United States Patent [19]
Kedar

[11] Patent Number: 6,165,778
[45] Date of Patent: Dec. 26, 2000

[54] REACTION VESSEL AGITATION APPARATUS

[75] Inventor: Haim Kedar, Palo Alto, Calif.

[73] Assignee: Affymax Technologies N.V., Greenford, United Kingdom

[21] Appl. No.: 09/109,613

[22] Filed: Jul. 2, 1998

Related U.S. Application Data

[63] Continuation of application No. 08/432,312, May 1, 1995, abandoned, which is a continuation-in-part of application No. 08/146,886, Nov. 2, 1993, Pat. No. 5,639,603, and a continuation-in-part of application No. 08/149,675, Nov. 2, 1993, Pat. No. 5,503,805.

[51] Int. Cl.$^7$ ..................................................... C12M 1/02
[52] U.S. Cl. ................................... 435/289.1; 435/287.2; 422/104; 366/110; 366/111; 366/211
[58] Field of Search .............................. 435/286.7, 287.2, 435/288.6, 809; 422/104, 101, 102; 366/110, 111, 210, 211

[56] References Cited

U.S. PATENT DOCUMENTS

| | | |
|---|---|---|
| 3,430,926 | 3/1969 | Freedman et al. . |
| 4,182,654 | 1/1980 | Royer ....................................... 435/272 |
| 4,315,074 | 2/1982 | Royer ......................................... 435/70 |
| 4,587,044 | 5/1986 | Miller et al. ............................. 530/211 |
| 4,597,412 | 7/1986 | Stark . |

(List continued on next page.)

FOREIGN PATENT DOCUMENTS

| | | | |
|---|---|---|---|
| 0 319 618 | 6/1989 | European Pat. Off. | ......... F16K 31/06 |
| 0 369 712 | 5/1990 | European Pat. Off. | ........ A61M 5/168 |
| 0 392 546 | 12/1990 | European Pat. Off. | .......... C12Q 1/68 |
| 0 529 504 | 3/1993 | European Pat. Off. | ......... B01J 19/00 |
| WO 90/00626 | 1/1990 | WIPO | .............................. C12Q 1/68 |
| WO 90/14441 | 11/1990 | WIPO | .............................. C12Q 1/68 |
| WO 90/15070 | 12/1990 | WIPO | .............................. C07K 1/04 |
| WO 91/17823 | 11/1991 | WIPO | .............................. B01J 19/00 |
| WO 92/00091 | 1/1992 | WIPO | ............................. A61K 37/02 |
| WO 92/03461 | 3/1992 | WIPO | ............................. C07H 17/00 |

(List continued on next page.)

OTHER PUBLICATIONS

*Advances in Analytical Chemisrty and Instrumentation*, Charles N. Reilley, Ed., John Wiley & Sons, Inc., 1964, pp. 56–59.

Amato, 1992, *Science*, 257:330–331 Speeding up a chemical game of chance.

Arnold et al., Mar. 15, 1991, *Optics Letters* 16(6):420–422 Room–temperature microparticle–based persistent spectral hole burning memory.

Baldwin et al., 1990, *Tetrahedron* 46(19):6879–6884 New photolabile phosphate protecting groups.

Barr et al., 1986, *BioTechniques* 4(5):428–432 7–Deaza–2'–deoxyguanosine–5'–triphosphate: Enhanced resolution in M13 dideoxy sequencing.

(List continued on next page.)

*Primary Examiner*—William H. Beisner
*Attorney, Agent, or Firm*—Darin J. Gibby; Matthew B. Murphy; Lauren L. Stevens

[57] ABSTRACT

A device and method for efficiently synthesizing diverse molecular products on substrates. A parent vessel 200 contains a suspension of substrates. The suspension is pressurized with argon and transferred to a plurality of reaction vessels 201–209 in one or more reaction vessel banks where monomer addition reactions take place. Optionally, the substrates may be tagged with a tag monomer. A vortexing motor 300 vortexes the contents of reaction vessels 201–209 during monomer addition reactions to enhance synthesis. After the desired monomer and/or tag monomer addition reaction, the suspension is pressurized with argon and transferred back to parent vessel 200 for mixing. Thereafter, the suspension may be pressurized with argon and reallocated among reaction vessels 201–209 for further synthesis.

16 Claims, 50 Drawing Sheets

Microfiche Appendix Included
(3 Microfiche, 200 Pages)

U.S. PATENT DOCUMENTS

| | | | |
|---|---|---|---|
| 4,631,211 | 12/1986 | Houghten | 428/35 |
| 4,671,941 | 6/1987 | Niina et al. | 422/131 |
| 4,701,304 | 10/1987 | Horn et al. | 422/62 |
| 4,713,326 | 12/1987 | Dattagupta et al. | 435/6 |
| 4,723,712 | 2/1988 | Egli et al. | |
| 4,741,354 | 5/1988 | DeMild, Jr. | |
| 4,755,558 | 7/1988 | Kalbag | 525/54.1 |
| 4,762,881 | 8/1988 | Kauer | 525/54.11 |
| 4,780,423 | 10/1988 | Bluestein | 436/527 |
| 4,794,150 | 12/1988 | Steel | 525/54.11 |
| 4,818,681 | 4/1989 | Dattagupta | 435/6 |
| 4,833,092 | 5/1989 | Geysen | 436/501 |
| 4,855,225 | 8/1989 | Fung et al. | 435/6 |
| 4,882,269 | 11/1989 | Schneider et al. | 435/6 |
| 4,965,188 | 10/1990 | Mullis et al. | 435/6 |
| 4,997,014 | 3/1991 | Weiler et al. | |
| 5,010,175 | 4/1991 | Rutter et al. | 530/334 |
| 5,143,854 | 9/1992 | Pirrung et al. | 436/518 |
| 5,182,366 | 1/1993 | Huebner et al. | |
| 5,192,269 | 3/1993 | Poli et al. | |
| 5,203,368 | 4/1993 | Barstow et al. | |
| 5,252,296 | 10/1993 | Zuckerman et al. | |
| 5,264,563 | 11/1993 | Huse | 536/25.3 |
| 5,316,034 | 5/1994 | Farnsworth et al. | |
| 5,320,139 | 6/1994 | Paul et al. | |
| 5,324,483 | 6/1994 | Cody et al. | 422/131 |
| 5,364,068 | 11/1994 | Farnsworth et al. | |
| 5,498,392 | 3/1996 | Wilding et al. | 422/68.1 |

FOREIGN PATENT DOCUMENTS

| | | | |
|---|---|---|---|
| WO 92/06176 | 4/1992 | WIPO | C12N 1/24 |
| WO 92/10092 | 6/1992 | WIPO | A01N 1/02 |
| WO 93/20242 | 10/1993 | WIPO | C12Q 1/70 |
| WO 94/02515 | 2/1994 | WIPO | C07K 17/06 |
| WO 94/08051 | 4/1994 | WIPO | C12Q 1/68 |
| WO 97/19283 | 5/1997 | WIPO | F16K 11/24 |

OTHER PUBLICATIONS

Bashkin et al., 1991, *J. Org. Chem.* 56:3168–3176 Synthesis and characterization of oligonucleotide peptides.

Borchardt et al., 1994, *J. Am. Chem. Soc.* 116:373–374 Synthetic receptor binding elucidated with an encoded combinatorial library.

Brenner et al., 1992, *Proc. Natl. Acad. Sci. USA* 89:5381–5383 Encoded combinatorial chemistry.

Crick et al., 1957, *Proc. Natl. Acad. Sci. USA* 43:416–421 Codes without commas.

Cwirla et al., 1990, *Proc. Natl. Acad. Sci. USA* 87:6378–6382 Peptides on phage: A vast library of peptides for indentifying ligands.

Eritja et al., 1991, *Tetrahedron* 47(24):4113–4120 Synthesis of defined peptide–oligonucleotide hybrids containing a nuclear transport signal sequence.

Farrall et al., 1976, *J. Org. Chem.* 41(24):3877–3882 Bromination and lithiation: Two important steps in the functionalization of polystyrene resins.

Fodor et al., 1991, *Science* 251:767–773 Light–directed, spatially addressable parallel chemical synthesis.

Frank and Doring, 1988, *Tetrahedron* 44(19):6031–6040 Simultaneous multiple peptide synthesis under continuous flow conditions on cellulose paper discs as segmental solid supports.

Frank et al., 1983, *Nuc. Acids. Res.* 11(13):4365–4377 A new general approach for the simultaneous chemical synthesis of large numbers of oligonucleotides: Segmental solid supports.

Frank et al., 1990, *Peptides* (Giralt & Andreu, eds., ESCOM Science Pub.), pp. 151–152 Facile and rapid 'spot–synthesis' of large numbers of peptides on membrane sheets.

Furka et al., Jul. 10–15, 1988, *14th Intl. Congress of Biochemistry,* Prague, Czechoslovakia, Abstract No. FR:013 Proteins and nucleic acids in three dimensions: Cornucopia of peptides by synthesis.

Furka et al., Aug. 15–19, 1988, *Xth Intl. Symp. on Medicinal Chem.,* Budapest, Hungary, Abstract No. P–168, p. 288 More peptides by less labour.

Furka et al., 1991, *Int. J. Peptide Protein Res.,* 37:487–493 General method for rapid synthesis of multicomponent peptide mixtures.

Geysen et al., 1987, *J. Immunol. Meth.,* 102:259–274 Strategies for epitope analysis using peptide synthesis.

Geysen et al., 1984, *Proc. Natl. Acad. Sci. USA,* 81:3998–4002 Use of peptide synthesis to probe viral antigens for epitopes to a resolution of a single amino acid.

Gordon et al., 1994, *J. Med. Chem.,* 37(10):1385–1401 Applications of combinatorial technologies to drug discovery. 2. Combinatorial organic synthesis, library screening strategies, and future directions.

Haralambidis et al., 1990, *Nuc. Acids Res.* 18(3):493–505 The synthesis of polyamide–oligonucleotide conjugate molecules.

Hayakawa et al., 1990, *J. Am. Chem. Soc.* 112:1691–1696 The allylic protection method in solid–phase oligonucleotide synthesis: An efficient preparation of solid–anchored DNA Oligomers.

Hodgson, 1992, *Bio/Technology* 10:973–974 Receptor screening and the search for new pharmaceuticals.

Houghten et al., 1991, *Nature* 354:84–86 Generation and use of synthetic peptide combinatorial libraries for basic research and drug discovery.

Houghten, 1985, *Proc. Natl. Acad. Sci. USA* 82:5131–5135 General method for the rapid solid–phase synthesis of large numbers of peptides: Specificity of antigen–antibody interaction at the level of individual amino acids.

Juby et al., 1991, *Tetrahedron Letters* 32(7):879–882 Facile preparation of 3' oligonucleotide–peptide conjugates.

Kaiser et al., 1989, *Science* 243:187–192 Peptide and protein synthesis by segment synthesis–condensation.

Kerr et al., 1993, *J. Am Chem Soc.,* 115:2529–2531 Encoded combinatorial peptide libraries containing non–natural amino acids.

Lam et al., 1991, *12th Amer. Pep. Symp.,* Abstract LW3 Rapid selection and structure determination of acceptor binding ligands from a large synthetic peptide library.

Lam et al., 1992, *Pept.: Chem. Bio., Proc. Am. Pept. Symp. 12th,* pp. 492–495 The selectide process: Rapid generation of large synthetic peptide libraries linked to identification and structure determination of acceptor–binding ligands.

Lam et al., 1991, *Nature* 354:82–84 A new type of synthetic peptide library for indentifying ligand–binding activity.

Mathur et al., 1980, *Polymers as Aids in Organic Chemistry,* Academic Press, New York, Ch. 9–12:138–197.

Needels et al., 1993, *Proc. Natl. Acad. Sci. USA,* 90:10700–10704 Generation and screening of an oligonucleotide–encoded sythetic peptide library.

Nikolaiev et al., 1993, *Peptide Research,* 6(3):161–170 Peptide–encoding for structure determination of nonsequenceable polymers within libraries synthesized and tested on solid phase supports.

Ohlmeyer et al., 1993, *Proc. Natl. Acad. Sci. USA*, 90:10922–10926 Complex synthetic chemical libraries indexed with molecular tags.

Tjoeng et al., 1990, *Int. J. Pept. Protein Res.* 35:141–146 Multiple peptide synthesis using a single support (MPS3).

Van Brunt, Nov. 16, 1993, *BioWorld Today* pp. 3–5 Affymax creates new large–scale drug screen.

Van der Zee et al., 1989, *Eur. J. Immunol.* 19:43–48 Efficient mapping and characterization of a T cell epitope by the simultaneous synthesis of multiple peptides.

Zuckermann et al. (1992), "Design, construction and application of a fully automated equimolar peptide mixture synthesizer," Intl. J. Peptide Protein Res. 40:497–506.

VALVE DIAGNOSTICS

Solvent Delivery Valves:
☐ 0  ☐ 1  ☐ 2  ☐ 3
☐ 4  ☐ 5  ☐ 6  ☐ 7
☐ 8  ☐ 9  ☐ 10 ☐ 11
☐ 12 ☐ 13 ☐ 14 ☐ 15
☐ 16 ☐ 17 ☐ 18 ☐ 19
☐ 20 ☐ 21 ☐ 22 ☐ 23
☐ 90 ☐ 91 ☐ 129

Pressurization Valves:
☐ 80 ☐ 81 ☐ 82 ☐ 83
☐ 84 ☐ 85 ☐ 86 ☐ 87
☐ 88

Bank 1 Valves:
☐ 100 ☐ 101 ☐ 102 ☐ 103 ☐ 104 ☐ 105 ☐ 106 ☐ 107
☐ 108 ☐ 109 ☐ 110 ☐ 111 ☐ 112 ☐ 113 ☐ 114 ☐ 115
☐ 116 ☐ 117 ☐ 118 ☐ 119 ☐ 120 ☐ 121 ☐ 122

Bank 2 Valves:
☐ 200 ☐ 201 ☐ 202 ☐ 203 ☐ 204 ☐ 205 ☐ 206 ☐ 207
☐ 208 ☐ 209 ☐ 210 ☐ 211 ☐ 212 ☐ 213 ☐ 214 ☐ 215
☐ 216 ☐ 217 ☐ 218 ☐ 219 ☐ 220 ☐ 221 ☐ 222

Bank 3 Valves:
☐ 300 ☐ 301 ☐ 302 ☐ 303 ☐ 304 ☐ 305 ☐ 306 ☐ 307
☐ 308 ☐ 309 ☐ 310 ☐ 311 ☐ 312 ☐ 313 ☐ 314 ☐ 315
☐ 316 ☐ 317 ☐ 318 ☐ 319 ☐ 320 ☐ 321 ☐ 322

Bank 4 Valves:
☐ 400 ☐ 401 ☐ 402 ☐ 403 ☐ 404 ☐ 405 ☐ 406 ☐ 407
☐ 408 ☐ 409 ☐ 410 ☐ 411 ☐ 412 ☐ 413 ☐ 414 ☐ 415
☐ 416 ☐ 417 ☐ 418 ☐ 419 ☐ 420 ☐ 421 ☐ 422

[ Close All ]   [ ✗ Cancel ]

FIG. 39

SENSOR DIAGNOSTICS

Bank 1 Sensors:
☒ 101 ☒ 102 ☒ 103 ☒ 104 ☒ 105 ☒ 106 ☒ 107
☒ 108 ☒ 109 ☒ 110 ☒ 111 ☒ 112 ☒ 113 ☒ 114
☒ 115 ☒ 116 ☒ 117 ☒ 118 ☒ 119 ☒ 120

Bank 2 Sensors:
☒ 201 ☐ 202 ☒ 203 ☐ 204 ☒ 205 ☐ 206 ☐ 207
☐ 208 ☐ 209 ☒ 210 ☒ 211 ☒ 212 ☒ 213 ☒ 214
☒ 215 ☒ 216 ☒ 217 ☒ 218 ☒ 219 ☒ 220

Bank 3 Sensors:
☒ 301 ☒ 302 ☒ 303 ☒ 304 ☒ 305 ☒ 306 ☒ 307
☒ 308 ☒ 309 ☐ 310 ☐ 311 ☐ 312 ☐ 313 ☐ 314
☐ 315 ☒ 316 ☒ 317 ☒ 318 ☒ 319 ☒ 320

Bank 4 Sensors:
☐ 401 ☐ 402 ☐ 403 ☐ 404 ☐ 405 ☐ 406 ☐ 407
☐ 408 ☒ 409 ☒ 410 ☐ 411 ☐ 412 ☐ 413 ☐ 414
☐ 415 ☐ 416 ☐ 417 ☐ 418 ☒ 419 ☒ 420

Misc. Sensors:
☐ 9 ☐ 12 ☐ 90 ☐ 99

✗ Cancel

Amino & Oligo Setup

RV01: V ATGCGT
RV02:
RV03:
RV04:
RV05:
RV06:
RV07:
RV08:
RV09:
RV10:
RV11:
RV12:
RV13:
RV14:
RV15:
RV16:
RV17:
RV18:
RV19:
RV20:
RV21:
RV22:
RV23:
RV24:
RV25:
RV26:
RV27:
RV28:
RV29:
RV30:
RV31:
RV32:
RV33:
RV34:
RV35:
RV36:

✓ OK — 1382
✗ Cancel — 1383
? Help 1380
1381

REACTION VESSEL AGITATION APPARATUS

RELATED APPLICATIONS

This application is a continuation of U.S. patent application Ser. No. 08/432,312, filed May 1, 1995, now abandoned, which is a continuation-in-part of U.S. application Ser. Nos. 08/146,886 and 08/149,675, both filed on Nov. 2, 1993, now U.S. Pat. Nos. 5,639,603 and 5,503,805, respectively, each of which is incorporated herein by reference for all purposes.

MICROFICHE APPENDIX

This specification includes microfiche Appendix 1 having 3 sheets with 200 frames.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD OF THE INVENTION

The present invention relates generally to methods and devices for synthesizing very large collections of diverse molecules and for identifying and isolating compounds with useful and desired activities from such collections. The invention also relates to the incorporation of identification tags in such collections to facilitate identification of compounds with desired properties.

BACKGROUND OF THE INVENTION

Ligands for macromolecular receptors can be identified by screening diverse collections of peptides produced through either molecular biological or synthetic chemical techniques. Recombinant peptide libraries have been generated by inserting degenerate oligonucleotides into genes encoding capsid proteins of filamentous bacteriophage and the DNA-binding protein Lac I. See Cwirla et al., 1990, *Proc. Natl. Acad. Sci. USA* 87: 6378–6382; Scott & Smith, 1990, *Science* 249: 386–390; Devlin et al., 1990, *Science* 249: 404–406; Cull et al., 1992, *Proc. Natl. Acad. Sci. USA* 89:1865–1869; and PCT publication Nos. WO 91/17271, WO 91/19818, WO 93/08278, each of which is incorporated herein by reference. These random libraries may contain more than 109 different peptides, each fused to a larger protein sequence that is physically linked to the genetic material encoding it. Such libraries are efficiently screened for interaction with a receptor by several rounds of affinity purification, the selected exposition or display vectors being amplified in *E. coli* and the DNA of individual clones sequenced to reveal the identity of the peptide responsible for receptor binding. See also PCT publication Nos. WO 91/05058 and WO 92/02536.

Chemical approaches to generating peptide or other molecular libraries are not limited to syntheses using just the 20 genetically coded amino acids. By expanding the building block set to include unnatural amino acids and other molecular building blocks, the accessible sequence and structural diversity is dramatically increased. In several of the strategies described for creating synthetic molecular libraries, the reaction products are spatially segregated and the identity of individual library members is unambiguously defined by the nature of the synthesis (see Geysen et al., 1984, *Proc. Natl. Acad. Sci. USA* 81: 3998–4002; Geysen et al, 1986, in *Synthetic Peptides as Antigens;* Ciba Foundation Symposium 119, eds. Porter, R. & Wheelan, J. (Wiley, New York) pp. 131–146; Fodor et al., 1991, *Science* 251: 767–773; U.S. Pat. No. 5,143,854; and PCT patent publication Nos. WO 84/03564; 86/00991; 86/06487; 90/15070; and 92/10092, each of which is incorporated herein by reference).

Libraries of more than 30 million soluble peptides have been prepared by the "tea-bag" method of multiple peptide synthesis. See Houghten, 1985, *Proc. Natl. Acad. Sci. USA* 82: 5131–5135; and U.S. Pat. No. 4,631,211, each of which is incorporated herein by reference. Each library is synthesized and screened as degenerate peptide mixtures in which individual amino acids within the sequence are explicitly defined. An iterative process of screening (e.g., in a competition binding assay) and resynthesis is used to fractionate these mixtures and define the most active peptides within the library. See Houghten et al., 1991, *Nature* 354: 84–86; Pinilla et al., 1992, *Peptide Research* 5: 351–358; Blake, J. & Litzi-Davis, 1992, *Bioconjugate Chem.* 3: 510–513; and PCT patent publication No. WO 92/09300, each of which is incorporated herein by reference.

Using the split-synthesis protocol of Furka et al., 1988, *Abstr. 14th Int. Congr. Biochem.*, Prague, Czech. 5: 47 (see also Furka et al., 1991, *Int J. Peptide Protein Res.* 37: 487–493; and Sebestyen et al., 1993, *Bioorg. Med. Chem. Lett.* 3: 413–418), Lam and coworkers have prepared libraries containing ~$10^6$ peptides attached to 100–200 $\mu$m diameter resin beads. See Lam et al., 1991, *Nature* 354: 82–84; Lam et al., 1993, *Bioorg. Med. Chem. Lett.* 3: 419–424; and PCT patent publication No. WO 92/00091, each of which is incorporated herein by reference. The bead library is screened by incubation with a labeled receptor: beads binding to the receptor are identified by visual inspection and are selected with the aid of a micromanipulator. Each bead contains 50–200 pmol of a single peptide sequence which may be determined directly either by Edman degradation or mass spectrometry analysis. In principle, one could create libraries of greater diversity using this approach by reducing the dimensions of the beads. The sensitivity of peptide sequencing techniques is limited to ~1 pmole, however, placing a clear limitation on the scope of direct peptide sequencing analysis. Moreover, neither analytical method provides for straightforward and unambiguous sequence analysis when the library building block set is expanded to include D- or other non-natural amino acids or other chemical building blocks.

High throughput screening of collections of chemically synthesized molecules and of natural products (such as microbial fermentation broths) has traditionally played a central role in the search for lead compounds for the development of new pharmacological agents. The remarkable surge of interest in combinatorial chemistry and the associated technologies for generating and evaluating molecular diversity represent significant milestones in the evolution of this paradigm of drug discovery. See Pavia et al., 1993, *Bioorg. Med. Chem. Lett.* 3: 387–396, incorporated herein by reference. To date, peptide chemistry has been the principle vehicle for exploring the utility of combinatorial methods in ligand identification. See Jung & Beck-Sickinger, 1992, *Angew. Chem. Int. Ed. Engl.* 31: 367–383, incorporated herein by reference. This may be ascribed to the availability of a large and structurally diverse range of amino acid monomers, a relatively generic, high-yielding solid phase coupling chemistry and the synergy with biological approaches for generating recombinant peptide libraries. Moreover, the potent and specific biological activities of many low molecular weight peptides make these molecules attractive starting points for therapeutic drug discovery. See Hirschmann, 1991, *Angew. Chem. Int. Ed. Eng.* 30: 1278–1301, and Wiley & Rich, 1993, *Med. Res. Rev.* 13: 327–384, each of which is incorporated herein by reference. Unfavorable pharmacodynamic properties such as poor oral bioavailability and rapid clearance in vivo have limited the more widespread development of peptidic compounds as drugs however. This realization has recently inspired workers to extend the concepts of combinatorial organic synthesis beyond peptide chemistry to create libraries of known pharmacophores like benzodiazepines (see Bunin & Ellman, 1992, *J. Amer. Chem. Soc.* 114: 10997–10998, incorporated herein by reference) as well as polymeric molecules such as oligomeric N-substituted glycines ("peptoids") and oligocarbamates. See Simon et al., 1992, *Proc. Natl. Acad. Sci. USA* 89: 9367–9371; Zuckermann et al., 1992, *J. Amer. Chem. Soc.* 114: 10646–10647; and Cho et al., 1993, *Science* 261:1303–1305, each of which is incorporated herein by reference.

Despite the great value that large libraries of molecules can have for identifying useful compounds or improving the properties of a lead compound, the difficulties of screening such libraries, particularly large libraries, has limited the impact access to such libraries should have made in reducing the costs of, e.g., drug discovery and development. Consequently, the development of methods for generating and screening libraries of molecules in which each member of the library is tagged with a unique identifier tag to facilitate identification of compounds (see PCT patent publication No. WO 93/06121, incorporated herein by reference; see also U.S. patent application Ser. No. 946,239, filed Sep. 16, 1992, and Ser. No. 762,522, filed Sep. 18, 1991, supra) met with great enthusiasm. In the method, products of a chemical synthesis procedure, typically a combinatorial synthesis on resin beads, are explicitly specified by attachment of an identifier tag to the beads coincident with each coupling or other product generating reaction step in the synthesis. Each tag specifies what happened in a reaction step of interest, e.g., which amino acid monomer was coupled in a particular step of a peptide synthesis procedure. The structure or identity of a compound, e.g., the sequence of a peptide, on any bead can be deduced by reading the set of tags on that bead. Ideally, such tags have a high information content, are amenable to very high sensitivity detection and decoding, and are stable to reagents used in the synthesis. The concept of an oligonucleotide-encoded chemical synthesis was also proposed by Brenner and Lerner, 1992, *Proc. Natl. Acad. Sci. USA* 89: 5181–5183, incorporated herein by reference.

The encoding method has been employed to show that, starting with an orthogonally differentiated diamine linker, parallel combinatorial synthesis can be used to generate a library of soluble chimeric peptides comprising a "binding" strand and a "coding" strand. See Kerr et al., 1993, *J. Amer. Chem. Soc.* 115: 2529–2531, incorporated herein by reference. The coupling of either natural or unnatural amino acid monomers to the binding strand was recorded by building an amino acid code comprised of four L-amino acids on the "coding" strand. Compounds were selected from equimolar peptide mixtures by affinity purification on a receptor and were resolved by HPLC. The sequence of the coding strand of individual purified molecules was then determined by Edman degradation to reveal the structure of the binding strand. An analogous peptidic coding scheme was also recently reported by Nikolaiev et al., 1993, *Peptide Research* 6: 161–170.

Constraints on the sensitivity and throughput of the Edman procedure will ultimately restrict the scope of this aspect of the encoding method to analyzing libraries of limited diversity. The use of oligonucleotide tags offers greater promise, but improved methods for synthesizing oligonucleotide-tagged molecular libraries are needed. Moreover, there remains a need for alternate methodology for synthesizing and screening very large tagged molecular libraries.

Where it is desirable to synthesize diverse collections of molecules on a plurality of solid supports such as beads, additional problems can arise. Examples of the use of beads with diverse molecular products synthesized thereon are disclosed in, for example, the following applications, incorporated herein by reference for all purposes: U.S. application Ser. No. 07/876,792, filed on Apr. 29, 1992; U.S. application Ser. No. 071762,522, filed on Sep. 18, 1991; and U.S. application Ser. No. 07/946,239, filed on Sep. 16, 1992.

While meeting with substantial success, the techniques described above have also met with certain limitations. For example, when the synthesis of diverse products takes place on beads, many manual manipulations of such beads become necessary. For example, in U.S. application Ser. No. 07/876,792, filed on Apr. 29, 1992, incorporated by reference herein for all purposes, one must suspend a collection of beads in a carrier, divide the beads, perform monomer addition reactions on the divided sets of beads, sometimes redivide and selectively recombine the beads thus synthesized, mix the recombined beads, and repeat the process. When large numbers of monomers are involved and when the reactions involve many monomer addition steps, manual techniques become extremely tedious. In addition, the "accounting" for the many products that have been synthesized becomes a daunting task.

From the above, it is seen that improved methods and devices for synthesizing and screening very large tagged molecular libraries are desired. The present invention meets these and other needs.

SUMMARY OF THE INVENTION

The present invention provides improved methods for generating and screening molecular libraries in which the individual molecules in the library are tagged with unique, easily decoded identifier tags. Also provided is an apparatus and method for rapidly and efficiently synthesizing diverse molecular products.

In one embodiment, the present invention provides methods and reagents for tagging the products of combinatorial chemical processes to construct encoded synthetic chemical libraries. In an important embodiment, the invention provides a method for performing peptide and oligonucleotide synthesis on microscopic beads through an alternating and compatible synthetic procedure. The large oligonucleotide-encoded synthetic peptide library produced by this combinatorial synthesis is composed of many beads, each of which contains many copies of a single peptide (with a defined sequence) and a single-stranded DNA tag whose sequence artificially and unambiguously codes for the structure of the associated peptide. The library can be efficiently interrogated for interaction with fluorescently-labeled biological receptors by flow cytometry, and individual beads selected by exploiting the ability of FACS instrumentation to sort single beads. The DNA tag on a sorted bead is amplified by the PCR and sequenced to determine the structure of the encoded peptide ligand. The library can be used, for example, to find high affinity (nanomolar) ligands for a receptor such as an anti-peptide monoclonal antibody.

A synthetic molecular library of the invention can be produced by synthesizing on each of a plurality of solid supports a compound, the compound being different for different solid supports. The compound is synthesized in a process comprising the steps of: (a) apportioning the supports in a stochastic manner among a plurality of reaction vessels; (b) exposing the supports in each reaction vessel to a first chemical building block; (c) pooling the supports; (d) apportioning the supports in a stochastic manner among the plurality of reaction vessels; (e) exposing the supports in each reaction vessel to a chemical building block; and (f) repeating steps (a) through (e) from at least one to twenty times. Typically, substantially equal numbers of solid supports will be apportioned to each reaction vessel. In one embodiment of the method, the chemical building blocks are chosen from the set of amino acids, and the resulting compound is a peptide oligomer.

More particularly, the invention relates to certain improvements in the coupling chemistries associated with such methods. One such improvement relates to the chemistry used to remove the Fmoc protecting group from the alpha-amino group of a bead, linker, or growing peptide chain in such syntheses. Preferably, such removal is effected by treatment with 5 to 15%, preferably 10%, piperidine for 5 to 60 minutes, preferably 5 to 10 minutes, although other conditions may be employed, e.g., 15 to 30% piperidine for 5 to 30 minutes. Other improvements relate to the activation chemistry of the peptide coupling reactions, in that when certain automated instrumentation is used to perform the synthesis of an oligonucleotide tagged peptide library, the invention provides for a simple mixture of HOBt/HBTU to reduce reagent supply bottles.

In another aspect, the present invention relates to methods of synthesizing a tagged molecular library, wherein each molecule in the library is covalently attached to a solid support and is tagged with one or more different chemically inert hydrocarbon tags, wherein said tags comprise a variable hydrocarbon region and a molecular hook. Preferably, such tags comprise a cleavable linker attaching said tag to said solid support, a molecular hook, and a variable length hydrocarbon chain linking said molecular hook to said cleavable-linker. More preferred are those embodiments wherein said tag comprises the formula:

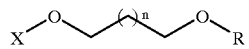

wherein n is from 1 to 10 or more, X is a cleavable linker and R is a molecular hook. Such molecular hooks are preferably selected from the group consisting of biotin, a complement of a high association peptide pair and a protected activatable group, such as a photoactivatable group. Preferred cleavable linkers are photocleavable linkers Also provided is a method of detecting the presence of such chemically inert hydrocarbon tags. The method comprises cleaving the one or more different tags from the solid support, followed by immobilizing the tags to a second solid support. The immobilized tags are then treated with an oligonucleotide sequence whereby the oligonucleotide sequence selectively binds to the immobilized tag. The oligonucleotide sequence is then amplified, and its presence is detected, wherein the presence or absence of the oligonucleotide sequence is indicative of the presence or absence of the tag.

Another embodiment of the present invention provides a method of determining the sequence of synthesis steps for a synthesized molecule attached to a solid support in tagged molecular library, tagged with chemically inert hydrocarbon tags. The method comprises individually detecting the presence of one or more different tags on said solid support, the presence or absence of said individual tags being indicative of the occurrence of a particular synthesis step in the synthesis of said molecule.

In another aspect, the invention relates to methods and instrumentation for synthesizing encoded synthetic chemical libraries on beads too small to be separated on conventional flow cytometry instrumentation. Such small beads allow the resulting library size to increase from the more typical range of $10^9$ to $10^{13}$ for bead based libraries up to a size of $10^{18}$ members for bead-free libraries. The invention also relates to methods for screening such libraries.

The invention also relates to methods for screening encoded synthetic libraries to identify useful compounds. In one important aspect, the invention provides important advances in the field of natural product screening relating to methods for generating, tagging, and screening natural product libraries to characterize and identify compounds with useful activity.

In another aspect, the invention relates to an improved process for rapidly and efficiently identifying a pool of compounds from a molecular library of the invention. In this method, the oligonucleotide tags from a pool of tagged compounds that exhibit a desired property (e.g., binding to a receptor) are concatemerized and cloned to facilitate sequencing of a plurality of tags in a single sequencing reaction. If the tagged compounds are peptides, and an encoding scheme based on the genetic code is employed, then one can subclone individual tags from the concatemer into other selection and expression systems, such as the plasmid and phage-based systems described in the background section above, for further analysis of the peptide.

In another embodiment, the present invention provides an apparatus and method for rapidly and efficiently synthesizing diverse molecular products. According to specific aspects of the invention, diverse polymers are synthesized on substrates such as glass beads. Optionally, the beads may be simultaneously "tagged" during the synthesis reactions with a molecular tag. Merely by way of example, the synthesized molecules on the beads may comprise peptides, while the molecular tags may comprise oligonucleotides. Of course, other molecular products may also be synthesized using the techniques described herein whenever a molecule has a basic "building block" common to other related molecules. Examples include benzodiazapines, prostaglandins, and beta turn mimetics.

According to one embodiment of the invention, a parent vessel is used to mix bead suspensions. The mixed beads are distributed through a common manifold to a plurality of separate reaction vessels. In the reaction vessels, the beads are exposed to different, selected monomers, which react on the beads to be coupled thereto, preferably covalently. The beads may, optionally, be exposed to chemical "tags" which also couple, covalently or otherwise, to the beads. The beads are then recombined through the manifold back to the parent vessel and mixed. The mixed bead suspension is then again divided among the plurality of reaction vessels, and the process of monomer addition, bead mixing, and redistribution continues. The process results in the formation of a collection of beads or other substrates with a diverse set of molecules formed on the surfaces thereof.

According to one aspect of the invention, the invention includes an apparatus and a method for synthesizing diverse molecules on substrates. The substrates are distributed to selected reaction vessels from a parent vessel. Reagents are then introduced into the reaction vessels to synthesize a portion of the molecules. The substrates are then moved to the parent vessel for mixing. The substrates are then redistributed to the reaction vessels for further synthesis. The cycles continue until a desired set of molecules are synthesized. During synthesis, the entire synthesizer is sealed from the external atmosphere.

In general, the invention provides apparatus and improved methods for generating and screening molecular libraries in which the individual molecules in the library are tagged with unique, easily decoded identifier tags.

A further understanding of the nature and advantages of the invention may be had with reference to the description and drawings below.

DESCRIPTION OF THE DRAWINGS

FIG. 39 depicts the valve diagnostic screen.

FIG. 40 depicts the sensor diagnostic screen.

FIGS. 42–44 show the dialog boxes involved in setting up a synthesis, allowing the user to select the reaction vessels to be used in the synthesis (FIG. 42), select the start, loop and end macros (FIG. 43) and enter the amino acid symbol and oligonucleotide code for each reaction vessel (FIG. 44).

DESCRIPTION OF THE SPECIFIC EMBODIMENTS

Figure 1:
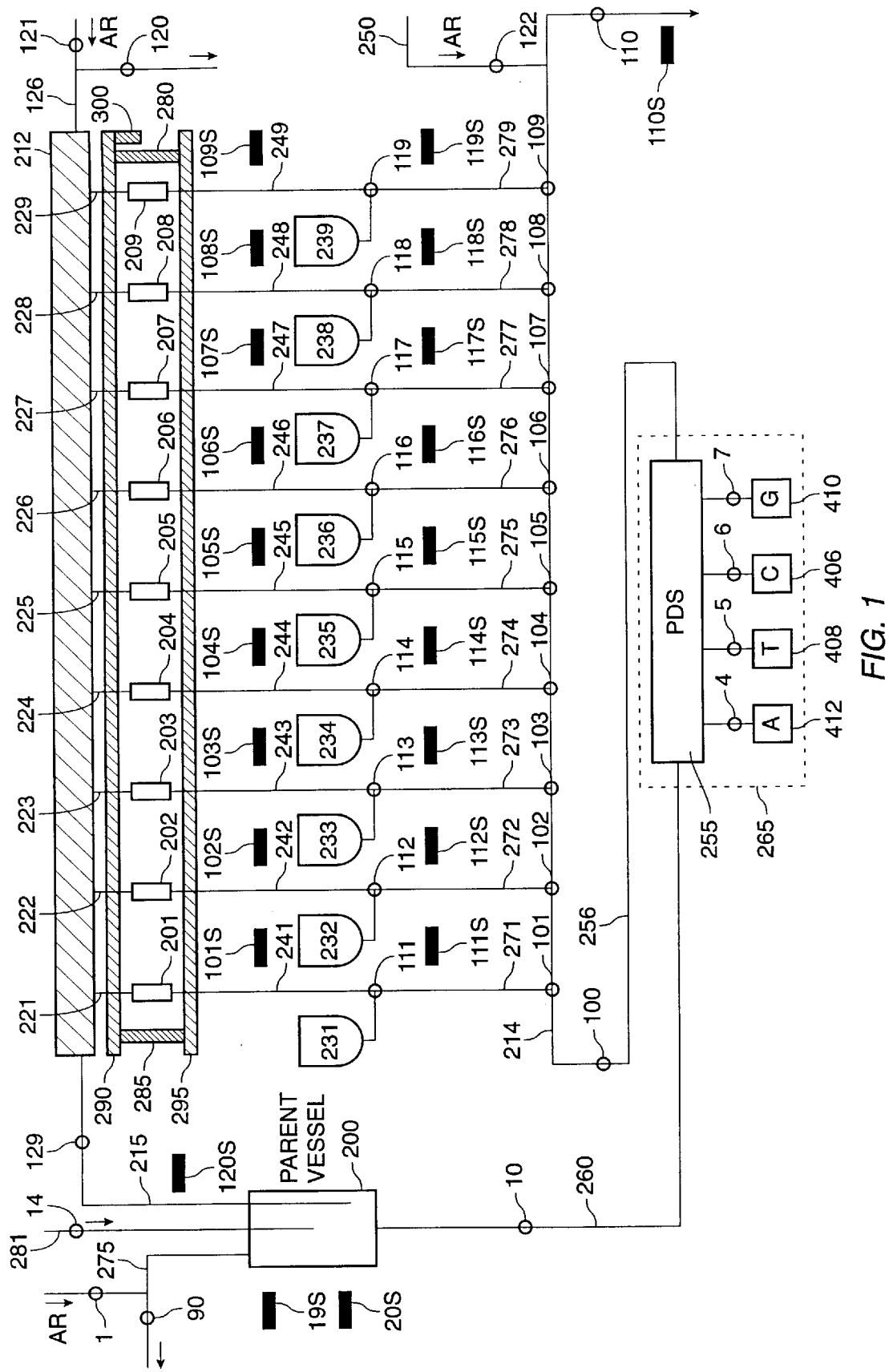
FIG. 1 shows a schematic diagram of the synthesizer of the present invention.

The present invention relates generally to improved methods for generating and screening tagged chemical libraries. The present invention also relates to a device useful in synthesizing collections of diverse molecules, such as the described tagged chemical libraries.

To appreciate the value of the improved methods, one must understand not only the basic methodology for making and using tagged libraries but also how the various steps of synthesis and screening interact and how the selection of reagents impacts the results achieved. Tagged chemical libraries are often synthesized on a solid support, and the choice of support and linker is critical to success. A linker can be used to attach the support to the tag, to attach the support to a library molecule, or, in an embodiment where there is no solid support, to attach the tag to a library molecule. The choices relating to chemical building blocks, tags, and synthesis methods can be equally critical and are also impacted by the nature of the solid supports and linkers available. The assays and applications for which the tagged libraries are intended also impact these choices, as well as the instrumentation and reagents available.

Although the apparatus and methods of the present invention are illustrated primarily with regard to the synthesis of oligonucleotides and peptides, the invention is not so limited. The invention will find application in the synthesis of materials such as polysaccharides, phospholipids, polyurethanes, benzodiazapines, prostaglandins, and beta turn mimetics, and other materials. Cyclic materials may be formed as disclosed in U.S. Pat. No. 5,242,974 (Holmes), incorporated herein by reference.

The use and synthesis of diverse materials such as oligonucleotides and peptides is disclosed in further detail in the following copending applications, which are incorporated herein by reference for all purposes: U.S. application Ser. No. 07/876,792, filed on Apr. 29, 1992; U.S. application Ser. No. 07/762,522, filed on Sep. 18, 1991; and U.S. application Ser. No. 07/946,239, filed on Sep. 16, 1992.

The description of the invention is provided as indicated by the following outline:

OUTLINE

I. Overview of a Synthesis of a Tagged Chemical Library
II. The Solid Support
   A. Types
   B. Linkers
   C. Molecular Supports
III. The Chemical Building Blocks
   A. Oligomers and Monomers
   B. Other Building Blocks
IV. The Tag
V. Synthesis Methods
   A. Oligonucleotide Tagged Peptide Libraries
   B. Improved Method for Synthesizing Oligonucleotide-Tagged Peptide Libraries
   C. Small Molecule Synthesis
   D. Methods for Generating Soluble Libraries
VI. Assay Methods
   A. Screening Assays for Bead-based Libraries
   B. Screening Soluble Molecules
   C. Screening Natural Product Libraries
VII. Instrumentation and Reagents
VIII. Apparatus for Parallel Coupling Synthesis Reactions
IX. Apparatus and Methods for Apportioning Individual or Select Number of Library Beads
Examples
End of Outline In addition to the outline above, the following glossary is provided to facilitate the description of the invention, and a number of abbreviations and terms are defined to have the general meanings indicated as used herein to describe the invention.

Abbreviations: HBTU, O-(benzotriazol-1-yl)-1,1,3,3-tetramethyluronium hexafluorophosphate; HOBt, 1-hydroxybenzotriazole; HATU, [O-(7-azabenzotriazol-1-yl)-1,1,3,3-tetramethyluroniumhexafluorophosphate; TFA, trifluoroacetic acid; TCA, trichloroacetic acid; DIEA, diisopropylethylamine; DMF, dimethylformarnide; Fmoc, 9-fluorenylmethyloxycarbonyl; DMT, dimethoxytrityl; Trt, trityl; Bz, benzoyl; Pmc, 2,2,5,7, 8-pentamethylchroman-6-sulfonyl; 'BOc, tert-butyloxycarbonyl; PBS, phosphate-buffered saline; BSA, bovine serum albumin; mAb, monoclonal antibody.

Complementary or substantially complementary: These terms refer to the ability of one compound to bind to another, e.g., as a ligand binds to its complementary receptor. Typically, these terms are used in connection with a description of base pairing between nucleotides of nucleic acids, such as, for instance, between the two strands of a double stranded DNA molecule or between an oligonucleotide primer and a primer binding site on a single stranded nucleic acid to be sequenced or amplified. "Complementary" nucleotides are, generally, A and T (or A and U), and C and G, but there are a wide variety of synthetic or modified nucleotides with binding properties known to those of skill in the art. "Substantial complementarity" exists when an RNA or DNA strand will hybridize under selective hybridization conditions to a complementary nucleic acid. Typically, hybridization will occur when there is at least about 55% complementarity over a stretch of at least 14 to 25 nucleotides, but more selective hybridization will occur as complementarity increases to 65%, 75%, 90%, and 100%. See Kanehisa, 1984, *Nucl. Acids Res.* 12:203, incorporated herein by reference. Highly selective hybridization conditions are known as "stringent hybridization conditions", defined below.

Epitope: This term is used to describe a portion of an antigen molecule delineated by the area of interaction with the subclass of receptors known as antibodies.

Identifier tag: In the most general sense, this term is used to denote a physical attribute that provides a means whereby one can identify a chemical reaction, such as a monomer addition reaction an individual solid support has experienced in the synthesis of an oligomer on that solid support. The identifier tag serves to record a step in a series of reactions used in the synthesis of a chemical library. The identifier tag may have any recognizable feature, including for example: a microscopically or otherwise distinguishable shape, size, mass, color, optical density, etc.; a differential absorbance or emission of light; chemically reactivity; magnetic or electronic properties; or any other distinctive mark capable of encoding the required information, and decipherable at the level of one (or a few) molecules. A preferred example of such an identifier tag is an oligonucleotide, because the nucleotide sequence of an oligonucleotide is a robust form of encoded information. An "identifier tag" can be coupled directly to the oligomer synthesized, whether or not a solid support is used in the synthesis. In this latter embodiment, the identifier tag can conceptually be viewed as also serving as the "support" for oligomer synthesis.

Ligand: This term is used to denote a molecule that is recognized by, typically by binding to, a particular receptor. The agent bound by or reacting with a receptor is called a "ligand", a term which is definitionally meaningful only in terms of its counterpart receptor. The term "ligand" does not imply any particular molecular size or other structural or compositional feature other than that the substance in question is capable of binding or otherwise interacting with the receptor. Also, a "ligand" may serve either as the natural ligand to which the receptor binds, or as a functional analogue that may act as an agonist or antagonist. Ligands that can be investigated by this invention include, but are not restricted to, agonists and antagonists for cell membrane receptors, toxins and venoms, viral epitopes, hormones, sugars, cofactors, peptides, enzyme substrates, cofactors, drugs (e.g., opiates, steroids, etc.), and proteins.

Monomer: This term is used to denote any member of a set of molecules that can be joined together to form another molecule or set of molecules, such as a set of oligomers or polymers. Sets of monomers useful in the present invention include, but are not restricted to, for the example of peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. Those of skill in the art will recognize that a "monomer" is simply one type of "chemical building block" and that any type of chemical building block can be employed in the present method, regardless of whether one is synthesizing an oligomer or a small organic molecule or some other molecule.

Oligomer or Polymer: These terms are used to denote molecules that are formed by a process involving the chemical or enzymatic addition of monomer subunits. Such oligomers include, for example, both linear, cyclic, and branched polymers of nucleic acids, polysaccharides, phospholipids, and peptides having either alpha-, beta-, or omega-amino acids, heteropolymers, polyurethanes, polyesters, polycarbonates, polyureas, polyamides, polyethyleneimines, polyarylene sulfides, polysiloxanes, polyimides, polyacetates, or other polymers, as will be readily apparent to one skilled in the art upon review of this disclosure.

Peptide: This term is used to denote an oligomer in which the monomers are alpha amino acids joined together through amide bonds. A "peptide" can also be referred to as a "polypeptide." In the context of this invention, one should appreciate that the amino acids may be the L-optical isomer or the D-optical isomer. Peptides are more than two amino acid monomers long, but more often are more than 5 to 10 amino acid monomers long and can be even longer than 20 amino acids, although peptides longer than 20 amino acids are more likely to be called "polypeptides." Standard single letter abbreviations for amino acids are used (e.g., P for proline). These abbreviations are included in Stryer, *Biochemistry,* Third Ed. (1988), which is incorporated herein by reference.

Oligonucleotides: This term is used to denote a single-stranded DNA or RNA molecule, typically prepared by synthetic means. Oligonucleotides employed in the present invention will usually be 50 to 150 nucleotides in length, preferably from 80 to 120 nucleotides, although oligonucleotides of different length may be appropriate in some circumstances. For instance, an oligonucleotide tag can be built nucleotide-by-nucleotide in coordination with the monomer-by-monomer addition steps used to synthesize the oligomer. In addition, very short, i.e., 2 to 10 nucleotides, oligonucleotides may be used to extend an existing oligonucleotide tag to identify a monomer coupling step. Suitable oligonucleotides may be prepared by the phosphoramidite method described by Beaucage and Carruthers, 1981, *Tetr. Lett.* 22: 1859–1862, or by the triester method, according to Matteucci et al., 1981, *J. Am. Chem. Soc.* 103:3185, both incorporated herein by reference, or by other methods such as by using commercial automated oligonucleotide synthesizers.

Operably linked: This terms refers to a functional relationship between one segment of a nucleic acid and another. For instance, a promoter (or enhancer) is "operably linked" to a coding sequence if the promoter causes or otherwise positively influences the transcription of the coding sequence. Generally, operably linked means that the nucleic acid segments or sequences being linked are contiguous and, where necessary to join two protein coding regions, contiguous and in reading frame.

Parallel Coupling: This phrase refers to the simultaneous coupling of two building block compounds to separate distinct points on a substrate. Such a substrate may be a solid support having distinct groups to which these building blocks are attached, or may constitute another chemical compound possessing two distinct groups where each building block independently attaches. Simultaneous coupling refers to the coupling of two compounds to such distinct points prior to the addition of a new building block compound to the first coupled building block. Thus, the term "simultaneous" as used in this context is not strict in the sense that the two building blocks are coupled with precise coincidence.

Receptor: This term refers to a molecule that has a specific affinity for a given ligand. Receptors may be naturally occurring or synthetic molecules. Receptors can be employed in their unaltered natural or isolated state or as aggregates with other species. Receptors may be attached, covalently or noncovalently, to other substances. Examples of receptors that can be employed in the method of the present invention include, but are not restricted to, antibodies, cell membrane receptors, monoclonal antibodies, antisera reactive with specific antigenic determinants (such as on viruses, cells, or other materials), polynucleotides, nucleic acids, lectins, polysaccharides, cells, cellular membranes, and organelles. Receptors are also known as "anti-ligands." A "ligand-receptor pair" is formed when two molecules, typically macromolecules, have combined through molecular recognition to form a complex. Other examples of receptors include, but are not restricted to specific transport proteins or enzymes essential to survival of microorganisms for which antibiotics are needed; the binding site of any enzyme; the ligand-binding site on an antibody molecule; a nucleic acid; a catalytic polypeptides as described in Lerner et al., 1991, *Science* 252: 659, incorporated herein by reference; and hormone receptors such as the receptors for insulin and growth hormone.

Substrate or Solid Support: These terms denote a material having a rigid or semi-rigid surface. Such materials will preferably take the form of small beads, pellets, disks, or other convenient forms, although other forms may be used. In some embodiments, at least one surface of the substrate can be substantially flat. A roughly spherical shape is preferred.

Stringent hybridization conditions: This phrase refers to highly selective hybridization conditions in which nucleic acids remain stably bound in association with other nucleic acids (or other segments of the same nucleic acid) only if the associated sequences are perfectly or highly (i.e., greater than 80%) complementary. Such conditions typically include salt concentrations of less than about 1 M, such as less than 500 mM, and will often include salt concentrations of less than 200 mM. The hybridization temperature for oligomers will typically be greater than 22° C., such as greater than about 30° C., and will often be in excess of about 37° C. Longer fragments may require higher hybridization temperatures for specific hybridization. As other factors may dramatically affect the stringency of hybridization (such factors include base composition, length of the complementary strands, presence of organic solvents, and extent of base mismatching), the combination of factors is more important than the absolute measure of any one factor alone.

Synthetic: A compound is "synthetic" when produced by in vitro chemical or enzymatic synthesis. The synthetic libraries of the present invention may be contrasted with those in viral or plasmid vectors, for instance, which may be propagated in bacterial, yeast, or other living hosts.

I. Overview of the Synthesis of a Tagged Chemical Library

The present invention relates generally to methods for synthesizing and screening tagged chemical libraries. In essence, each "book" of a chemical library of the invention consists of a chemical or molecule of interest, a tag identifying the chemical or molecule of interest or some important aspect thereof, and a linkage between the chemical or molecule of interest and the tag. In one important embodiment, the chemical or molecule of interest is an oligomer such as a peptide, the tag is an oligomer such as a nucleic acid, and the linkage is a solid support or particles, from which oligomers and tags may optionally be cleaved, e.g., to facilitate detection or to provide a soluble library. Such libraries can be screened to isolate individual oligomers that bind to a receptor or possess some other desired property. A general method for producing a tagged chemical library is illustrated by the production of a large, highly diverse collection of oligomers, in which each different library member is an oligomer with a unique monomer sequence relative to other library members (although the library will typically comprise duplicate "books"). Such a library or collection may contain, for example, all combinations of X different monomers in a set of monomers assembled into length n oligomers yielding, $X^n$ different compounds. The collection may also contain oligomers having different monomer units at, for example, only one or a small number of positions, while having an identical sequence at all other positions.

A general method for synthesizing such collections of oligomers typically involves a random combinatorial ("stochastic") approach and the chemical and/or enzymatic assembly of monomer units. One process comprises the steps of: (a) apportioning a plurality of solid supports among a plurality of reaction vessels; (b) coupling to the supports in each reaction vessel a first monomer and a first tag using different first monomer and tag combinations in each different reaction vessel; (c) pooling the supports; (d) apportioning the supports among a plurality of reaction vessels; (e) coupling to the first monomer a second monomer and coupling to either the solid support or to the first tag a second tag using different second monomer and second tag combinations in each different reaction vessel; and optionally repeating the coupling and apportioning steps with different tags and different monomers one to twenty or more times. Typically, substantially equal numbers of solid supports will be apportioned to each reaction vessel. Those of skill in the art recognize that the same chemical building block can be employed in different coupling steps and that the same chemical building block can be employed in more than one coupling reaction (reaction vessel) of a single coupling step.

To visualize the method more readily, one might first consider the stochastic synthesis of an untagged library of all oligomers three residues in length, assembled from a monomer set of three different monomers: A, B, and C. Three aliquots of beads are apportioned among three reaction vessels, and monomer A is coupled to the beads in the first reaction vessel, B is coupled in the second, and C in the third. The beads from all the reaction vessels are then pooled. The pool contains approximately equal numbers of three different types of beads, with each type characterized by the monomer coupled to the bead. The pool is mixed and redistributed to the separate monomer reaction vessels, each containing A, B, or C as the next monomer to be coupled.

Following this coupling reaction, each reaction vessel now has beads with all three different monomers in position one and the monomer contained in each particular second reaction vessel in position 2. All beads are pooled again, producing a mixture of beads each bearing one of the nine possible dimers. The pool is again distributed among the three reaction vessels and coupled to the three different monomers, producing the complete set of all trimers of the three monomers ($3^3$=27). As can be readily appreciated, the use of a sufficiently large number of synthesis beads helps to ensure that the set completely represents the various combinations of monomers employed in this random, stochastic, combinatorial synthesis scheme.

Modifications of this completely random approach are also possible. For example, the monomer set may be expanded or contracted from step to step; or the monomer set could be changed completely for the next step (e.g., amino acids in one step, nucleosides in another step, carbohydrates in another step), if the coupling chemistry were available. A monomer unit for peptide synthesis, for example, may include single amino acids or larger peptide units, or both. One variation is to form several pools of various sequences on solid supports to be distributed among different monomer sets at certain steps of the synthesis. By this approach, one can also build oligomers of different lengths with either related or unrelated sequences, and one can fix certain monomer residues at some positions while varying the other residues, to construct oligomer frameworks wherein certain residues or regions are altered to provide diversity.

The synthesis of a tagged chemical library often involves such combinatorial synthesis steps. Because the identifier tag can be easily decoded to report the identity of each oligomer, however, tagged chemical libraries can be significantly larger and more complex than untagged libraries. In fact, the present methods for synthesizing encoded synthetic libraries of compounds makes possible the screening of large collections of non-sequenceable compounds produced by multi-step synthesis.

In particular, the use of oligonucleotide tags and oligonucleotide encryption provides a powerful mechanism for recording the structural identity of every member of vast library of tethered compounds, especially peptides, generated through a combinatorial synthesis. The methods are broadly applicable to encoding the combinatorial assembly of other non-peptidic structures, providing the parallel synthetic schemes remain orthogonal and compatible. The net outcome of a combinatorial synthesis is unambiguously defined only for a sequence of reactions that each proceed in very high yield to afford single products. This situation is approximated with standard peptide and DNA synthesis chemistries, and the resulting product structures are explicitly specified by the order of the building blocks and/or coupling reactions used in the synthesis.

However most synthetic organic reactions are more idiosyncratic, giving variable yields and frequently multiple products (such as regio- and stereoisomeric structures). Using such chemistry to synthesize combinatorial libraries on solid supports yields a mixture of products on each bead in the library. In the most general case, the encryption of a synthesis may not uniquely specify the chemical structure of an associated entity. Rather, the encryption process may more accurately be viewed to encode the exact synthetic protocol (e.g., reagents, reaction conditions, etc.) by which a member of the library was constructed. The library is screened to identify "active recipes" that then can be reproduced on a preparative scale and fractionated (if necessary) to isolate the bioactive component(s). The encoded library technologies have considerable potential to expand the scope of combinatorial chemistry and its applications to drug discovery and the development and isolation of a wide variety of useful compounds. With this overview of the synthesis of tagged molecular libraries, one can better appreciate important aspects of the invention, such as the use and choice of solid supports in library synthesis.

II. The Solid Support

A. Types

Typically, the tagged chemical libraries of the invention are composed of a collection of "solid supports", such as beads or particles. Such solid supports may be of any shape, although they will preferably be roughly spherical. The supports need not necessarily be homogenous in size, shape, or composition; although the supports usually and preferably will be uniform. In some embodiments, supports that are very uniform in size may be particularly preferred. In another embodiment, however, two or more distinctly different populations of solid supports may be used for certain purposes, i.e., the solid supports may be composed of a single particle, or two or more linked particles.

Solid supports may consist of many materials, limited primarily by capacity for derivatization to attach any of a number of chemically reactive groups and compatibility with the chemistry of oligomer or other molecular synthesis and tag attachment. Suitable support materials include glass, latex, heavily cross-linked polystyrene or similar polymers, gold or other colloidal metal particles, and other materials known to those skilled in the art. Except as otherwise noted, the chemically reactive groups with which such solid supports may be derivatized are those commonly used for solid state synthesis of the respective molecule or oligomer and thus will be well known to those skilled in the art. The term "solid support" as used herein embraces a particle with appropriate sites for oligomer synthesis and, in some embodiments, tag attachment and/or synthesis. There are various solid supports useful in preparation of the synthetic oligomer libraries of the present invention. Solid supports are commonly used for solid phase synthesis of, for example, peptides and nucleic acids and other oligomers as enumerated above, and thus are well known to those skilled in the art. The solid supports of the present invention do not include living cells, viruses, or cloning vectors such as phage vectors or plasmids. Monobeads™ (commercially available from Pharmacia Fine Chemicals AB, Uppsala Sweden) or their equivalent, are particularly useful as solid supports for the various aspects of the present invention. Monobeads™ provide good size homogeneity and a small size, 10 µm. Further, these Monobeads™ do not clump in either organic or inorganic solvents, and provide a suitable support for both oligonucleotide and peptide synthesis. Finally, Monobeads™ provide very high loading of primary amines (100 nmole/mg).

One important aspect of the particular solid support chosen for practicing the invention is the size of the support. With enough solid supports and efficient coupling, one can generate complete sets of certain oligomers, if desired. In general, the solid support size is in the range of 1 nm to 100 µm, but a more massive solid support of up to 1 mm in size may sometimes be used. The appropriate size of the solid support depends on (1) the number of oligomer synthesis sites and identifier tag attachment sites desired; (2) the number of different compounds to be synthesized (and the number of solid supports bearing each oligomer that are needed for screening); and (3) the effect of the size of the solid supports on the specific screening strategies [e.g., fluorescence-activated cell sorters (FACS)] to be used.

As a specific example, solid supports of 1 µm in diameter may be used in the method. If each reaction vessel contains approximately 0.2 mL of solid supports, and the oligomers are synthesized from a set of 50 monomers (50 parallel reactions), then a total of 10 mL of solid supports, or approximately $10^{13}$ solid supports, would be required. If one wishes to make hexamers with these 50 monomers, then there are over $1.5 \times 10^{10}$ possible sequences, and each specific sequence would be represented on about $10^3$ solid supports. An estimated capacity of each bead, based on the capacity of commonly used peptide synthesizing resins, is about 0.1 pg of peptide per bead. By this estimation, then, each solid support would have about 100 amol or $10^8$ oligomer chains.

To improve washing efficiencies, one could employ nonporous beads or other solid supports less porous than typical peptide synthesis; however, for certain applications of the invention, quite porous beads or resins work well and are often preferable. Nonporous supports will have a lower density of growing chains, but even with a decrease in capacity of several orders of magnitude, sufficient oligomer densities can be produced for efficient screening. With the less porous supports, a greater proportion of the oligomers will be accessible for binding to the receptor during the screening process. Also, the less porous supports will reduce the carryover of tags from one reaction to the next, thus improving the accuracy of reading the dominant (correct) tags.

As noted above, another embodiment involves the use of two solid supports, such as beads, that are physically linked together, one with synthesis sites (or linkers) for the molecule or oligomer and one with attachment sites (or linkers) for the identifier tag(s). This arrangement allows the segregation of molecules or oligomers and identifier tags into discrete "zones" and permits the use of widely different chemically reactive groups and chemistries for attachment. The solid supports can be derivatized separately and then linked under conditions where all or nearly all of the synthesis solid supports will have a tag-attachment solid support in tow. The solid supports can be of different sizes, as for example a large synthesis bead with several (or many) smaller tag-attachment beads linked. In one embodiment, the first solid support will have at least one attached amino acid and the second solid support will have at least one attached nucleotide.

The mode of linking the two beads is constrained by the chemistry of oligomer synthesis. The most obvious means of linking the beads is with a heterobifunctional cross-linking agent (for examples of such agents, see *Pierce ImmunoTechnology Catalog and Handbook* pp. E10–E18 (1991)) interacting with the dominant chemically reactive groups on each species of solid support. Such cross-linking agents can serve a variety of purposes, as indicated by the following section.

B. Linkers

When bound to a solid support, the oligomer and its associated tag are usually attached to the support by means of one or more molecular linkers. The linker molecule, prior to attachment, has an appropriate functional group at each end, one group appropriate for attachment to the support and the other group appropriate for attachment to the oligomer or tag. In some embodiments, cleavable linkers will be used to facilitate an assay or detection step.

Given the wide availability of diverse linking reagents, one can link the identifier tags either to the oligomer or other library compound of interest or to the solid support or to a pre-existing tag. For instance, the identifier tag may be attached to a monomer incorporated into an oligomer or to a building block incorporated into a non-oligomeric compound. For peptidic oligomers, the side chain of a cysteine residue provides a convenient site for tag attachment. In other instances, the tag could even be attached so as to cap a small number of the oligomer chains, providing the decreased amount of net synthesis of the desired oligomer could be readily tolerated. One can attach the tag directly to the linker that binds the oligomer (or other compound of interest) to the solid support. In this embodiment, the linker has, prior to attachment, a third functional group appropriate for the attachment of the identifier tag.

One can of course incorporate a wide variety of linkers, depending upon the application and effect desired. For instance, one can select linkers that impart hydrophobicity, hydrophilicity, or steric bulk to achieve desired effects on properties such as coupling or binding efficiency. In one aspect of the invention, branched linkers, i.e., linkers with bulky side chains such as the linker Pmoc-Thr(tBu), are used to provide rigidity to or to control spacing of the molecules on a solid support in a library or between a molecule and tag in the library.

As noted above, cleavable linkers can be employed to useful effect. Preferred photocleavable linkers of the invention include 6-nitroveratryloxycarbonyl (NVOC) and other NVOC related linker compounds (see PCT patent publication Nos. WO 90/15070 and WO 92/10092; see also U.S. patent application Ser. No. 971,181, filed Nov. 2, 1992, incorporated herein by reference). In another embodiment, the linkers are nucleic acids with one or more restriction sites, so that one portion of a library member (either the tag, the oligomer or other compound of interest or both, or the solid support) can be selectively cleaved from another by the appropriate restriction enzyme. This novel nucleic acid linker illustrates the wide variety of linkers that may be employed to useful effect for purposes of the present invention.

C. Molecular Supports

As noted above, the invention can also be carried out in a mode in which there is no solid support, and the tag is attached directly (typically through a linker) to the oligomer or other molecule being synthesized. Alternatively, the oligomer or other molecule and its associated tag can be synthesized on a solid support and then cleaved or otherwise removed from the solid support prior to screening or other use. Such methods are described more fully below. Regardless of whether a solid support is present, the size and composition of the library will be determined by the number of coupling and mixing steps and the monomers or other building blocks used during the synthesis.

III. The Chemical Building Blocks

A. Oligomers and Monomers

The wide applicability of the present inventions is perhaps most readily grasped by considering the synthesis and screening of large libraries of diverse oligomers and polymers. Oligomers are polymeric compounds composed of monomers; for biological polymers, the sequence of the monomers in an oligomer often specifies important biological properties. Preferred oligomers of interest include peptides, oligonucleotides, oligo N-substituted glycines, and polycarbamates. As noted above, for purposes of the present invention a monomer is any member of a set of molecules that can be joined together to form an oligomer or polymer, i.e., amino acids, carbamates, sulfones, sulfoxides, nucleosides, carbohydrates, ureas, phosphonates, lipids, esters, combinations of the same, and the like. Thus, the monomers may be of any type that can be appropriately activated for chemical coupling or accepted for enzymatic coupling.

This method of assembling oligomers from many types of monomers requires using the appropriate coupling chemistry for a given set of monomer units or building blocks. Any set of building blocks that can be attached to one another in a step-by-step fashion can serve as the monomer set. The attachment may be mediated by chemical, enzymatic, or other means, or by a combination of any of these means. The resulting oligomers can be linear, cyclic, branched, or assume various other conformations as will be apparent to those skilled in the art.

B. Other Building Blocks

The invention is described herein primarily with regard to the preparation of molecules containing sequences of amino acids, but the invention can readily be applied to the preparation of other oligomers and to any set of compounds that can be synthesized in a component-by-component fashion, as can be appreciated by those skilled in the art. For instance, compounds such as benzodiazepines, hydantoins, and peptidylphosphonates can be prepared using the present methods (see U.S. patent application Ser. No. 08/119,700, filed Sep. 9, 1993, which is a continuation-in-part of Ser. No. 081,577, filed Jun. 21, 1993, now abandoned, which is a continuation-in-part of U.S. Pat. No. 5,339,115, each of which is incorporated herein by reference.

In one embodiment, the present method can be used to create libraries of branched polymers. While in many instances libraries of linear polymers, such as peptides, are quite useful, with more than 3–4 residues, the shape of these linear molecules becomes long and narrow. Most drugs do not have such an extended shape, perhaps due in part to the high degree of flexibility of the molecules. Branched backbone polymers can result in molecular shapes similar to known drugs. Thus, in one embodiment, the present invention relates to the incorporation of monomers with at least three functional groups to which other monomers can be attached.

If one uses such monomers exclusively, however, then the fully branched synthesis will always result in a high ratio (relative to the other monomers used in the synthesis) of the last monomer coupled. One could of course incorporate mixtures of different branching monomers to alter this ratio, but then one might have more difficulty in identifying the structure of a compound of interest, i.e., the more complex the mixture of branched monomers, the less information the tag may provide about the particular compound synthesized. In an improved method of the invention, one incorporates a mixture of two monomers—one capable of branching and one not—at each monomer coupling step, producing a library comprising a great diversity of shapes with highly informative tags. In this case, the tag would specify the monomers present at each coupling step but not whether the monomer was capable of branching. However, a simple resynthesis using only those monomers contained in the selected set of compounds from the first library would readily identify the structure of those compounds.

IV. The Tag

The identifier tag has a recognizable feature that is, for example, microscopically or otherwise distinguishable in shape, size, mass, charge, or color. This recognizable feature may arise from the optical, chemical, electronic, or magnetic properties of the tag, or from some combination of such properties. In essence, the tag serves to label a molecule and to encode information decipherable at the level of one (or a few) molecules or solid supports. By using identifier tags to track the synthesis pathway that each member of a chemical library has taken, one can deduce the structure of any chemical in the library (i.e., the sequence of monomers of any oligomer) by reading the identifier tag.

One can construct microscopically identifiable tags as small beads of recognizably different sizes, shapes, or colors, or labeled with bar codes. The tags can be "machine readable" luminescent or radioactive labels. The identifier tag can also be an encodable molecular structure. The information may be encoded in the size (the length of a polymer) or the composition of the molecule. Perhaps the best example of this latter type of tag is a nucleic acid sequence, i.e., RNA or DNA assembled from natural or modified bases.

To illustrate the role played by the tag in the synthesis and screening of a chemical library, consider for example, the use of microscopically recognizable, alphanumeric tags that are attached to each bead in an oligomer synthesis. The tag "A1" means that a bead participated in the A-monomer reaction at step 1, "C2" means that a bead participated in the C-monomer reaction at step 2, and "B3" means B-monomer was added in step 3, and so on. At the end of a 3-step synthesis, one bead would have three tags attached, e.g., A1, C2, and B3, indicating that the sequence of the peptides on the bead is ACB. This scheme requires a number of distinct identifier tags equal to at most the product of the number of different monomers and the number of synthesis steps (nine in this example). The number of identifier tags is reduced if the symbols are attached to one another in the order of the steps: A, A-C, A-C-B, in which case only as many identifier tags are needed as monomers, and the identifier tag is assembled in a way that preserves the record of what monomer was added, and in which addition step.

In another example, the tag is comprised of a variety of light-addressable molecules, such as fluorescent or phosphorescent compounds, the spectral properties of which can be changed (e.g., photobleaching) and therefore used to store information, which are used to mark each bead or other solid support in the library. In one such mode, a bead incorporates a variety of fluorophors, each of which can be selectively photobleached, and so rendered incapable of fluorescence or of diminished fluorescence. During each coupling or chemical reaction step, the bead is irradiated (or not) to photobleach (or not) one or more particular types of fluorophors, thus recording the monomer identity in the oligomer synthesized. See *Science* 255: 1213 (Mar. 6, 1992), incorporated herein by reference.

The identifier tags therefore identify each monomer coupling or other reaction step that an individual library member or solid support has experienced and record the step in the synthesis series in which each monomer was added or other chemical reaction performed. The tags may be attached immediately before, during, or after the monomer addition or other reaction, as convenient and compatible with the type of identifier tag, modes of attachment, and chemistry of oligomer or other molecular synthesis. As noted above, the identifier tag can be associated with the oligomer through a variety of mechanisms, either directly, through a linking molecule, or through a solid support upon which the oligomer is synthesized. In the latter mode, one could also attach the tag to another solid support that, in turn, is bound to the solid support upon which the oligomer is synthesized. The identifier tag is added when the solid supports that have undergone a specific monomer addition or other chemical reaction step are physically together and so can be tagged as a group, i.e., prior to the next pooling step.

In some cases, of course, when only a small number of monomer units of an oligomer are varied, one may need to identify only those monomers which vary among the oligomers, as when one wants to vary only a few amino acids in a peptide. For instance, one might want to change only 3 to 6 amino acids in peptides 6 to 12 amino acids long, or one might want to change as few as 5 amino acids in polypeptides up to 50 amino acids long. One may uniquely identify the sequence of each peptide by providing for each solid support an identifier tag specifying only the amino acids varied in each sequence, as will be readily appreciated by those skilled in the art. In such cases, all solid supports may remain in the same reaction vessel for the addition of common monomer units and apportioned among different reaction vessels for the addition of distinguishing monomer units.

Synthetic oligodeoxyribonucleotides are especially preferred information-bearing identifier tags. Oligonucleotides are a natural, high density information storage medium. The identity of monomer type and the step of addition or any other information relevant to a chemical synthesis procedure is easily encoded in a short oligonucleotide sequence. Oligonucleotides, in turn, are readily amenable for attachment to a wide variety of solid supports, oligomers, linkers, and other molecules. For example, an oligonucleotide can readily be attached to a peptide synthesis bead.

One outstanding advantage inherent in using an oligonucleotide-based coding scheme is the ability to achieve tremendous levels of target amplification through the polymerase chain reaction (PCR, see *PCR Protocols: A Guide to Methods and Applications* (Innis, M., Gelfand, D., Sninsky, J. and White, T., Academic Press, San Diego 1990); see also U.S. Pat. Nos. 4,683,202 and 4,965,188, each of which is incorporated herein by reference) and other nucleic acid replication and amplification techniques. Although the most commonly used in vitro DNA amplification method is PCR, suitable alternate amplification methods include, for example, nucleic acid sequence-based amplification (Compton, 1991, *Nature* 350:91–92, incorporated herein by reference) and amplified antisense RNA (Van Gelder et al., 1988, *Proc. Nat. Acad. Sci. USA* 85:7652–7656, incorporated herein by reference), and the self-sustained sequence replication system (3SR, see Guatelli et al., 1990, *Proc. Natl. Acad. Sci. USA* 87: 1874–1878, incorporated herein by reference). Only tiny quantities (with highly selective and efficient methods, even a single copy is sufficient) of DNA template is required for PCR, enabling one to use solid supports of microscopic dimensions and obtain larger libraries.

The use of nucleic acid tags facilitates the construction and screening of synthetic libraries that far exceed the diversity accessible through other tethered library techniques. Moreover, these libraries employ manageable quantities of bead material and can therefore be assayed for receptor binding using practical volumes of biological reagents. One improved method of the invention relates to a limiting step in the processing of ESL libraries with oligonucleotide tags—the amplification, strand separation, and sequencing of tags from individual beads. The method increases sequencing efficiency by at least an order of magnitude, and relates to the incorporation of a tag concatamerization (concatenation) step, in which a number of different tags typically amplified from a selected set of library members are ligated together prior to either cloning or sequencing of the oligonucleotide tags.

In one embodiment of the method, the amplified tags are concatenated and then cloned as linear arrays of 10 to 20 (or even more) tags in a conventional sequencing vector. Preferably, appropriate restriction sites are installed adjacent to the "coding regions" (sequences with information content) of the oligonucleotide tags; after amplifying the tags on a group of beads, the restriction sites are cut, and the fragments ligated to form concatamers. The concatamers are then cloned into an appropriate sequencing vector. Each template can then be used for bidirectional sequencing of a total of, for example, 500 to 800 bases, allowing the identification of more than at least 10 tags per template. This approach will also provide the option of avoiding the isolation of individual beads with FACS. Beads or tagged compounds can be sorted into pools, the pool of tags amplified, concatenated, and cloned for sequencing. In addition, because the requirement to manipulate individual beads is relieved, one can use beads smaller than 1 $\mu$m (typically, this size is too small for conventional FACS analysis) for library construction and screening. The selection can be conveniently accomplished by affinity purification methods (panning, magnetic beads, etc.) and the enriched pools of beads then amplified and cloned as above.

Oligonucleotide identifier tags can be assembled base-by-base before, during, or after the corresponding monomer coupling (for oligomer synthesis) or other chemical reaction step. In one case of base-by-base synthesis of an oligonucleotide tag, the tag for each step is a single nucleotide, or at most a very few nucleotides (i.e., a block of 2 to 5 nucleotides). In the block-by-block approach, encoded sets of nucleotides ("codons") of 2 to 5 to 10 or more bases are added as protected, activated blocks. Each block carries the monomer-type or other information, and the order of addition of one tag block to the next represents the order of the monomer addition or other reactions. Alternatively, the block may encode the oligomer synthesis or other reaction step number as well as the monomer-type or other building block information. This strategy preserves the order of the steps in the linear arrangement of the oligonucleotide chain grown in parallel with the oligomer. To preserve the chemical compatibility of the parallel synthetic steps (oligonucleotides and peptides, for example), one can modify the standard synthesis chemistries, an important aspect of the present invention discussed in further detail below.

One can also attach protected (or unprotected) oligonucleotides containing amplification primer sites, monomer-specific information, and order-of-reaction information, from 50 to 150 bases (nucleotides) in length, at each step. At the end of a series of n oligomer synthesis (monomer coupling) or other chemical synthesis steps, there would be n differently encoded sets of oligonucleotide identifier tags associated with each oligomer sequence or other chemical in the library. After identifying the oligomers with ligand activity, the associated oligonucleotides could be amplified by PCR and sequenced to decode the identity of the oligomer or other compound.

As discussed more fully below, the choice of bases used in an oligonucleotide identifier tag is dictated by the chemistry of oligomer synthesis or other chemical reaction conditions to which the tag will be exposed. For example, the use of strong acid can depurinate nucleic acids. Therefore, when chemistries requiring the use of strong acid are employed, the use of an oligonucleotide composed of only the pyrimidines C and T and a binary code can prove of value. In similar fashion, the lability of purine nucleotides to strong acid may be overcome through the use of the purine nucleoside analogs, such as 7-deaza-2'-deoxyadenosine and 7-deaza-2'-deoxyguanosine (see Barr et al., 1986, *Techniques* 4:428–432, and Scheit, *Nucleotide Analogs: Synthesis and Biological Function* pp. 64–65 (John Wiley and Sons, New York), both of which are incorporated herein by reference). Use of these or other analogs would permit the use of a quaternary or other, as opposed to a binary, encoding scheme. Thus, in a preferred embodiment, the identifier tag will be an oligonucleotide about 50 to 150 nucleotides in length and composed of pyrimidines or pyrimidines and purine analogs or any type of nucleoside that will not degrade under the coupling conditions used to assemble the oligomer library. The oligonucleotide identifier tag may contain a 5' and a 3' amplification site, and optionally a DNA sequencing primer site, which may be specific for each step of the oligomer synthesis.

Encoding a combinatorial synthetic procedure with oligonucleotides provides a mechanism for addressing the major limitations of ambiguity and sensitivity encountered in the direct structural analysis of minute quantities of ligands isolated from large libraries. The high capacity of DNA for information storage can be exploited to archive the precise details of a library's construction. In Example 1 below, a "codon" structure of 2 contiguous nucleotides comprising three bases ($c^7dA$, dC, T), capable of encoding a synthesis incorporating up to $3^2=9$ amino acid building blocks was used (only seven building blocks were used in the synthesis of this library). If $c^7dG$ was also included in the coding template, then a combinatorial synthesis employing 1000 different monomers could be accommodated by using a "codon" size of just 5 nucleotides ($4^5=1024$).

Information may be encoded in the length rather than, or in addition to, the sequence of the oligonucleotide, or for that matter any other polymeric or oligomeric, tag. If only length is utilized to represent each specific monomer addition to the oligomer, then the identity of the oligomer can be decoded by, for example, amplifying an oligonucleotide tag, as described above, and identifying the tags through any of a variety of size-separation techniques, including polyacrylamide gel or capillary gel electrophoresis. Each different monomer added at a given step in an oligomer synthesis or each different chemical reaction step is represented by an oligonucleotide tag of unique length. The oligonucleotide tag contains amplification sites, such as PCR priming sequences, the sequences of which are designed to be characteristic of the given step-number in the oligomer or other chemical synthesis. Determination of the oligomer composition at any given position in the sequence then involves amplifying the tag using the PCR priming sequence characteristic for that step in the synthesis and size-separating the amplification products utilizing techniques well known in the art, such as gel or capillary electrophoresis (using the tagging oligonucleotides as standards) This embodiment is particularly useful when one desires to make a library of compounds related to a lead sequence. One need only tag during steps in which a site being analoged is synthesized.

In addition to length, oligomer sequence information can also be encoded in the sequence of bases comprising the oligonucleotide tag. This type of encryption is of value not only in the embodiment in which one attaches a different oligonucleotide tag at each coupling step but also in the embodiment in which one extends a pre-existing oligonucleotide tag at each coupling step. For example, one may use oligonucleotides of up to about 100 bases (or somewhat longer), each having seven (or more) regions, as described below.

Region 1 is a 3'-PCR primer site (20 to 25 bases). This site is used in conjunction with another PCR site (at the 5'-end of the oligonucleotide) to prime amplification by PCR. Other amplification methods may also be used.

Region 2 is a "step-specific" DNA sequencing primer site (15–20 bases). This site is specific for the particular numbered step in the synthesis series. All the oligonucleotides added to all the beads at a particular step will have this sequence in common. Each numbered step will have a highly specific primer site representing that step.

Region 3 is a spacer (20–30 bases). A spacer segment of variable length, but preferably 20 to 30 bases long, places the coding site sufficiently distant from the sequencing primer site to give a good "read" through the monomer encoding or identification region.

Region 4 is a monomer identification region (8 bases). In this illustrative embodiment, each base in the 8-bit string represents one bit of binary code, where, for example, T=0 and C=1. Each set of step-specific identifier tags consists of 8 bases with a 1 (C) or a O (T) at each of the 8 positions. These may be thought of as switches set to "on" or "off" at the different positions. Each monomer type is encoded by a mixture of 1 to 8 of these "switches."

Region 5 is a step number confirmation region (4 bases plus 2 bases on either side for region distinction). Four bits in this short stretch encode the step number. This is redundant to the sequencing primer but can be used to confirm that the proper primers were used and that the right step is decoded.

Region 6 is a repeat of the monomer identification region (8 bases). This region has the same information as region 4, and is used to confirm monomer identity. Installing this second monomer encoding region also increases the probability that a good sequencing "read" will be obtained.

Region 7 is a 5'-PCR primer site (20 to 25 bases). This site serves as a site for annealing the second PCR primer for amplification of the sequence. The length of oligonucleotides with all seven of these features, some of which are optional, will commonly be between 75 and 125 bases.

An 8 bit format can encode 256 different monomer types. The number of steps that can be encoded is determined by the number of step-specific sets (8 per set) of oligonucleotides on hand. With 10 sets (80 oligonucleotides) one can encode up to 256 different monomers assembled into oligomers up to 10 units long (thus providing encoding capability for up to $256^{10}=1.2\times10^4$ oligomer sequences). The coded identifier tags may be used so that each monomer is assigned a specific binary number (e.g., Ala=00000001, Gly= 00000110, etc.). The appropriate oligonucleotides are combined to give the correct binary code.

To facilitate oligonucleotide tag identification, one has a variety of options. For instance, one could read the tag directly from the bead by sequencing or hybridization. One can also amplify oligonucleotide tags to facilitate tag identification. The oligonucleotide identifier tags carried by a single solid support or oligomer can be amplified in vivo, by cloning, or in vitro, e.g., by PCR. If the limit of detection is on the order of 100 molecules, then at least 100 or more copies of each oligonucleotide tag on a bead would be required. Copies of the tag are produced, either as single stranded oligonucleotides, double-stranded nucleic acids, or mixtures of single and double-stranded nucleic acids, by any of a variety of methods, several of which are described below, and the amplified material is sequenced. In the embodiment of the invention in which a separate and distinct oligonucleotide tag is added at each monomer addition step (as opposed to extending an existing tag at each step), one can amplify all tags at once and then divide the amplified material into as many separate sequencing reactions as there were oligomer synthesis steps (employing a different sequencing primer for each type of tag). In this embodiment, one could also design the tags so that each tag could be amplified separately from the other tags by appropriate choice of primer sequences. The sequencing reactions are performed and run on a standard sequencing gel, and the oligomer sequence is deduced from the code revealed in the resulting sequence information.

An alternative strategy is to use common PCR primers and common sequencing primers (the sequencing primer may even overlap completely or partially with a PCR primer site) and identify the step by hybridization to oligonucleotide probes that are complementary to each step-specific sequence in the oligonucleotides from the bead. A single set of sequencing reactions is performed on all of the amplified oligonucleotides from a single bead, and the reaction products are run in a single set of lanes on a gel. The reaction products are then transferred to a suitable hybridization membrane and hybridized to a single step-specific probe (see Maniatis et al., *Molecular Cloning: A Laboratory Manual*, Cold Spring Harbor Laboratory, Cold Spring Harbor, N.Y. (1982), which is incorporated herein by reference). After detection of the resulting signal, the probe is washed from the membrane and another step-specific probe is hybridized. One could also use the procedure described in EPO publication No. 237,362 and PCT publication No. 89/11548, each of which is incorporated herein by reference.

Parallel hybridization provides an alternative to sequential hybridization. The sequencing reactions are divided into a number of aliquots equal to the number of peptide synthesis steps and run in a separate set of lanes for each on the sequencing gel. After transfer of the reaction products to a suitable membrane, the membrane is cut to separate the sets of lanes. Each lane set is then hybridized to one of a plurality of step-specific oligonucleotide probes (see "Uniplex DNA sequencing" and "Multiplex DNA sequencing," in *Plex Luminescent Kits Product Catalog*, Bedford, Mass., 1990, incorporated herein by reference).

As noted above, a single synthesis solid support (or an attached bead bearing a tag, or in solution in a "well") may only comprise a few hundred copies of each oligonucleotide tag. These tags may be amplified, e.g., by PCR or other means well known to those skilled in the art, to provide sufficient DNA to be sequenced accurately. The ability to decode the oligomers depends on the number of available oligonucleotide identifier tags, the level of amplification that can be achieved from the available tags, and the accuracy of sequencing that amplified DNA.

If PCR amplification of an oligonucleotide identifier tag is employed, one may encounter "PCR product contamination," caused by the product of one PCR reaction contaminating a subsequent PCR reaction mixture designed to amplify other tags having the same PCR primer binding sites. One may prevent this problem by introducing lability into the product sequences and treating subsequent reactions so as to destroy potential contamination carried over from previous reactions. A specific example of this strategy, for which commercial kits are sold by PECI and Life Technologies, is to introduce dUMP into the product. Treating each new PCR reaction with uracil-N-glycosidase degrades any dU-containing DNA present, preventing amplification of the contaminant. The template DNA, which contains no dU (only dT) is not affected. Of course, the glycosidase is removed or inactivated before amplification is begun.

Some of the tags described above for peptide synthesis have the unusual characteristic of containing only pyrimidines. This means that the uracil glycosidase strategy (Perkin Elmer Cetus Instruments (PECI) Catalog, Alameda (1991), incorporated herein by reference) will work on only half of the strands produced—those containing T's (or U's). One cannot introduce dUMP into the complementary, purine-only strand; however, the purine strand is highly vulnerable to acid depurination and alkaline-mediated scission of the backbone. The combination of these treatments can greatly reduce problems with product contamination.

Another approach to preventing carryover contamination involves incorporation of a restriction site (EarI could be used for polypyrimidine tags) into the oligonucleotide tag and digestion with the corresponding restriction enzyme prior to amplification of a reaction suspected of being contaminated with the tag. This method only works if the tag to be amplified will not be cleaved by the enzyme, as would generally be the case for a single stranded oligonucleotide tag.

For sequencing amplified DNA, one usually desires to generate single stranded templates. This generation may be accomplished by any of several means. One such means is asymmetric PCR, where an excess of one of the primers is used to amplify one strand to a level 10 to 100-fold higher than the other (see, e.g., U.S. Pat. No. 5,066,584, incorporated herein by reference). Another means of providing a single stranded template is to by biotinylate one of the primers and purify or remove the resulting strand by adsorption to immobilized streptavidin (*Pierce Immunotechnology Catalog and Handbook*, 1991, incorporated herein by reference). Yet another means involves generation of RNA transcripts (representing only one of the strands) from an RNA polymerase promoter and sequencing the transcripts with reverse transcriptase (Sommer et al., Chapter 25, In *PCR Protocols: A Guide to Methods and Applications*, supra, incorporated herein by reference). If the tags are composed of only pyrimidine nucleotides, then all purine strands can be eliminated by acid/base treatment, leaving the pyrimidine strand for sequencing.

The use of separate sequencing primers for each step-specific oligonucleotide requires a separate, conventional sequencing reaction for each step-specific primer. Using primers that are differentially labeled would allow the identifier tags from a single solid support to be sequenced in a single reaction and run in a single lane set (2 lanes if only polypyrimidines are used; 4 lanes if 4 different bases are used) on a gel. There are now commercially available primers labeled with distinguishable fluorophores that are suitable for this purpose (ABI Catalog, incorporated herein by reference). Sets of chemiluminescent labels now distributed commercially may also be used (Bronstein et al., *BioTechniques* 8:310–314 (1990), incorporated herein by reference).

The amplified product can be easily sequenced or otherwise identified to decode the identity of the peptide or other molecule on the bead or otherwise attached to the oligonucleotide tag. For this purpose, one can use any of a variety of sequencing methods, including sequencing by sequence-specific probe hybridization. DNA sequencing enzymes which may be employed in the present invention include Taq DNA polymerase, *E. coli* DNA polymerase I (or the Klenow fragment), T7 polymerase, SequenaseW and Sequenase II™ (Modified T7 DNA polymerases), Bst DNA polymerase, and reverse transcriptase (from AMV, MMLV, RSV, etc., see *USB Enzymes for DNA Sequencing*, U.S. Biochemical Corp, 1991, Cleveland Ohio, incorporated herein by reference). The sequence of an oligonucleotide tag may also be identified by a high fidelity DNA hybridization technique. To this end, very large scale immobilized polymer synthesis with oligonucleotides may be useful (see PCT patent publication Nos. 92/10587 and 92/10588, each of which is incorporated herein by reference).

The choice of tag, whether the tag is an oligonucleotide or some other molecular structure, depends upon the nature of the molecules of which the library is composed and the method by which those molecules are to be synthesized, as discussed in the following section.

Where synthesis chemistries involve the use of reagents and reaction conditions incompatible with the above described oligonucleotide tags, it may be desirable to utilize an alternate tagging method. Thus, the methods for synthesizing a tagged molecular library of the present invention also envision utilizing chemically inert hydrocarbon tagging molecules which are discretely resolvable by a variety of methods, such as chromatographic methods.

The use of such inert hydrocarbon tags in molecular libraries has been described. See Michael H. J. Ohlmeyer, et al., *Proc. Nat'l. Acad. Sci.* 90:10922–26 (December 1993), and published PCT Application No. WO 94/08051, both references incorporated herein by reference for all purposes.

The tags described utilize a binary coding scheme like that described herein. Specifically, a binary code is assigned to each chemical building block, i.e., an amino acid, to be added in the synthesis. The length of the code may be dependent upon the total number of building blocks to be added. For example, where only seven total building blocks are to be added, a three bit binary code may be used. This allows for seven separate specific codes, 001 through 111, each one being assigned to one of the seven building blocks, e.g., lysine=001. Where the number of building blocks is greater, a larger code can be utilized, e.g., an eight bit binary code, as described herein.

A number of tags are prepared, each having a different resolution or separation pattern from the others using chromatographic methods. If a particular tag is present, it will represent a "1" in each position of the final tag code for a given synthesized molecule. Thus, where a molecule has four building blocks and is coded in a three bit coding system, there are 12 potential code digits, each building block having three bits. For each step in the synthesis, the solid support upon which the molecule is to be synthesized is tagged so as to indicate not only the building block added, but also the step at which it was added. For example, the presence of tag no. 1 or "T1" indicates that there is a "1" in the first position of the binary tag code for the building block added at the first step. Similarly, the presence of T7 indicates that there is a "1" in the seventh position of the overall code, which, in a three digit code, would also correspond to the first position of the third added building block. Thus, the building block assigned the code 111, if added at position one, would be encoded by the presence of tags T1, T2 and T3. Alternatively, if added in step 2, the same building block would be encoded by the presence of tags T4, T5 and T6.

The specific hydrocarbon tags described by Ohlmeyer have the following structure:

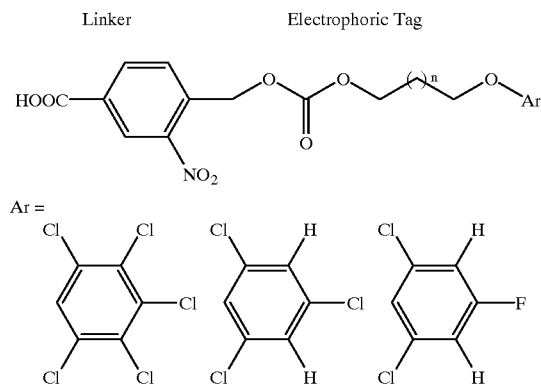

where n is from 1 to 10. The varying length of the hydrocarbon chain and the varied halogenated group allow physical separation or resolution of the tags by chromatographic methods, specifically, electron capture gas chromatography.

Detection of these hydrocarbon tags is, however, limited by the sensitivity of the detection method. Thus, to ensure detection of the tags, larger amounts of tag must be used. This requires larger sized beads, thus reducing the size of the overall library which can be synthesized, and increased reaction times to ensure maximum coupling of the tags to the solid support. Finally, where larger molecules are screened, more hydrocarbon tags are added to the solid support. The incorporation of large amounts of hydrocarbons on a solid support, e.g., for large synthetic compounds having numerous tags, will likely have adverse effects on continued synthesis and/or screening of the compound on the solid support due to steric, hydrophobic or ionic interactions.

The problems of detectability, tagging time, and screening or synthesis interference associated with these hydrocarbon tags may be circumvented utilizing the methods of the present invention. Specifically, the present invention, in one embodiment, provides a method of tagging using hydrocarbon tags wherein such tags have a "molecular hook," instead of a detectable electrophore as described in Ohlmeyer, et al. This "molecular hook" is defined herein as a functional group on the tag which allows for the attachment of an amplifiable, detectable group, thus permitting detection of smaller amounts of tag on the solid support. The hook will generally comprise a stable functional group or molecule which will either form a covalent linkage with the amplifiable, detectable group, or will have a high affinity for a portion of that group. Examples of such hooks include, e.g., biotin, to which a streptavidin linked amplifiable, detectable group may be bound or one complement of a high association peptide. Such high association peptides generally comprise a complementary pair of peptides each having a high affinity for the other. Thus, one complement denotes one peptide of such a pair. High association peptides are generally described in U.S. application Ser. No. 08/321,933, filed Oct. 12, 1994, which is a continuation-in-part of U.S. application No. 08/067,387, filed May 24, 1993, each of which is incorporated herein by reference for all purposes. Alternatively, the hook may comprise a protected activatable group, which may be activated to covalently attach the amplifiable, detectable group to the tag. Photoprotected activated groups are particularly useful in this application. Activated groups are generally well known in the art, and include such groups as carboxyl, hydroxyl, amino, thiol and the like. These groups may be protected using photolabile protecting groups such as those described in published PCT Application No. WO 93/22680, incorporated herein by reference for all purposes. The resulting group is photoactivatable.

In addition to the above, the molecular hooks may comprise multifunctional groups. For example, the molecular hook may comprise two or more different functional groups capable of being coupled to two separate entities. This may be the case where for example, it is desirable to recouple the tag to another solid support for detection purposes, e.g., a reaction well in a microtiter plate. The first functional group may be used to selectively bind a complementary group on the solid support. Once coupled, the second functional group may be used for selective coupling of the amplifiable detectable group. Such hooks may generally comprise combinations of the functional groups described herein, or other groups which are capable of being selectively bound to another such group. As an example, such a hook might comprise both biotin and digoxin, orthogonally linked to the hydrocarbon tag. Once separated, these tags may be contacted with a solid support, e.g., a microtiter well, which is coated with a group capable of binding to one of the functional groups on the tag, e.g., an anti-digoxin antibody, and allowed to bind thereto. After repeated washing steps, the solid support is contacted with the oligonucleotide coupled to a group capable of binding to the second functional group, e.g., streptavidin linked oligonucleotide as described previously. The bound oligonucleotide is then detected as previously described. The synthesis of the hydrocarbon tags of the present invention may be carried out by methods well known in the art. See, e.g., March, Advanced Organic Chemistry (John Wiley & Sons, 3rd Ed., 1985), Larock, Comprehensive Organic Transformations (VCH Publishers, 1989).

Because the inert hydrocarbon tags of the present invention provide for more sensitive detection of the hydrocarbon tags, the amount of a particular tag on a solid support may be reduced without affecting its detectability. Further, by reducing the amount of tag on the solid support, time required for the coupling of the tag to the support may be reduced.

Tags useful in the present invention will generally comprise a variable hydrocarbon region and a molecular hook. More preferably, such tags will comprise a cleavable linker attaching the tag to the solid support, a molecular hook as described, and a varied length hydrocarbon chain connecting the molecular hook to the linker. Different tags will have a different length hydrocarbon chain, or a different molecular hook, so as to allow for their physical separation and detection.

Tags having the following general structure are preferred:

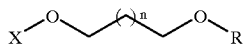

where n is from 1 to 10, or more, X is a cleavable linker and R is a molecular hook. Preferred molecular hooks comprise, e.g., biotin, a high association peptide, and activatable groups, such as a photoactivatable group, or a combination thereof.

Examples of cleavable linkers which are useful in the present invention include, for example, the photocleavable linkers described in U.S. application Ser. No. 08/265,090, filed Jun. 23, 1994, and incorporated herein by reference for all purposes. Examples of such photocleavable linkers include those having the following structures:

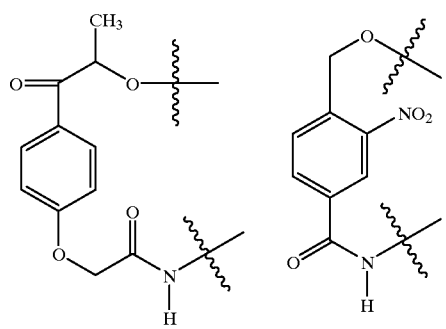

-continued

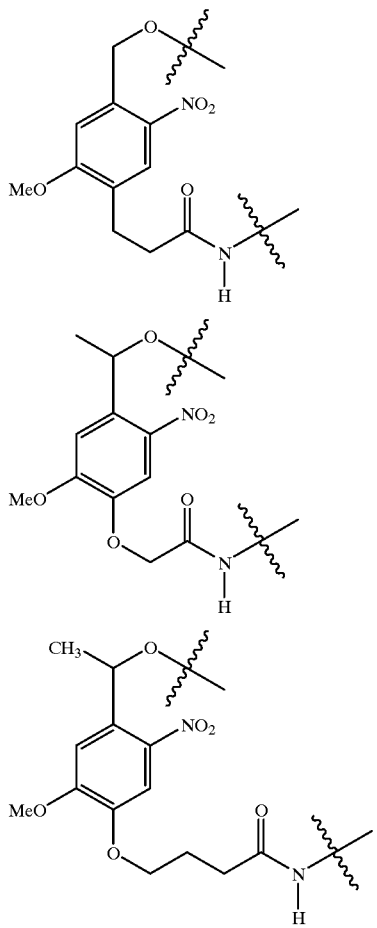

Following synthesis and tagging, the tags are removed from the solid support, e.g., by photolysis of the linker. The tags are then separated from each other using a method which preserves the separation pattern of the tags, e.g., HPLC with fraction collection, or other chromatographic methods, such as gel or capillary electrophoresis. Because the tags are generally present in amounts undetectable by normal means, e.g., absorbance, etc., they must be separated in a manner which allows subsequent detection and correlation to their separation pattern. As an example, the tags cleaved from a solid support, are separated on an HPLC column and collected in a fraction collector. When the tags are eventually detected, as described in further detail below, the fractions which indicate the presence of a tag are correlated against the known elution profile, or separation pattern, for all of the tags used in the tagging/synthesis.

The separated tags are then immobilized according to their separation pattern. Such immobilization may take the form of spotting individual fractions, blotting for gel based separations, or immobilization within reaction wells, i.e. on a microtiter plate.

Once immobilized, the tags may be "hooked" to an amplifiable, detectable group. Amplifiable/detectable groups generally include a compound or structure which is capable of being amplified, or produces a signal which is capable of being amplified. Compounds capable of exponential amplification are preferred. A particularly useful amplifiable, detectable group is an oligonucleotide sequence. Hooking of the amplifiable, detectable group may take a variety of forms. For example, where the hook comprises a biotin group, the oligonucleotide may be coupled to streptavidin which will tightly bind the biotin. Alternatively, the streptavidin may be added in an intermediate step followed by addition of biotinylated oligonucleotide. In alternative embodiments, the tag may comprise a complement of a high association peptide. In this case, the oligonucleotide is linked to the other complement to that peptide so that the oligonucleotide may tightly bind to the tag. In yet another embodiment, where the tag comprises an activated group protected by a photolabile protecting group such as those described in published PCT Application No. WO 93/22680, previously incorporated by reference, this group may be activated, i.e., by photolysis of the photolabile group, allowing the oligonucleotide to then be coupled to the tag by methods well known in the art. Where this is the case, it may be desirable to select a photolabile protecting group having different photolysis characteristics from a the photocleavable linker, if one is being used. This will allow selective cleavage of the tag from the solid support without activation of the molecular hook.

Once hooked to the tag, the oligonucleotide sequence may be amplified using the PCR techniques described herein. Where the immobilization is in a blotting format, the amplification must be carried out so as to preserve the local concentration and avoid diffusion of the amplified oligonucleotide, thus allowing its detection and correlation to the separation pattern. This may be accomplished by performing the amplification reaction in, for example, a gel overlay of the blot.

Detection of the hooked oligonucleotide, and thus the tag, may be carried out by incorporating a label into the amplified oligonucleotide or by probing for the amplified oligonucleotide sequence where such sequence is known. Detection of a tag is correlated to the known separation pattern for the tags. A tag so identified is then incorporated in the overall tag code for the synthesized molecule. For example purposes only, if following HPLC separation, hooking, amplification and probing, fraction #17 indicates the presence of a tag, this is correlated to the tag which is known to separate into fraction #17. If, for example, this is tag # 5, then a "1" may be assigned to position # 5 of the overall binary code for the molecule synthesized on the particular support. The coding schemes described herein are for example purposes, and those of skill in the art will recognize that a variety of coding schemes may be applied to the methods of the present invention.

Those of skill in the art will also recognize that there is no requirement that the code reporting the sequence of a synthesized molecule be contained in a single polymeric sequence of individual tags. Instead, the code may be embodied by the presence or absence of individual different tags on the solid support. While these tags may potentially be coupled sequentially to each other, those of skill will recognize the benefit of having each different tag individually attached to the solid support. Specifically, only a single coupling chemistry would be required for any and all tagging steps. Further, complex protocols of protecting\deprotecting reactions for tags having different reactive groups may be avoided.

V. Synthesis Methods

The method of the present invention can be applied to any set of synthetic chemical reactions performed in a sequence to generate diverse compounds. While the invention is typically illustrated using chemical building blocks, more typically monomer building blocks, the general nature of the invention should be appreciated. The majority of synthetic chemical reactions proceed quite differently than the typical monomer coupling reaction; the typical organic chemical reaction gives variable yields and leads to multiple products, such as regio- and stereoisomeric structures. The present invention can be used to identify useful products of such series of chemical reactions, because one can practice the methods so that the tag encodes the protocol for synthesizing the compound instead of explicitly specifying the structure of the reaction product.

To simplify discussion, however, the invention is most readily viewed as a series of monomer coupling steps. Because the various coupling reactions of the present method can be carried out in separate reaction vessels at separate times, even building blocks, such as monomers, with very different coupling chemistries can be used to assemble the compounds of interest in a library. While the invention can be practiced by exposing solid supports to a building block and an identifier tag at the same time, or sequentially (either building block and then tag or tag and then building block), the sequential approach allows one additional flexibility with respect to coupling chemistries. In any event, the preferred arrangement for conducting coupling reactions is one in which the diverse coupling reactions are carried out in parallel.

After each parallel series of coupling steps is performed, the solid supports on which the oligomers or other compounds of the library are synthesized are pooled and mixed prior to re-allocation to the individual vessels for the next coupling step. This shuffling process produces a large library of compounds with each distinct member of the library on a distinct solid support. If each synthesis step has high coupling efficiency, then substantially all the compounds on a single solid support have the same structure or, if the compounds are oligomers, monomer sequence. That structure or sequence is determined by the synthesis pathway (type and sequence of monomer or other building block coupling reactions) for any given solid support at the end of the synthesis. The maximum length of oligomers is typically less than about 20, usually from 3 to 15 monomers in length, but in some cases a length of 8 to 12 monomers (residues) is preferred.

Given the diverse numbers of tags and building blocks suitable for use with the present invention, there are a number of chemical methods by which one can prepare chemical libraries of the invention. However, one must ensure that each coupling step, whether of tag or oligomer, does not produce unacceptable levels of unwanted reactions or destroy tags or oligomers already present on the support. In one embodiment, one ensures that only desired reactions occur by using solid supports with chemically reactive groups for tag and oligomer attachment that are protected using two different or "orthogonal" types of protecting groups. The solid supports are exposed to a first deprotection agent or activator, removing the first type of protecting group from, for example, the chemically reactive groups that serve as oligomer synthesis sites. After reaction with a first monomer, and after any optional blocking steps, the solid supports are then exposed to a second activator that removes the second type of protecting group, exposing, for example, the chemically reactive groups that serve as identifier tag attachment sites. The tag is then coupled, and these steps are repeated, typically from one to about 20 times.

A. Oligonucleotide Tagged Peptide Libraries

In one important embodiment, the present invention relates to the synthesis of large libraries of diverse peptides. While many other compounds and oligomers can be made by the method (see Gait, *Oligonucleotide Synthesis: A Practical Approach*, IRL Press, Oxford (1984); Friesen and Danishefsky, 1989, *J. Amer. Chem. Soc.* 111:6656; and Paulsen, 1986, *Angew. Chem. Int. Ed. Engl.* 25:212, all of which are incorporated herein by reference), techniques for solid state synthesis of peptides are particularly important and well known (see Merrifield, 1963, *J. Am. Chem. Soc.* 85:2149–2154, incorporated herein by reference), and peptide libraries are highly useful for a variety of purposes. In the Merrifield method, an amino acid is covalently bonded to a support made of an insoluble polymer. Another amino acid with an alpha-amino protecting group is reacted with the covalently bonded amino acid to form a dipeptide. The protective group is removed, and a third amino acid with an alpha protective group is added to the dipeptide. This process is continued until a peptide of a desired length and sequence is obtained. Protective groups known to those skilled in the art may be used to prevent spurious coupling (see *The Peptides*, Vols. 1 & 3 (eds. Gross, E., and J. Meinhofer, Academic Press, Orlando (1979 & 1981), which is incorporated herein by reference) or to allow one to control coupling. Photolabile, base-labile, and acid-labile protecting groups, and combinations of the same can all be employed for various purposes of the present invention.

Additionally, both L and D forms of amino acids may be employed in peptide synthesis methods described herein. Employing D-amino acids may be useful in the synthesis of "retro-inverso peptides," as described in U.S. application Ser. No. 08/309,451, filed Sep. 21, 1994, incorporated herein by reference for all purposes. Such retro-inverso peptides will comprise the same amino acid sequence, but having reversed stereochemistry from a peptide which is synthesized using L-amino acids.

When the present invention is used to make and screen peptide libraries, the tag of choice is a nucleic acid. There are a variety of compatible chemistries for peptide synthesis and round by round attachment of oligonucleotide identifier tags. However, to maintain the integrity of an oligonucleotide tag during peptide synthesis, one may need to use different combinations of protecting groups and/or synthetic nucleotides to avoid degradation of the tag or the oligomer synthesized. In general, polypyrimidine oligonucleotide tags are relatively stable under typical peptide synthesis conditions, as opposed to oligonucleotide tags that contain natural purine nucleotides, but a polypyrimidine nucleotide tag may be somewhat refractory to amplification by PCR. One may need to incorporate purine bases, or analogs such as 7-deaza-deoxyadenosine, and 7-deaza-deoxyguanosine, tested for ability to withstand peptide coupling (and deprotection) conditions, into the tag to achieve a desired efficiency of amplification. For purposes of the present invention, the tag optionally may contain from 10 to 90%, more preferably 35 to 50%, and most preferably 33 to 35%, purine or purine analog nucleotides. The oligonucleotide tags may optionally incorporate a biotin or other reporter group to facilitate purification, hybridization, amplification, or detection (see *Pierce ImmunoTechnology Catalog and Handbook*, 1991, incorporated herein by reference).

Thus, in selecting the chemistries used to create an oligonucleotide-tagged peptide library of the invention, one must (1) select a solid support with appropriate functional groups; (2) select the amino acid coupling chemistry; (3) select the oligonucleotide tag coupling chemistry; (4) select the protecting groups for the various tags, monomers, and oligomers; and (5) select the deprotection and, in some embodiments, cleavage chemistry (for either the tag or peptide). Those of skill in the art recognize that not all of the above selections need be made in every case, as some applications may not present the same issues as others. For instance, one or more protecting groups may not be required for all applications. In the general case, however, each of these selections is important.

To consider factors relevant to the selection of coupling chemistries and protecting groups for the synthesis of oligonucleotide tagged peptide libraries, consider a synthesis in which commercially available Fmoc protected amino acids are coupled using standard Merrifield chemistry, and the oligonucleotide tags are coupled using standard phosphoramidite chemistry. The process can be viewed as having the following steps: (1) removal of the amino-terminal Fmoc protecting group from the linker or peptide attached to the bead; (2) coupling an Fmoc protected (the side chains may be protected as well) amino acid to the free amino group produced in step (1); (3) optional capping of unreacted free amino groups; (4) removal of the DMT protecting group from the hydroxyl group on the bead or tag to which the nucleotide tag is to be attached; (5) coupling a nucleotide phosphoramidite with a 5'-DMT protecting group as well as protecting groups on the phosphate and exocyclic amines of the bases; (6) optional capping of any unreacted free hydroxyl groups; (7) oxidation of the phosphorous of the oligonucleotide tag; and (8) deprotection of the peptide and oligonucleotide tag. Each of these steps is discussed below.

(1) Removal of the amino-terminal Fmoc protecting group from the linker or peptide attached to the bead is necessary prior to the attachment of the next amino acid monomer. Typically, treatment with 30% piperidine in DMF for about one hour is used to achieve this deprotection (see also step 8), but one aspect of the present invention relates to the use of reduced concentrations of piperidine or reduced deprotection times for the synthesis of oligonucleotide tagged peptide libraries. Piperidine may cause deprotection of methyl triester protected oligonucleotide tags, and O-methyl phosphate protecting groups have greater base stability than the standard beta-cyanoethyl group, known to be susceptible to piperidine cleavage. Preferred Fmoc deprotection conditions of the invention are 5 to 15%, preferably 10%, piperidine for 5 to 60 minutes, preferably 10 to 20 minutes, and 15 to 30% piperidine for 15 to 30 minutes. Another treatment known to effect Fmoc removal is treatment with DBU (1,8-diazabicyclo[5.4.0]undec-7-ene), e.g., 5% DBU for 5 min. However, a report by Palom et al., *Tetr. Lett.* 34: 2195–2198, incorporated herein by reference, suggests that such treatment can result in methylation at N-3 of thymidine. While DBU-mediated Fmoc removal can be effective in some applications, the potential for base modification should be recognized.

(2) Coupling an Fmoc protected amino acid to the free amino group on the bead or peptide can be achieved using standard BOP coupling chemistry (see *The Peptides*, supra). Typically, a mixture of an Fmoc protected amino acid (110 mM), HBTU (100 mM), HOBt (100 mM, and DIEA (300 mM) in a solution composed of 1:1 DMF/DCM is employed to effect amino acid coupling. Other activation chemistries may also be applied in this instance, for example substitution of HBTU/HOBt with HATU. In one embodiment of the invention, however, the reaction mixture is composed of 55 mM Fmoc-protected amino acid, 50 mM HBTU, and 150 mM DIEA in a solution composed of 3:1 DMF/DCM; this embodiment is preferred for use with instruments where reagent delivery bottles may be limited. The side chains may be protected as well; Fmoc/$^t$Bu protection is preferred for most purposes, due to the commercial availability of building blocks. Other useful amino acid building blocks with side chain protection included Arg(Pmc), Gln(Trt), His(Trt), Asn(Trt), Asp(O$^t$Bu), Glu(O$^t$Bu), and Lys($^t$Boc) and amino acids with side chain protecting provided by photolabile protecting groups.

(3) Optional capping of unreacted free amino groups can be achieved by treatment with acetic anhydride and i-methyl imidazole or by other methods known in the art.

(4) Removal of the DMT protecting group from the hydroxyl group on the bead or tag to which the nucleotide tag is to be attached can be achieved by treatment with trichloroacetic acid (TCA), i.e., 1% TCA in $CH_2Cl_2$. If one uses acid-labile protecting groups on phosphates and exocyclic amines of the nucleotides (i.e., deoxycytidine, 7-deaza-deoxyadenosine, and 7-deaza-deoxyguanosine), then those groups should be sufficiently robust to resist the TCA (typically 1–3%) used in 5'-0-detritylation.

(5) Coupling a nucleotide phosphoramidite with a 5'-DMT protecting group can be achieved using standard phosphoramidite chemistry, although one must take into consideration the need for protecting groups on the phosphate oxygen as well as on the exocyclic amines of the bases of the oligonucleotide tags. For photolabile protecting groups for nucleic acids, see PCT patent publication WO 92/10092 and Baldwin et al., 1990, *Tetr. Lett.* 46: 6879–6884, each of which is incorporated herein by reference. As noted above, suitable phosphate protecting groups include the O-methyl and beta-cyanoethyl groups, but O-allyl and/or N-allyloxycarbonyl groups (i.e., by incorporating 3-(allyl N,N'-diisopropyl) phosphoramidites) can also be used to protect phosphate oxygens and the exocyclic amines of the nucleoside bases, respectively (see Hayakawa et al., 1990, *J. Amer. Chem. Soc.* 112: 1691–1696, incorporated herein by reference). Allylic protecting groups can be removed using THF containing tris (dibenzylideneacetone) dipalladium-chloroform complex, triphenylphosphine, and n-butylamine/formic acid, followed by a THF wash, an aqueous sodium N,N-diethyldithiocarbamate wash, and a water wash. Phosphoramidite coupling is mediated with agents such as 1H-tetrazole; 4-nitrophenyl tetrazole; pyridinium hydrochloride/imidazole. The latter phosphoramidite activator leads to selective 5'-O-phosphitylation at the expense of low levels of spurious reaction at nitrogen on the peptide or oligonucleotide (see Gryaznov and Letsinger, 1992, *Nucleic Acids Research* 20: 1879–1882, incorporated herein by reference).

(6) Optional capping of any unreacted free hydroxyl groups can be achieved by treatment with acetic anhydride and 1-methyl tetrazole or by treatment with acetic anhydride/lutidine/DMAP.

(7) Oxidation of the phosphorous of the oligonucleotide tag can be achieved by treatment with iodine and pyridine or by treatment with $I_2$, collidine, MeCN in $H_2O$. Alternatively, by employing the mild oxidant 'BuOOH for oxidation at the phosphorous, one can minimize oxidation of the amino acids methionine, tryptophan, and histidine (see Hayakawa et al., 1990, *Tetr. Lett.* 27:4191–4194, incorporated herein by reference).

(8) Deprotection of the peptide and oligonucleotide tag can be effected by sequential treatment with 1% TCA in dichloromethane, then with thiophenol/$NEt_3$/dioxane (1:2:2), then with ethylenediamine/EtOH (1:1) at 55 degrees C, to remove the protecting groups from the tag, and then trifluoroacetic acid (95:5 TFA/water, with cation scavengers) is used to remove acid-labile amino acid protecting groups. The lability of purine nucleotides to strong acid (e.g., TFA) can be avoided by use of phosphoramidites of the purine nucleoside analogs 7-deaza-2'-deoxyadenosine and 7-deaza-2'-deoxyguanosine (see Barr et al., 1986, *BioTechniques* 4:428432, and Scheit, *Nucleotide Analogs: Synthesis and Biological Function* pp. 64–65 (John Wiley and Sons, New York), both incorporated herein by reference).

The next section illustrates one preferred embodiment for synthesizing oligonucleotide-tagged peptide libraries.

B. Improved Method for Synthesizing Oligonucleotide-Tagged Peptide Libraries

Establishing a practical bead-based oligonucleotide-encoded peptide library methodology demands that several key technical criteria be met. These include (i) the development of mutually compatible chemistries for parallel assembly of peptides and oligonucleotides; (ii) the selection of bead material with appropriate physical characteristics; (iii) the facile isolation of small beads bearing ligands that bind a target receptor; and (iv) successful reading of the tags from a single bead, i.e., by PCR amplification and sequencing of template tag DNA from single beads. The present invention provides an improved method for synthesizing such libraries, as illustrated in this section and Example 1, which show how to use single stranded oligonucleotide tags to encode a combinatorial peptide synthesis on 10 μm diameter polystyrene beads.

In this improved method, peptides and nucleotides are assembled in parallel, alternating syntheses so that each bead bears many copies of both a single peptide sequence and a unique oligonucleotide identifier tag. The oligonucleotides share common 5'- and 3'-PCR priming sites; the beads can therefore serve as templates for the PCR. To illustrate the method, an encoded synthetic library of some $8.2 \times 10^5$ hepta-peptides was generated and screened for binding to an anti-dynorphin B monoclonal antibody D32.39 (Cull et al., 1992, *Proc. Natl. Acad. Sci. USA* 89:1865–1869, incorporated herein by reference), using a fluorescence activated cell sorting (FACS) instrument to select individual beads that strongly bind the antibody. After PCR amplification of the oligonucleotide tags on sorted beads, the DNA was sequenced to determine the identity of the peptide ligands, as is described more fully below.

One important aspect of this method, which is described in additional detail in Example 1, below, is the solid support selected for synthesis of the peptide and tag. Solid supports, i.e., 10 μm diameter beads, fashioned from a macroporous styrene-divinylbenzene copolymer and derivatized with a dodecylamine linker are preferred. The amino group loading of these beads was estimated to be ~100 μmol/g by exhaustive acylation with Fmoc-glycine, followed by piperidine cleavage of the Fmoc group and spectrophotometric quantitation of the released piperidine-dibenzofulvene adduct ($e^{302}$=7,800 1 $mol^{-1}$ $cm^{-1}$). With $5 \times 10^9$ beads/g, this corresponds to a maximum peptide loading of ~20 μmole/bead. Acylation of the beads with a mixture of an appropriately protected amino acid and an omega hydroxy acid provide orthogonally differentiated amino and hydroxyl groups from which the peptide and nucleotide chains respectively can be extended. The average stoichiometry of peptide to oligonucleotide per bead is controlled by varying the ratio of amino and hydroxy acids coupled to the initial bead mass (vide inf@ra. Test peptide syntheses (5-mers to 12-mers) on these beads equipped with a trifluoroacetic acid-cleavable Knorr linker (Bematowicz et al., 1989, *Tetr. Lett.* 30: 4645–4648, incorporated herein by reference) using standard Fmoc chemistry were found to proceed with high fidelity that was indistinguishable from syntheses performed on conventional peptide synthesis resin, as determined by HPLC analysis of the crude cleaved peptide carboxamides.

Parallel synthesis strategies require the use of a set of protecting groups on the amino acids and nucleotide building blocks that are mutually orthogonal, and that each of the polymer chains be stable to the reagents used in the synthesis and deprotection of the second chain. Although, in principle, a variety of protection/deprotection schemes can be used (as discussed above), Fmoc/ᵗBu protection on the peptide building blocks is preferred, because of the extensive commercial availability of natural and unnatural amino acids protected in this manner. However, the ᵗBu-based peptide side chain protecting groups require treatment with strong acid (typically trifluoroacetic acid) for removal, conditions that can lead to rapid depurination of oligonucleotides containing either 2'-deoxyadenosine (dA) or 2'-deoxyguanosine (dG) (see Capon, 1969, *Chem. Rev.* 69: 407–498, incorporated herein by reference). This problem has been circumvented by using 7-deaza-2'-deoxyadenosine ($c^7$ dA) in place of dA in the template oligonucleotide tag. The glycosidic bonds of deazapurine nucleosides are resistant to acid-catalyzed hydrolysis (see Scheit, 1980, *Nucleotide Analogs: Synthesis and Biological Function* (John Wiley and Sons, New York) pp. 64–65, incorporated herein by reference), and oligonucleotides incorporating these monomers are faithfully copied by thermostable polymerases used in the PCR (see McConlogue et al., 1988, *Nucl. Acids Res.* 16: 9869, and Barr et al., 1986, *BioTechniques* 4: 428–432, each of which is incorporated herein by reference). Acid-resistant guanosine analogs can also be incorporated into the template DNA.

5'-O-dimethoxytrityl 2'-deoxynucleoside 3'-(O-methyl-N,N-diisopropyl) phosphoramidites were used in all parallel syntheses. The reagent ($I_2$/collidine/$H_2O$/acetonitrile) used to convert the nucleotide phosphite intermediates to phosphotriesters in the DNA synthesis protocol was not found to adversely affect either the readily oxidized residues Trp and Met or any of the other protected amino acids. Complete removal of the 5'-O-DMT group from the growing oligonucleotide chain was achieved in ~40 sec using 1% trichloroacetic acid (TCA) in dichloromethane, while all of the acid-labile side chain protecting groups used conventionally in Fmoc/ᵗBu chemistry, excepting the ᵗBu ether derivative of tyrosine, were inert to treatment with 1% TCA for 1 hour. Fmoc-Tyr(O-Bz) proved a suitable replacement in the synthesis of tyrosine-containing peptides, the O-benzoyl ester being robust towards both TCA and the piperidine used for removal of the alpha-N-Fmoc protecting group in peptide synthesis. Quantitative deprotection of the alpha-amino residues required 5–10 minute treatment with piperidine/DMF (10% v/v) and also resulted in partial demethylation of the protected polynucleotide phosphotriesters ($t_{1/2}$ 45 min). Control experiments indicated that any aberrant phosphitylation of the resulting phosphodiester species during subsequent nucleotide chain elongation was reversed by the final oligonucleotide deprotection steps (see Lehmann et al., 1989, *Nucl. Acids Res.* 17: 2379–2390, incorporated herein by reference). At the completion of the parallel synthesis, the DNA was fully deprotected by treatment with thiophenolate (phosphate O-demethylation) then ethanolic ethylenediamine (debenzoylation of protected cytidine and 7-deazaadenine residues). These mild, anhydrous aminolysis conditions did not adversely affect protected peptide sequences (see Juby et al., 1991, *Tetr. Lett.* 3: 879–882, incorporated herein by reference), which were deblocked using TFA under standard conditions.

The carboxy-terminal region of opioid peptide dynorphin B (YGGFLRRQFKVVT) (SEQ ID NO: 1) has been previously shown to represent the epitope of anti-dynorphin B mAb D32.39 (see Cull et al., supra): the soluble heptapeptide RQFKVVT (SEQ ID NO:2) binds D32.39 with high affinity ($K_d$ ~1 nM). A parallel synthesis of this peptide and a 69 base oligodeoxynucleotide was performed on orthogonally differentiated beads bearing an acid-cleavable Fmoc-protected carboxamide (Knorr) linker. After addition of the first 20 nucleotides, the beads were treated with piperidine/DMF and the first peptide residue (Fmoc-Thr(ᵗBu)-OH) coupled to the free amines. The beads were then subjected to two cycles of phosphoramidite chemistry and coupling of the next amino acid (Fmoc-Val-OH). This process was repeated until the heptapeptide sequence and nucleotide coding region had been fully elaborated, and then the DNA was extended by a further 35 nucleotides to provide a spacer region and 5'-priming site for the PCR. The beads were finally exposed to full oligonucleotide and then peptide deprotection conditions, and the TFA supernatant containing the cleaved peptide was analyzed by reverse-phase HPLC. The HPLC results showed that the crude peptide from the parallel synthesis consists of a single major component (co-eluting with authentic RQFKVVT, (SEQ ID NO:2)) and that this crude product is not significantly different from that generated in a control peptide synthesis in which no oligonucleotide chemistry occurred.

The stability to parallel synthesis chemistries of template DNA containing T, dC and $c^7$ dA was compared with an analogous target containing the standard purine nucleotide dA. Using the single bead cloning capability of a FACStar Plus cytometer, individual deprotected beads from the two syntheses were sorted into microfuge tubes and the tethered oligonucleotide template amplified through 45 cycles of the PCR. A "clean" amplification product of the expected size and nucleotide sequence was obtained only from template containing the deazapurine. Thus the integrity of this oligonucleotide was maintained through the course of a parallel peptide synthesis, demonstrating that template from a single bead can be readily amplified and sequenced.

An encoded library designed to contain 823,543 ($7^7$) different hepta-peptides attached to 10 μm beads was constructed by a combinatorial synthesis using seven amino acid building blocks Arg, Gln, Phe, Lys, Val, D-Val and Thr. Alpha-N-Fmoc-Thr(tert-butyl)-oxybenzotriazole (protected threonine) and succinimidyl 4-O-DMT-oxybutyrate residues were first coupled to all the beads to provide the orthogonally differentiated amino and hydroxyl groups for this synthesis. On average, each bead bore 20 molecules of a single peptide sequence per molecule of DNA tag. Every amino acid addition was encoded by building a characteristic dinucleotide unit, and after the seventh cycle of peptide coupling the beads were pooled, and the DNA synthesis completed. Starting with a total bead mass of 35 mg (1.75× $10^8$ beads) ensured that each peptide sequence appeared on ~200 different beads in the library. Peptide microsequencing analysis of an aliquot of the library confirmed that the seven amino acids were stochastically distributed among every position of the degenerate hepta-peptide mixture (note that L-valine and D-valine are not distinguished in the Edman degradation procedure).

The binding of mAb D32.39 to control beads and to the bead library was analyzed by flow cytometry. Beads carrying the positive control sequence RQPKVVT (SEQ ID NO:2) and a 69-mer oligonucleotide tag were strongly stained by the antibody whereas blank beads were unstained. By contrast, only a small fraction of the encoded library bound D32.39. Analysis of $10^5$ events indicated ~2% of the library stained above background levels. Significantly, this binding to D32.39 was specific for the combining site as it could be completely blocked by preincubating the mAb with soluble RQFKVVT peptide (SEQ ID NO:2). Individual beads from the library having fluorescence intensities comparable with the positive control beads were sorted into microfuge tubes for tag amplification by PCR (beads with fluorescence in the top 0.17% of the population were collected). The amplification reactions contained dUTP and uracil DNA glycosidase to prevent carryover contamination with soluble product from previous amplifications (see Longo et al., 1990, Gene 93: 125–128, incorporated herein by reference). Nucleotide sequences were obtained from 12 sorted beads and the deduced peptide sequences are given in Table 1. Representative peptide sequences obtained from single beads having fluorescence which was not significantly above background are also tabulated for comparison.

TABLE 1

| Sequence | | Kd,nM |
|---|---|---|
| High Fluorescence Intensity Beads | | |
| (SEQ ID NO:3) | TFRQFKVT | 0.29 |
| (SEQ ID NO:4) | TTRRFRVT | 4.3 |
| (SEQ ID NO:5) | TVRQFKTT | 8.8 |
| (SEQ ID NO:6) | QvRQFKTT | 16 |
| (SEQ ID NO:7) | RQFRTVQT | 76 |
| (SEQ ID NO:8) | KQFKVTKT | 340 |
| (SEQ ID NO:9) | QQFKVVQT | 370 |
| (SEQ ID NO:10) | KQFKVTQT | 410 |
| (SEQ ID NO:11) | TQFKVTKT | 560 |
| (SEQ ID NO:12) | TFRvFRVT | 1400 |
| (SEQ ID NO:13) | FRRQFRVT | not tested |
| (SEQ ID NO:14) | RQFKQVQT | not tested |
| Low Fluorescence Intensity Beads | | |
| (SEQ ID NO:15) | QTvTvKKT | >1 |
| (SEQ ID NO:16) | QQVQRQTT | >0.4 |
| (SEQ ID NO:17) | KTQvVQFT | not tested |
| (SEQ ID NO:18) | QvTQvRVT | not tested |
| (SEQ ID NO:19) | FVVTVRVT | not tested |

The data in Table 1 is consistent with earlier studies demonstrating that the preferred recognition sequence of D32.39 is localized to the six amino acid fragment RQFKVV of dynorphin B (see Cull et al., supra). The positively charged residues arginine and lysine are strongly preferred in the first and fourth positions of the epitope and phenylalanine appears exclusively as the third residue of this motif. At the second position glutamine is the favored residue in this library, while the aliphatic b-branched amino acids valine (L-enantiomer only) and threonine are clearly preferred as the fifth and six residues. D-Valine appears to be best tolerated at positions outside of the consensus motif. The range of affinities of peptides that were selected ($K_b$~0.3–1400 nM) was not unexpected given the design of the binding assay: bivalent primary antibody with labeled second antibody detection. Manipulation of the binding valency (for example, by using directly labeled monovalent receptor) and the stringency of wash conditions will improve the capacity to isolate only the highest affinity ligands.

C. Small Molecule Synthesis

Although primarily described in terms of the synthesis of peptide or other large polymer libraries, as noted previously, the various aspects of the present invention are equally applicable to other chemical syntheses. Specifically, the apparatus and methods of the present invention may be used to carry out a variety of chemical synthesis steps in many synthetic protocols, including, for example, the synthesis of other oligomers or small molecules. The apparatus may be employed in a chemical synthesis scheme to selectively add reagents in conformance with the synthesis protocol for the particular molecule.

Further, different synthesis protocols may be carried out in parallel, as with the peptide synthesis described above, where different reagents are added at different steps to yield a diverse library of small molecules on solid supports. These diverse libraries may be screened for desired properties by the methods described herein. Additionally, where such a diverse library of small molecules is desired, the library may be tagged so as to encode the synthesis steps which were involved in the synthesis of each discrete member of the library of molecules.

Examples of the synthesis of such small molecules on solid supports include, for example, thiazolidinones, metathiazolidinones, and derivatives thereof, as described in Example 2, included herein, and U.S. patent application Ser. No. 08/265,090, filed Jun. 23, 1994, and incorporated herein by reference for all purposes.

In a preferred aspect, the present invention provides methods of synthesizing small molecule libraries, using N-substituted glycine ("NSG") oligomers as a scaffold. In brief, the combinatorial synthesis methods of the present invention can be used to synthesize N-substituted glycine oligomers having a wide variety of pharmacophores attached at one end. For a particular pharmacophore, the libraries diversity is supplied by varying the nature of the side-chain groups on the amine building blocks (e.g., acidic, basic, hydrophobic, neutral H-bonding, etc.), as well as the nature of the connection between the scaffold and the pharmacophore. See, e.g., J. Med. Chem. (1994) 37(17):2678–2685.

Although the NSG libraries described herein may comprise a range of different oligomer lengths, typically, these NSG libraries will comprise a diverse collection of dimeric, trimeric or tetrameric compounds, wherein the NSG scaffold comprises one, two or three NSG units is attached via a connecting group to a pharmacophore, respectively. The basic structure of the N-substituted glycines is shown below:

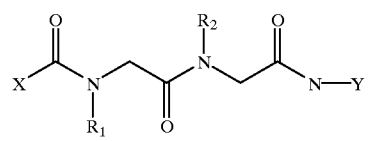

where X is a pharmacophore, and Y is a solid support, e.g., a bead, and the R groups, e.g. $R_1$, $R_2$ and $R_3$, are the varied side chain groups of the amine building blocks.

The particular screening application, i.e. the goal of the screen, will generally dictate the nature of the pharmacophore attached to the oligomer. One of skill in the art will recognize that a wide variety of pharmacophores may be attached to the NSG libraries. For example, mercapto alcohol or carboxylate moieties can be used in screening for inhibitors of matrix metalloproteases ("MMP") (see U.S. patent application Ser. No. 08/329,420 filed Oct. 27, 1994), while N-acetyl-p-malonyl($CH_2$)-Phe-OH, a phosphotyrosine isostere, could be used in screening for inhibitors of SH2/phosphorylated ligand interactions, e.g., Grb2 SH2, and the like (see U.S. patent application Ser. No. 08/382,100, filed Feb. 1, 1995). Examples of pharmacophore-connector building blocks for such libraries include those shown below:

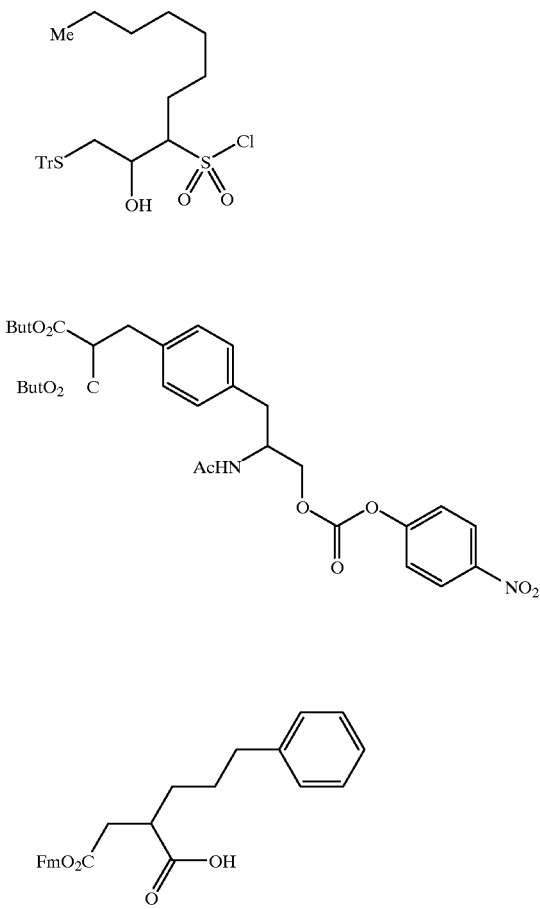

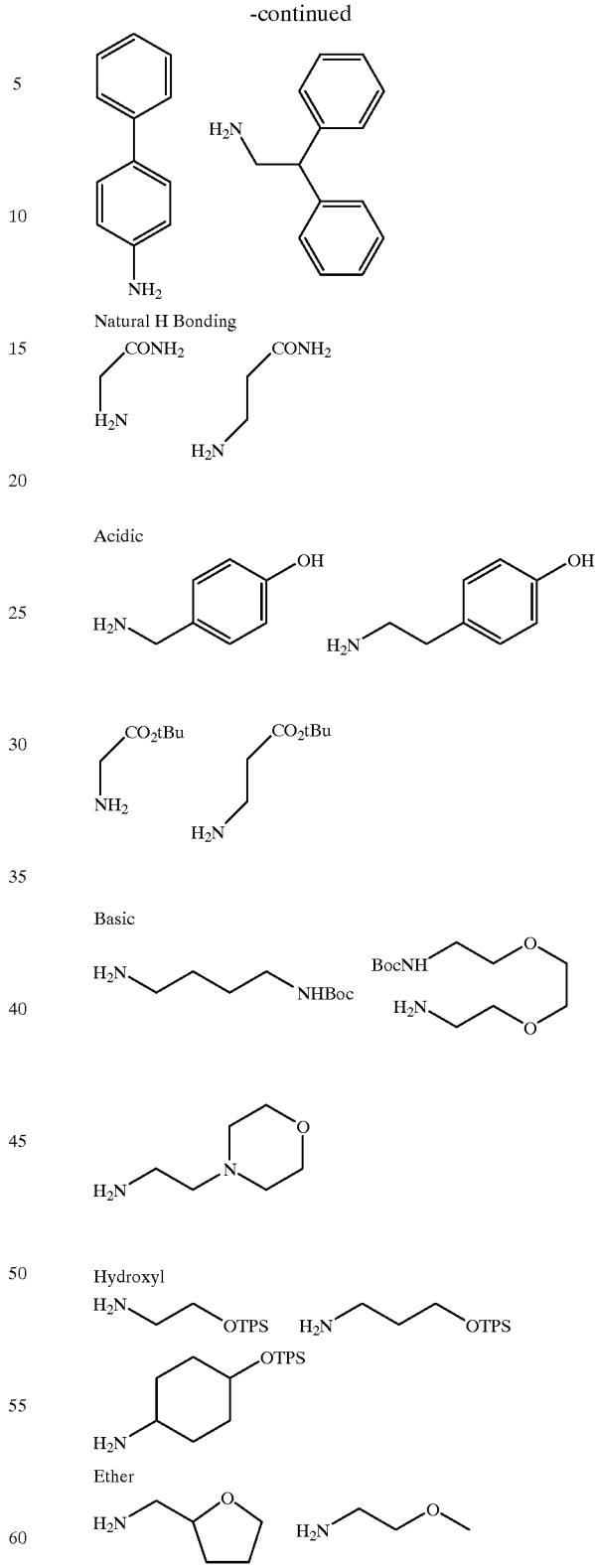

As noted above, the diversity of a particular individual library, will generally be supplied by tile substitution of the side chains of the NSG scaffold. Typically, these substituents will comprise a range of structural, chemical and physical properties. For example, the side chains may be acidic, basic, hydrophobic or neutral H-bonding side chains. Examples of amines possessing these properties which may be readily incorporated in the NSG scaffolds described herein include the following:

Hydrophobic

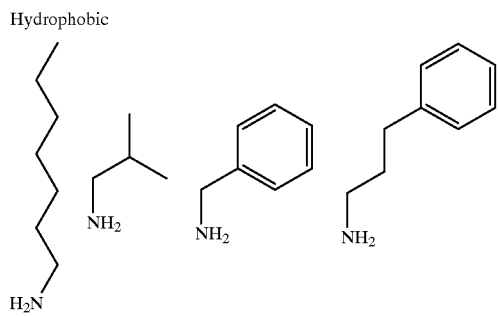

Another source of diversity of the various NSG based libraries may be supplied by the choice of connecting groups linking the particular pharmacophore with the scaffold. A variety of amide and non-amide linkages are available to supply this connection, including ally, amine, amide, sulfonamide, urea, carbamate, amino amide, or other linkages may be used. A variety of other linkages preparable by standard methods will be apparent to those in the art. Several exemplary linkages, and their syntheses are illustrated, below:

in the art. See, e.g., Zuckerman, et al., *J. Med. Chem.* (1994) 37:2678–2685. For example, acylation of amines bound to solid supports using bromoacetic acid, followed by alkylation of the ce-bromoamides on the supports with alkylamines. See Zuckerman.

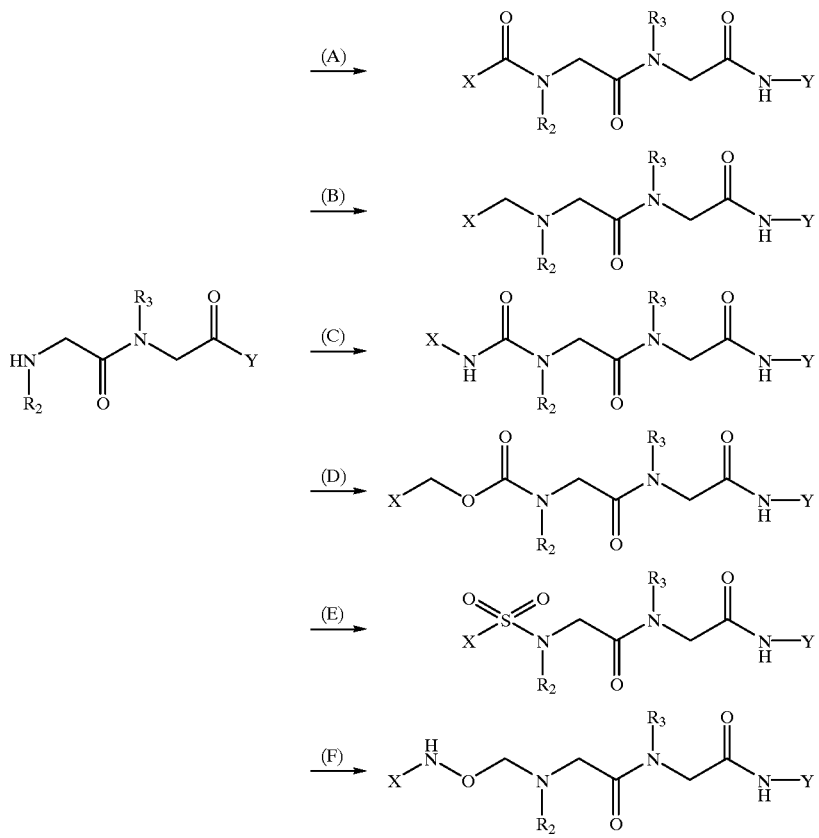

(A) X-CO$_2$H, HATU
(B) X-CHO, NaBH$_3$CN
(C) X-N=C=O
(D) X-CH$_2$OCOPNP
(E) X-SO$_2$Cl
(F) BrCH$_2$CO$_2$H, X'NH$_2$

Again, the pharmacophore is shown as X, whereas the solid support is denoted by Y.

Synthesis of amide (A), amine (B), urea (C), carbamate (D), sulfonamide (E), and NSG (F) linkages to N-substituted glyince scaffolds are shown.

The preparation of the NSG based libraries described herein, will generally be carried out by methods well known Examples of NSG libraries include those shown below for mercapto ketone based libraries biased toward MMP inhibitors (top) (U.S. application Ser. No. 08/329,420, filed Oct. 27, 1994), and malonic acid based NSG inhibitors biased toward SH2 ligands (bottom)(U.S. application Ser. No. 08/382,100, filed Feb. 1, 1995):

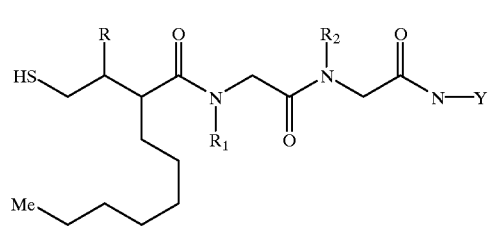

-continued

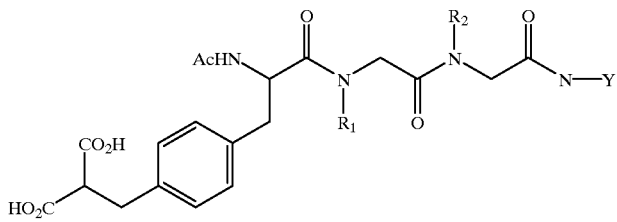

where Y is a solid support and R is OH, H or double bonded oxygen.

D. Methods for Generating Soluble Libraries

For some applications, one may desire a "bead-free" or "soluble" library of molecules. Soluble molecules, both tagged and untagged, can be useful for a variety of purposes, including assaying the activity of a compound (see Section VI.B, below) and amplifying a tag. There are a variety of ways one to generate soluble molecular libraries, both tagged and untagged, and to solubilize compounds, both tagged and untagged, synthesized on a solid support. Typically, cleavable linkers are employed in such methods.

For instance, and as noted above in Section II.B, cleavable linkers can be used to cleave tagged or untagged molecules from a bead or other solid support, thus solubilizing the molecule of interest. To produce a soluble tagged molecule, the cleavable linker will be attached to the bead or other solid support and have at least two functional groups: one for synthesizing the molecule of interest and the other for synthesizing the tag. Thus, the molecule and tag are synthesized attached to a common linker, which, in turn, is bound to the solid support. Once the molecule and tag are synthesized, the linker is cleaved to provide a soluble tagged molecule.

A single, planar solid support can be used to synthesize the library, and the members can be cleaved from the support prior to screening using very large scale immobilized polymer synthesis (VLSIPS™) technology. See U.S. Pat. No. 5,143,854 and PCT patent publication No. 92110092, each of which is incorporated herein by reference. In one embodiment, an array of oligonucleotides is synthesized on the VLSIPS™ chip, and each oligonucleotide is linked to the chip by a cleavable linker, such as a disulfide (see U.S. patent application Ser. No. 874,849, filed Apr. 24, 1992, incorporated herein by reference). The oligonucleotide tag has a free functional group, such as an amine, for attachment of the molecule to be tagged, which is typically an oligomer and preferably a peptide. The tag may optionally contain only pyrimidine or pyrimidine and purine analog bases. The tag also contains binding sites for amplification, i.e., PCR primer sites, optionally a sequencing primer site, and a short section uniquely coding the monomer sequence of the oligomer to be tagged. Then, the oligomer is synthesized, i.e., from a free terminal amine groups on the tag or a linker linked to the tag, so that each oligomer is linked to a tag. The collection of tagged oligomers can be released from the chip by cleaving the linker, creating a soluble tagged oligomer library.

Other advantages can be realized by generating soluble libraries of molecules. In any bead-based library, the size (mass) of the bead will impose practical limits on the size of the library that can be assembled. For instance, several grams of beads may be required to assemble a library containing $10^9$ different tagged molecules. The present invention provides an improved method for synthesizing tagged molecular libraries that enables one to obtain much larger libraries much more practically. This improved method provides a means whereby the compounds are released from the solid support prior to the mixing steps but are reattached to the solid support prior to each coupling step.

In this method, the tagged molecule is immobilized on a solid support in a reversible manner, allowing one to release the tagged molecule from the support during each of the mixing steps of the method. In one embodiment, this reversible binding is provided by an ultrafiltration membrane (for suitable membranes, see, e.g., the "Commercial Compatibility Chart" in the Millipore catalogue, which shows membranes inert to a variety of solvents and chemicals used in synthesis methods). A membrane with a molecular weight cut-off of about 2,000 to 10,000 daltons (such as the Amicon YM5 membrane) would be suitable for most libraries. During the coupling steps, the molecules of the library would be retained by the membrane, while the coupling and other reagents would be drawn through the membrane by vacuum suction. The vacuum would be released to allow the molecules to be mixed during the mixing steps.

In another embodiment of the method, a reversible covalent linkage is used to attach the tagged molecules to the support during the coupling steps. Examples of suitable reversible chemical linkages include (1) a sulfoester linkage provided by, e.g., a thiolated tagged-molecule and a N-hydroxy-succinimidyl support, which linkage can be controlled by the $NH_2OH$ concentration; and (2) a disulfide linkage provided by, e.g., a thiolated tagged-molecule and a 2-pyridyl disulfide support (e.g., thiolsepharose from Sigma), which linkage can be controlled by the DOT (dithiothreitol) concentration.

VI. Assay Methods

The utility of large combinatorial libraries for ligand discovery depends critically on the availability of robust and affinity-sensitive biochemical assay methodologies. The present invention provides a number of novel assays for use with encoded synthetic molecular libraries, which in turn have a wide variety applications. By way of example, such libraries can be used in assays to identify ligands that bind receptors, such as peptides and nucleic acids that bind to proteins, drugs that bind therapeutic target receptors, and epitopes (both natural and synthetic) recognized by antibodies, as well as to identify a variety of compounds with pharmaceutical, agricultural, and medical diagnostic applications. Given these diverse applications, there are a wide variety of assay methods relevant to the present invention. Two important types of assays, albeit with some overlap, include bead-based assays and assays of soluble molecules.

In general, however, such assays typically involve the following steps. The libraries are screened by assays in each different molecule in the library is assayed for ability to bind to a receptor of interest. The receptor is contacted with the library of synthetic molecules, forming a bound member between the receptor and any molecule in the library able to bind the receptor under the assay conditions. The bound molecule is then identified by examination of the tag associated with that molecule. In one embodiment, the receptor to which the library is exposed under binding conditions is a mixture of receptors, each of which is associated with an identifier tag specifying the receptor type, and consequently two tags are examined after the binding assay.

A. Screening Assays for Bead-based Libraries

When specific beads are isolated in a receptor screening, the beads can be segregated individually by a number of means, including infinite dilution, micromanipulation, or preferably, flow cytometry. Libraries of tethered ligands are most effectively evaluated in binding assays with soluble labeled receptors. By adopting cell-sized solid supports or beads, one can use flow cytometry for high sensitivity receptor binding analysis and facile bead manipulation.

Flow cytometry, commonly referred to as fluorescence activated cell sorting or FACS should be viewed as equivalent to "fluorescence activated molecular sorting" or "fluorescence activated bead sorting" for purposes of the present invention. One of ordinary skill in FACS methods for cloning mammalian cells expressing cell surface antigens or receptors can readily practice the assay methods of the present invention. In general, these assays involve the binding of a receptor labeled with a fluorescent tag to a mixture of beads displaying the diverse molecules of a molecular library. After washing away unbound or non-specifically bound receptors, one then employs a FACS instrument to sort the beads and to identify and isolate physically individual beads showing high fluorescence. See *Methods in Cell Biology*, Vol. 33 (Darzynkiewicz, Z. and Crissman, H. A., eds., Academic Press); and Dangl and Herzenberg, 1982, *J. Immunol. Meth.* 52:1–14, both incorporated herein by reference. Once the desired beads have been isolated, one identifies the tag to ascertain the identity (or molecular structure, composition, or conditions of synthesis) of the molecule of interest on the bead.

Standard FACS instrumentation permits bead (cell) fluorescence analysis rates of $\sim 10^4$ events/sec. and, when operated in single bead cloning mode, sort rates that are 5–10 fold slower. In assaying very large libraries (e.g., $>>10^7$ beads) some form of affinity-selective pre-screen can be used prior to individual bead isolation with the cell-sorter. For example, receptor-coated sub-micron sized superparamagnetic particles are frequently used to affinity purify specific cells from large, mixed populations by magnetic activated sorting (see Miltenyi et al., 1990, *Cytometry* 11: 231–238, incorporated herein by reference). To have a high probability of detecting very rare binding events, each different compound in the library should be present on many beads in the library. A practical upper limit for the size of an encoded library constructed from 10 μm particles, assuming a hundred-fold redundancy, is probably $10^8$–$10^9$ compounds synthesized on $\sim 10^{10}$–$10^{11}$ beads. Even larger libraries can be prepared using smaller beads, but conventional cytometers are unlikely to detect or manipulate particles much less than $\sim 1$ μm in diameter. Of course, as noted elsewhere herein, the present invention provides a variety of applications for such small beads in the synthesis and screening of libraries of molecules. For instance, by using the oligonucleotide tag concatenation method of the invention, one need not use FACS methodology to sort the molecules in the library.

Nonetheless, one should not underestimate the power of FACS instrumentation for purposes of the present invention. In one assay method of the invention, the tagged molecular library is synthesized on fluorescent beads. The beads are smaller than cells and composed of a fluorescent material. The library is incubated with a suspension of cells expressing a high level of a cell surface receptor of interest, such as a G-protein-linked receptor. Of course, one can also perform a variety of controls, such as conducting all steps with cells that do not express a high level of the cell surface protein, and use those controls to identify false positives.

In any event, cells expressing the receptor can bind to any library members presenting a ligand for the receptor. Fluorescently labeled cells can be readily distinguished and separated from fluorescent unbound library beads and from unlabeled cells with a FACS instrument based on light-scattering or another fluorescent signal, e.g., from a cell nucleus. After sorting, the tags from the beads attached to the cells are examined to identify the ligands specific for the receptor. Depending on the application, one would sort for cells expressing the highest level of the desired receptor, e.g., by selecting only the brightest cells, and would adjust the binding conditions to maximize specific binding events. To discriminate between ligands specific for the receptor of interest and those specific for other cell surface receptors, one could examine tags associated with beads binding to cells expressing high levels of the receptor of interest and cells that do not.

The methods of the present invention also enable one to use FACS instrumentation to sort tagged molecular libraries synthesized on beads much smaller than the smallest beads current FACS instrumentation are capable of sorting. In this method, encoded synthetic libraries are screened for effector activity on signal transduction pathways. The synthetic library is constructed with several modifications: (a) the beads are 1 μm or smaller and need not be sortable in the FACS, allowing rather small beads to be used in some instances; (b) the tags are oligonucleotides resistant to the intracellular environment (most particularly nuclease resistant), phosphorothioates are preferred for this purpose; and (c) the peptides (or other diverse chemical entities) are attached to the bead support via a linker that cleaves in the intracellular environment. Such linkers include linkers that can be cleaved upon the application of an external factor, such as light, that does not harm the cells and linkers labile to the intracellular environment, such as a phosphodiester bond or a disulfide bond, but in any case, the cleavable linker must be stable to the parallel synthesis process.

The library beads are introduced into the reporter cells preferably by a mechanical process such as, for example, biolistic projection. In some cases, a biochemically-mediated process leading to internalization can be employed, but this route usually results in incorporation into an undesirable cellular compartment (i.e., lysozomal localization). Once the beads are in the cells, the peptides or other compounds of interest are released. Given that 10 μm beads have a demonstrated capacity of $10^{10}$ peptide (or other) synthesis sites, then if the capacity scales with volume, a 1 μm bead of the same material would contain $10^7$ molecules of the synthesized peptide. If all of the synthesized peptide is released in a single (spherical) cell of $\sim 10$ μm diameter (a volume of $\sim 0.5$ pL), then a concentration of free peptide of $\sim 30$ μM would result. This concentration would be controllable by the synthesis density on the beads, and a lower loading density could provide for a more stringent screening format (i.e., a screen for more active compounds). The recipient cells are engineered to generate a fluorescent signal upon activation or inactivation of the pathway of interest. The individual cells producing the desired effect are selected by FACS instrumentation, and the tags, which are still attached to the beads and contained within the cells, are amplified and sequenced to identify the active synthetic compounds.

In another embodiment, large beads are employed and used to screen a population of cells that express a receptor (i.e., the enzyme beta-galactosidase) capable of generating a fluorescent or other detectable signal, i.e., by cleavage of a substrate to produce a detectable compound. The beads are then mixed with a population of the cells, which are allowed to attach to the beads. If the receptor on the cell surface is stimulated by the compound on the bead, then the detectable compound is produced, providing a basis for sorting activated cells attached to the beads from unactivated cells. One could employ appropriate reagents (i.e., free labeled or unlabeled receptor) to maximize selection of high affinity ligands.

There are of course a variety of alternatives to flow cytometry for purposes of screening and selecting for library molecules of interest. In one embodiment, an encoded synthetic library is screened for antimicrobial activity to find compounds that retard the growth or kill bacteria or any other microorganism that can be plated in two dimensions, such as virus-infected cells, many eukaryotic cells including cancer cells, and some protozoa. Large libraries of related or unrelated chemical structures can be screened against cells in agar culture by controlled release of the peptide or compound from the bead on which it was synthesized.

The steps of the method follow: (1) plate the cells of interest on agar plates; (2) overlay the cells with another layer of agar in which the beads bearing the synthesized peptide/drug are suspended at a dilution that provides for even dispersion so that individual beads can be picked, e.g., with a capillary tube, from the solid agar; (3) initiate release of the peptide/drug from the beads; (4) culture the plate to allow diffusion of the peptide/drug from the bead immobilized in agar into the surrounding agar and into the agar below containing the indicator cells; (5) read the extent to which the diffused test compounds from individual beads have affected the growth/morphology/phenotype of the indicator cells; (6) choose zones where the indicator cells exhibit the desired response (e.g., death of a bacterial lawn) and using a capillary tube or similar, pick out the zone of agar that contains the original bead from which the test drug had diffused; (7) read the tag, e.g., by PCR amplification of the encoded material on the individual bead, to determine the structure of the peptide/drug that elicited the desired response; and (8) optionally chemically synthesize the appropriate drug/peptide and verify desired effect.

There are a variety of ways to release the test compound from beads. For instance, one could partially cleave the peptides/drugs from beads using TFA and allowing cleaved peptide to dry down onto the bead surface in such a form that subsequent resuspension in water (agar) will allow release of the peptide/drug and localization of the released compound to the zone of agar around a particular bead. Alternatively, one can expose beads spread upon a surface to gaseous TFA to effect release of the library compounds, followed by neutralization or removal of the TFA, e.g., by treatment in vacuo. One can also link the drug/peptide to the bead using chemistry that is sensitive to a particular change in bead environment that can be initiated upon plating onto the agar and indicator cells or after plating and agar solidification, e.g., a photosensitive linkage, a thiol sensitive linkage, a periodate sensitive linkage, etc. These chemical agents could themselves be diffused in through another thin agar overlay, if necessary. Such release chemistry must be compatible with the integrity of the test substance, integrity of the encryption on the bead, and health of the underlying indicator cells. The particular release chemistry used will also of course depend on the type of chemistry used for synthesizing the library and the nature of the indicator cells. The method is especially preferred for screening libraries of beta-lactam antibiotics for identification of new antibiotics that might kill newly evolved strains of bacteria resistant to existing beta-lactams and for screening peptide libraries of analogues of known anti-bacterial peptides such as the magainins.

Other methods can also be used to screen bead-based molecular libraries. Affinity adsorption techniques can be employed in conjunction with the libraries of the invention. For example, the mixture of beads can be exposed to a surface on which a receptor has been immobilized (see PCT patent publication No. 91107087, incorporated herein by reference). After washing the substrate to remove unbound beads, one can then elute beads bound to the surface using conditions that reduce the avidity of the oligomer/receptor interaction (low pH, acid treatment, or base treatment, for example). The process of affinity adsorption can be repeated with the eluted beads, if desirable. These methods, and related variants, such as the use of magnetic selection, described above, can be practiced in diverse ways; for instance the solid support can be a resin packed into a chromatographic column.

In another method of the invention, libraries of "tethered" compounds are used as a source of structural diversity in a form suitable for affinity purification of families of related molecules, such as families of receptors of pharmacologic interest. In general, this method relates to the use of a tagged and tethered molecular library to screen a second library of untagged molecules. The tagged, tethered library molecule serves as an affinity purification reagent to screen complex mixtures of soluble proteins, oligonucleotides, carbohydrates, antibodies, etc. Subsequent to affinity purification, molecules that bind to the combinatorial library members are identified by elution and appropriate separation and identification methods. The combinatorial library is then divided into smaller fractions of combinatorially synthesized compounds to determine, through repeated cycles as necessary, reductively and precisely which compound(s) mediate the binding process.

In similar fashion, combinatorial chemical libraries can be used to identify and clone novel receptors. Many receptors are members of families of proteins that share sequence homology (usually reflecting divergent evolution from an ancestral parent) but exhibit differences in their specificity/affinity for structurally related sets of ligands/cognate receptors. Each member of a receptor family ($R_n$) may represent a separate target for specific pharmacologic action and hence for drug discovery and development by virtue of their different properties, i.e., locations in the body, specificities, affinities for ligands, etc. If one identifies a receptor ($R_1$) whose binding properties are of sufficient interest so that the identification of other receptors in the same family would be beneficial, then one can employ the following method to identify receptors related to $R_1$ in their binding site properties. One first identifies a ligand that binds to $R_1$ and then creates a tagged combinatorial compound library of molecules closely related structurally to the ligand.

Next, one prepares polysome preparations from cells believed likely to express additional members of the receptor family. Such polysomes comprise ribosomes attached to mRNA with pendant receptor in various stages of protein synthesis from nascent peptide to almost fully elaborated protein. The receptor protein nearing completion of synthesis will express the specific receptor property of binding to one or more members of the combinatorial library. Using the combinatorial library tethered to solid support, affinity purification of polysomes bearing receptors with affinity for any member of the combinatorial library is performed. Such affinity purification may involve column chromatographic methods, batchwise separation of immobilized components from the liquid phase, or aqueous two phase separation methods to achieve separation of the solid phase bearing attached receptor and relevant mRNA encoding the receptor from non-adherent polysomes.

Next, one performs cDNA synthesis from the mRNAs that encode the cognate receptor population using standard technology (reverse transcriptase, etc.) and clones the cDNA population into a vector suitable for rapid sequence analysis. Dependent on prior knowledge of the receptor sequences that are likely and the degree of sequence conservation that can be anticipated, one may attempt to use PCR or another amplification to amplify the cDNAs enriched by this method. By sequence analysis of a suitable number of cDNA clones, one can identify cDNAs (whether full length or not) that show sufficient sequence homology with the sequence of the already known receptor $R_1$ to represent putative additional members of the same receptor family ($R_n$). One prepares optionally full length cDNA clones of these novel cDNAs (or relevant portions thereof, such as the portion encoding the extracellular domain of relevance to ligand binding) by standard cloning methods and expresses these cDNAs by standard methods (i.e., in eukaryotic expression systems as soluble or membrane bound proteins as appropriate). Using standard formats for testing receptor ligand interaction, one tests for binding of populations of mixed compounds from the combinatorial library or individual compounds. In this way, one can identify precisely which compound(s) from the library bind to the newly identified receptor.

Individual beads can be physically separated, for example, by limited dilution or by methods similar to those in which cells are incubated with a receptor coupled to small superparamagnetic beads and then cells expressing a ligand for the receptor are extracted using a high power magnet (see Miltenyi et al., 1990, *Cytometry* 11: 231–238 incorporated herein by reference). As noted above, magnetically selected cells can be further analyzed and sorted using FACS. Radionucleotides may also serve to label a receptor, allowing one to identify and isolate beads by selecting beads that are radioactively labeled.

B. Screening Soluble Molecules

One can also employ tagged molecular libraries to useful effect in novel assays of the invention in which a ligand is solubilized in either tagged or untagged form prior to binding to a receptor of interest. For screening very large libraries of soluble (bead-free) tagged molecules, one preferably employs affinity chromatography under conditions of weak affinity. For example, a 30 mg library of $10^{18}$ molecules can be screened with a simple 10 mL affinity chromatography column containing a few hundred μg of a receptor of interest. Oligonucleotides are preferred tags for such libraries, being readily PCR amplified and cloned into the commercially available TA cloning vector (Invitrogen, Inc.), a convenient form for storing tag information prior to analysis by DNA sequencing. In addition, oligonucleotide tags can be concatenated, as described above, allowing one to collect pools of soluble tagged molecules, clone the concatenated tags from the selected pools, and then sequence the tags to identify the desired compounds.

Soluble tagged molecules can also be screened using an immobilized receptor. After contacting the tagged molecules with the immobilized receptor and washing away non-specifically bound molecules, bound, tagged molecules are released from the receptor by any of a wide variety of methods. The tags are optionally amplified and then examined and decoded to identify the structure of the molecules that bind specifically to the receptor. A tagged oligomer in solution can be assayed using a receptor immobilized by attachment to a bead, for example, by a competition assay with a fluorescently labeled ligand. One may recover the beads bearing immobilized receptors and sort the beads using FACS to identify positives (diminished fluorescence caused by the library molecule competing with the labeled ligand). The associated identifier tag is then amplified and decoded.

The soluble molecules of the library can be synthesized on beads and then cleaved prior to assay. In one embodiment, the microscopic beads of a molecular library are placed in very small individual compartments or wells that have been "nanofabricated" in a silicon or other suitable surface. Beads are loaded in the wells by dispersing them in a volume of loading buffer sufficient to produce an average of one bead per well. In one embodiment, the solution of beads is placed in a reservoir above the wells, and the beads are allowed to settle into the wells. Cleavage of the oligomers from the beads may be accomplished using chemical or thermal systems, but a photocleavable system is preferred. The molecules of interest can be cleaved from the beads to produce either untagged molecules in solution (the tag remaining attached to the bead) or tagged molecules in solution. In either event, the molecules of interest are cleaved from the beads but remain contained within the compartment along with the bead and the identifier tag(s).

In one embodiment, a surface or a portion of the surface of the well is coated with a receptor. Binding buffer and a fluorescently labeled known ligand for the receptor is added to the well to provide a solution phase competition assay for ligands specific for the receptor. The binding of the fluorescently labeled ligand to the receptor can in one embodiment be estimated by confocal imaging of the monolayer of immobilized receptor. Wells with decreased fluorescence on the receptor surface indicate that the released ligand competes with the labeled ligand. The beads or the tags in wells showing competition are examined to reveal the identity of the competitive ligand.

Recovery of identifier-tagged beads from positive wells may optionally be effectuated by a micromanipulator to pluck individual beads out of wells. Another mode involves the use of beads that have incorporated a fluorescent molecule, either during bead manufacture or through labeling. A laser of the appropriate wavelength is used to bleach the resident beads in only the positive wells. All the beads are then removed en masse and sorted by FACS to identify the bleached positives. The associated tags may then be amplified and decoded to identify the molecules that bind specifically to the receptor.

In alternative aspects, the present invention provides methods for screening soluble library molecules from individual beads, without the need for mechanical separation and actual isolation of the individual library beads. In a first example, the target molecule, e.g., the receptor, enzyme, antibody, or the like, is attached to the same solid support as the molecules of the library. That is, the target molecules are attached to the library beads along with the library compounds. The library compounds bound to the individual beads may then be released by cleavage of the linker group, e.g., photolysis of a photocleavable linker or chemical cleavage. The release of the library compounds from the bead will create a "zone" of that compound in the immediate vicinity of the bead. The beads are then suspended in a solution which contains a ligand of the target molecule. Active compounds, e.g., compounds which bind the target molecule, receptor, enzyme, or antibody which is also bound to the same bead, will compete for binding with the fluorescently labeled ligand. Those of skill in the art will appreciate that the release of the library molecules and the contacting with the target ligand, may be carried out in either order. The result of this competition will be beads which are lower in fluorescence, or "dark" beads, than those which are exposed to inert compounds. The darker beads may be selected by FACS sorting methods, and the tagging groups on the beads may be decoded, as described herein.

A variety of modifications of this method may also be practiced. For example, the target molecule may be either directly attached to the library bead, or, alternatively, may be attached to a separate bead which is, in turn, attached to the library bead. Screening of the library compounds is then carried out as above. In some embodiments, it may often be desirable to provide the target molecule expressed upon the surface of a cell as described for the general screening methods, above, e.g., to more closely approximate physiological conditions of receptor/ligand interaction. For example, certain receptors, e.g., the multi-transmembrane receptors linked to G-proteins, and the many ion-channel families of receptors, often recognize small molecules that bind in deep pores formed by these transmembrane domains. Accordingly, these receptors may be particularly suited as targets for screening soluble small molecule libraries. Again, these bead-bound cells are suspended in a solution which contains a detectable ligand to the receptor, e.g., a fluorescent ligand. Upon release from the library beads, competition by effective receptor binding library molecules will result in beads/cells that are lower in fluorescence, and thereby separable by FACS techniques already described. These cell-based screening methods can also be particularly useful in screening library molecules for intracellular activity. Those of skill will appreciate based upon the instant discussion, that libraries may be screened for agonistic as well as antagonistic effects on target/ligand interaction. By changing the selection conditions, i.e. to select for beads/cells having higher fluorescence, or "bright" beads, as compared to a control, one can select compounds which may have a positive effect on target/ligand interaction.

In another aspect, the screening methods described herein may employ the target molecule expressed upon the surface of a "reporter" cell, which cell will produce a detectable response upon receptor/ligand binding. A variety of reporter cell systems may be used in the screening methods described herein. Typically, any suitable detectable reporter gene whose expression may be assayed can, if desired, be used for constructing the reporter cells of the present invention. Examples of readily detectable reporter gene products include, e.g., the green fluorescent protein (GFP), β-galactosidase, luciferase, and the like. The reporter system may also result in the expression of a binding protein upon the reporter cell surface, thereby providing an affinity ligand for isolation of the cell and attached bead. Similarly, the reporter cell may separate from the library bead, and receptor ligand interaction may result in the expression of a bivalent binding protein, having one complement on the surface of the library bead. Thus, activation of the reporter system will result in the expression of the binding protein, and consequent binding of the cell to the bead. The second binding aspect of the reporter protein may then supply the basis for selecting the active bead/cell complexes.

Alternatively, the receptor ligand/interaction may result in the expression of a protein necessary for producing a chemotactic response by the reporter cell in response to an externally supplied attractant, or away from a repellant. Specific chemotactic proteins will vary depending upon the reporter cell used. Examples of chemotactic proteins include, for example, flagellar proteins, e.g., flagellin, basal structure proteins, and the like. The chemotaxis of the reporter cells and attached beads, as a result of activation of the reporter system would greatly enrich for library beads possessing active compounds. Similarly, the reporter system may encode for a protein which blocks chemotaxis upon receptor/ligand binding. These methods could be readily applied in screening for agonists or antagonists of the particular receptor using methods known to those of skill in the art.

Release of active library compounds will create a zone of higher library molecule concentration surrounding the bead and reporter cell. Active library molecules, e.g., those capable of binding he receptor of interest, will result in the expression of the detectable gene product, or other cellular response, by the reporter cell. The reporter cells and associated beads may then be selected based upon their response, e.g., fluorescence, movement toward an attractant, etc. Reporter systems will generally be constructed to respond generically to activation of the transfected receptor system (target/ligand binding), e.g., G-protein linked receptors in CHO cells. However, differentiated cells having intrinsic response pathways for the receptor of interest may also be used.

Attachment of reporter cells or target molecule beads to the library beads may be carried out by a variety of methods, including, e.g., adsorption or covalent binding of antibodies upon the surface of the library beads, which antibodies recognize and tightly bind a structure on the surface of the reporter cell or target molecule bead. The structure on the surface of the reporter cell may be either naturally, or recombinantly expressed by the reporter cell. In the case of a target molecule bead, the binding epitope may be adsorbed or covalently attached to the target molecule bead, by methods known in the art.

In the above described methods for screening libraries of soluble molecules, release of the library compound from the bead will generally result in a high concentration of the library compound in the immediate vicinity of the bead. However, it may often be desirable to physically isolate small groups or even individual library beads for screening, to avoid excess diffusion of the library molecule after release from the bead, or to eliminate any washing of the library compound from the vicinity of the bead by convective effects. Methods for such isolation include, e.g., the use of "nanofabricated" microtiter plates, and other methods described previously, herein. However, it may often be desirable to avoid the micromanipulation which may be associated with the separation and screening of individual beads. In particular, such methods may be limited in their ability to screen very large libraries, due to their ability to only screen a limited number of beads at a time. Limitations on the ability to sort and isolate individual beads may in some applications, effectively place commercial limitations on the ability to screen very large libraries. Therefore, in an alternate aspect, the library beads (and in some cases, the associated cells or target beads) can be encapsulated in a permeable microcapsule to reduce potential convective forces which may disturb the concentration of the library compound around the library bead. Preferred encapsulation compositions result in reduced convective forces without overly restricting diffusion of the library compound upon release from the bead. As a result, upon release from the library bead, the library molecules will maintain a zone of higher concentration in the immediate vicinity of the bead, without being washed away by convective forces associated with the screening methods. Examples of useful encapsulation compositions and methods for preparing them, include those well known in the art, i.e., agarose or calcium alginate encapsulation methods and compositions. While these encapsulation compositions will generally not inhibit the diffusion rate of small molecules, it will generally prevent convective effects which can perturb the layer of library compound which diffuses from the beads upon release. Further, these encapsulated beads may also comprise indicators of library molecule/target molecule interaction. For example, pH indicators which will indicate pH effects of binding may be incorporated into the encapsulated composition whereby slight pH changes resulting from binding can be detected. See Weaver, et al., *Bio/Technology* (1988) 6:1084–1089. Methods for encapsulating particles in gel capsules are well known in the art, and are readily applicable here. See, e.g., Weaver, et al., supra, and M. F. A. Goosen, *Fundamentals of Animal Cell Encapsulation and Immobilization*, Ch. 6, pp 114–142 (CRC Press, 1993).

Alternatively, thin layer gel methods, as described above for cell based screening methods may also be used for screening the effects of soluble molecules upon a target molecule. In particular library beads may be spread over a surface or thin layer of immobilized target molecules. The target molecules are then exposed to a known ligand of the target molecule, e.g., a fluorescently labeled ligand. Library molecules which possess the desired activity, i.e., the ability to compete with the fluorescent ligand for binding to the target molecule, are collected, and their tagging groups are decoded to yield the structure of the effective library molecule. The surface of target molecules may comprise target molecules immobilized upon a surface, e.g., nitrocellulose or a PVDF membrane, or alternatively, it may comprise a thin layer of gel, e.g., agarose, polyacrylamide, or the like, which has incorporated therein an amount of target molecule, or which simply overlays the target molecule immobilized upon the membrane. The library beads are then spread or spotted upon the surface or thin layer, followed by release of the library compounds from the beads. The surface is then contacted with a solution containing a fluorescent ligand for the target molecule. In some aspects, the contacting of the surface with the fluorescent ligand will be carried out by methods which avoid disturbing the localization of the individual beads, thus allowing later collecting and decoding. For membrane immobilized target proteins, this can involve introduction of the fluorescent ligand from the side of the membrane opposite to the beads. A similar approach can also be used for gel suspended target molecules, or membranes which are overlaid with a gel layer. However, beads may also be embedded in the gel surface to prevent their migration during the screening process by, for example, lightly heating the gel over which the beads are spread, prior to the introduction of the fluorescent ligand.

In a specific example, the screening methods described herein, can be used to screen libraries for selective inhibitors of human IMP type II dehydrogenase. Human IMP dehydrogenase is a target for anticancer, antiviral, antiparasitic and immunosuppressive therapies. See Natsumeda and Carr, *Ann. N.Y. Acad. Sci.* (1993) 696:88–93. This enzyme catalyzes oxidation of IMP to XMP, a step necessary for the de novo synthesis of GTP. It occurs in two isoforms, types I and II, which are 84% identical at the amino acid level. The type II enzyme is the most promising chemotherapeutic target, as it is induced in neoplastic and replicating cells. However, the type I enzyme is constitutively expressed in many cells. A selective inhibitor of the type II enzyme would be expected to have reduced side effects over a non-selective inhibitor, due to the reduced inhibition of the type I enzyme. The present invention provides methods for screening libraries for compounds which selectively inhibit only the type-II enzyme.

In *E. coli,* IMP dehydrogenase is encoded by the guaB gene. Knockout mutations in the guab gene lead to a requirement for guanine in the growth medium of these cells. Expression in *E. coli,* of either human type I or type II IMP dehydrogenase can complement this mutation, allowing growth on medium lacking guanine. See Carr, et al., *J. Biol. Chem* (1993) 268:27286–27290. Inhibitors of the IMP dehydrogenase enzymes would prevent the growth of cells carrying a sensitive enzyme, growing on guanine deficient medium. To assay for selective inhibitors of one of the enzyme types, a mixture two strains of guanine deficient cells is constructed, where one strain expresses he human type I enzyme and the other expresses the human type II enzyme. Selective inhibition of one of the enzyme types will result in inhibited growth of the cell type which expresses only that enzyme type. The screening method comprises mixing the two types of cells together, and contacting the cells with the library beads described herein. The library compounds are released from the beads, and inhibition of growth of one or the other cell type can be detected. In particular, the beads and cell mixture may be suspended in, e.g., minimal medium agar lacking guanine, and the library compounds may be released. When the lawn of cells grows, those beads bearing library compounds which are selective inhibitors will inhibit the growth of only one cell type. The different cell types may be engineered with additional markers which allow detection by simple methods, e.g., color indicators of cell type. Once a region possessing effective inhibitors of the desired enzyme type have been identified, the bead or beads within that region may be collected, and decoded to elucidate the structure of the effective compound.

In another embodiment of the invention, one employs relatively large tagged beads, from which the molecules of interest are cleaved in a series of reactions. In this method, the beads are 50 to 500 $\mu$m in diameter, with capacities equivalent to 100 to 500 pmol of peptide per bead; preferably, one uses 100 $\mu$m beads with a capacity of about 200 pmol, if constructing a peptide library. The typical size of such a library is from about $10^6$ to $10^8$, preferably $10^7$ different molecules. The library is divided into about 100 pools, each containing about 100,000 beads. A certain percentage, about 25%, of the molecule of interest is cleaved from the pool, producing, in the case of a peptide library, for example, each peptide at 50 nM in a volume of 1 mL.

The cleaved pool is then tested in a competition or functional assay. One identifies the pools with the highest activity, and then retrieves the remainder of the original pool and aliquots the remainder into 100 pools of 1000 beads per pool. The process is repeated until one has a single bead, from which one reads the tag and identifies the compound of interest. This method avoids the resynthesis and frame limitations of the Houghten method and is advantageous in that the pools are random, rather than related, compounds. The chances of a mixture being active because of the cumulative potency of many low affinity related molecules is reduced.

C. Screening Natural Product Libraries

With the automated high flux assays that are now available, the present limitations in natural product screening are first, the ability to obtain and handle (dispense, dissolve, label, etc.) the samples; and second, the substantial effort required to characterize the active components of positive samples. The present invention provides methods for generating and screening natural product libraries that can provide a huge number of samples in readily screened form and to identify active components in the samples. The basis of the method is the combination of biochemical and chemical diversity with metabolic diversity from "natural products", i.e., from nature. The simplest example involves feeding collections of peptides to cultures of microorganisms. Each microbial strain might create many modified peptides (a metabolite library). Because each culture would (potentially) contain a very complex mixture of metabolites, an efficient method of screening is required.

Several approaches are available and might be orthogonally classified as factored or tagged, and soluble or tethered. For the sake of illustration, consider as the "feedstock" a library of soluble peptides. An aliquot of the library is incubated with each of the many strains typical of a microorganism fermentation screening program, and the media screened in typical fashion. Positive cultures are then incubated with subsets of the libraries and rescreened. This process of factoring continues until the input_peptides generating the most active metabolites are identified. The characterization of the active metabolites then proceeds aided by the knowledge of the likely precursor molecules. Thus, the first screening identifies the active organism(s), subsequent steps identify the active precursors, and finally, the active metabolites are identified by standard analytical means.

In all its formats, however, factoring is a tedious process. Libraries produced by split synthesis and cleaved free of the resin produce soluble compounds amenable to cellular uptake and metabolism by intact organisms. However, the concentrations of the individual compounds is quite low (inversely related to the diversity of the collection), leading to inefficient enzymatic turnover and very low concentrations of the resulting metabolites. The concentrations of the compounds may be increased by producing subsets of the libraries and fermenting each subset separately with each microbial isolate. Sub-libraries are constructed by fixing one or more of the positions and randomizing the remaining positions. For example, there are 500 pentapeptide sublibraries containing all permutations of 2 fixed positions utilizing 50 building blocks. Each of these sublibraries contains 125,000 compounds. The use of tagged libraries offers a major advantage in ease and sensitivity, but requires modifications in the method of exposing the compound collections to the metabolic activities. The combinatorial feedstock need not be only peptides but could consist of any type of combinatorial chemical collections.

Oligomer and other molecular libraries can be constructed in a combinatorial process and each step encoded with identifying tags. This may be done via a direct linkage and parallel synthesis of the oligomer to the tag. If oligonucleotides are used as the tags, then the complexes will be relatively large but small enough to insert actively into the cells via liposome fusion, electroporation, solvent permeabilization, etc,. Once inside, the complexes would be subject to the metabolic machinery of the cells. One would avoid the vulnerability of the oligonucleotide tags to degradation by the use of modified nucleotides and nucleotide linkages. Upon recovery of the active metabolites from the culture of from lysed cells, the samples are screened and the tags decoded to reveal the precursor compound. Scaled-up fermentation of the active organism with the active precursors should produce sufficient quantities of the active metabolites to characterize. Libraries of compounds made by an encoded combinatorial process on beads can be exposed to lysates of bacteria, fungi, plant cells, etc. With this format, the need to insert the tagged complexes into intact cells is avoided, and only a relatively few of the many molecule on the bead need be processed to be detected (e.g., in a fluorescence-activated binding assay).

Another useful method of the invention involves the utilization of the products of one microbial culture as feed for another culture. To illustrate, consider a collection of 100 different microbial isolates from large scale cultures (~1 liter). The supernatant of each culture is recovered by filtration and divided into one hundred 10 mL aliquots. Each aliquot is inoculated with one of the 100 strains and incubated. 10,000 samples (metabolites of metabolites) are thereby generated from the 100 microbial isolates. This method of combinatorial metabolism can be extended to sequential metabolism by greatly different species: subjecting the product of microbial fermentation to incubation with exotic plant lysates or incubating extracted fractions of plant tissues with fungal cultures, for example. These methods can be used in combination; any product of a chemical diversity generating method can be subjected to these sequential metabolism product exposure steps.

In another aspect of the invention, natural product diversity is screened by creating a mixture of combinatorially-tagged liposomes, each liposome preferably encapsulating only one member or a simple mixture of a natural product compound library. The invention allows for the simultaneous assay of 1000's–10,000's of chemical compounds or natural product extracts and assay of 100's of chromatographically separated fractions derived from natural product extracts that are signal-positive. In this connection, "simultaneous" means assayed together in the same tube with the cells of the readout system.

The mixture of combinatorially tagged liposomes is prepared as follows. For each individual natural product extract or chemical from an inventory, one prepares separate liposomes encapsulating the test substance in aqueous phase. A unique liposome tag is incorporated into the liposome preparation at the time of encapsulation. The liposomes can be lyophilized for long-term storage at low-temperature, a significant advantage to the collection and storage of natural product samples near the site of collection, as well as for the long term storage of the natural product extract in a form suitable for subsequent combinatorial experimentation. The lipids in the liposome preparations are preferably identical for all samples and chosen in terms of types and composition to produce unilamellar liposomes of the desired size and integrity. Agents such as trehalose can be included at the time of liposome formation to allow lyophilization and subsequent reconstitution of intact liposomes by addition of water. At the time of generation/regeneration of tagged liposomes encapsulating the extract/chemical, one can also use a high pressure technique that allows for the encapsulation of greater volume of aqueous phase than the calculated volume enclosed by the liposome. A 3–5 fold increase in volume-equivalent can be encapsulated by this pressure method, allowing greater volume of test material to be tested, hence greater signal in the cell-based readout.

Existing liposome technology allows for creation of liposomes that incorporate a high percentage (>80%) of the aqueous phase (relevant to the efficiency of use of each test substance). Unincorporated aqueous phase can be removed by diverse "wash" methods. In addition, one can create liposomes that do not leak or exchange encapsulated aqueous phase (relevant to the specificity of tagging and absence of mixing enclosed aqueous phases), as well as liposomes that do not exchange components inserted into their lipid monolayer (glycolipid/protein antigens inserted as tags cannot be exchanged).

A wide variety of tags can be employed with the method. For example, the tags can be: (a) different fluorophores with excitation and emission properties that allow the fluorophores of each to be measured in the presence of each of the others, or combinations thereof—the fluorophores can be selected to partition in the encapsulated aqueous phase or in the membrane phase of the reconstituted liposomes, facing outwards; (b) different metal cations of rare earth elements that can be distinguished individually by atomic absorption spectrometry—the rare metal atoms would be designed to partition as salts in the encapsulated aqueous phase of the reconstituted liposomes; (c) different antigens, that can be distinguished by their specific reactions with appropriate monoclonal antibodies and primary/secondary florescent detecting antibodies/fluorophores, as necessary—the antigens, borne on proteins, glycoproteins and/or glycolipids, can be selected to partition in the membrane phase of the reconstituted liposomes, facing outwards; and (d) combinations of antigens, fluorophores, and/or metal ions can greatly increase the number of possible signatures for simultaneous screening, and an additional level of tagging of different liposomes (increased numbers) can result from use of different levels of fluorophores/metal ions/antigens, such that the different "quanta" of each component in the signature mixture could be identified.

One can also employ a general fluorescent tag that shared by all liposomes that enables rapid selection of cells fused with a liposome from those that did not fuse with a liposome. This tag is distinct from any tags used in combinatorial labelling of the individual liposome preparations and is mixed in with the liposome-generating lipids, the signature tags, and the aqueous sample of drug/natural product at the time of liposome generation. One can also employ a fluorescent tag that is self-quenched at high density (i.e., in the liposome membrane) but that will exhibit fluorescence in the outer cell membrane of a cell after a liposome fusion event and lateral diffusion of the fluorophore in the cell membrane. Depending on the mode of liposome fusion with cells, one can also incorporate a fusogenic protein of viral origin, or a glycolipid, for example, that will mediate tight adhesion of liposome to cell (dependent on a lectin like adhesion process mediated by a suitable receptor incorporated as necessary into the cell line used for read out). Such an element would not affect liposome-liposome interaction (an event to be avoided) but can enhance the efficiency of liposome-cell fusion.

The method can employ a cell read-out system that utilizes a cell line that contains a reporter gene (e.g., luciferase, beta-galactosidase) downstream of a promoter that is activated in response to addition of an exogenous hormone or ligand, such as a steroid, cytokine, prostaglandin, antibody, antigen, etc. to the cells. Binding of the activating ligand to either a cell surface receptor or an intracellular receptor activates a signal cascade that leads ultimately to activation of the responsive promoter and transcription of the signal gene. Expression of the signal protein leads to generation of a signal from the individual activated cell that can be detected quantitatively. In a search for compounds that act on any part of the intracellular signal transduction cascade as antagonists, the entire population of cells can be pretreated by addition of the exogenous signal agonist (cytokine, hormone, etc.), and one measures a decrease in signal output on an individual cell basis after the liposome fusion event. In a search for compounds that act on any part of the intracellular signal transduction cascade as agonists, no exogenous signal need be added to the cells, and one can measure the appearance of a signal on an individual cell basis after the liposome fusion event.

The mixture of tagged liposomes is mixed with a very large number excess of read-out cells. Cell number excess is critical such that after liposome-cell fusion only the following products will result: (i) cells that did not fuse with a liposome; and (ii) cells that fused with one liposome (acceptor cells). Efficient mixing is essential at this step and can be performed using a continuously stirred or linear-flow cell suspension to which the liposome mixture is added at a slow rate. Fusion is initiated by standard methods such as addition of PEG or application of a high voltage. Fusion may be enhanced if necessary by inclusion of a fusogen or a ligand-receptor recognition pair into the cell-liposome membranes. The fusion step effectively adds the aqueous phase compartment of a single liposome to an acceptor cell. Hence, the aqueous natural product extract, test compound from a chemical inventory, or fraction from chromatographic separation of a natural product extract is now able to act at any point in the intracellular signal transduction pathway. The fusion step also adds the specific tags that provide the signature of the particular test compound sample to the individual acceptor cell. If those tags were in the lipid membrane of the liposome, then the tags are distributed in the outer cell membrane of the acceptor cell. Antigens at this location are accessible to panels of specific monoclonal antibodies. Rare earth metal ions that were in the aqueous phase of the particular liposome are in the acceptor cell cytoplasm. The fusion step also adds the shared liposome tag that identifies cells that acted as acceptors from those, the excess, that did not undergo a liposome fusion event. The tag can be a fluorophore that moves from the liposome membrane to the acceptor cell membrane.

The mixture of cells, cells fused to individual liposomes, and any unfused liposomes is next incubated with the exogenous ligand (e.g., in the case of testing for an antagonist) or incubated without any addition (e.g., in the case of testing for an agonist). The time of this incubation is determined using control compounds at defined concentrations and incubation times.

Preferably, one uses FACS to select compounds (cells) of interest. For instance, one can first use forward or side light scatter to sort cells (whether acceptors or not) from any unfused liposomes. Large cells can be readily separated from small liposomes. Next, one can sort cells that were liposome acceptors from those, the excess, that were not liposome acceptors. Cells that were acceptors bear the shared liposome-derived fluorescent label, whereas the non-acceptor cells are non-fluorescent with L this label. This step is of course optional but, if performed as a presort, allows separation of the (typically) majority of cells that are irrelevant to subsequent analysis from the minority that were acceptors. For identification of an antagonist, one can sort on the basis of light emission from the reporter protein (e.g., beta-galactosidase or luciferase), separating the majority of fluorescence-positive cells (rendered such by addition of the exogenous ligand earlier), from the minority of fluorescence-negative cells or low fluorescence cells. The latter two cell categories result from presumed antagonist effects of compounds that were encapsulated in the particular liposomes that fused with these individual cells. For identification of an agonist, one can sort on the basis of light emission from the reporter protein, separating the majority of fluorescence-negative cells from the minority of fluorescence-positive cells. The latter cells have resulted from a presumed agonist effect of liposome-derived compounds.

In some experiments, one can sort all cells of interest according to the criteria above as a population and collect occasional cells as cloned individuals using standard FACS methods. These individual cells can be analyzed as single cells for the particular tags that they bear, allowing precise identification of the particular liposome that mediated the desired effect. In other applications, one can analyze the tag distribution in the entire sorted event-positive population and dependent on the design of the experiment and particular tags that had been incorporated in samples from different times/locations/inventories, be able in a first pass to determine the diversity of tag types in the total event-positive population.

Collected single cells or populations of cells can be analyzed by methods appropriate to the particular tag combinations used. Fluorescence tags can be analyzed by FACS and/or traditional spectrophotometry. Antigen tags can be analyzed by addition of appropriately labeled monoclonal antibodies and ELISA, FACS, radioisotopic, or luminescence assisted assays. Metal ion tags can be analyzed last by atomic absorption spectrometry. After tag decoding, the tests can be repeated either with mixtures of only those liposomes that yielded a positive event on first pass or with pure liposomes of each member of interest added to separate cell samples.

These and other methods of the invention can be automated to facilitate practice of the invention, as discussed in the following section.

VII. Instrumentation

The coupling steps for some of the monomer sets (amino acids, for example) can in some embodiments require a relatively lengthy incubation time, and for this and other reasons a system for performing many monomer additions in parallel is desirable. The present invention relates to automated instrumentation for use in generating and screening encoded synthetic molecular libraries. One preferred instrument, able to perform 50 to 100 or more parallel reactions simultaneously, is described in U.S. patent application Ser. No. 081149,675, filed Nov. 2, 1993, incorporated herein by reference. Such an instrument is capable of distributing the reaction mixture or slurry of synthesis solid supports, under programmable control, to the various channels for pooling, mixing, and redistribution.

In general, however, the instrumentation for generating synthetic libraries of tagged molecules requires plumbing typical of peptide synthesizers, together with a large number of reservoirs for the diversity of monomers and the number of tags employed and the number of simultaneous coupling reactions desired. The tag dispensing capability translates simple instructions into the proper mixture of tags and dispenses that mixture. Monomer building blocks are dispensed, as desired, as specified mixtures. Reaction agitation, temperature, and time controls are provided. An appropriately designed instrument also serves as a multichannel peptide synthesizer capable of producing 1 to 50 mgs (crude) of up to 100 specific peptides for assay purposes. See also PCT patent publication 91/17823, incorporated herein by reference.

Typical instrumentation comprises (1) means for storing, mixing, and delivering synthesis reagents, such as peptide and oligonucleotide synthesis reagents; (2) a sealed chamber into which the various reagents are delivered and inside of which the various reactions can proceed under an inert atmosphere; (3) a matrix of sealed reaction vessels; (4) means for directing the flow of reagents to the appropriate reaction vessels: (5) means for combining and partitioning small (0.1–100 $\mu$m) beads; and (6) means for washing the beads in each reaction vessel at the conclusion of each chemical reaction. The matrix of reaction vessels can have any one of several designs. For example, the vessels can be arranged in a circle so that the vessels can be made to rotate about a central axis (i.e., a centrifuge). Alternatively the vessels can be arranged in a 12×8 matrix (96-well microtiter plate format). Any arrangement amenable to accessibility by robotic delivery, aspiration, and transfer functions is useful for some applications.

The system used for combining and redistributing particles can have one of several designs. For instance, the beads can be suspended in a solvent of appropriate surface tension and density such that a robotic pipetting instrument can be used to transfer the beads to a combining vessel. After mixing, the beads can be redistributed to the reaction vessels by the same robotic pipettor. Alternatively, the beads can be combined by using a special valved reaction chamber. The valve is opened to allow solvent flow to transfer the beads to a combining vessel. After mixing, the beads are repartitioned by reversing the flow to each reaction vessel.

In another embodiment, the beads are combined using closely spaced reaction vessels with open top ends. Flooding the vessels allows the beads to mix. If the beads are magnetic, then the beads are re-partitioned by pulling the beads back down to the bottom of the vessels by application of a magnetic field. Non-magnetic beads are re-partitioned by vacuum suction through the bottom of the reaction vessels. In yet another embodiment, the beads are partitioned by distributing them on a flat surface and then restricting them to certain sectors by covering them with a "cookie-cutter" shaped device, described more fully below.

The system for washing the beads can also have one of several designs. The beads can be washed by a combination of liquid delivery and aspiration tubing. Each reaction vessel has its own set of tubing, or a single set can be used for all reaction vessels. In the latter case, the liquid delivery and aspiration lines can be mounted on a robotic arm to address each vessel individually. The beads in each vessel can be made to form a single pellet by either centrifugation or the use of magnetic beads and application of a magnetic field. One can also employ a reaction vessel with a bottom wall composed of a chemically inert membrane so that reagents can be removed from the vessels by application of a vacuum. Reagents can also be removed from each vessel by using vessels that can accommodate continuous flow through of reagents and washing solutions, i.e., a vessel with luer fittings and membranes on each end.

Any automated combinatorial instrument that relies on an individual reaction chambers, each connected to reagent delivery systems and to a "mother pot" to which the beads are pumped for pooling and from which the beads are reallocated among the reaction chambers for successive rounds of monomer addition faces a very important practical limitation. There is a wealth of monomer or other building block units, and the difficulty of partitioning beads and reagents among the potentially large number of reactions may limit such instruments to fewer than 100 separate parallel reactions.

The present invention provides an instrument that avoids the need to pump beads between chambers to mix and reallocate, simplifies reagent delivery, and allows the simple and accurate partitioning of very small numbers of tiny beads. The basic design consists of a plate with an array of reaction "sites" located on the surface; the surface may be planar or may consist of an array of shallow wells that form reaction sites. In one embodiment, there are 256 sites in a 16×16 array. Each reaction site is a spot, or well, on the surface to which a group of synthesis beads is attracted. The attractive force may be magnetism, vacuum filtration, gravity with passive mechanical sorting, or various other simple means. The beads are initially applied as a dilute slurry in a shallow reservoir evenly covering the array of reaction sites. Upon application of the attractive force, beads are concentrated at each site.

Figure 29:
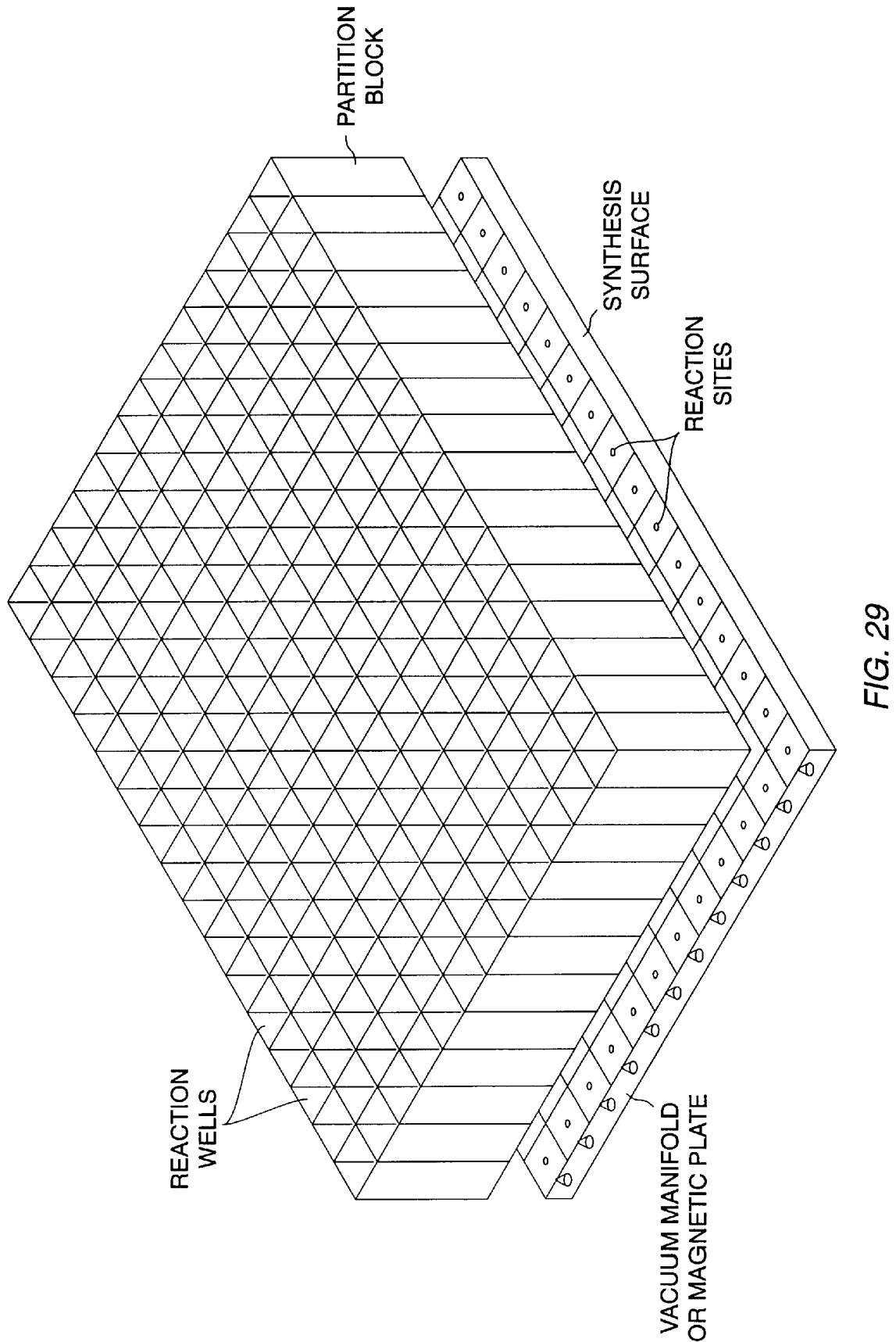
FIG. 29 shows a device for synthesizing combinatorial chemical libraries on microscopic beads. The device is composed of a vacuum manifold or magnetic plate attached to a solid substrate having a synthesis surface having an array of reaction sites at which compounds can be synthesized. The partition block is composed of an array of reaction wells corresponding to said reaction sites and is used to partition library members after each mixing step. The device can also be used to aid the synthesis of tagged chemical libraries.

After positioning all the beads on the reaction sites, the sites are then separated by mechanical partitions to create (temporarily) the individual reaction chambers as shown in FIG. 29. A variation provides partitions permanently affixed to the surface to form shallow wells. The reaction components are delivered to each chamber, the beads released into suspension, and the reaction initiated. When desired, the beads can be reattached to the surface and the reagents removed. After all steps for a coupling cycle are completed, the chamber partitions are removed, and the beads are released into the common reservoir above the array of sites.

Mixing of the beads is caused by induced convection of the reservoir fluid, and the beads are then reattracted to the surface sites for the next round of coupling. Subsequent steps, including the wash steps, are accomplished in a similar fashion. Addition and removal of reagents is done with a combination of plumbing and automated pipetting. Addition of reaction specific reagents (monomers, for example) may be done with robotic multipipettors. Addition of common reagents and the removal of all reagents can be done with a fixed plumbing system not requiring valving at each reaction chamber. Some common steps such as washes can be done on the beads en masse, before installing or after removing the chamber partitions.

The use of large numbers of monomers or other building blocks places an additional burden on the encoding process. In one encoding scheme for oligonucleotide tags, a basis set of 1000 monomers might require a 5 base sequence to tag each reaction step; a set of more than 1024 monomers could require 6 bases to encode. To reduce the plumbing complexity of the synthesis instrument (i.e., to reduce the number of specific reaction additions), a special encoding strategy is provided by the present invention. To illustrate the method, consider an array of 16×16 reaction sites, an arrangement that allows 256 different reactions to be carried out simultaneously. To encode each reaction individually with multiple base coupling is a difficult undertaking.

The array consists of 16 rows and 16 columns, each site in the array having a unique geographical address. Each row of sites can be tagged as a group, and all 16 rows can be uniquely encoded with 2 base codons ("subcodons"). A striped template or channel block can serve to form the 16 reaction chambers for these 2-base additions (note that the bases are coupled as monomeric phosphoramidites, not as dimers). See PCT patent publication No. WO 93/09668, incorporated herein by reference. This form of addressing of the reaction sites is analogous to others; for example, an optical method can be used to label the beads, as in the striped masking process described in U.S. Pat. No. 5,143,854, incorporated herein by reference. If a template or channel block is employed, then the template is lowered onto the synthesis surface just as is the grid template that isolates the individual reactions during synthesis of the library molecule.

The beads are not released during the tagging reaction, however, as their spatial segregation must be maintained through the next step. When the rows have been tagged with subcodons, the template is lifted, rotated 90°, and lowered to form stripes covering the columns. The 16 columns are then labeled with 2-base subcodons, resulting in the unique tagging of each of the 256 reaction addresses with a 4-base "supercodon". By identifying the reaction addresses, the supercodons also specify the monomer that was added in each reaction.

VIII. Apparatus for Parallel Coupling Synthesis Reactions

In general, the device of the present invention provides for the synthesis of diverse materials on a solid substrate. By way of example, the present invention utilizes beads such as those described herein. Examples of a the synthesis of diverse peptides are discussed below to provide a framework for the discussion of the synthesizer.

The invention will utilize a plurality of substrates, referred to as "S," on which synthesis reactions take place. The substrates are optionally provided with a linker molecule "L" on which coupling reactions take place. The substrates are divided and reacted with diverse monomers, such as "A" and "B" to form collections of, for example, the following substrates:

S-A and S-B

Thereafter, the substrates are recombined, mixed, and divided again. After such mixing and dividing steps, two or more collections of substrates are formed, each containing both S-A and S-B.

Additional coupling reactions then take place. For example, the pooled products above may be reacted with monomers C and D to form the following collections of products:

1. S-A-C S-A-D
2. S-B-C S-B-D

From even the above simple example it becomes apparent that such synthesis techniques rapidly create large collections of diverse products. By carefully planning the synthesis of such diverse collections of molecules and/or by providing for the parallel synthesis of tags on such substrates, the substrates will find use in a variety of applications, as described above. In a particular embodiment, the present invention provides devices and methods that may efficiently generate substrates for these and other uses.

A. General

FIG. 1 illustrates a device used to synthesize diverse collections of molecules. The device includes a parent mixing vessel 200 coupled to a plurality of reaction vessels 201–209 by a top common manifold 212 and tubes 215, and 221–229. Top common manifold 212 couples to tubes 221–229 and 215. Reaction vessels 201–209 also selectively couple to monomer addition reagent supply reservoirs 231–239 via valves 111–119 and tubes 241–299. A pressurized delivery system (PDS) 265 is coupled to both parent vessel 200 and reaction vessels 201–209 via tubes 260 and 256 respectively.

A synthesis reaction begins when a bead suspension is transferred from parent vessel 200 to reaction tubes 201–209. A valve 129 opens (all valves are closed as default), and the bead suspension enters top common manifold 212 from parent vessel 200 through tube 215. The bead suspension is thereafter distributed among reaction vessels 201–209 through tubes 221–229. Selected reagents from monomer reservoirs 231–239 then enter respective reaction vessels 201–209 through respective tubes 241–249. Coupling reactions then take place inside reaction vessels 201–209 on beads contained therein.

FIG. 1 shows pressurized delivery system 265 coupled to parent vessel 200 via a tube 260. Pressurized delivery system 265 delivers pressurized reagents to parent vessel 200 from delivery system 265 via tube 260 when valve 10 and vent valve 90 open.

Pressurized delivery system 265 is also coupled to reaction vessels 201–209 through a tube 256, an isolation valve 100, lower manifold valves 101–109, lower tubes 271–279, injection valves 111–119, and tubes 241–249. To deliver a reagent from PDS 265 to selected reaction vessels 201–209, the pressurized reagent enters tube 256 and a lower manifold 214 through open valve 100. Thereafter, the pressurized reagent is forced up selected tubes 271–279 through selected open valves 101–109. The pressurized reagent is then forced into selected reaction vessels 201–209 through selected tubes 241–249.

To deliver a reagent from, for example, a given monomer reservoir 231 to a respective reaction vessel 201, a quantity of pressurized activating solution from PDS 265 is forced into tube 256, into lower manifold 214, and up tube 271. At an appropriate moment, a quantity of monomer reagent from monomer reservoir 231 is injected into the stream of activating solution travelling up tube 271. Following the reagent injection, the stream of solution including the monomer reagent injected from reagent reservoir 231 enters reaction vessel 201 through a tube 241 to participate in the coupling reactions.

To optionally tag the beads inside selected reaction vessels 201–209 with a monomer from monomer reservoirs 406–412, a pressurized tag monomer reagent from monomer reservoirs 406–412 enters a common manifold 255 of PDS 265 through an open valve 4–7. Thereafter, the pressurized tag monomer and an appropriate activation reagent enter lower manifold 214 through open valve 100 and tube 256. The pressurized monomer tagging reagent and its appropriate activation reagent travel up selected tubes 271–279 and 241–249 through selected open valves 101–109 into selected reaction vessels 201–209 where the synthesis of tags on beads takes place.

After desired monomer and/or tag addition reactions, the bead suspension in reaction vessels 201–209 is transferred back to parent vessel 200 for pooling and mixing. To move the bead suspension from reaction vessels 201–209 to parent vessel 200, the bead suspension is pressurized with argon from tube 250 via open valve 122 and 101–109. Valves 100 and 110 are closed, thereby pushing the pressurized bead suspension into tubes 221–229, top common manifold 212, tube 215 through open valve 129, and finally parent vessel 200. In parent vessel 200, the bead suspension is mixed in preparation for re-allocation among reaction vessels 201–209 to further synthesize the desired set of molecules.

In an alternative embodiment, a plurality of three-way valves can be provided between each of the reaction vessels 201–209 and the parent vessel 200. Such valves will preferably be held in the top common manifold 212. In this way, certain vessels can be isolated from the parent vessel 200. This may be particularly advantageous when redistributing the bead suspension for further synthesis. For example, if the beads were initially allocated to all the reaction vessels 201–209 for synthesis and then returned to the parent vessel 200, during re-allocation only certain of the three-way valves could be opened so that, for instance, only reaction vessels 201, 205 and 209 received the bead suspension for further synthesis.

FIG. 1 also shows nonconcentric agitators 280 and 285 coupled to a top reaction vessel bracket 290 and a bottom reaction vessel bracket 295. Top reaction vessel bracket 290 is held stationary while bottom reaction vessel bracket 295 is permitted to follow the motion of nonconcentric agitators 280 and 285. Each nonconcentric agitator cooperates with a vortexing motor 300 to exert an agitation force on bottom vessel bracket 295 and the bottom end of reaction vessels 201–209. Since the tubes between the brackets are flexible, this agitation force causes the contents of each individual reaction vessel 201–209 to vortex inside the reaction vessel thereby enhancing synthesis reactions.

Top common manifold 212 connects to tube 215 at one end to provide a conduit for transferring material between parent vessel 200 and top common manifold 212. At the other end, top common manifold 212 connects to a tube 126. Tube 216 provides pressurized argon to top common manifold 212 through a valve 121. Tube 216 also allows top common manifold 212 to vent its contents through a valve 120.

Two capacitive sensors 90S and 99S are located near the exterior surface of parent vessel 200 to detect the level of liquid in parent vessel 200. If a fluid exists within the detection envelope of a capacitive sensor, that capacitive sensor is turned on. Conversely, the capacitive sensor is off if no fluid exists within the detection envelope.

Sensors 101S–119S are optical sensors for detecting the presence of a fluid within a substantially translucent tube. These optical sensors are on when a column of fluid is present in the tube. The optical sensors are off when no fluid is detected.

Likewise, an acoustic sensor 120S detects the presence of a fluid in its detection envelope. Fluid, including bead suspension, flowing through a tube which has been placed in the acoustic sensor's detection envelope turns acoustic sensor 120S on. Conversely, acoustic sensor 120S is off when no fluid is present in the tube which has been placed in the detection envelope of the sensors. Acoustic sensor is used for sensor 120S because optical sensors cannot reliably distinguish, under certain conditions, between an empty translucent teflon tube and a translucent teflon tube containing a bead suspension. Further, although an acoustic sensor is chosen for sensor 120S, any sensor which can distinguish the difference between an empty tube and a tube filled with either a fluid or a bead suspension may be used. Because acoustic sensors are fairly costly relative to other types of sensor such as optical sensors, there is only one acoustic sensor 120S per synthesizer.

The reaction vessel bank is designed such that there is only one or fewer valve between the parent vessel and the reaction vessels. In fact, valve 129 is optional. This design is advantageous because it reduces the possibility of the mechanical opening and closing action of valves damaging the fragile beads and the synthesized polymers. Also, if the size of the beads are large enough, they may become lodged in the valve and clog the system. Furthermore, some polymers are temperature sensitive and may be adversely affected by the heat generated by the valves during operation. Accordingly, it is desirable to reduce the number of valves through which the bead suspension must traverse. If valve 129 is not included, pressurization techniques can be used to prevent fluids from flowing between the parent vessel and the reaction vessel banks.

As discussed earlier, the valves used in this embodiment are closed in their default state. Absent a specific command to open, the valves always remain in this default closed state.

B. Mechanical Components

Mechanically speaking, the automated synthesizer may be roughly divided into three subsystems: the reaction vessel bank, the parent vessel, and the pressurized delivery system.

As mentioned above, coupling synthesis takes place at the reaction vessel bank inside the reaction vessels. The parent vessel holds, pools and mixes the beads from all reaction vessels. The delivery system ensures that the proper solvent and/or reagent solution in an appropriate reagent/solvent concentration is delivered to either the parent vessel or the reaction vessel bank at an appropriate step in the synthesis process. Furthermore, the entire system is sealed during operation. Pressurization, where necessary, is done with an inert gas such as argon. Argon is the preferred pressurizing agent because of its availability and low chemical reactivity.

For ease of discussion, the automated synthesizer will now be described with reference to a specific example. The specific example used throughout this disclosure involves the synthesis on beads of a set of polypeptides. The beads are tagged for identification following each amino acid coupling reaction with four nucleotide monomers: A, T, C, and G.

It must be recognized, however, that the automated synthesizer is neither limited to the synthesis of the particular polymer described in the above specific example nor to tagged polymer synthesis. Although reference will be made throughout this disclosure to the synthesis of polypeptides and the tagging of beads with the above nucleotides utilizing a reaction vessel bank having nine reaction vessels, there is no inherent upper or lower limit in the number of reaction vessels which may be included in each reaction vessel bank. In fact, modular construction of the device permits easy addition of additional reaction vessel banks. Further, many other molecules and tags may be synthesized on the beads, or the tags may be eliminated entirely.

1. The Pressurized Delivery System

The detailed description of a pressurized delivery system 265, which has been specifically tailored to synthesize the polypeptides according to the specific example, has been divided into three parts: reservoirs for use synthesizing polypeptides, reservoirs for use in tagging beads, and the delivery valves.

a. Reservoirs for use in synthesizing polypeptides

In addition to the nine amino acid monomers used to synthesize the peptides of the specific example, several other additional "common" reagents will be employed in the synthesis. In a typical peptide synthesis, for example, the following reagents may be employed:

TABLE 2

| Function | Chemical |
|---|---|
| Deprotection | 10% Piperidine in DMF |
| Activation | 0.2M HBTU and 0.6M DIEA in DMF/DCM mixture having a 3:1 ratio |
| Capping | acetic anhydride in THF n-methyl imidazole in THF |
| Washing | DMF THF | b. Reservoirs for use in tagging beads

In the specific example, the beads are optionally tagged. In a peptide synthesis reaction, the beads are in one embodiment tagged with a nucleic acid comprising nucleotides from the group A, T, C, and G. In addition to the four nucleotide reagents, the following solvents and reagents are used during the synthesis of tags.

TABLE 3

| Function | Chemical |
|---|---|
| Deprotection | trichloroacetic acid in DCM |
| Oxidation | $I_2$, collidine, $H_2O$, and MeCN |
| Activation | 0.5M tetrazole in MeCN |
| Capping | acetic anhydride in THF N-methyl imidazole in THF |
| Washing | MeCN |

These nucleotide reagents are contained in reservoirs having sufficient volume and quantity to accomplish the synthesis of tags utilizing the automated synthesizer.

Figure 2:
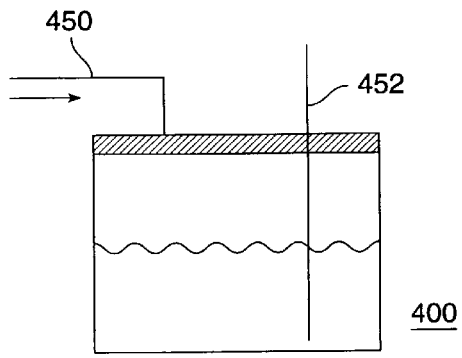
FIG. 2 shows a schematic diagram of a reagent reservoir.

FIG. 2 shows a representative reservoir 400 for containing, for example, the MeCN solution in Table 3. There are two tubes associated with each reservoir listed in Tables 2 and 3. As shown in FIG. 2, a tube 450 contains pressurized argon for pressurizing the reservoir to force the contents of the reservoir up a second tube 452. In some embodiments, the reagent reservoirs are always pressurized. In other embodiments, the argon tube is controlled by a local on/off valve to pressurize a reagent reservoir only when the contents of that reservoir are needed.

c. Delivery Valves

Figure 3:
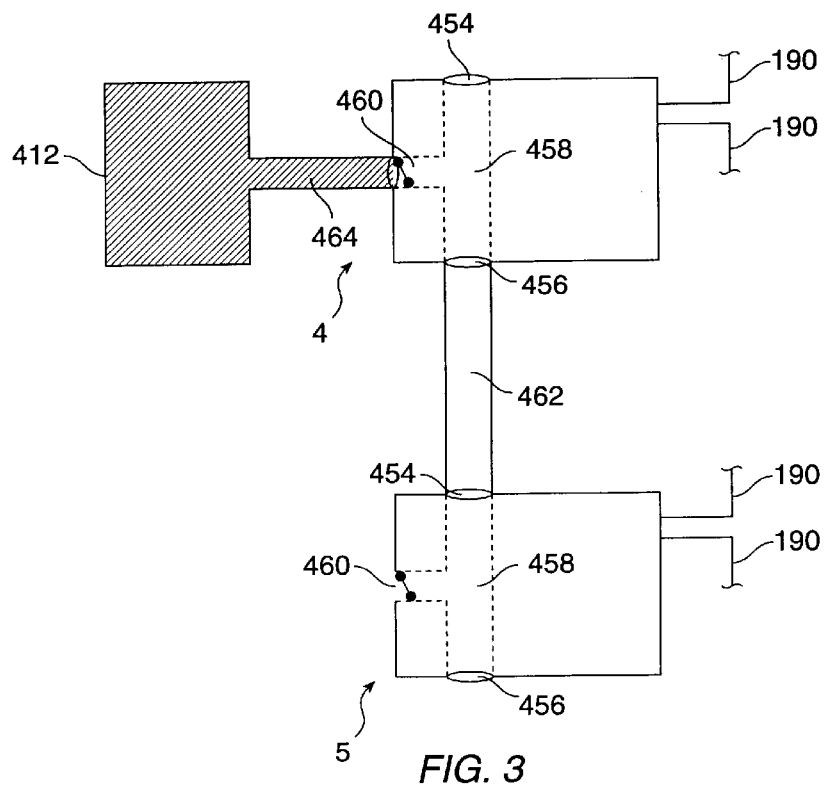
FIG. 3 shows a 3-port valve used in the synthesizer.

FIG. 3 shows a representative 3-port solenoid valve in greater detail. The valve may be, for example, a Model 2-110-900 by General Valve Corp. of Fairfield, N.J. Further, the 3-port valve of FIG. 3 represents, for example, valve 4 which deliver,; a reagent from reservoir 412. Three-port valves are used in the pressurized delivery system 265 of FIG. 1. The 3-port solenoid valve employed in the present embodiment includes a first port 454 and a second port 456. The 3-port solenoid valve also has a channel 458 through its body that communicates with first port 454 and second port 456 and always permits a fluid to flow freely between the first and second port. To form a common manifold 462, second port 456 is coupled with, for example, first port 454 of another 3-port valve. The other 3-port valve may be, for example, valve 5 of FIG. 1. A solenoid inside the valve, responsive to a control signal through wires 190, selectively permits a third port 460 to communicate with channel 458. Third port 460 of valve 4 is coupled to reservoir 412 of FIG. 1.

To control the injection of a reagent from reservoir 412 into manifold 462, a line 464 carrying the pressurized reagent is connected to third port 460 of valve 4. At an appropriate moment, the solenoid opens and permits third port 460 to communicate with channel 458, thereby causing the pressurized reagent from third port 460 to be injected into channel 458 of valve 4 and into common manifold 462.

Figure 4:
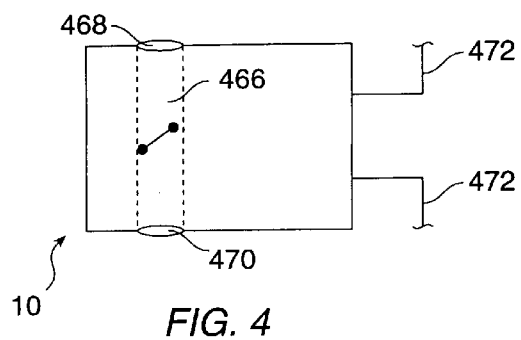
FIG. 4 shows a 2-port valve used in the synthesizer.

FIG. 4 shows a representative on/off 2-port solenoid valve 10. This valve may be, for example, a Model 2-17-900 by General Valve Corp. of Fairfield, N.J., for selectively permitting a fluid or a gas to flow in a channel between its two ports. As shown in FIG. 4, valve 10 includes two ports 468 and 470. Valve 10 also has a channel through its body that communicates between a first port 468 and a second port 470 to permit a fluid or a gas to flow between the two ports. A solenoid inside valve 10, responsive to a control signal through wires 472, selectively permits first port 468 to communicate with second port 470. When one port of valve 10 is connected to a tube carrying a pressurized gas or fluid, valve 10 can be used to permit or inhibit flow from that port to the other port of valve 10.

Figure 5:
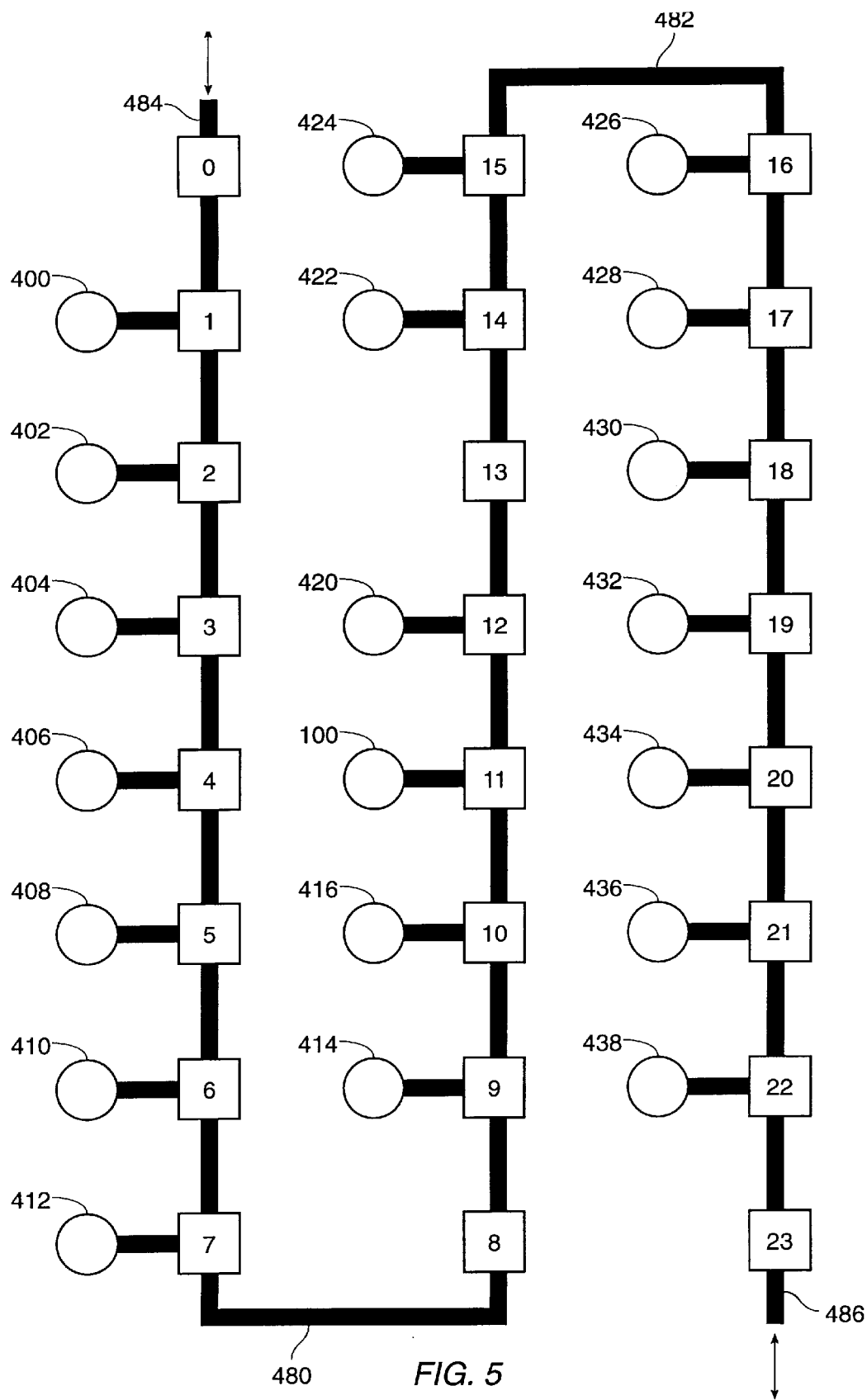
FIG. 5 shows a pressurized delivery system according to one aspect of the present invention.

FIG. 5 shows in greater detail a pressurized delivery system 265 according to one aspect of the present invention. FIG. 5 shows 24 valves 0–23 through which a common manifold is formed. The 2-port and 3-port valves are daisy-chained by coupling their first and second ports together so as to form a common manifold through which reagent flows. Three-port valves 1–7, 9–12, and 14–22 may be, for example, substantially similar to valve 4 of FIG. 3. Two-port valves 0, 8, 13, 23 may be, for example, substantially similar to valve 10 of FIG. 4. The common manifold includes the through channels of the 3-port valves and of the on/off valves, as well as the coupling tubes between adjacent valves. As previously mentioned, the third port of a 3-port valve is controlled by a solenoid in the valve. The third port of each 3-port valve is coupled to a tube from a reagent or solvent reservoir to transfer a reagent or solvent to and from PDS 265. Alternatively, the third port of a 3-port valve may serve as an exit port for delivering reagents to, for example, valve 100 of a reaction vessel bank. Two-port valves are used primarily as isolation valves or argon supply valves.

As shown in FIG. 5, the 24 valves are physically arranged in three separate banks to save space. The delivery system of FIG. 5 also includes a tube 480 for connecting the left bank of valves with the center bank. A tube 482 connects the right bank with the center bank. Table 4 lists the valves used in the delivery system, specifying the types of valves used and the reagent reservoir controlled by each valve in a typical embodiment.

TABLE 4

| Valve | Type | Reservoir | Reservoir Content |
|---|---|---|---|
| 0 | On/Off | -) | Argon |
| 1 | FWO 60 | 400 | MeCN |
| 2 | FWO 60 | 402 | 1% trichloroacetic acid in DCM |
| 3 | FWO 60 | 404 | Tetrazole |
| 4 | FWO 30 | 406 | C |
| 5 | FWO 30 | 408 | T |
| 6 | FWO 30 | 410 | G |
| 7 | FWO 30 | 412 | A |
| 8 | On/Off | — | — |
| 9 | FWO 30 | 414 | Waste |
| 10 | FWO 30 | 416 | Bottom of Parent Vessel |
| 11 | FWO 30 | 100 | RV Banks |
| 12 | FWO 30 | 420 | Waste |
| 13 | On/Off | — | — |
| 14 | FWO 60 | 422 | Top Parent |
| 15 | FWO 60 | 424 | $I_2$, collidine, $H_2O$, MeCN |
| 16 | FWO 60 | 426 | Acetic anhydride in THF |
| 17 | FWO 60 | 428 | n-methyl imidazole in THF |
| 18 | FWO 60 | 430 | Piperidine |
| 19 | FWO 60 | 432 | HBTU |
| 20 | FWO 60 | 434 | DIEA |
| 21 | FWO 60 | 436 | MeCN |
| 22 | FWO 60 | 438 | DMF |
| 23 | On/Off | — | Argon |

For example, valve 22 is shown to be a FWO60 valve or a fast wash out (FWO) 3-port valve having a $^{60}/_{1000}$-inch through channel. Furthermore, valve 22 controls a reagent from pressurized reservoir 438 which, as indicated by Table 4, contains DMF. As a further example, valve 23 is an on/off valve controlling the flow of pressurized argon from an argon supply source (not shown) to the common manifold of DS 265.

FIG. 5 shows a tube 484 connected to valve 0 for pressurizing the common manifold of PDS 265 from one end. Another tube 486 is connected to valve 23 and pressurizes the common manifold of PDS 265 with argon from the other end.

As an illustration, the operation of pressurized delivery system 265 during a peptide synthesis deprotection cycle is described below. For deprotection of polypeptides, a solution of 10% piperidine in DMF is delivered to the reaction vessels in the reaction vessel (RV) bank. Table 4 indicates that valve 18 permits the flow of piperidine from reservoir 430. Consequently, valve 18 needs to open to permit piperidine from pressurized reservoir 430 to flow into the common manifold of PDS 265. To force the solution to enter RV bank valve 11, isolation valve 8 is closed and isolation valve 13 opens to force the pressurized piperidine to enter open RV bank valve 11.

As shown in FIG. 5 and Table 4, RV bank valve 11 and parent vessel valve 10 are centrally located in the chain of valves. This arrangement advantageously minimizes the length of the manifold section between these valves and a given reagent valve. Consequently, a smaller volume of reagent is required to fill up this manifold section. Isolation valves 8 and 13 can be closed to prevent the reagent from one end of the manifold from overshooting RV bank valve 11 or parent vessel valve 10 and from unnecessarily entering another portion of the common manifold.

Table 4 also shows valves 4–7 and 9–12 to be 3-port valves having a through channel dimension of $^{30}/_{1000}$ inch. In contrast, the remaining valves in the manifold have a through channel dimension of $^{60}/_{1000}$ inch. The reduced channel cross section further reduces the volume in the respective portion of the manifold. Consequently, less reagent is needed to fill up the manifold.

For example, nucleotides A, T, C, and G are relatively costly. It is therefore desirable to keep the volume of reagent used to the necessary minimum. Nucleotide valves 4–7 are located proximate to RV bank exit valve 11 to keep the distance between a nucleotide valve and RV bank exit valve 11 short and the required volume of reagent low. The cross section of the manifold along the path from any nucleotide valve to RV bank exit valve 11 is also kept small to further reduce the volume of nucleotide reagent present in the manifold. In fact, tube 480 of FIG. 5 as well as the portion of the manifold between the nucleotide valves and isolation valve 8 have a reduced cross section of $^{30}/_{1000}$ inch.

C. Reaction Vessel Banks

Figure 6:
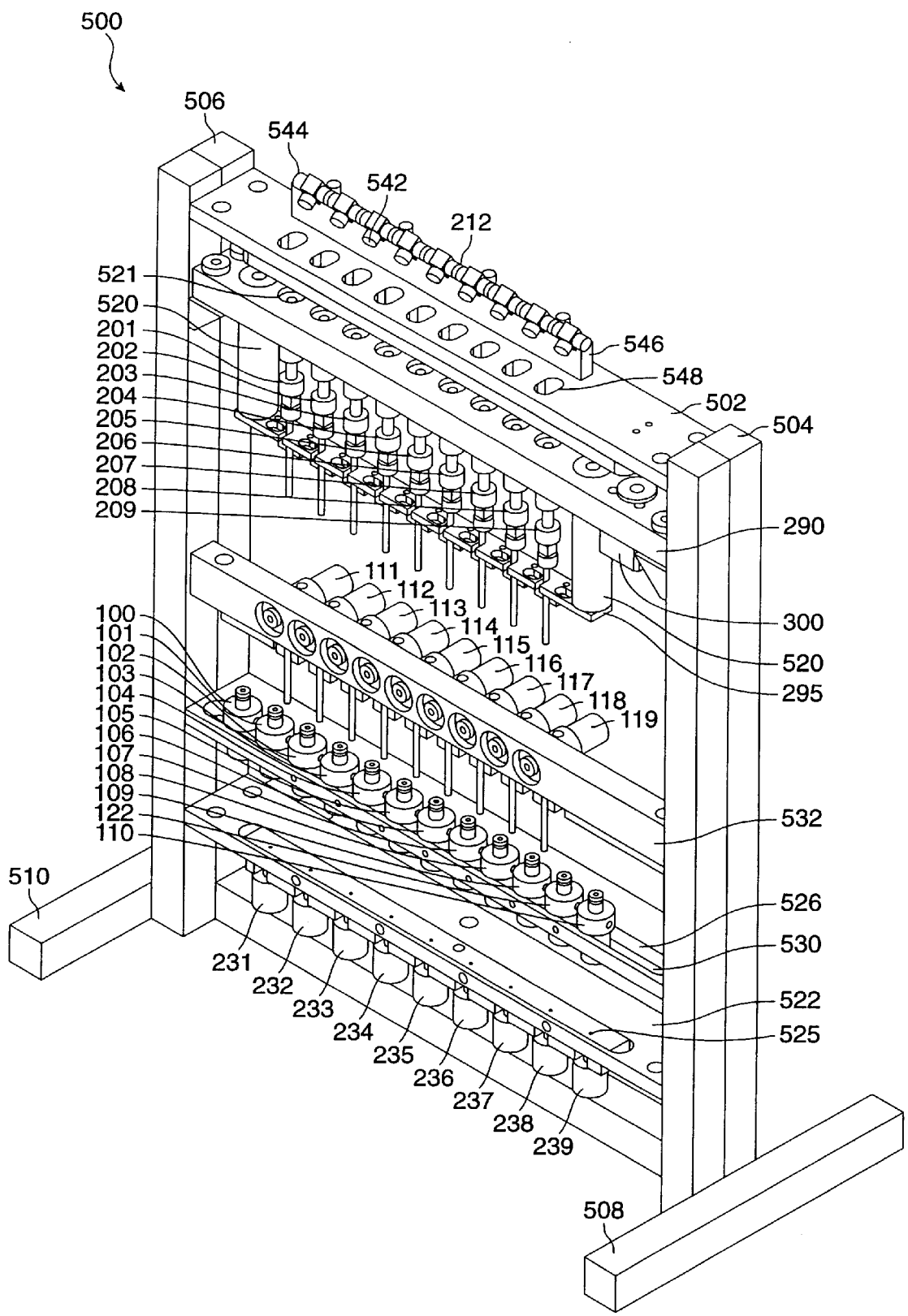
FIG. 6 shows a reaction vessel bank.

FIG. 6 shows a simplified reaction vessel bank 500 according to one aspect of the present invention. For ease of illustration, tubes through which solution flows have been partially deleted. Reaction vessel bank 500 includes a top bracket 502, two side brackets 504 and 506, and two bases 508 and 510. A top reaction vessel bracket 290 attaches to side brackets 504 and 506. A vortexing motor 300 attaches to top reaction vessel bracket 290 for supplying an agitation force to a plurality of reaction vessels 201–209 via a drive belt 521. The bottom of reaction vessels 201–209 are attached to a bottom reaction vessel bracket 295. Brackets 502, 504, 506, 290, and bases 508 and 510 may be constructed from any suitable material. For ease of machining, strength, and light weight, aluminum is used to construct the above-mentioned brackets in the present embodiment.

Bottom reaction vessel bracket 295 is attached to top reaction vessel bracket 290 by two nonconcentric shafts 280 inside shaft housings 520. Nonconcentric shafts 280 are rotatably mounted through apertures (not shown) in top reaction vessel bracket 290. Nonconcentric shafts 280 are operatively coupled to a vortexing motor 300 through belt 521. As will be discussed later, nonconcentric shafts 280 translate the rotational force supplied by vortexing motor 300 to an agitation force for urging bottom reaction vessel bracket 295 to move in a circular pattern. This circular motion exerts a vortexing effect upon the contents of reaction vessels 201–209. Because every reaction vessel 201–209 is attached at its respective lower end to bottom reaction vessel bracket 295, all reaction vessels are agitated uniformly and simultaneously.

FIG. 6 also shows a bottom bracket 522. Bottom bracket 522 is attached to side brackets 504 and 506 and may also be constructed from any suitable material, including aluminum. A plurality of amino acid reservoirs 231–239 are mounted beneath bottom bracket 522. The amino acid reagents in amino acid reservoirs 231–239 are used as building blocks for synthesizing the set of polypeptides of the specific example. The present embodiment contemplates using nine different amino acid monomers per bank for synthesizing the set of polypeptides.

FIG. 6 also shows an isolation valve bracket 526 attached to side brackets 504 and 506. Isolation valve bracket 526 includes a channel 530 for mounting a plurality of lower manifold valves 101–109. As shown in FIG. 6, each lower manifold valve 101–109 is secured within channel 530 in the present embodiment. However, lower manifold valves 101–109 may be secured to isolation bracket 526 using commercially available mounting hardware or other mounting methods. Lower manifold valves 101–109 are 3-port solenoid valves and are the same as the 3-port valve discussed earlier in connection with FIG. 3. As used in reaction vessel bank 500, the through channels of lower manifold valves 101–109 are coupled together to form a common lower manifold 214 through which solution from the pressurized delivery system 265 flows.

Three 2-port valves 100, 110, and 122 are also shown in FIG. 6. Nine valves 101–109 control the flow of solution from lower manifold 214 to the nine reaction vessels 201–209. Isolation valve 110 at a first end of the common lower manifold 214 opens to a waste line (not shown in FIG. 6). Isolation valve 100 at a second end of common lower manifold 214 selectively inhibits or permits the flow of solution from PDS 265 to the rest of the common lower manifold 214. An optional isolation valve 122 supplies local argon pressure to assist in the delivery of solution to and from various portions of reaction vessel bank 500.

In another embodiment, the eleven isolation valves 100–110 and 122 are provided for in an 11-valve block such as model P/N601374, by ABI of Foster City, Calif. The block comes preassembled and thus simplifies construction. The eleven valves of the 11-valve block function substantially as discussed above.

An injection valve bracket 532 made of a suitable material such as aluminum is attached to side brackets 504 and 506. A plurality of injection valves 111–119 are mounted through apertures in injection valve bracket 532. FIG. 6 shows a total of 9 injection valves 111–119 to control the injection of amino acids from nine amino acid reservoirs 231–239. Injection valves 111–119 are 3-port solenoid valves and are the same as the 3-port valve discussed earlier in connection with FIG. 3. The first port of each injection valve couples to a reaction vessel 201–209 while the second port of each injection valve is coupled to the third port of a lower manifold valve 101–109. The coupling is accomplished with appropriately sized tubes, such as the 1/16-inch teflon tubes employed in the present embodiment. As is apparent from the foregoing, the through channel of each injection valve 111–119 permits a solution to flow freely between a reaction vessel 201–209 and the third port of a lower manifold valve 101–109. The third port of each injection valve 111–119 is connected to an amino acid reservoir 231–239 to selectively inhibit or permit an amino acid to be injected into a stream of solution flowing between a lower manifold valve 101–109 and a reaction vessel 201–209.

FIG. 6 also shows a top common manifold 212. Top common manifold 212 includes nine manifold ports 542 for connecting top common manifold 212 to the nine reaction vessels 201–209. In the present embodiment, 1/8-inch flexible teflon tubes are used to couple manifold ports 542 to the top end of reaction vessels 201–209. Top common manifold 212 also includes a first end port 544 for connecting with a parent vessel (not shown in FIG. 6) where the beads from individual reaction vessels 201–209 are pooled and mixed together. A second end port 546 connects top common manifold 212 with a 3-port pressure/vent valve (not shown in FIG. 6). The pressure/vent valve and second end port 546 provide another route through which pressurized argon, solutions, reagents, etc., may be supplied to top common manifold 212. Alternatively, the pressure/vent valve and second end port 546 provide an additional route through which pressurized argon, solutions, etc., may be vented from top common manifold 212 to the appropriate reservoir.

Figure 6A:
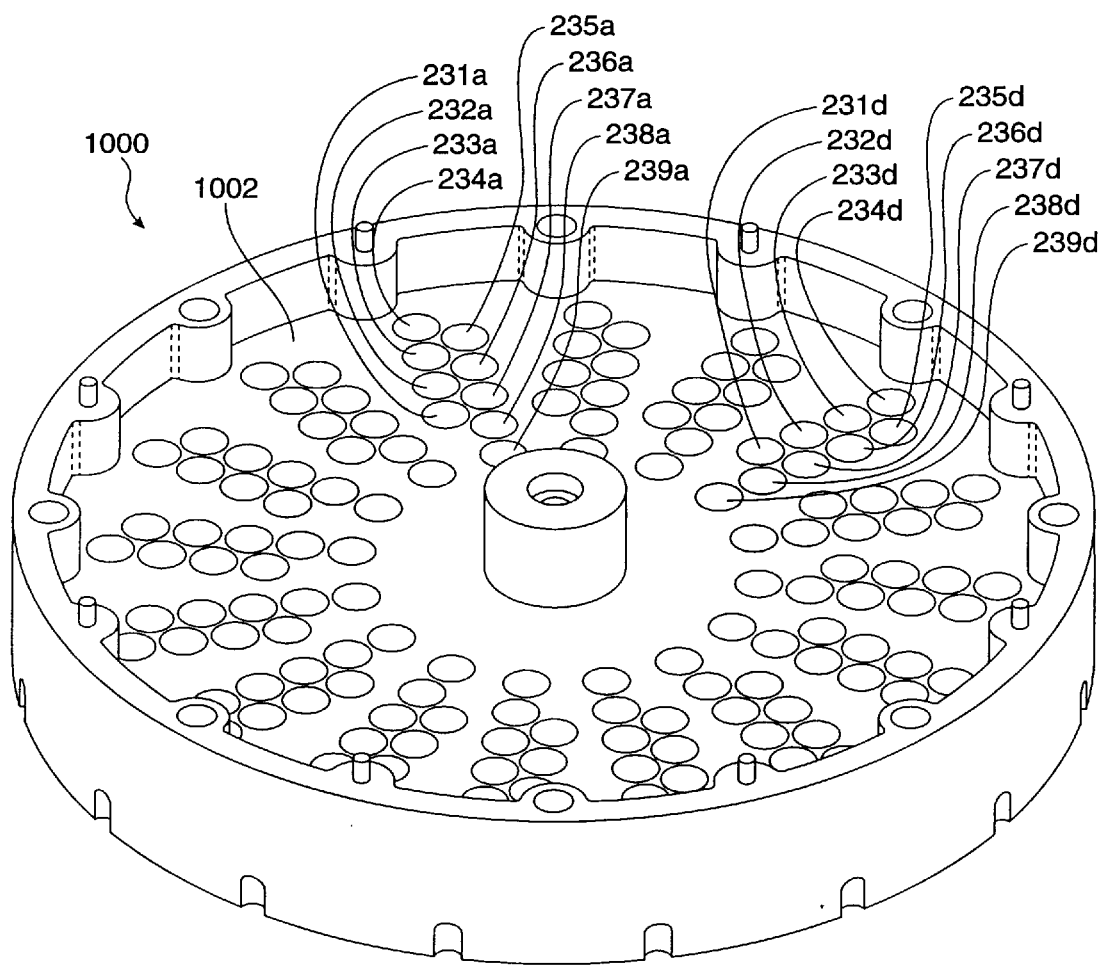
FIG. 6A shows an alternative arrangement of a reaction vessel bank having a rotatable carousel holding a plurality of groups of reagent reservoirs.

An alternative arrangement for the reservoirs 231–239 is shown in FIG. 6A. Instead of employing a single group of reservoirs, e.g., reservoirs 231–239, a plurality of groups of reservoirs can be provided, e.g., 231a–239a, 231b–239b, etc. The reservoirs are held within a rotatable carousel 1000. The reservoirs are open at a top surface 1002 of the carousel 1000 so that the reagents held in the reservoirs can be accessed from the top surface 1002. The carousel 1000 is held within a pressure vessel (not shown) so that each of the reservoirs are subjected to the same pressure within the pressure vessel. To transfer the reagents in the reservoirs to the reaction vessels 201–209, a plurality of tubes in communication with the tubes 241–249 are disposed within the pressure vessel. The tubes within the pressure vessel are placed into the reservoirs of a selected group of reservoirs, e.g., reservoirs 231a–239a. The tubes can be placed into the reservoirs by translating the tubes toward the reservoirs or by translating the carousel 1000 toward the tubes. The carousel 1000 is rotated to align the tubes with the selected group of reservoirs. The pressure within the pressure vessel is such that a pressure gradient exists between the reservoirs and the tubes 241–249. When the tubes are placed into the reservoirs, and when selected valves 111–119 are opened, the pressure gradient drives the reagents in the reservoirs into the tubes 241–249 for delivery to the reaction vessels 201–209 as previously described. The carousel 1000 thus provides flexibility to the synthesizer by allowing the reagents to be selectively chosen from a variety of different reagents, e.g., allowing a different set of building blocks to be used at each synthesis step.

Figure 7:
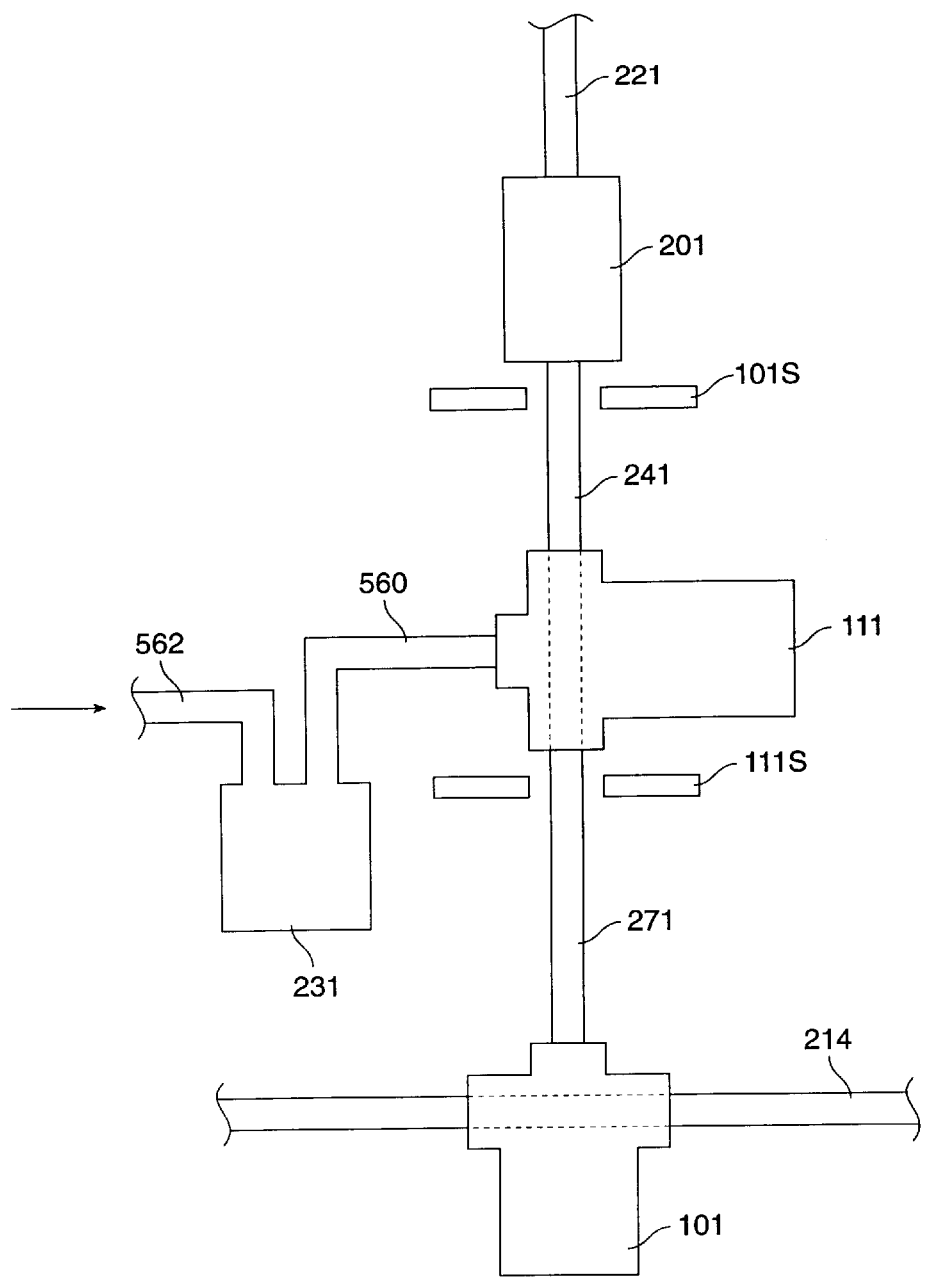
FIG. 7 shows the interconnections among a lower manifold valve, an injection valve, a reagent reservoir, and a reaction vessel.

FIG. 7 shows in greater detail the interconnections among an amino acid reservoir 231–239, an injection valve 111–119, a lower manifold valve 101–109, and a reaction vessel 201–209. A lower manifold valve, for example, valve 101, which is a three-port valve, is connected to common lower manifold 214 so as to permit a solution to flow freely between the first port and the second port of lower manifold valve 101. The third port of lower manifold valve 101 is connected via tube 271 to either the first or second port of the 3-port injection valve 111. The other port of either the first or second port is connected to one end of reaction vessel 201 via tube 241. The other end of reaction vessel 201 is connected to a manifold port 542 of top common manifold 212 (not shown in FIG. 7) via a tube 221. Tubes 271, 241, and 221 are made from a chemically resistant material such as teflon. In fact, the present embodiment employs translucent PTFE and FEP teflon tubes of various cross-sectional dimensions throughout because of the low reactivity and optical characteristics of the translucent teflon material.

Amino acid reservoir 231 is pressurized with an inert gas such as argon via tube 562. The pressurized amino acid solution in amino acid reservoir 231 enters the third port of 3-port injection valve 111 through tube 560. Upon receipt of an appropriate command, injection valve 111 opens to permit the pressurized amino acid solution to enter the through channel of injection valve 111.

FIG. 7 also shows two optical sensors 111S and 101S. Optical sensors 111S and 101S detect the presence or absence of a liquid within substantially translucent teflon tubes 271 and 241. As shown in FIG. 7, optical sensor 111S is positioned below injection valve 111 and optical sensor 101S is positioned below reaction vessel 201. Data from optical sensors 111S and 101S are sent to a control computer (not shown in FIG. 7) for use in controlling various phases of the synthesis reaction.

Figure 8:
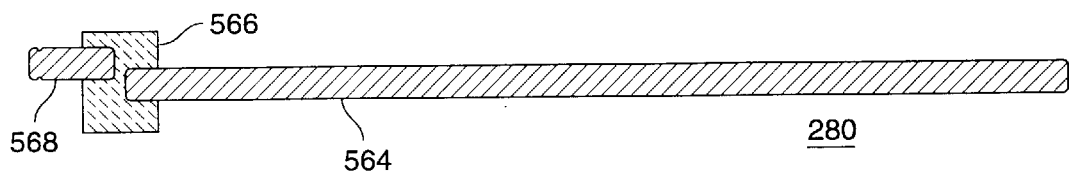
FIG. 8 shows a nonconcentric agitator.

FIG. 8 shows in greater detail the nonconcentric agitator 280 of FIG. 1. Nonconcentric agitator 280 includes two cylindrical shafts 564 and 568 coupled to a cylindrical knuckle 566. Shaft 564 aligns longitudinally with the radial axis of cylindrical knuckle 566 and is coupled at one of the two planar surfaces of cylindrical knuckle 566. Shaft 568 is coupled to the other planar surface of cylindrical knuckle 566 and is offset from the radial axis of cylindrical knuckle 566. In one embodiment, shafts 564 and 568, and cylindrical knuckle 566 are machined from a single piece of metal stock.

When cylindrical shaft 564 is torqued to rotate within a fixed rotary support such as a roller bearing, cylindrical shaft 568, which is offset from the axis of rotation of cylindrical shaft 564, moves in a circular path around the axis of rotation of cylindrical shaft 564. More than one nonconcentric agitator 280 may be operatively coupled, for example, by a belt-and-pulley arrangement to allow a plurality of nonconcentric agitators 280 to move in unison. In the present embodiment, shafts 568 of two nonconcentric agitators 280 are connected to a single bracket to move the bracket in a circular path when shafts 564 are rotated. Furthermore, shafts 568 and vortexing motor 300 are designed to move the bottom of each reaction vessel in a circular path at approximately 1500 revolutions per minute. To prevent damage to beads, the circular path of the present embodiment is preferably limited to a radius of approximately 3.5 mm.

Figure 9:
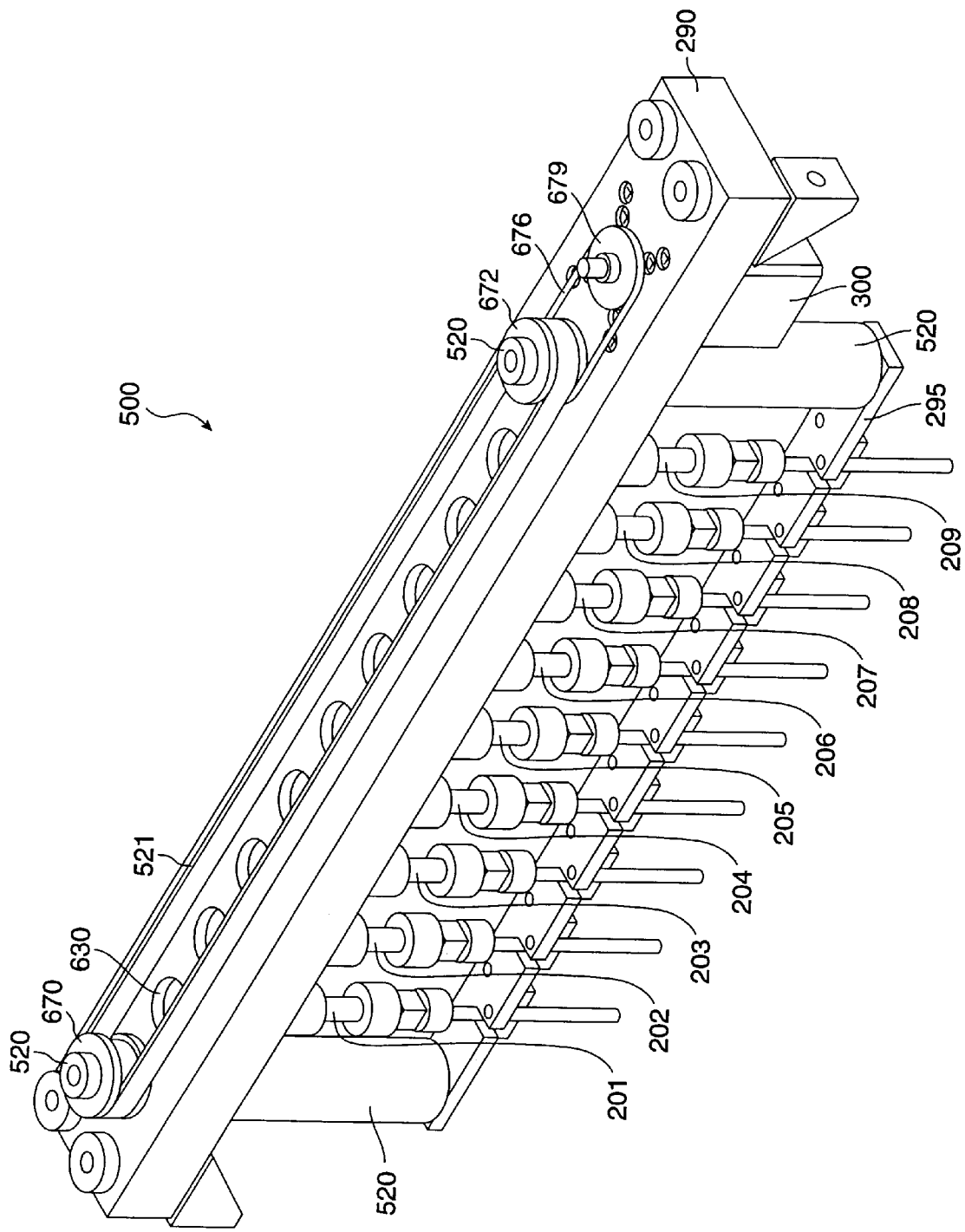
FIG. 9 shows the upper portion of a reaction vessel bank.

FIG. 9 shows in greater detail the upper portion of the reaction vessel bank 500 including reaction vessels 201–209 and vortexing motor 300 of FIG. 6. As discussed in connection with FIG. 6, reaction vessel bank 500 includes a plurality of reaction vessels 201–209 connected to top bracket 290. Top bracket 290 has a plurality of apertures 630 at which reaction vessels 201–209 connect. A teflon tube from above the aperture (not shown) connects to the upper end of each reaction vessel 201–209 at aperture 630 in a manner that permits a fluid to flow freely between the teflon tube and reaction tube 201–209.

Figure 10A:
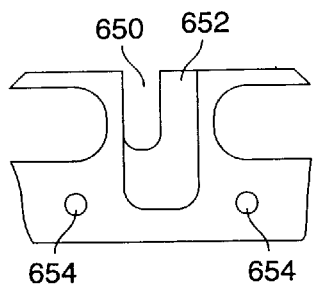
FIGS. 10A and 10B show a lower reaction vessel bracket.
Figure 10B:
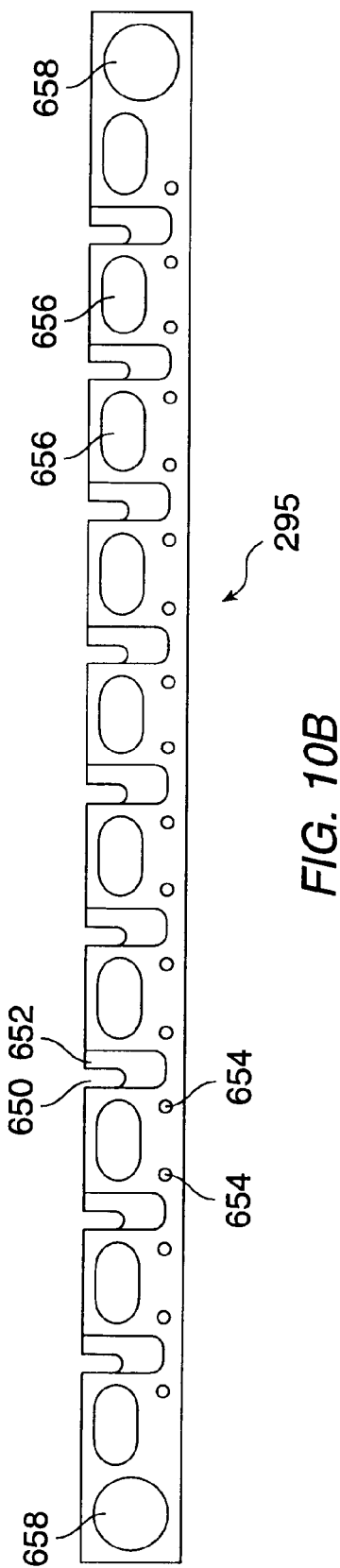

The lower ends of reaction vessels 201–209 are connected to lower reaction vessel bracket 295. FIGS. 10A and 10B show in greater detail a bottom view of the lower reaction vessel bracket 295 of FIG. 6. FIG. 10A is a close-up bottom view of a portion of lower reaction vessel bracket 295.

FIG. 10B shows a plurality of channels 650 in lower reaction vessel bracket 295. A flexible and substantially translucent teflon tube (omitted from FIG. 10B for ease of illustration) extends from the lower end of each reaction vessel 201–209 (also omitted from FIG. 10B for ease of illustration) and fits in a channel 650. A groove 652 for mounting an optical sensor is associated with each channel 650. Groove 652 is clearly illustrated in FIG. 10A.

FIG. 10B shows a plurality of mounting holes 654 for securely fastening optical sensors to lower reaction vessel bracket 295. Also shown in FIG. 10B is a plurality of optional holes 656 for reducing weight. As discussed earlier, lower reaction vessel bracket 295 follows the motion of the nonconcentric agitators in a circular path to vortex the contents of the reaction vessels. Optional holes 656 may be machined through lower reaction vessel bracket 295 to reduce the mass of the bracket, thereby reducing the amount of power needed to move the bracket.

A through hole 658 near each end of lower reaction vessel bracket 295 connects a nonconcentric agitator 280 to lower reaction vessel bracket 295. The lower ends of reaction vessels 201–209, which are extended by flexible teflon tubes 241–249 to fit through channels 650 in lower reaction vessel bracket 295, follow the circular movement of lower reaction vessel bracket 295. As lower reaction vessel bracket 295 moves in a circular path, the contents of all reaction vessels 201–209 in a reaction vessel bank are vortexed in a parallel manner.

FIG. 9 also shows optional nonconcentric agitator housings 520 for fitting over nonconcentric agitators 280. Optional nonconcentric agitator housings 520 enclose the nonconcentric shafts within a hollow cylindrical housing to prevent possible injury to human users and damage to equipment when the nonconcentric shafts are in motion.

The present embodiment uses a stepper motor (Model PX245-01AA by Oriental Motor U.S.A. Corp. of Torrance, Calif.) along with a stepping motor controller (Model RD122 by Semix Corp., of Fremont, Calif.) for supplying the rotational force to the nonconcentric agitators. As shown in FIG. 9, three pulleys 670, 672, and 674 cooperate with vortexing motor 300 and two drive belts 521 and 676 to rotate the two nonconcentric agitators 280 in unison inside optional nonconcentric agitator housings 520. Although the present embodiment utilizes a stepper motor and a stepping motor controller, the rotational force may be supplied by any other suitable type of motors, including other electrical or pneumatic motors. Furthermore, the force supplied by vortexing motor 300 may be transmitted to nonconcentric agitators 280 by any suitable transmission means including chains and sprockets, pulleys and belts, gears, etc.

Figure 11A:
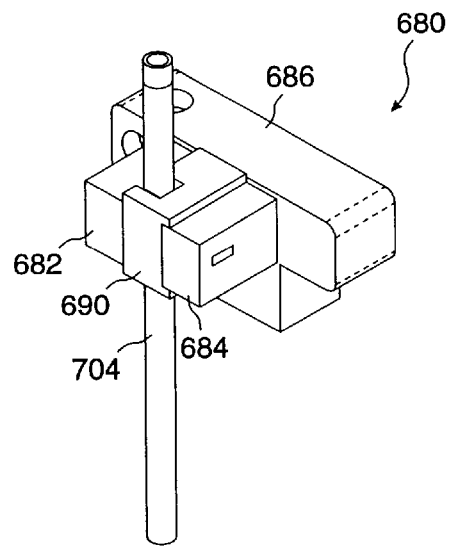
FIGS. 11A–11D show an optical alignment block for use with optical sensors to detect the presence of a liquid within a substantially translucent tube according to one aspect of the present invention.

FIG. 11A shows a representative optical sensor 680 for use in detecting the presence or absence of a fluid within a substantially translucent teflon tube. Optical sensor 680 is the same as optical sensors 101S–119S of the present embodiment. Optical sensor 680 (Model EE-SX671 by Omron, Inc. of Schaumburg, Ill.) includes two forked ends 682 and 684 for housing a light transmitter and a collector, respectively. Optical sensor 680 also has a body 686 for housing the appropriate electronic circuitry to transmit sensor data to a control computer and for attaching optical sensor 680 to a bracket.

Figure 11B:
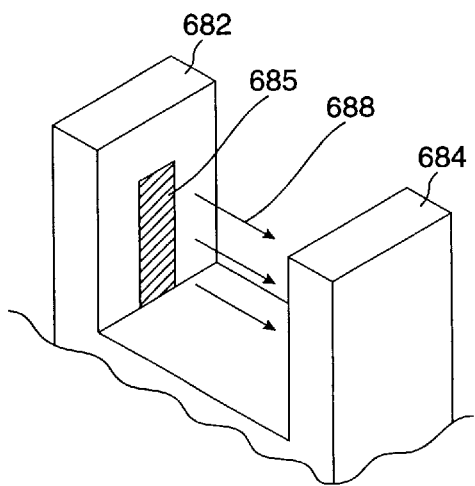

FIG. 11B shows in greater detail forked ends 682 and 684 of optical sensor 80. Located at the interior surface of forked end 682 is a substantially rectangular transmitter 685 for transmitting light to a substantially rectangular collector (not shown in FIG. 11B) in the direction of arrows 688. The collector is located at the interior surface of forked end 684 and is likewise of a substantially rectangular shape. To detect the presence of a fluid within a substantially translucent teflon tube, the teflon tube is fitted through the gap between the two forked ends 682 and 684. When a fluid is present within the substantially translucent teflon tube, the collector is triggered signifying detection of a fluid within the teflon tube.

In practice, it was discovered that the substantially translucent teflon material may, when empty, cause optical sensor 680 to fail to trigger. To advantageously use common optical sensors to sense the presence of a liquid inside a substantially translucent tube, a novel optical alignment block is used. FIG. 11 C shows in greater detail an optical alignment block 690. Optical alignment block 690 is made of an opaque material which substantially blocks any light emitted by transmitter 685. Optical alignment block 690 includes two retaining walls 692 and 694 at a first surface 696 for frictionally engaging block 690 with one of the forked ends of optical sensor 680, and to securely hold optical alignment block 690 between the forked ends. In one embodiment, retaining walls 692 and 694 are designed to engage the collector forked end 684 of FIG. 11B.

Optical alignment block 690 also includes a channel 698 built into a second block surface 700. Second block surface 700 is the surface opposite the above-mentioned first surface 696. The axis of channel 698 is orthogonal to retaining wall 692 and 694. Channel 698 is sized to grip the teflon tube snugly. As a result, the teflon tube is secured within channel 698 and is aligned at a right angle with respect to the above-mentioned transmitter strip 685 when optical alignment block 700 is fitted into the gap between forked ends 682 and 684.

Figure 11C:
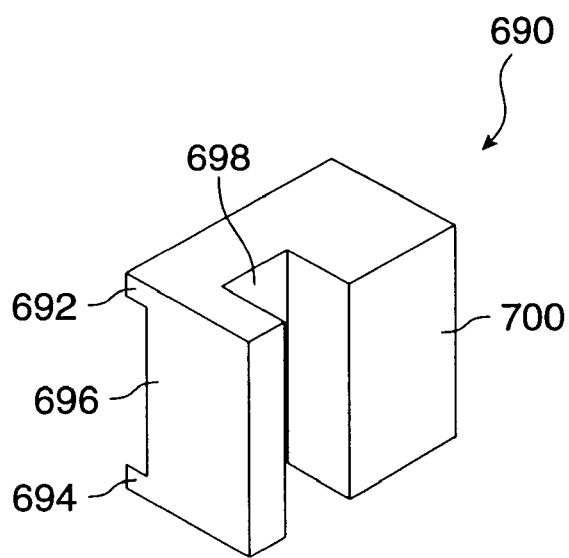
Figure 11D:
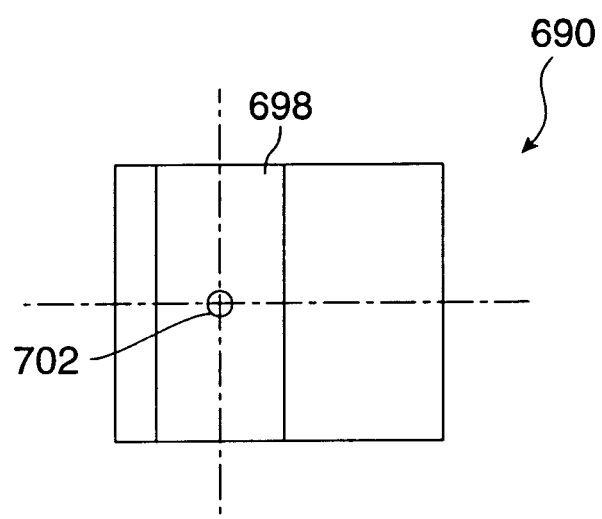

FIG. 11D shows an aperture 702 located along the center line of channel 698. Aperture 702 permits a small amount of light to travel through optical alignment block 690 along its bore between first surface 696 and second surface 700. When a substantially translucent teflon tube such as tubes 241–249 or 271–279 is fitted snugly within channel 698, the axis of aperture 702 runs through the center of the teflon tube.

The shape and size of aperture 702 is a function of the optical properties of the tubes.

When optical alignment block 690 is fitted between forked ends 682 and 684 in the manner shown in FIG. 11A, light from transmitter 685 in forked end 682 travels through a substantially translucent tube 704. Most of the light is blocked by optical alignment block 690 after passing through tube 704. Some of the light passing through tube 704 reaches aperture 702 (hidden from view in FIG. 11A) and travels along the bore of aperture 702 to reach the collector within forked end 684.

Since the axis of aperture 702 runs through the center of substantially translucent tube 704, light passing through the center of the tube reaches a portion of the collector in forked end 684. Since light going through empty tube 704 is diffracted, an insufficient amount of light reaches the collector to trigger the sensor. When a fluid is present within translucent teflon tube 704, light passing through the filled tube is focused by the fluid within. The focused light enters aperture 702 from the direction of forked end 682 to trigger the collector in forked end 684. When a fluid is absent, the focusing effect is less pronounced. Consequently, less light enters aperture 702. In fact, when there is no fluid in teflon tube 704, there is insufficient light passing through aperture 702 to trigger the collector in forked end 684.

As discussed earlier, optical alignment block 690 is sized to snugly grip teflon tube 704. When optical alignment block 690 is fitted between forked ends 682 and 684, the teflon tube is securely gripped, as shown in FIG. 11A, by optical sensor 680 and block 690. By securing optical sensor 680 to a bracket, teflon tube 704 is thereby secured to the bracket. In this manner, the teflon tubes 241–249 extending from the bottom of reaction vessels 201–209 of this embodiment are secured to the bottom reaction vessel bracket 295.

Figure 12:
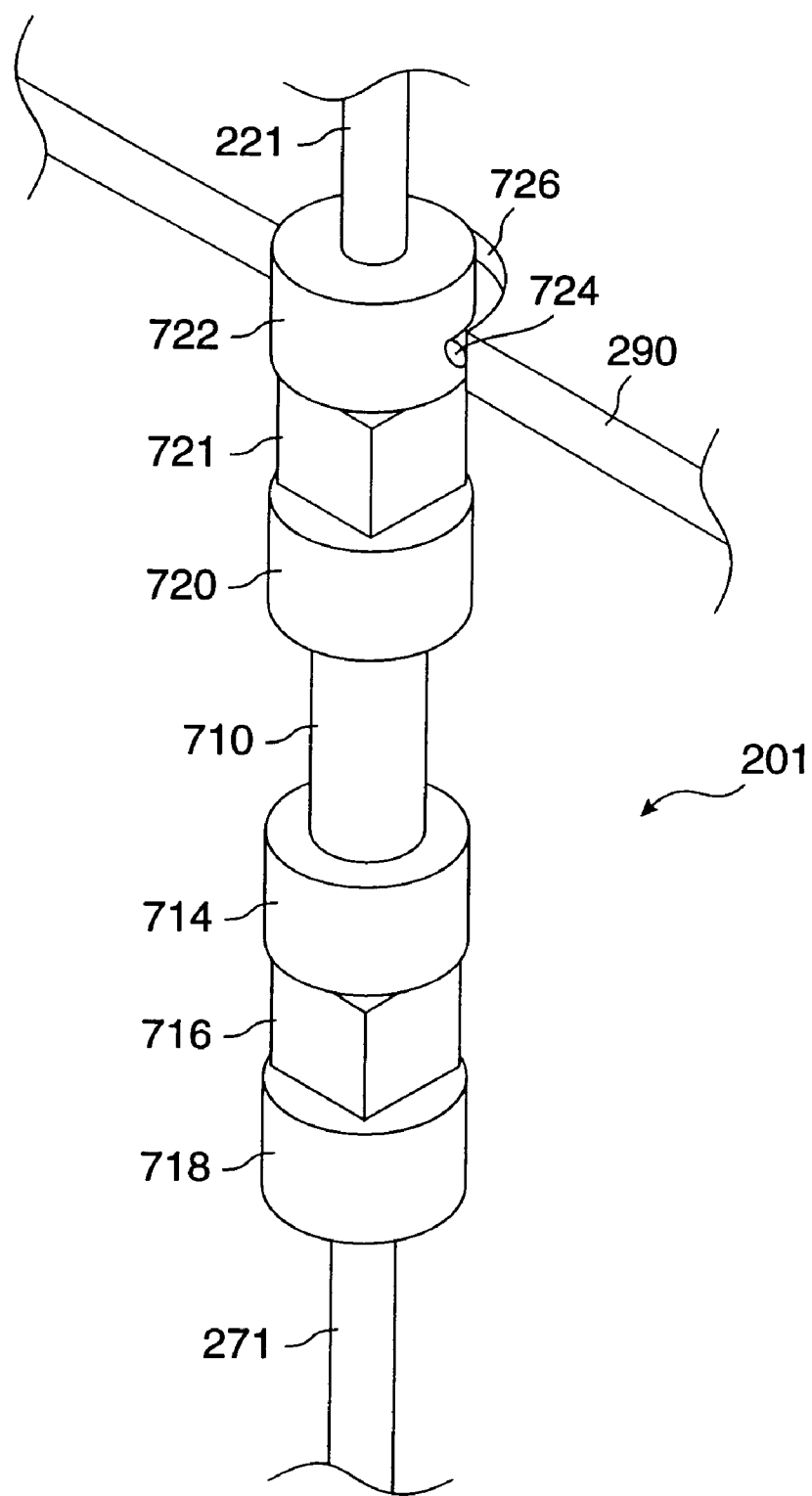
FIG. 12 shows a reaction vessel according to one aspect of the present invention.

As shown in FIG. 12, a reaction vessel such as reaction vessel 201 of the present embodiment consists of a segment of FEP teflon tube 710. Tube 710 has an outside diameter of ¼ inch and an inside diameter of 0.19 inch. As described in greater detail hereinafter, the diameter of tube 710 can alternatively be made much larger for applications where two or more reagents are simultaneously mixed in the reaction vessel 201. Tube 710 is sealingly coupled with a flexible teflon tube 271. Flexible teflon tube 271 is secured to lower reaction vessel bracket 295 of the reaction vessel bank. As the lower reaction vessel bracket 295 moves in a circular motion, the bottom of the flexible teflon tube 271 follows the circular motion described by the bottom reaction vessel bracket 295 to vortex the contents within tube 710.

In this embodiment, tube 271 has an outside diameter of ⅛ inch and an inside diameter of ¹⁄₁₆ inch. FIG. 12 shows a tube connector comprising a first coupler 714, a second interconnector 716, and a third coupler 718 for sealingly connecting tubes of different cross-sectional dimensions together. The aforementioned tube connector is available from Norton, Inc. of Akron, Ohio. There is a frit or filter 1102 (hidden from view in FIG. 12) located at the bottom end of tube 710 for preventing substrates within tube 710 from entering flexible tube 712. The frit may be, for example, 2 micron titanium frit.

At the other end of tube 710, a fourth coupler 720, a fifth interconnector 721, and a sixth coupler 722 sealingly connect tube 710 to a tube 221. The couplers 720 and 722 as well as interconnector 721 are necessary because tube 221 of the present embodiment has different cross-sectional dimensions from tube 710. Tube 221 connects to a manifold port 542 of top manifold 212 (not shown in FIG. 6).

A flexible O-ring 724 is fitted within a hole 726 in bracket 290 (shown in FIG. 12 in a cutaway view). O-ring 724 flexibly grips coupler 722, thereby flexibly securing reaction vessel 201 to bracket 290. When the bottom end of reaction vessel 201 is agitated, O-ring 724 serves as a pivot point and holds the top end of reaction vessel 201 relatively immobile to enhance the vortex effects.

Figure 12A:
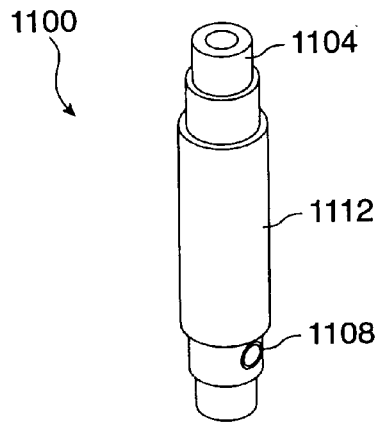
FIG. 12A shows a temperature controlling jacket around the reaction vessel of FIG. 12.
Figure 12B:
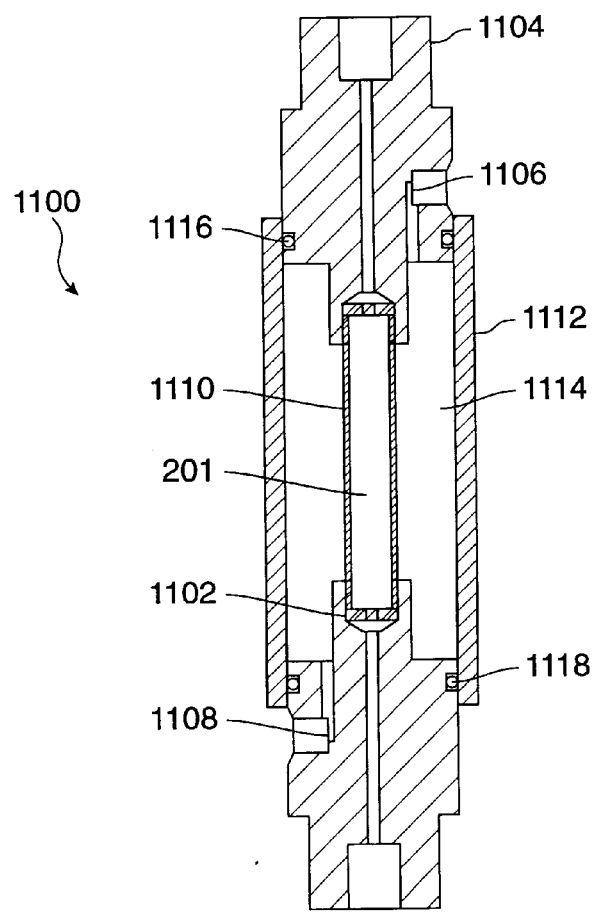
FIG. 12B shows a cross-sectional view of the jacket and vessel of FIG. 12A.

As shown in FIGS. 12A and 12B, the reaction vessel 201 in one particular embodiment can optionally be provided with a temperature control jacket 1100 for controlling the temperature of the reaction vessels 201–209. The temperature control jacket 1100 in this embodiment includes a fitting 1104 for connecting the reaction vessel 201 to the lines 221 and 241 (not shown). Inlet/outlet ports 1106, 1108 are provided for supplying a thermally conductive fluid to the reaction vessel 201. The thermally conductive fluid can be used to either heat or cool the reaction vessel 201. In this embodiment, the reaction vessel 201 is formed from a teflon tube 1110, preferably having an outer diameter of ¼ inch and a wall thickness of ¹⁄₃₂ inch. Spaced-apart from the tube 1110 is an outer tube 1112, preferably constructed of teflon and having an outer diameter of ¾ inch and a wall thickness of ¹⁄₃₂ inch. The outer tube 1112 is positioned over the fitting 1104 to form an annular space 1114 for receiving the thermally conductive fluid. O-rings 1116, 1118 are placed between the outer tube 1112 and the fitting 1104 to form a fluid tight seal. In this way, the thermally conductive fluid can be introduced into the annular space 1114 through either of the ports 1106, 1108 for heating or cooling the reaction vessel 201. The ports 1106, 1108 also allow the thermally conductive fluid to be continuously circulated through the annular space 1114.

Figure 12C:
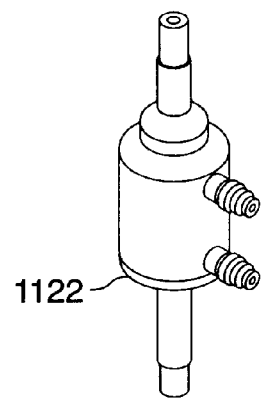
FIG. 12C shows an alternative embodiment of reaction vessel having a temperature controlling jacket.
Figure 12D:
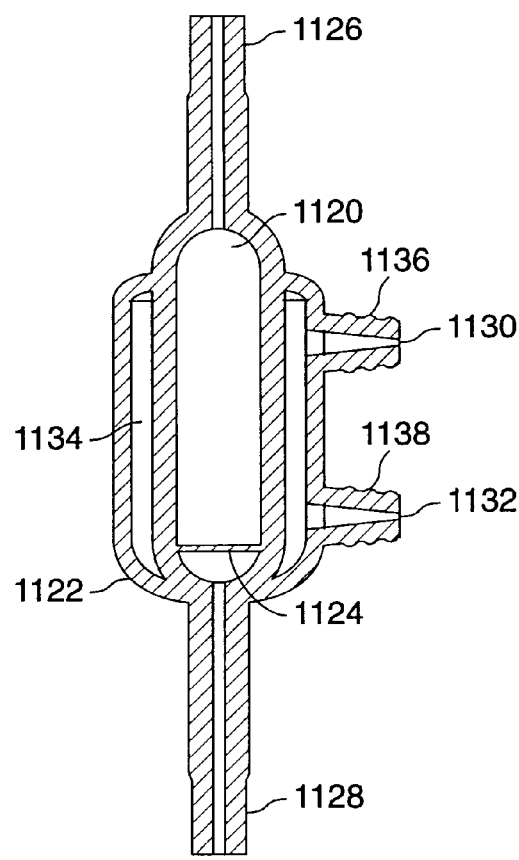
FIG. 12D shows a cross-sectional view of the jacket and vessel of FIG. 12C.

An alternative embodiment of a reaction vessel 1120 having an integrally formed temperature control jacket 1122 is shown in FIGS. 12C and 12D. The reaction vessel 1120 functions substantially identical to the vessel 201 except that the reaction vessel 1120 is preferably constructed of glass. The temperature control jacket 1122 is also preferably constructed of glass. Such a configuration allows the reaction vessel 1120 and the temperature control jacket 1122 to be formed as an integral unit. The reaction vessel 1120 includes a frit 1124, and connections 1126 and 1128 for connection to lines 221 and 241 (not shown). Inlet/outlet ports 1130, 1132 are provided for circulating thermally conductive fluid through an annular space 1134 between the jacket 1122 and the reaction vessel 1120. Hose barbs 1136, 1138 are conveniently provided for connection of the inlet/outlet ports 1130, 1132 to a suitable fluid source. In this way, thermally conductive fluid can be circulated through the annular space 1134 to heat or cool the reaction vessel 1120.

D. Parent Vessel

Figure 13:
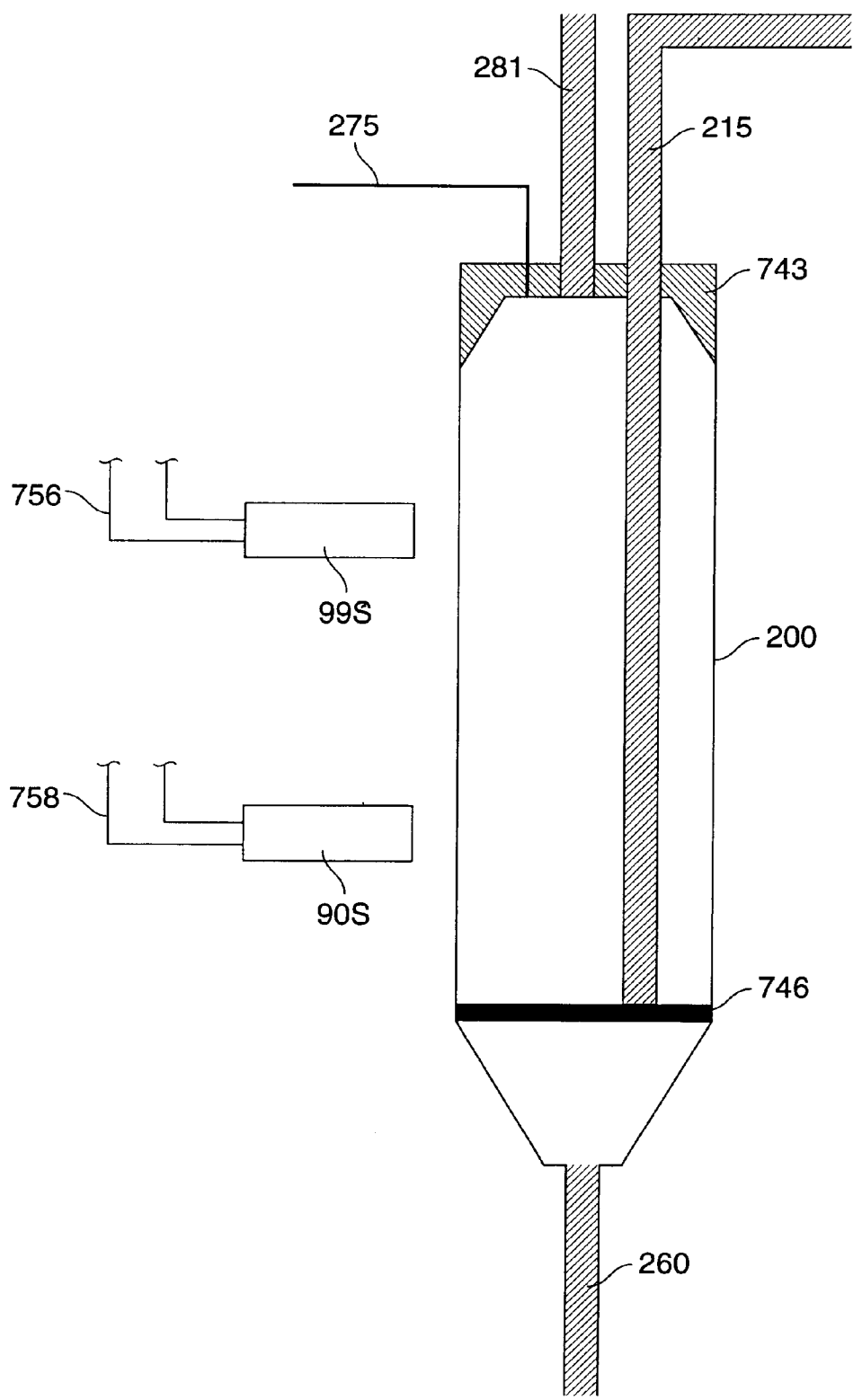
FIG. 13 shows a parent vessel.

FIG. 13 shows in greater detail the parent vessel of the present embodiment. Parent vessel 200 has, for example, a volume of approximately 30 mL. A tube 260 is sealingly connected to the bottom end of parent vessel 200 for transferring a reagent or argon to and from delivery system PDS 265 (not shown in FIG. 13). A frit or filter 746 is fitted near the bottom of parent vessel 200 to prevent substrates from entering tube 260. There is a removable cap 743 fitted on the top end of parent vessel 200 for adding and removing material. Tube 215 fitted through cap 743 transfers material between parent vessel 200 and top common manifold 212 in a reaction vessel bank (not shown in FIG. 13). Tube 215 extends through cap 743. A pressurized argon/vent line 275 also extends through cap 743. An optional rinse line 281 connects to a solvent source for delivering pressurized solvent to the interior walls of parent vessel 5 to rinse the interior walls.

FIG. 13 shows two capacitive sensors 90S and 99S (Model 18-08 by Electromatic Control Corp. of Hoffman Estates, Ill.) mounted near the exterior of parent vessel 200. Each capacitive sensors 90S or 95S detects the presence of a liquid in its vicinity and transmits sensor data to a control computer (not shown) via wires 756 and 758 respectively. Capacitive sensor 99S is used for detecting the level of reagents added to the parent. Capacitive sensor 90S is for detecting the level of bead suspension for redistribution. Both sensor levels can be adjusted according to amount of beads and the number of reaction vessels used. The capacitive sensor data is utilized by the software to control various cycles of the synthesis process.

E. Control System

1. Control Computer

The automated synthesizer utilizes a control computer to acquire data from the sensors, and to control the valves and the vortexing motor during the various cycles of the synthesis process. When used in conjunction with the automated synthesizer, any computer including those popularly known as microcomputers, minicomputers, workstations, mainframes, and the like, may be used to process the sensor data and to issue commands to control the valves and the vortexing motor.

Furthermore, sensor data from the sensors in the synthesizer may be acquired by any number of commercially available data acquisition devices using common data acquisition methods. Likewise, the valves and the vortexing motor may be controlled, responsive to an appropriate computer command, by commercially available input/output controllers.

In one embodiment, an IBM-compatible microcomputer (also known as a personal computer or PC) is used as the control computer (Model Gateway 2000 4DX2-50V, by Gateway 2000 Inc. of No. Sioux City, S. Dak.). Within the PC, there are a plurality of expansion slots permitting the addition of various expansion boards. These boards tap into the bus resources of the PC and permit the PC to communicate with the circuitry on the card to perform an electronic function. Certain expansion boards also permit the PC to communicate with external devices and circuitry. For example, a board popularly known as a modem board plugs into an expansion slot on a PC and permits the PC to communicate with another computer having a modem. The use of expansion boards with a personal computer is a matter of common engineering knowledge.

In one embodiment, the automated synthesizer communicates with the PC via a multichannel digital I/O board (Model PCDIO120-P by Industrial Computer Source of San Diego, Calif.). The specification of the PCDIO120-P board is described in detail in Product Manual No. 00431-050-20A which is also available from Industrial Computer Source.

Each PCDIO120-P provides 120 channels of buffered inputs/outputs (I/O) in five 24-channel groups. Each 24-channel group is controlled by a programmable peripheral interface (PPI) 8255A chip. The channels are selectable in set of 8 for either input or output.

Figure 14:
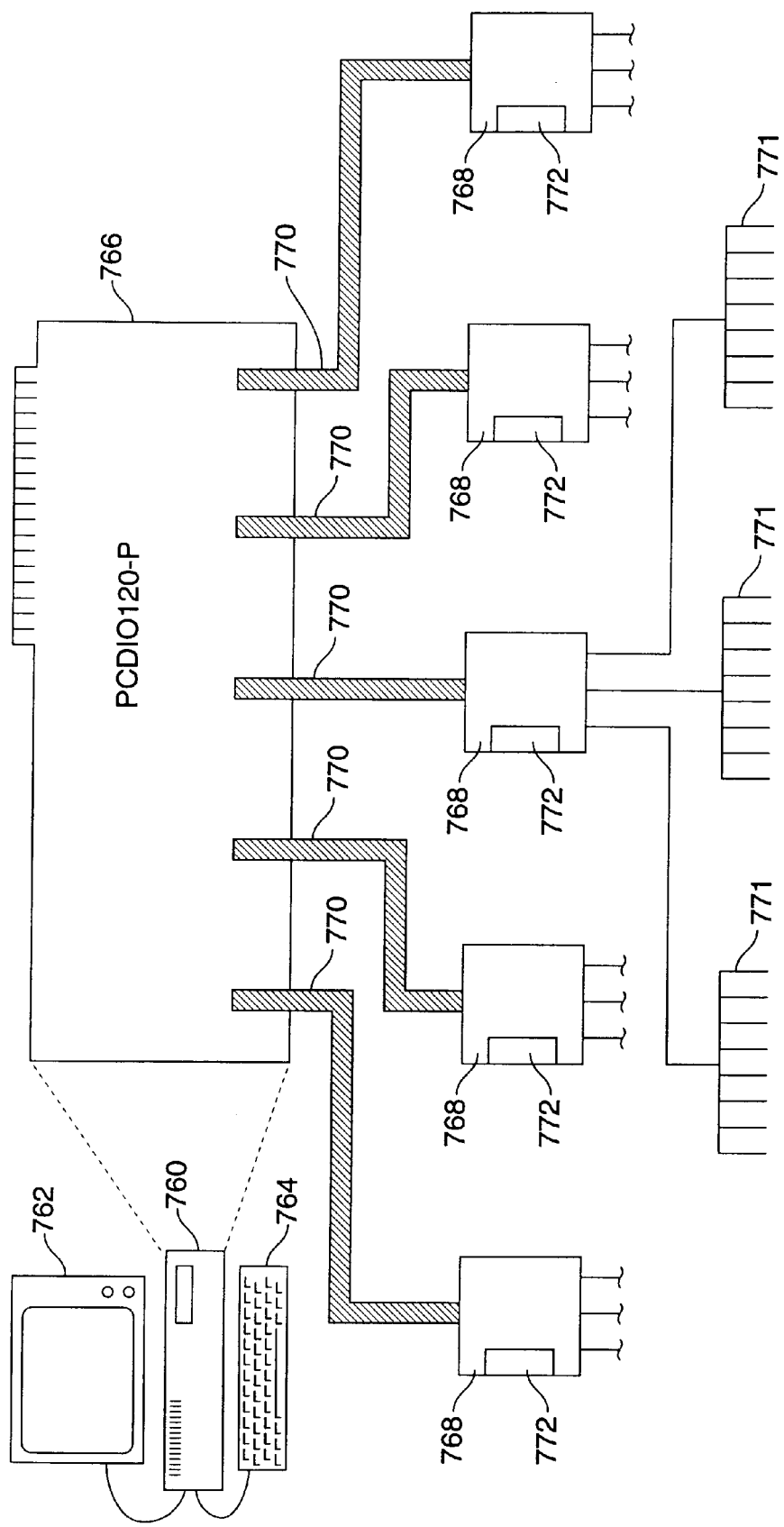
FIG. 14 is a simplified diagram of the electronic hardware for controlling the synthesizer.

FIG. 14 shows a simplified diagram of a portion of the control hardware. A computer 760, such as the PC, having a plurality of expansion slots, connects to a display monitor 762 and a keyboard 764. A PCDP120-P I/O board 766 is inserted into one of the expansion slots to permit the PC to communicate with five controller circuits 768. Each controller circuit 768 communicates with I/O board 766 via a conductor channel 770. In the present embodiment, conductor channel 770 includes a 50-conductor ribbon having the capability to service 24 I/O channels.

2. Controller Circuits

The output signals from I/O board 766, typically 15 mA of source current and 24 mA of sink current, are inadequate to operate solenoid valves. Consequently, controller circuits 768 convert the output signals coming from I/O board 766 into power signals having adequate power to actually operate the solenoid valves. Controller circuit 768 has the capability to receive 24 output signals from I/O board 766 and in turn outputs 24 power signals 771 to control various devices of the synthesizer. The 24 power lines 771 of each controller circuit 768 are shown in FIG. 14.

Each controller circuit 768 also provides a central physical location into which sensor data from up to 24 sensor lines, one for each sensor, may be gathered. Data from up to 24 different sensors may be received by a sensor port 772 on each controller circuit 768.

Figure 15:
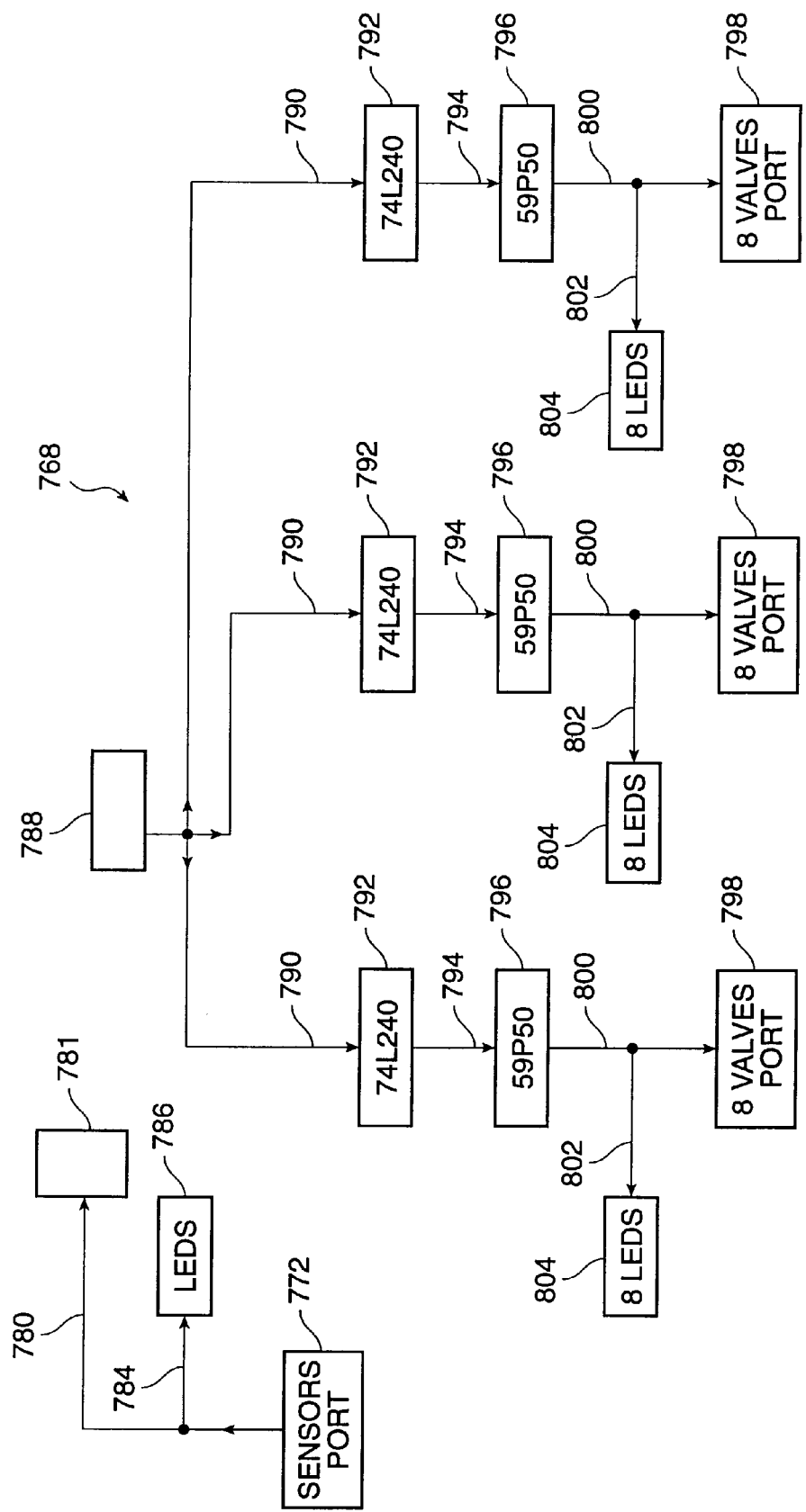
FIG. 15 shows a simplified diagram of the controller circuit.

Thus, each controller circuit 768 can service up to 48 I/O channels, 24 inputs and 24 outputs, of I/O board 766. FIG. 15 shows a representative diagram of a controller circuit 768 according to one aspect of the present invention. A 50-pin header 781 connects the controller circuit 768 to I/O board 766 (not shown in FIG. 15). Header 781 is an input header and is connected via a bus 780 to a sensors port 772. Sensors port 772 comprises headers or connectors for connecting controller circuit 768 with up to 24 input devices such as sensors. Each conductor on bus 780 carries a signal from one sensor to input header 781. FIG. 15 also shows an optional LED bus 784 for carrying LED indicator signals from sensors port 772 to an optional bank of light emitting diodes (LEDs) 786. Each conductor in optional LED bus 784 carries a signal to one LED in bank 786.

FIG. 15 also shows another 50-pin header 788 for connecting controller circuit 768 to I/O board 766 (not shown in FIG. 15). Header 788 is an output header for receiving output signals from I/O board 766. A bus 790 carries up to eight output signals from header 788 to an octal inverter 74LS240 chip 792. Octal inverter 74LS240 chips 792 are manufactured by Texas Instruments, Inc. of Dallas, Tex. A bus 794 carries the inverted buffered output signals from chip 792 to an octal latch driver 796. Latch driver chips 796 are Model MIC59P50, manufactured by Micrel, Inc. of San Jose, Calif. Output signals from each latch driver chip 796 are connected to an output port 798 via a bus 800. An optional LED bus 802 carries LED indicator signals from chip 796 to an optional bank of light emitting diodes (LEDs) 804. Each conductor in optional LED bus 802 carries a signal to one LED in bank 804.

3. The Valves

The solenoid valves such as, for example, valves 4–7, 10, 14, 90–91, 100–121, and 129, used in the present embodiment are normally closed unless commanded to open. Consequently, the default state for all valves in the synthesizer is off. Safety is ensured because no material is permitted to flow when the synthesizer is in its default state. When open, valves use power and heat up. Besides the obvious drain on the system power, hot valves may adversely affect the chemicals passing through their ports. Because it normally takes a greater amount of power to open a solenoid valve than to keep an already opened valve open, a strike relay such as, for example, a model D1D20 by Crydom, Inc. of Long Beach, Calif., is used to operate the valves. A strike relay such as the D1D20 supplies +12 volts to a valve for a specified period of time, typically 100 milliseconds, to open the solenoid valve from the off state. The period of time during which the strike relay supplies +12 volts can be specified through software control, and the strike is supplied via an I/O channel. Thereafter, the strike relay supplies a reduced voltage, typically half the rated voltage or approximately 6 volts in the present embodiment, to keep the solenoid valve open. Consequently, less energy is required to operate the valves and less heat is produced.

The present invention provides for four separate power supplies. A first power supply outputs +5 volts to power the TTL chips such as those found on controller circuits 768. A second power supply outputs +32 volts for use by the stepper motor. A third power supply provides +12 volts to activate the solenoid valves. An optional fourth power supply also provides +12 volts for use by the sensors. A separate fourth power supply for the valves ensures that any noise generated by the valves as they open and close does not interfere with sensor operation.

In its default state, all valves are closed. As an additional safety measure, the synthesizer further provides for a solid state watchdog relay to shut off all valves in the event the control computer malfunctions. A solid state watchdog relay such as a Model SM-WDT5 by Brentek International (available from Industrial Computer Source of San Diego, Calif.) is interposed between the control computer and the power supply to the valves. A software-generated pulse is transmitted from the control computer to the watchdog relay on one of the I/O channels. When the pulse is absent, e.g., upon CPU failure, latch-up or power failure, the watchdog relay shuts down the power supply for the valves, thereby closing all valves.

F. Control Software

The control software will now be discussed in detail with reference to the flow charts of FIGS. 16–24. These flow charts illustrate the commands issued by the control computers or completing relevant phases of the synthesis process. To simplify the discussion below, it is assumed that at all relevant times, the valves of the pressurized delivery system receive the appropriate commands from the control computer to deliver the desired reagent to the reaction vessel bank valve.

Figure 16:
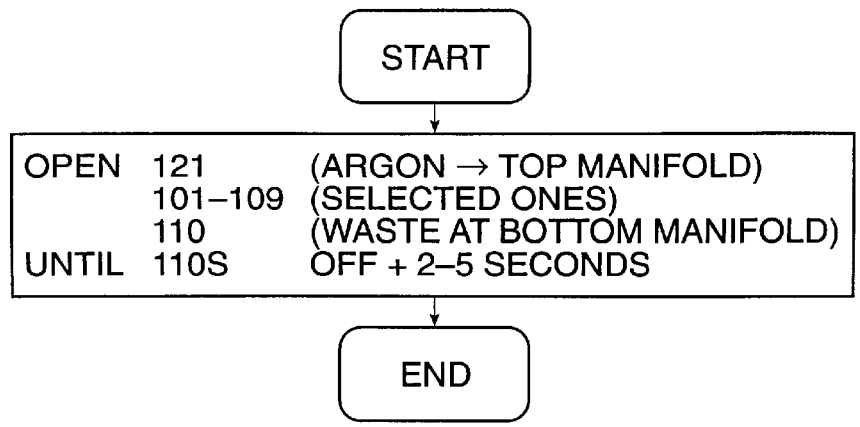
FIG. 16 shows the steps taken by the control computer to drain the reaction vessels of all liquids.

FIG. 16 is a flow chart illustrating the combination of commands issued by the control computer for draining reaction vessels 201–209 of their contents. Before draining, reaction vessels 201–209 contain a liquid or a bead suspension. An argon supply valve 121, connected to top common manifold 212, receives an open command and opens to pressurize top common manifold 212 with argon. At the same time, selected 3-port valves 101–109 open to permit a liquid from reaction vessels 201–209 to enter lower manifold 214. Only selected valves 201–209 open because not all reaction vessels 201–209 are used during some coupling reactions. If a reaction vessel sits empty throughout a synthesis session, there is no need to drain its contents. Waste valve 110 in bottom manifold 214 opens to permit fluid exit. As a consequence of the pressure differential, argon pressure pushes fluid from reaction vessels 201–209, through lower manifold 214, and out waste valve 110. When sensor 110S turns off, signifying that no liquid is left to drain, the valves stay open an additional 2–5 seconds to ensure all liquids are drained from the reaction vessel bank.

Figure 17:
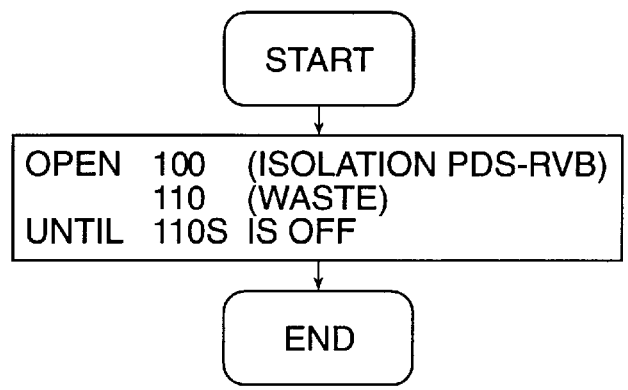
FIG. 17 shows the steps taken by the control computer to clear the bottom manifold of material.

FIG. 17 depicts the combination of commands issued by the control computer to clear lower manifold 214. At the start step, there is material in lower manifold 214. Thereafter, isolation valve 100 opens to permit pressurized argon from PDS 265 to enter lower manifold 214. Simultaneously, waste valve 110 opens to vent material from lower manifold 214. Material exits from lower manifold 214 until no material is left. The valves return to their default state when optical sensor 110S detects no material in the waste tube.

Figure 18:
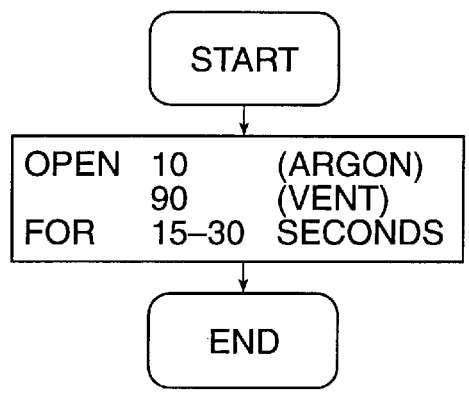
FIG. 18 shows the steps taken by the control computer to agitate the contents of the parent vessels.

FIG. 18 shows the set of commands issued by the control computer to mix the contents of parent vessel 200. The system introduces argon into parent vessel 200 from below to mix the contents. The argon bubbles agitate the contents of parent vessel 200 as they rise from the bottom of the parent vessel to the surface of the contents inside the parent vessel. Again, all valves which have not been expressly commanded to stay open are in their default state. Valve 100 opens to introduce pressurized argon from PDS 265 to the bottom of the parent vessel to agitate the contents within. Valve 90 also opens to vent argon from the parent vessel. Valves 100 and 90 return to their default state after approximately 15 to 30 seconds.

Figure 19A:
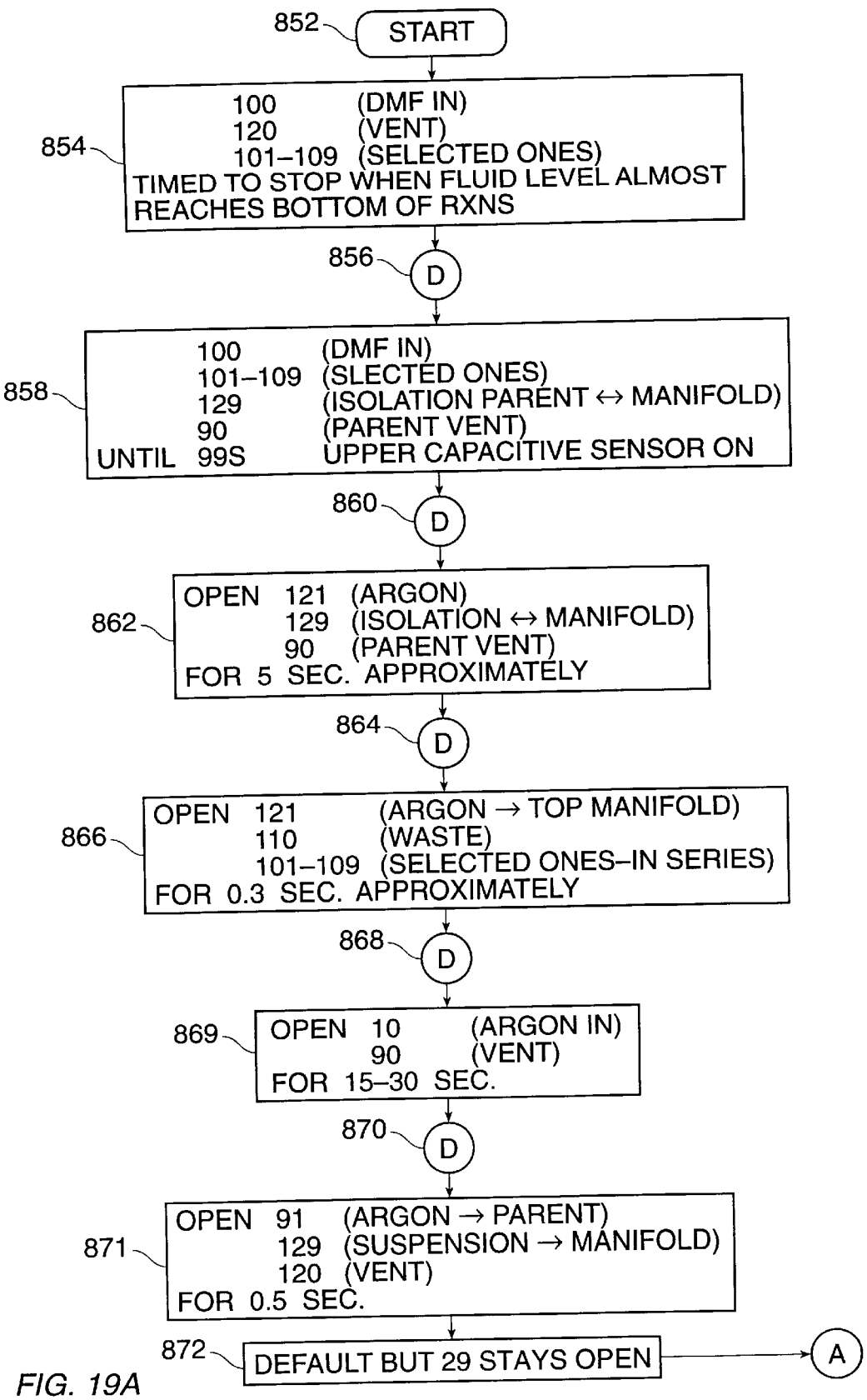
FIGS. 19A–19D show the steps taken by the control computer to reallocate the bead suspension from the parent vessel to the reaction vessels.
Figure 19B:
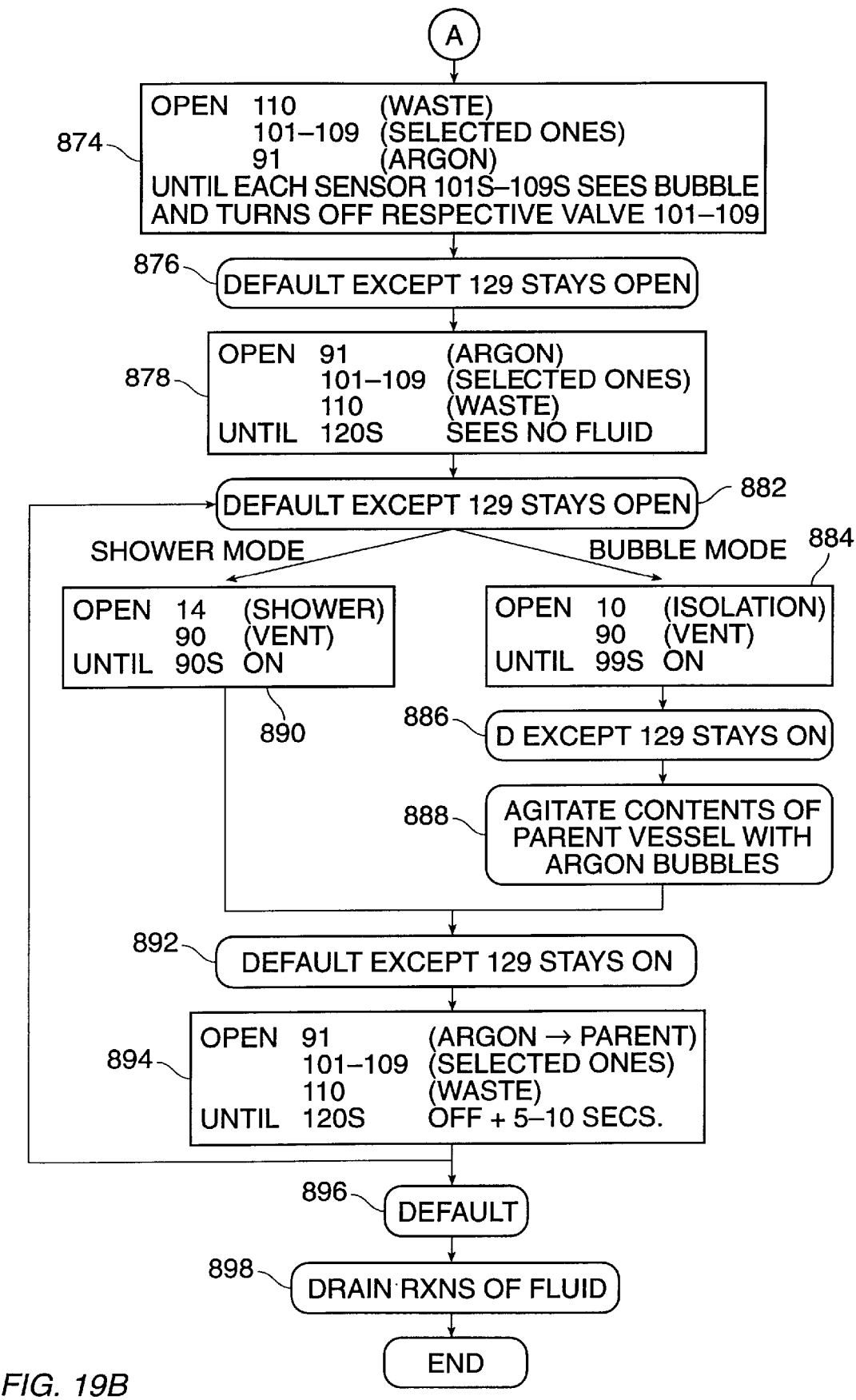

FIGS. 19A and 19B depict the sequence of commands issued by the control computer to allocate bead suspension from the parent vessel to the various reaction vessels. The sequence of commands implements a volumetric technique for filling the various reaction vessels with the bead suspension. Using this approach, the reactions vessels are filled with little dependence on flow rate. Thus, as will be seen, the bead suspension is distributed evenly among the reaction vessels regardless of the distance between that reaction vessel and the manifold port through which the bead suspension enters. At the start of the allocation cycle, the reaction vessel bank contains only argon, and the parent vessel contains a bead suspension at step 852.

At step 854, the reaction vessel bank is partially filled with DMF to displace the argon that exists in the reaction vessel bank prior to the reallocation phase. Isolation valve 100 opens to permit pressurized DMF to enter the lower manifold from the pressurized delivery system. Valves 101–109 open to permit DMF to rise toward the reaction vessels. Valve 120 opens to vent argon from the top common manifold. Valves 100, 101–109, and 120 return, preferably in series, to their default state after a preprogrammed time period, which may be about 3 seconds each. Reaction vessels 201–209 are then mixed to dislodge bubbles. Valves 100–109 open again for about 3 seconds. At the expiration of this preprogrammed time period, the level of DMF in each tube 241–249 leading to the reaction vessels will be near the top common manifold 212.

The reaction vessel bank and parent vessel 200 are then filled with DMF at step 858. Valve 100 opens to permit pressurized DMF to enter the reaction vessel bank from PDS 265. Valves 101–109 open to continue filling the reaction vessel bank with DMF. Valve 129 opens to permit the DMF which overflows the reaction vessel bank to enter parent vessel 200. Valve 90 also opens to vent the displaced argon from parent vessel 200. The filling continues until the level of fluid in parent vessel 200 rises to the level of upper capacitive sensor 99S when sensor 99S detects DMF within its detection envelope. The reaction vessel bank is then completely filled. Parent vessel 200 fills up to approximately the level of second capacitive sensor 99S. Valves 90, 100, 101–109 then return to their closed state at step 860.

Next, the top common manifold is cleared of DMF at step 862. Valve 121 opens to pressurize the top common manifold with pressurized argon. Valve 129 opens to permit DMF to enter the parent vessel from the top common manifold. Valve 90 opens to vent the displaced argon from the parent vessel. DMF from the top common manifold is thereby transferred to the parent vessel. The parent vessel is designed to have a sufficient volume to accept the additional DMF without overflowing. After a preprogrammed time period of, for example, about five seconds, valves 90, 121, and 129 return to their default state at step 864. The preprogrammed time period is variable but must equal or exceed the time it takes to clear the top common manifold of DMF.

Had the reaction vessels not been prefilled with DMF prior to the introduction of the bead suspension, i.e., had the reaction vessels been empty, an uneven distribution of bead suspension would occur. If the reaction vessels were empty, the reaction vessel which is the closest to the manifold port through which the bead suspension enters from the parent vessel would fill up first. There may be no bead suspension left for some reaction vessels if a few were allowed to fill up excessively.

The present invention employs a novel method for controlling the volume at which a reaction vessel accepts the bead suspension. First, at step 866, a small column of argon is introduced to the top of each tube which connects the reaction vessels to the top common manifold. To create this argon bubble, valve 121 opens to permit pressurized argon to enter the top common manifold. Selected valves 101–109 open in series to permit some DMF to drain from the reaction vessels to the lower manifold. Valve 110 opens to vent the displaced DMF from the bottom manifold. After about 0.3 seconds, a small column of argon appears at the top of the tube which connects the reaction vessel to the top common manifold. Valves 101–110, and 121 then return to their default state at step 868.

At step 869, the bead suspension in the parent vessel is mixed in preparation for distribution among the reaction vessels. The commands associated with this step are similar to those discussed in connection with FIG. 18. Valves 10 and 90 then return to their default state at step 870. This step ensures that a homogeneous bead suspension is evenly distributed among the selected reaction vessels.

A portion of the bead suspension is then introduced to the top common manifold at step 871. This step is timed according to a preprogrammed time period so that the bead suspension that enters the top common manifold displaces most of the argon existing within the top common manifold without flowing past the manifold port into which the last reaction vessel tube, e.g., the reaction tube associated with sensor 109S, connects. A preprogrammed period of about 0.5 seconds has been found to be satisfactory. To introduce this portion of the bead suspension to the top common manifold, valve 91 opens to pressurize the parent vessel with argon. Valve 129 opens to permit the bead suspension to flow into the top common manifold. Valve 120 opens to vent the argon existing in the top common manifold. After the expiration of the previously discussed preprogrammed time period, valves 91 and 120 return to their default state at step 872. Most importantly, valve 129 continues to stay open to prevent beads and polymers from being damaged due to the closing action of the valve. In the present embodiment, 2-port valve 129 continues to receive the command signal from the control computer to stay open in the manner discussed earlier. However, valve 129 may be a latch valve which toggles between the open and shut states upon receipt of a command pulse from the control computer. If valve 129 is a latch valve and is already open, no action needs to be taken by the control computer to keep latch valve 129 open.

FIG. 19B is a continuation of FIG. 19A. After some argon which existed in top common manifold 212 has been displaced, the rest of the bead suspension is transferred to top common manifold 212 at step 874. Valve 91 opens to pressurize parent vessel 200 with argon. Valve 129 which has been kept open permits the pressurized bead suspension to enter top common manifold 212. Selected valves 101–109 open to permit the DMF within reaction vessels 200 to exit into lower manifold 214. Valve 110 opens to drain DMF from lower manifold 214. Partly due to the resistance of the bead suspension, DMF recedes down selected reaction tubes 201–209 relatively slowly. The DMF displaced from selected tubes 221–229 connecting selected reaction vessels 201–209 with top common manifold 212 is replaced with the bead suspension. The column of suspension-bubble-DMF advances slowly downward towards lower manifold 214.

The column of bubble introduced earlier also advantageously serves as a volume marker, i.e., provides a way for the control computer to determine when each reaction vessel has received a sufficient amount of bead suspension. The column of bubble stays trapped between the column of DMF and the column of suspension because of the surface properties of the teflon and the high contact angle between the DMF and teflon. As discussed earlier, the optical sensors used in the present embodiment can detect the presence or absence of a liquid column inside a substantially translucent teflon tube. As DMF is replaced by the downwardly advancing mass of bead suspension, the bubbles move down into the reaction tubes and into the tubes which connect the reaction vessels to the lower manifold. At the moment the argon bubble is detected by an optical detector 101S–109S on its downward movement, that detector is momentarily turned off. The sensor data, as discussed earlier, is communicated to the control computer which promptly issues a command signal to shut off a respective valve 101–109. After all valves 101–109 have been turned off, the bead suspension transfer is restarted and continues at step 878 until acoustic sensor 120S detects no fluid in the tube connecting the parent vessel with the top common manifold. At step 882, all valves except valve 129 return to their default state. As discussed, valve 129 stays open to avoid damage to the beads and valve 129.

The synthesizer at this point has suspension in its reaction vessels, and possibly some bead suspension residue in the parent vessel. To make sure all the beads are transferred to the reaction vessels, a rinsing process comprising at least one rinse cycle is employed.

The rinsing cycle is initiated by showering the interior walls of the parent vessel at step 890 with DMF sprays to loosen any bead suspension residue which may have cling to the wall. Valve 14 opens to permit sprays of DMF to wash down the walls. Valve 90 opens to vent the replaced argon from the parent vessel. The interior wall continues to receive sprays of DMF until the level of DMF in the parent vessel rises to the level of lower capacitive sensor 90S and turns it on. This sensor data is received by the control computer which promptly issues a command at step 892 to return all valves except valve 129 to their default state. The contents of the parent are then stirred by argon bubbles in the manner previously discussed.

Alternatively, the parent vessel may be rinsed by refilling it with DMF and then mixing it to loosen any bead suspension residue which may have clung to the interior walls or frit of the parent vessel. First, at step 884 the parent vessel is refilled with fresh DMF. The refilling is accomplished by opening valve 10 to permit DMF to enter the parent vessel from the pressurized delivery system. Valve 90 also opens to permit displaced argon to exit the parent vessel. When the level of DMF in the parent vessel rises to the level of the top capacitive sensor 99S, top capacitive sensor 99S is turned on. This sensor data is received by the control computer which promptly issues a command at step 886 to return all valves except valve 129 to their default state. The parent vessel is then mixed at step 888 by introducing argon bubbles to the parent vessel in the manner previously discussed.

The mixture of DMF and bead suspension is then transferred to the reaction vessels at step 894 by opening valve 91 to pressurize the parent vessel with argon and to transfer the mixture to the top common manifold through valve 129 which has remained opened through out the rinsing process. Selected valves 101–109 open to permit fluid to flow from the reaction vessels to the lower manifold. Valve 110 opens to drain DMF from the bottom manifold. The frits at the bottom of the reaction vessels strain all beads inside the reaction vessels. Eventually, the parent vessel is drained. Sensor 120 turns off when no fluid is present in the tube connecting the parent vessel with the top common manifold. This sensor data is communicated to the control computer to signify that no fluid is left in the parent vessel to transfer. The control computer continues to open valve 91 for another 5–10 seconds to pressurize the top common manifold and to move any remaining mixture into the reaction vessels. After 5–10 seconds, all valves except valve 129 are returned to the default state. One rinse cycle is completed.

As discussed earlier, a plurality of rinse cycles may be employed to ensure that substantially all bead suspension from the parent vessel is transferred to the reaction vessels. Two to three rinse cycles have been found to be satisfactory.

When all rinse cycles are completed, all valves including valve 129 are returned to the default state at step 896. Note that valve 129 remains open throughout the bead suspension reallocation process, including the rinsing process, to minimize any damage to beads and polymers. The reaction vessel bank is then drained of all fluids in the manner earlier discussed at step 898.

From the steps in FIGS. 19A–19B, it can be seen that the use of the argon bubble allows the bead suspension to be distributed evenly among the reaction vessels regardless of the flow rate of each flow path between the parent vessel and reaction vessel. As long as the argon bubble remains stable between the bead suspension and the DMP reagent, a viable marker is provided, enabling the sensors to determine the status of the reaction vessels. The ability to maintain a stable argon bubble, as previously mentioned, is due to the favorable physical properties of DMF, i.e., high contact angle of DMF with teflon.

However, it may be desirable to use fluids other than DMF when delivering the beads to the reaction vessels. This may create problems, particularly if the substitute fluid does not have physical properties which are conducive to creating a stable argon bubble. For instance, acetonitrile (MeCN), which is used as a solvent for DNA synthesis, is unable to produce a stable argon bubble. Thus, a different approach for distributing the beads to the reaction vessels is required.

Figure 19C:
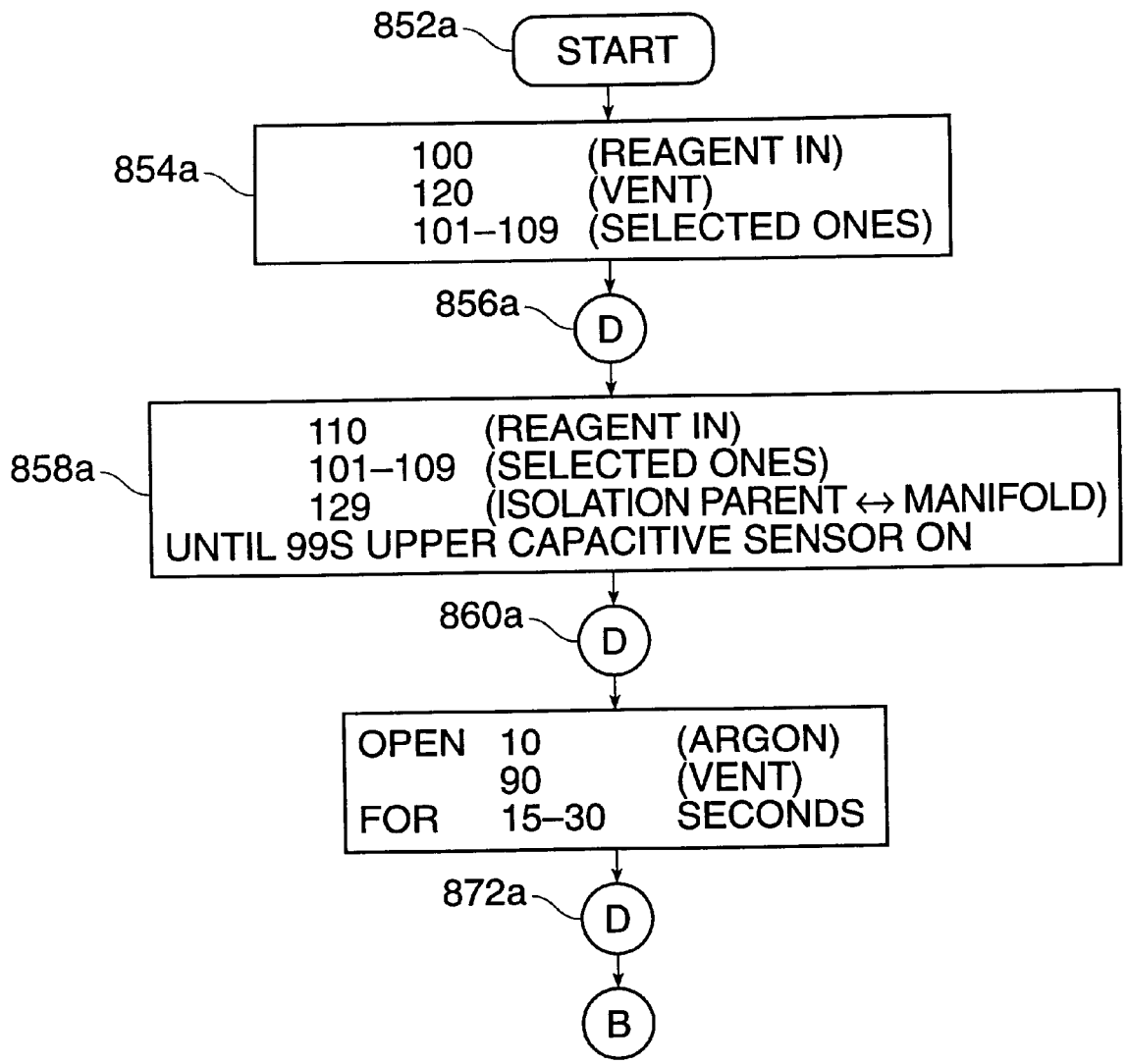
Figure 19D:
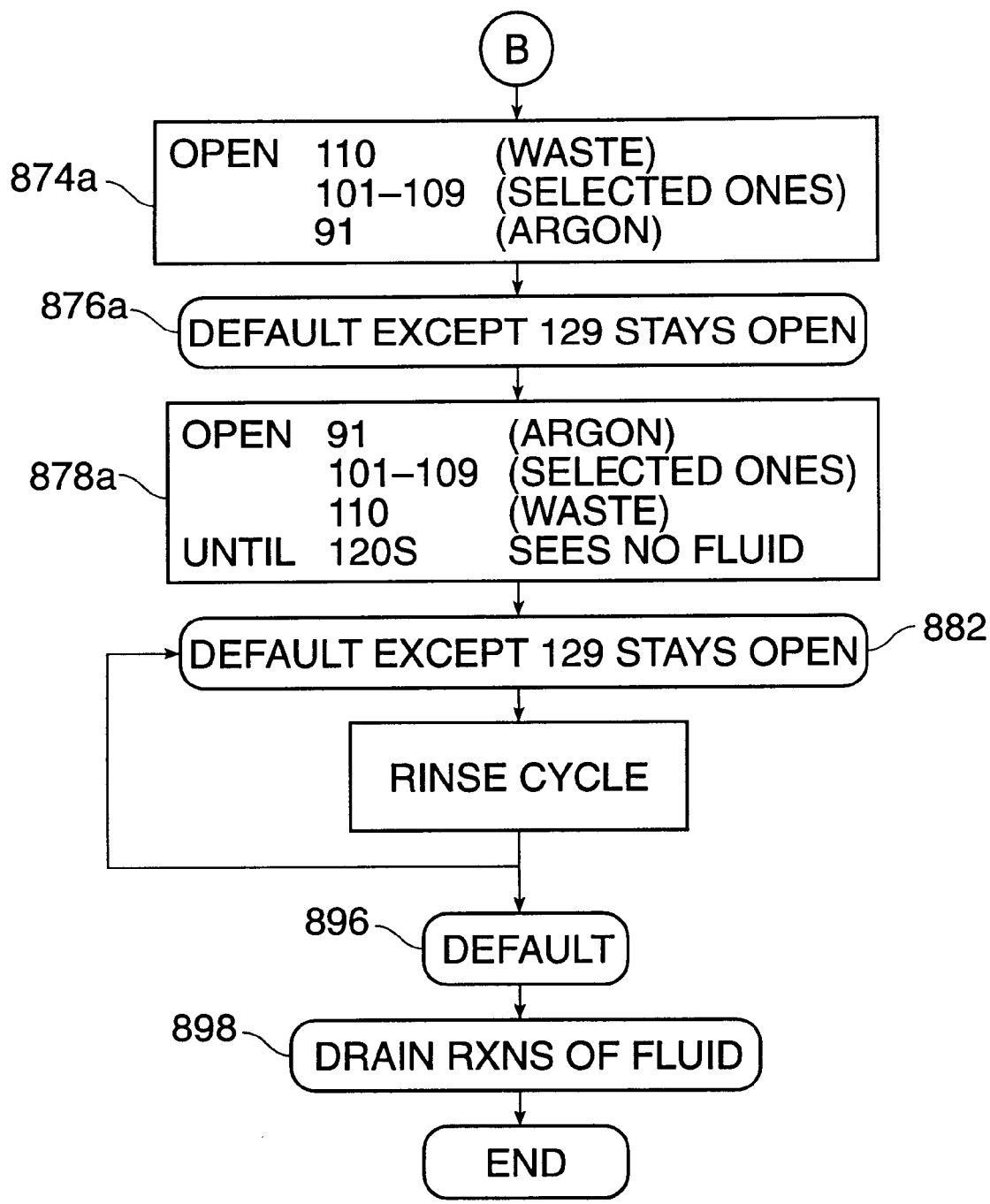

FIGS. 19C–19D illustrate an alternative set of commands issued by the control computer for mixing the contents of the parent vessel when a stable argon bubble cannot be produced. This technique is particularly useful when only a small number, e.g., up to four to five, of reaction vessels are employed.

Steps 854a–860a are similar to steps 854–860 in FIG. 19 except that only a smaller number of valves 101–109 are opened, i.e., only those corresponding to the selected reaction vessels. The selected reaction vessels are partially filled with a solvent, such as MeCN in order to displace the argon that exists in the reaction vessel bank prior to the reallocation phase. After which, the selected reaction vessels and the parent vessel are filled with MeCN. The flow of MeCN is stopped when the amount of MeCN in parent vessel 200 rises to the level of second capacitive sensor 99S, indicating that filling is completed. Upon completion, the selected valves then return to their closed state.

Next, at step 872a, the bead suspension located in the parent vessel is mixed in preparation for distribution to the selected reaction vessels. At step 874a, the bead suspension is then introduced to the top common manifold and distributed to the selected reaction vessels by opening valves 91,129, and selected ones of 101–109. These valves remain open until the sensor 120S detects the absence of fluid in the tube connecting the parent vessel with the top common manifold. Since no argon bubble is produced, sensors 110S–109S are not employed. Because only a small number of reaction vessels receive the beads, the time required for the beads to reach each of the reaction vessels is approximately equal, thereby ensuring a generally equal distribution for each of the reaction vessels.

At step 890a, a rinsing process, such at those already discussed in FIG. 19A–19B, is employed to make sure all the beads are transferred to the reaction vessels. Upon completion of the rinsing process, all valves including valve 129 are returned to the default state at step 896a. The reaction vessel bank is then drained of all fluids at step 898a.

Figure 20:
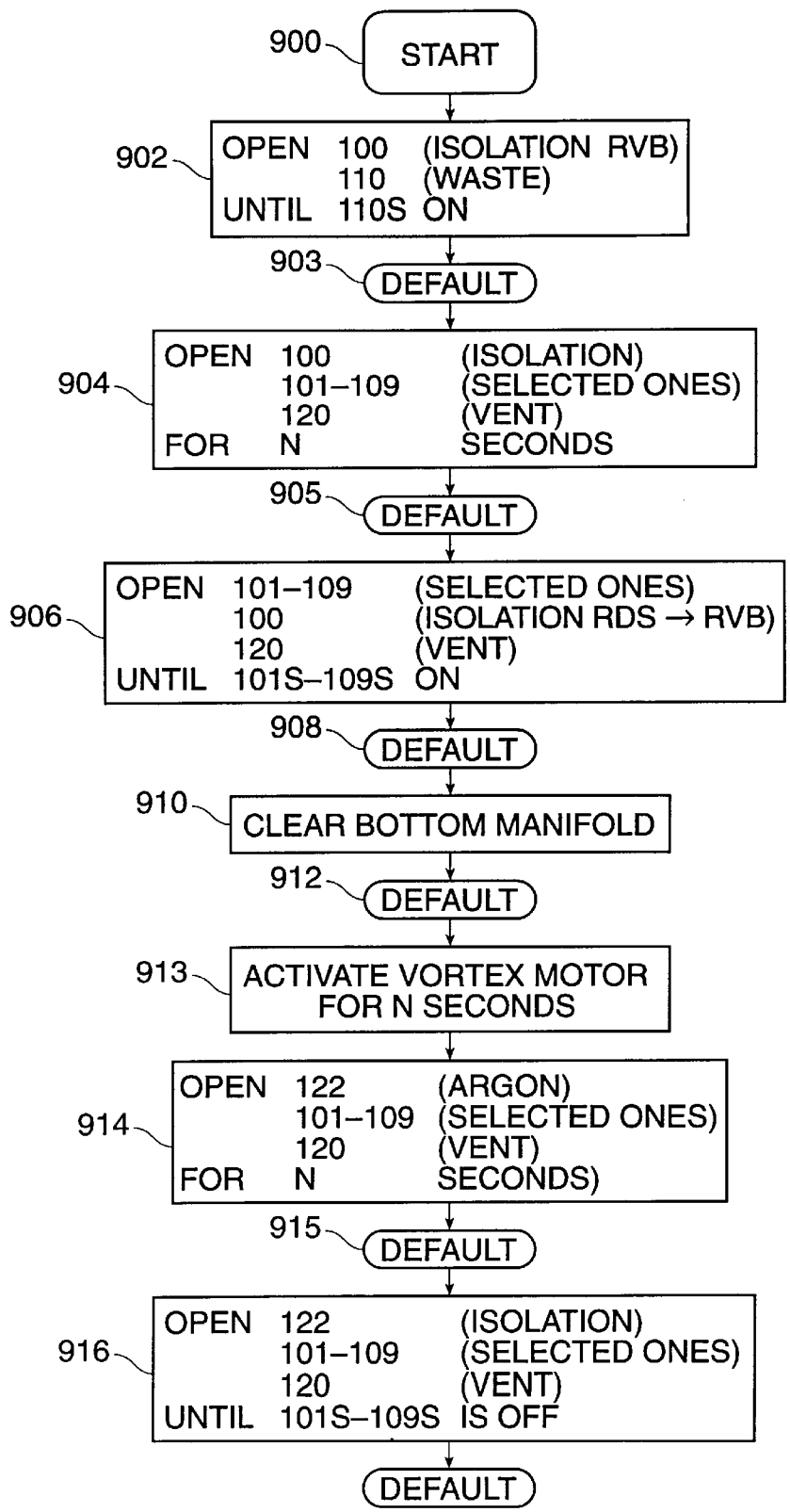
FIG. 20 shows the steps taken by the control computer to fill the reaction vessels with reagents from the pressurized delivery system.
Figure 21A:
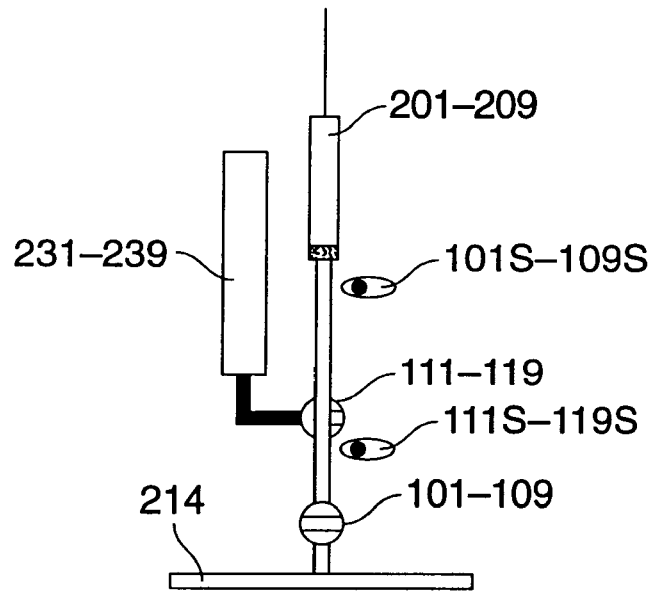
FIGS. 21A–21D schematically illustrate the steps taken by the control computer to fill the reaction vessels with reagents from the pressurized delivery system.

FIG. 20 is a flow chart showing the sequence of commands issued by the control computer to fill the reaction vessel with the desired reagent from the delivery system. The steps discussed in connection with FIG. 20 are also schematically illustrated in FIGS. 21A–21D. This process assumes that the lower manifold is filled only with inert argon at step 900. FIG. 21A graphically shows a relevant portion of the reaction vessel bank having an empty manifold. The lower manifold is first filled with a reagent at step 902. Valve 100 opens to permit the reagent to enter the lower manifold, and valve 110 opens to vent the argon displaced from the lower manifold. When the reagent is detected by sensor 110S, all valves return to default at step 903.

In some instances, the sensors 101S–109S may be tripped inadvertently or prematurely while filling the tubes connecting the reaction vessels with the lower manifold. For example, a sensor may be actuated by a stray droplet of reagent before the reagent actually reaches it. This can cause an insufficient amount of reagent to be present in the tubes for delivery into the reaction vessels.

To reduce or eliminate problems associated with premature sensor actuation, the control computer, at step 904, can optionally be programmed to open valves 101–109 for a set amount of time in order to prefill the tubes. Generally, the time is set so as to prefill the tubes to about 75%, before being detected by the sensors 101S–109S. As described, this step does not rely on the use of sensors 101S–109S. Thus, prefilling ensures that there is at least a sufficient amount of reagent present in the tubes to inject into the reaction vessels to adequately perform mixing, even if the sensors are prematurely actuated. At step 905, the valves return to default after the predefined time has expired in preparation for filling the tubes.

Figure 21B:
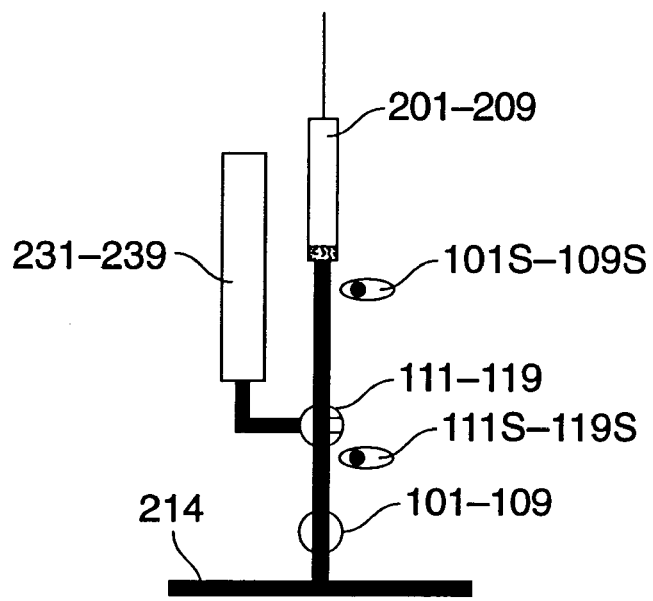

At step 906, the tubes connecting the reaction vessel with the lower manifold are filled to the sensors with reagent. The filling process may be carried out in parallel to save time or in series. Valve 100 opens to permit pressurized argon from the pressurized delivery system to enter the lower manifold. Selected valves 101–109 open, serially or in parallel, to permit the reagent to enter the tube connecting the reaction vessel with lower manifold. When the level of reagent in a tube reaches the upper light sensors 101S–109S, the light sensors turn on, and the control computer promptly turns off an associated valve 101–109. When all sensors 101S–109S are on, all valves are returned to the closed state at step 908. FIG. 21B schematically illustrates the result after this filling step is completed.

Figure 21C:
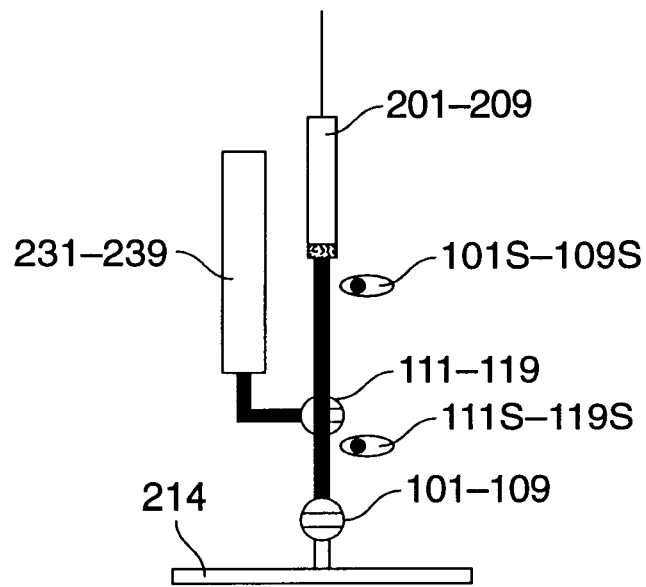

The bottom manifold is then cleared in the manner earlier discussed at step 910. FIG. 21C shows a relevant portion of the reaction vessel bank having a cleared manifold and a column of reagent inside the portion of the tube between a top optical sensor, e.g., 101S, and a valve, e.g., 101. After the bottom manifold is cleared, all valves are again returned to default at step 912. The reagent in the tubes are then pushed up into the reaction vessels through the frits.

To push the reagent into the reaction vessels, Argon valve 122 opens to permit argon from the pressurized delivery system to pressurize the lower manifold. Vent valve 120 also opens.

At step 913, the vortex motor is activated to commence agitating the reaction vessel bank for a predetermined amount of time. The time period is sufficient long to permit the contents within the reaction vessels to mix completely. Generally, a time of about 4 has been found to be adequate, but may vary depending on the type of synthesis.

During the above mentioned mixing period, at step 914, valves 101–109 open for a preprogrammed period of time to flow a small amount of reagent into the reaction vessels. Usually, the reaction vessels are filled and drained repetitively during a synthesis process. Each time the reaction vessels are drained, the beads therein become dry and clump together to form a "bead cake". Step 914 fluidizes the contents of the reaction vessel and dissolves the bead cake. Since vortexing is most effective when the beads are at or near the bottom of the reaction vessel, only a small amount of fluid should be injected. Otherwise, the bead cake may float to the top of the reaction vessel, requiring more time to dissolve it. At step 915, the valves return to default after the predefined time has expired.

At step 916, the remaining portion of the reagent is pushed up into the reaction vessel by opening valves 101–109. Each vessel is filled until its associated sensor 101S–109S detects the absence of a fluid and the control computer turns off that valve. When all sensors 101S–109S are off, all reaction vessels are filled. To improve mixing, the vessel bank is agitated while being filled. As noted before, the reaction vessels may be programmed so as to fill the vessels in parallel or in series by opening all the valves 101–109 at once or sequentially.

Figure 21D:
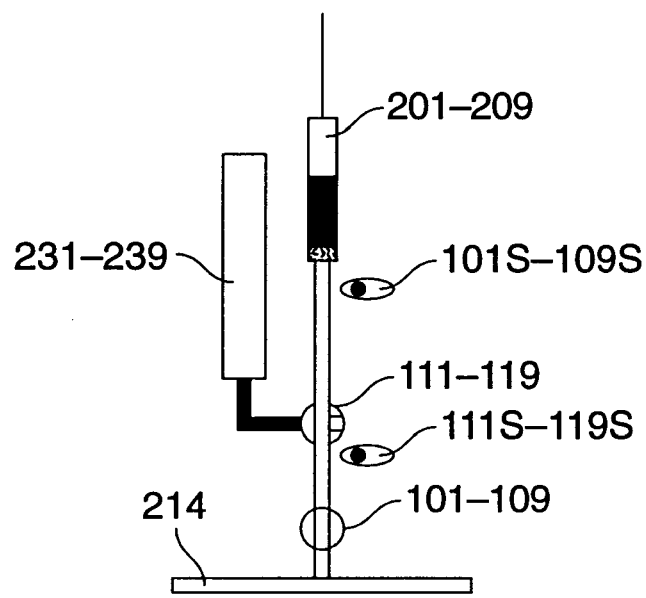

Alternatively, the reaction vessels may be filled without relying on sensors 101S–109S. For example, valves 101–109 may be opened for a preprogrammed time period which is sufficient to fill the vessels to the desired level. A time period of 0.5 seconds to 1 second has been found to be satisfactory. However, this time period may vary according to the number of vessels being used, i.e., the greater the number, the longer the time required. FIG. 21D shows a diagram of the reaction vessel after being filled.

Note that the volume of reagent to be pushed up into the reaction vessels also can be easily changed by varying the length or diameter of tubing between valves 101–109 and sensors 101S–109S. This change can be easily accomplished by substituting the tube which connects a reaction vessel to an injection valve, e.g., valve 111, with a tube having a different length or cross-sectional dimension.

It may also be advantageous in some instances to increase the diameter of reaction vessels themselves. For instance, it may be desirable to simultaneously mix the beads with two or more reagents. Such mixing can occur by following the steps described in FIGS. 21A–21D to introduce the first reagent to the reaction vessels. A second reagent is then introduced to the reaction vessel by repeating the steps described in FIGS. 21B–21D. In so doing, however, an argon bubble will be disposed between the bead suspension and the second reagent due to the argon left in the tubes 241–249 and 271–279 before introduction of the second reagent. To remove the argon bubble from the reaction vessel, the inner diameter of the reaction vessel can be made larger to reduce the height of the bead suspension within the reaction vessel, thereby making escape of the argon bubble through the bead suspension easier. After removal of the argon bubble, the bead suspension and the second reagent are mixed together by vortexing as previously described.

Figure 22:
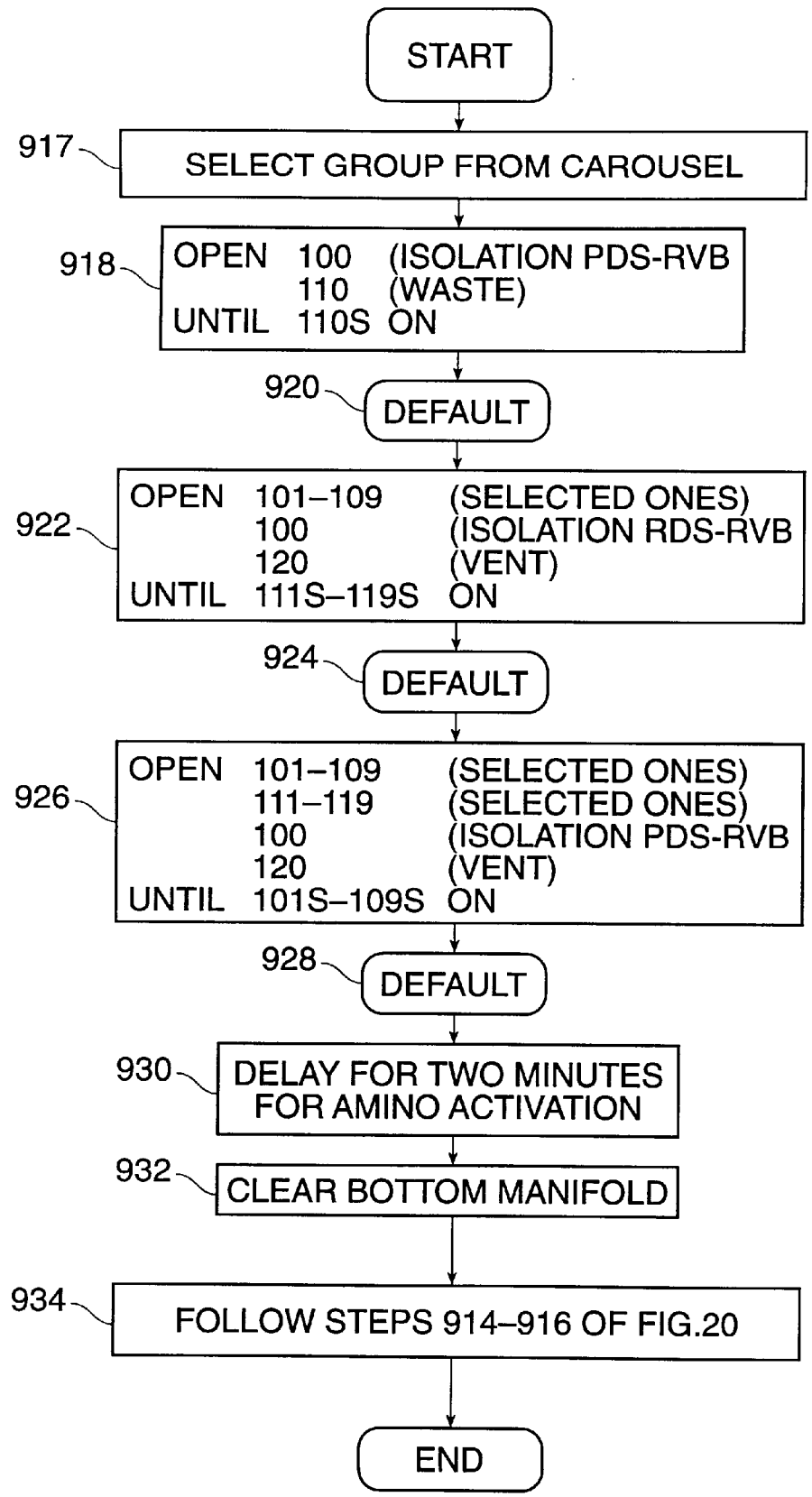
FIG. 22 shows the steps taken by the control computer to introduce amino acid monomers into the reaction vessels.
Figure 23A:
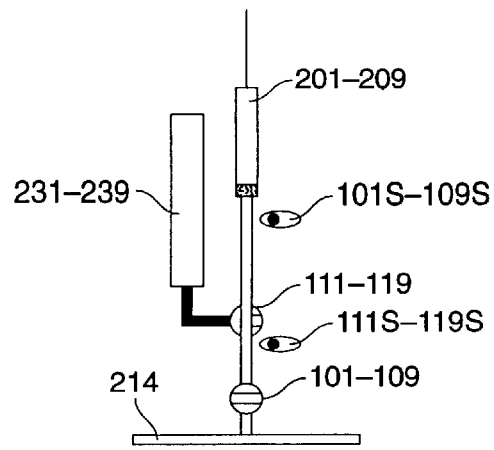
FIGS. 23A–23C schematically illustrate the steps taken by the control computer to introduce amino acid monomers into the reaction vessels.
Figure 23B:
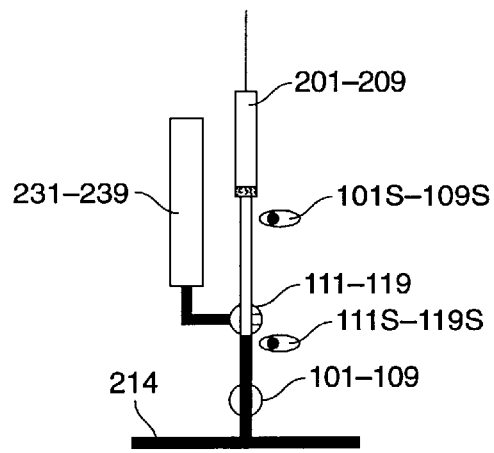
Figure 23C:
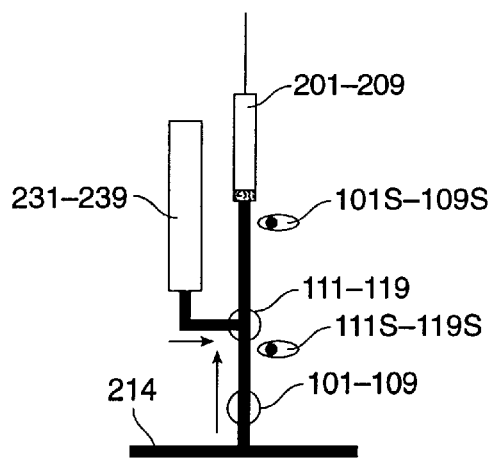

FIG. 22 is a flow chart showing the sequence of commands issued by the control computer to inject activated amino acid reagents into the reaction vessels. FIGS. 23A–23C schematically illustrate the relevant steps of the amino acid injection process. Again, it is assumed that the lower manifold is cleared, i.e., contains only argon, at the start. FIG. 23A shows a diagram of the reaction vessel, the lower manifold, the valves, the sensors, and associated tubes at the start.

An alternative arrangement for the reservoirs 231–239 is shown in FIG. 6A.

For embodiments implementing a rotatable carousel for holding a plurality of groups of reservoirs, the carousel is rotated to align the tubes with the selected group of reservoirs at step 917. Once the appropriate reservoirs are selected, the manifold is filled at step 918 with amino acid activating reagents such as 0.2M HBTU and 0.6M DIEA in a solution of 3:1 DMF to DCM. The manifold is filled in the manner discussed in connection with FIG. 20, i.e., open valves 100 and 110 until sensor 110S is turned on. Thereafter, all valves close at step 920.

The activating reagents then enter the tubes connecting the reaction vessels with the lower manifold. Valves 100 and 120 open to let pressurized activating reagent enter the lower manifold at step 922. Selected ones of valves 101–109 open until the lower optical sensors 111S–119S senses fluid presence. All valves again close at step 924. FIG. 23B graphically shows the presence of fluid in relevant portions of the reaction vessel bank after this initial filling step.

To accomplish the injection, valves 100 and 120 again open to let pressurized activating reagents enter the lower manifold at step 926. Selected ones of valves 101–109 open in parallel to permit a column of pressurized activating reagent to advance up the aforementioned tube. Simultaneously, associated ones of valves 111–119 open to inject amino acid into the upwardly advancing column of pressurized activating reagent and to mix with the activating reagent. FIG. 23C graphically shows this injection step.

When each sensor 101S–109S detects a fluid presence, the control computer turns off a valve 101–109 which is associated with that sensor. When all valves 101–109 lose at step 928, all valves of the reaction vessel bank return to the default mode. The mixture of amino acid and activating reagent is preferably permitted to stay in the aforementioned tube for about two minutes to ensure proper activation at step 930.

Thereafter, the bottom manifold is cleared at step 932 in the manner discussed earlier in connection with FIG. 17. The column of mixture between valves 101–109 and upper sensors 101S–109S are then pushed up into the reaction tubes in the manner discussed in connection with FIG. 20 at steps 913–916.

Figure 24:
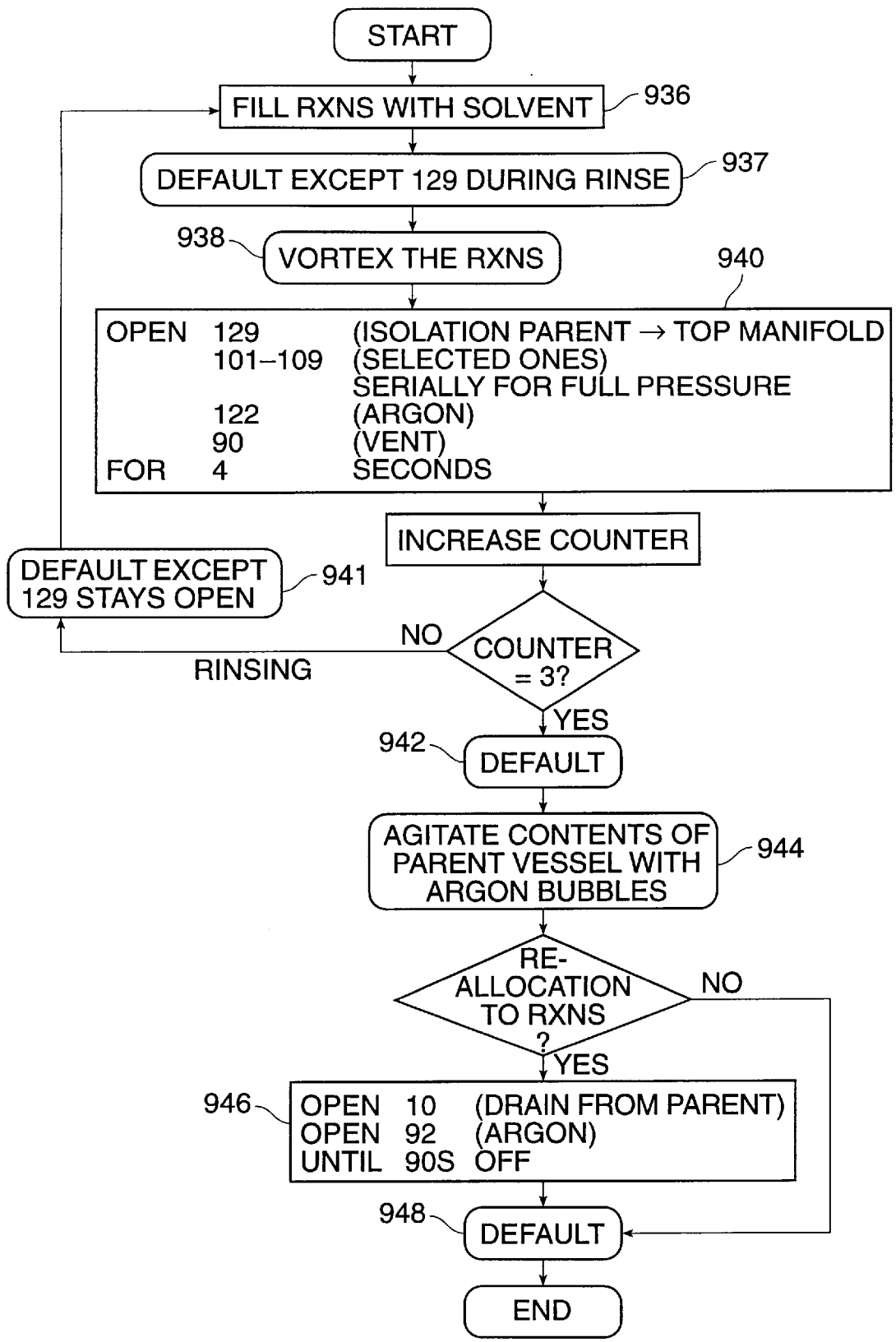
FIG. 24 shows the steps taken by the control computer to transfer the bead suspension from the reaction vessels to the parent vessel for mixing.

FIG. 24 shows the sequence of commands issued by the control computer for transferring the bead suspension within the reaction vessels back to the parent vessel. At the start, it is assumed that the reaction vessels have been drained, and the lower manifold is filled with argon. The reaction vessels are first filled with a solvent at step 936 in the manner discussed in connection with FIG. 20. Thereafter, all valves return to default.

Next, the mixture of beads and reagent is vortexed to create a suspension at step 938. Alternatively, the mixture of beads can be vortexed while the reaction vessels are being filled. Such a process improves the speed of suspension and helps prevent the beads from clumping together at the bottom of the vessel. The contents of the reaction tubes are transferred to the parent vessel at step 940. Valve 122 opens to pressurize the lower manifold with argon. Valve 129 opens to permit the bead suspension to move from the reaction vessel bank to the parent vessel. Selected ones of valves 101–109 open, preferably in series, to permit argon to blow the contents of each reaction vessel up toward the top common manifold and into the parent vessel. The contents of the reaction vessels are thus transferred to the parent vessel serially. Although the above transfer may also be performed in parallel by opening valves 101–109 simultaneously, serial transfer permits argon pressure within the reaction vessel bank to remain high and is therefore preferable. Furthermore, each of valves 101–109 preferably remains open for about four seconds to ensure that substantially all of the contents of a given reaction vessel are transferred to the parent vessel. During this process, valves 90, 122, and 129 remain open.

After the contents of all reaction vessels are transferred to the parent vessel, the reaction vessels may be rinsed and another transfer process may occur. To rinse the reaction vessels, the above steps are repeated, starting with the refilling of the reaction vessels with DMF at step 936. As shown in steps 937 and 941, valve 129 is kept open during the line cycles to prevent damage to the beads and valve 129. The parent vessel preferably has volume for at least three transfers. At the end of the recombination, the parent vessel is preferably drained by opening valves 110 and 91 until the level of fluid in the parent vessel reaches below lower capacitive sensor 90S and turns that sensor off. Three cycles of rinse have been found to be satisfactory.

Thereafter, all valves including valve 129 return at step 942 to the default state. The contents of the parent vessel are agitated at step 944 to mix the beads from the various vessels in the manner discussed in connection with FIG. 20. If the beads are to be removed from the parent vessel, the parent vessel is preferably drained at step 946 by opening valves 10 and 91 until the level of fluid in the parent vessel reaches below lower capacitive sensor 90S and turns that sensor off. All valves are subsequently returned at step 948 to their default state. The mixture containing beads may then be removed from the parent vessel for use.

Alternatively, the beads may be reallocated to the reaction vessels in the manner discussed in connection with FIGS. 21A–21B. Following the reallocation, all valves return to the default off state.

G. Overall Diagram of Software

Figure 25:
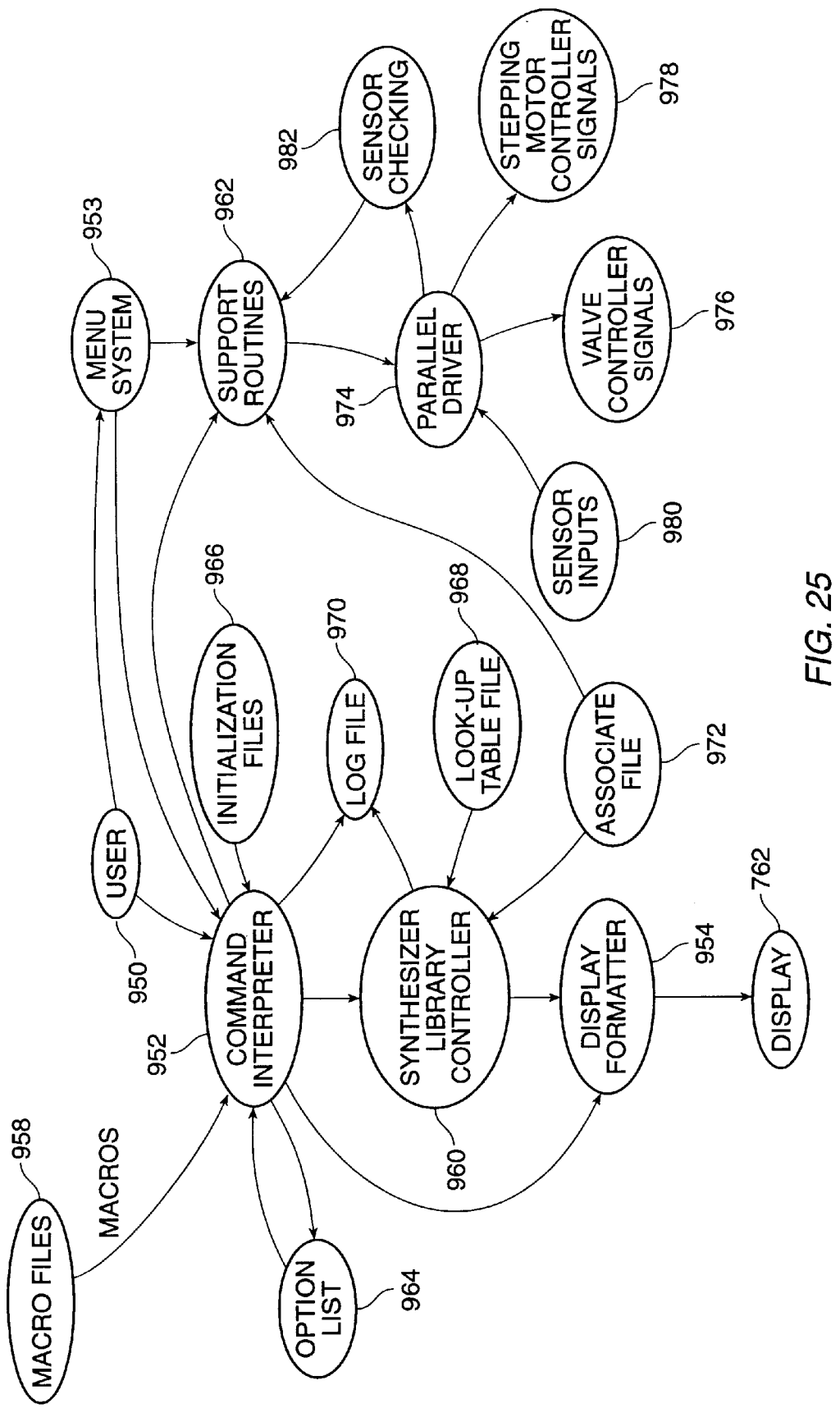
FIG. 25 schematically illustrates the data flow among the major modules of the control software.

FIG. 25 is a flow chart of the source code which is included herein as Appendix I. Module 950 represents the user. A command interpreter 952 accepts the textual commands from the user. Alternatively, the user may enter commands to run the synthesizer using a menu system 953. The commands received by menu system 953 are either converted to a format usable by command interpreter 952, or call a support routine in support routines module 962 directly. Command interpreter 952 also parses the commands entered, textually or otherwise, by the user. Thereafter, the parsed commands call and execute support routines in support routines module 962. Furthermore, the parsed commands are formatted by a display formatter 954 and displayed on a display 762.

Module 958 contains a plurality of macro files. A macro file defines, for example, the sequence of steps that must actually take place to run a synthesis or build a library. At its most basic level, a macro file contains, for example, macros which in turn contains sets of discrete commands for controlling valves and reading sensor information. Macros may utilize other basic macros to perform higher level functions such as draining reaction vessels 201–209.

The macros received by command interpreter 952 from macro files 958 are passed into a synthesizer library controller 960. Synthesizer library controller 960 calls the macros for actual synthesis. For example, one macro may specify the initial global variables that must be set before synthesis begins.

Figure 26:
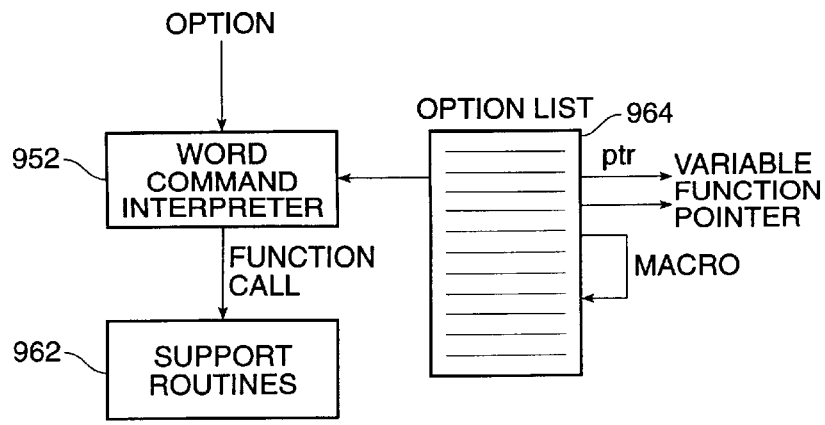
FIG. 26 schematically illustrates the command interpreter structure.

FIG. 25 shows a support routines module 962 for running a variety of support subroutines. One such subroutine is autofill, which is a subroutine for automatically filling the reaction vessels until all sensors are on. Support routines 962 accept inputs from either command interpreter 952 or menu system 953. Option list 964 contain pointers to functions, etc. FIG. 26 shows the inputs and outputs of option list 964 and its relationship with command interpreter 952 and support routines module 962.

There are also initialization files 966 for holding global variables and global settings. Initialization files 966 hold, for example, a value representing the amount of time during which a strike voltage is supplied to a valve to open a closed valve, etc. A lookup table file 968 cooperates with synthesizer command library controller 960 to, for example, permit a monomer to enter appropriate selected reaction vessels. Lookup table file 968 may contain, for example, a listing of each reaction vessel, its corresponding tag monomer, and the list of monomers necessary for synthesizing the desired polymer.

FIG. 25 also shows a log file 970. Log file 970 accepts inputs from command interpreter 952 and synthesizer library controller 960. Log file 970 contains operational data for diagnostic purposes. An entry in log file 970 contains, for example, information relating to the macros called.

An associate file 972 contains a listing of each reaction vessel and its associated valves and sensors. Associate file 972 cooperates with both synthesizer library controller 960 and support routines 962 to simplify the task of addressing each reaction vessel and its associated valves and sensors.

The digital commands outputted by support routines 962 enter a parallel driver 974. Parallel driver 974 may be, for example, PCDIO120-P I/O board 766. Parallel driver 974 outputs valve control signals 976 via its I/O channels to drive the solenoid valves. The valve control signals, as discussed, are further processed by controller circuit 768. Furthermore, parallel driver 974 outputs stepping motor controller signals 978 to control the vortexing stepper motor. Sensor inputs 980 from the optical sensors, the ultrasonic sensor, and the capacitive sensors of the synthesizer are also received by parallel driver 974 for processing by support routines 962 via sensor checking subroutines 982.

Figure 27:
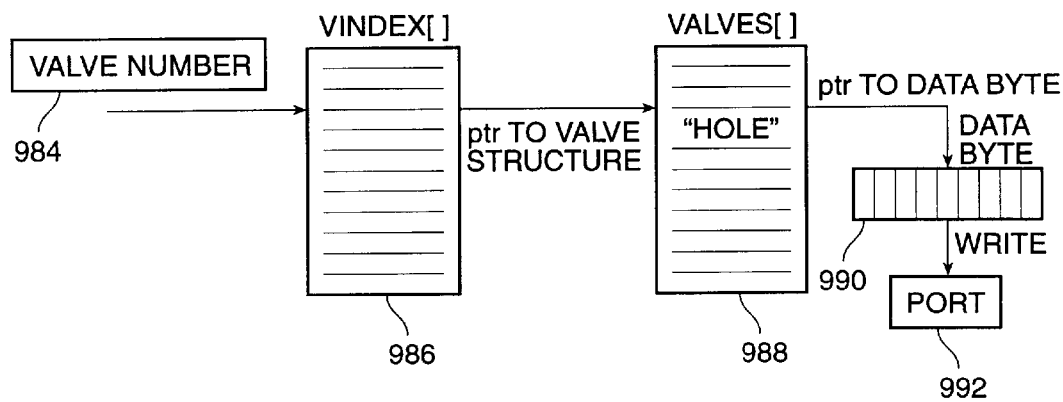
FIG. 27 schematically illustrates the scheme used to access valve data.

FIG. 27 illustrates the data structures necessary to control valves. A valve index VINDEX array 986 accepts a valve number 984 as input and provides a pointer to a VALVES array 988. Each element of VALVES array 988 contains a pointer to a data byte 990. Each data byte 990 contains 8 bits of valve data information. The bit containing valve data information for a given valve is accessible by the address of its data byte 990 and a shift value representing the relative location of that bit within data byte 990. Each bit of data byte 990 may be manipulated to appropriately turn on or off a valve. The valve data information in each bit controls a corresponding valve via output port 992.

Figure 28:
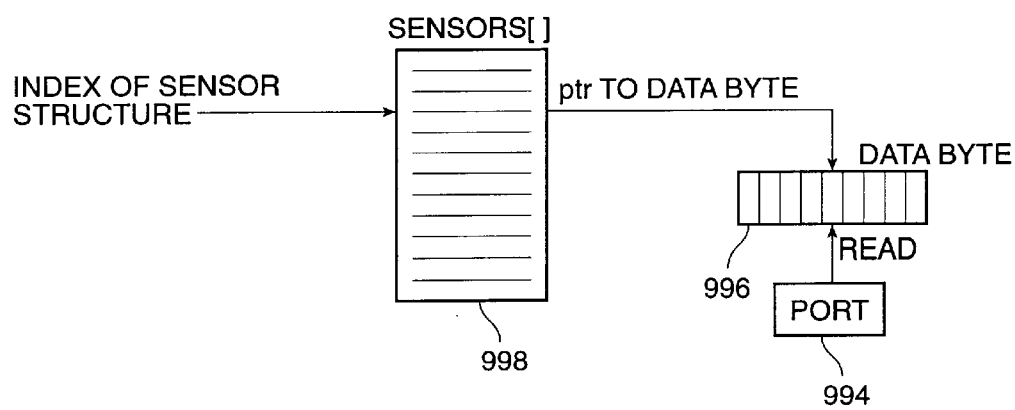
FIG. 28 schematically illustrates the scheme used to access sensor data.

FIG. 28 illustrates the data structures necessary for receiving sensor information from input port 994. The information representing the binary state of each sensor is stored in one bit in a data byte 996. To access the information in data byte 996, a sensor number is used to access SENSOR array 998. Each element of SENSOR array 998 contains a pointer to an appropriate data byte. Each data byte 996 contains 8 bits of sensor data information. The bit containing valve data information for a given valve is accessible by the address of its data byte 996 and a shift value representing the relative location of that bit within data byte 996.

H. Windows Interface

The control software may incorporate a Windows-type interface or workspace. Generally, the Windows interface is a rectangular, graphical user interface (GUI) providing one or more windows for display on the screen. Additional window objects may be displayed in various sizes and formats (e.g., tiled or cascaded), as desired. At the top of the window is a menu bar with a plurality of user-command choices, each of which may invoke additional submenus and software tools for use with application objects. The window also includes an area for displaying and manipulating screen objects. This area is a workspace or viewport for the user to interact with data objects which reside in the memory of the control computer system, The windows interface includes a screen cursor or pointer for selecting and otherwise invoking screen objects of interest. In response to user movement signals from a pointing device such as a mouse, the cursor floats (i.e., freely moves) across the screen to a desired screen location. During or after cursor movement, the user may generate user-event signals (e.g., mouse button "clicks" and "drags") for selecting and manipulating objects, as is known in the art. For example, the window may be closed, resized, or scrolled by "clicking on" (selecting) screen components. Keystroke equivalents, including keyboard accelerators or "hot keys", are provided for performing these and other user operations through the keyboard. Thus, a Windows interface provides a more intuitive approach to interacting with the control computer.

Underlying the Windows interface is a message or event-driven architecture. This model is perhaps best described by contrasting its operation with that of a modal or sequential architecture that has been traditionally employed, as exemplified by the command interpreter in FIG. 25. In this manner, the reader may appreciate the added flexibility as well as complexity of an event-driven system.

A modal program comprises a series of discrete operating blocks or modes having a well-defined beginning, middle, and end. Thus, the program follows a fairly rigid sequence of operation with each step necessarily being completed before the program proceeds to the next step.

While a modal program is relatively easy to design and implement, it is generally not easy to use. The design certainly ensures that all required information is entered, but only at the expense of forcing users to operate in a manner dictated by the program. Specifically, since the program is built around a pre-arranged set of modes, a user cannot get from one mode to another without first completing a previously-required mode. Any deviation from this sequence by the user is simply not permitted. This inflexibility of the modal programs may be inefficient for handling real-world tasks.

On the other hand, an event-driven architecture eschews a pre-selected sequence, opting instead for an "event loop." The event loop is a centralized mechanism for processing messages about user and system events. It includes an event queue and mechanisms for retrieving and dispatching messages to various window classes.

Messages are how the operating system manages and synchronizes multiple applications and hardware events, such as clicks of a mouse or presses of a keyboard, which in MS-Windows are converted to messages by Windows event handlers. From a programming perspective, a message is simply a data structure containing information about a particular event. The message structure may include a message identifier which serves as a symbolic constant for a particular event. For example, messages from a window object might include information about creating, closing, moving, and re-sizing the window. Additional event data are available as message parameters; the exact interpretation of a given parameter varies with each event type represented. Input messages are collected in a system-wide queue and then directed to the proper window. These messages, along with timer and screen paint (screen refresh) messages, are passed to the target application(s) of interest.

A mechanism is provided for retrieving messages from the system queue and dispatching them to the appropriate application which, in turn, may proceed to process any message that arrives. Each window belongs to a particular window type which defines certain characteristics common to all windows of that type. Associated with each type is a Windows function which processes all messages sent to windows of its type. An application queue is provided where Windows may place messages that belong to a specific application. When the application is ready to receive input, it simply reads the awaiting messages. If none are found or if there exists a message for other applications with higher priority, Windows passes control to the other applications.

The general mechanism for retrieving and dispatching messages in an event-based system, such as Microsoft®

Windows™, is known in the art; see, e.g., Petzold, C., *Programming Windows*, Second Edition, Microsoft Press, 1990 and Custer, H., *Inside Windows NT*, Microsoft Press, 1993. Additional information can be found in Microsoft's Window Software Development, available from Microsoft Corp. of Redmond, Wash. The disclosures of each of the foregoing are hereby incorporated by reference for all purposes.

Figure 33:
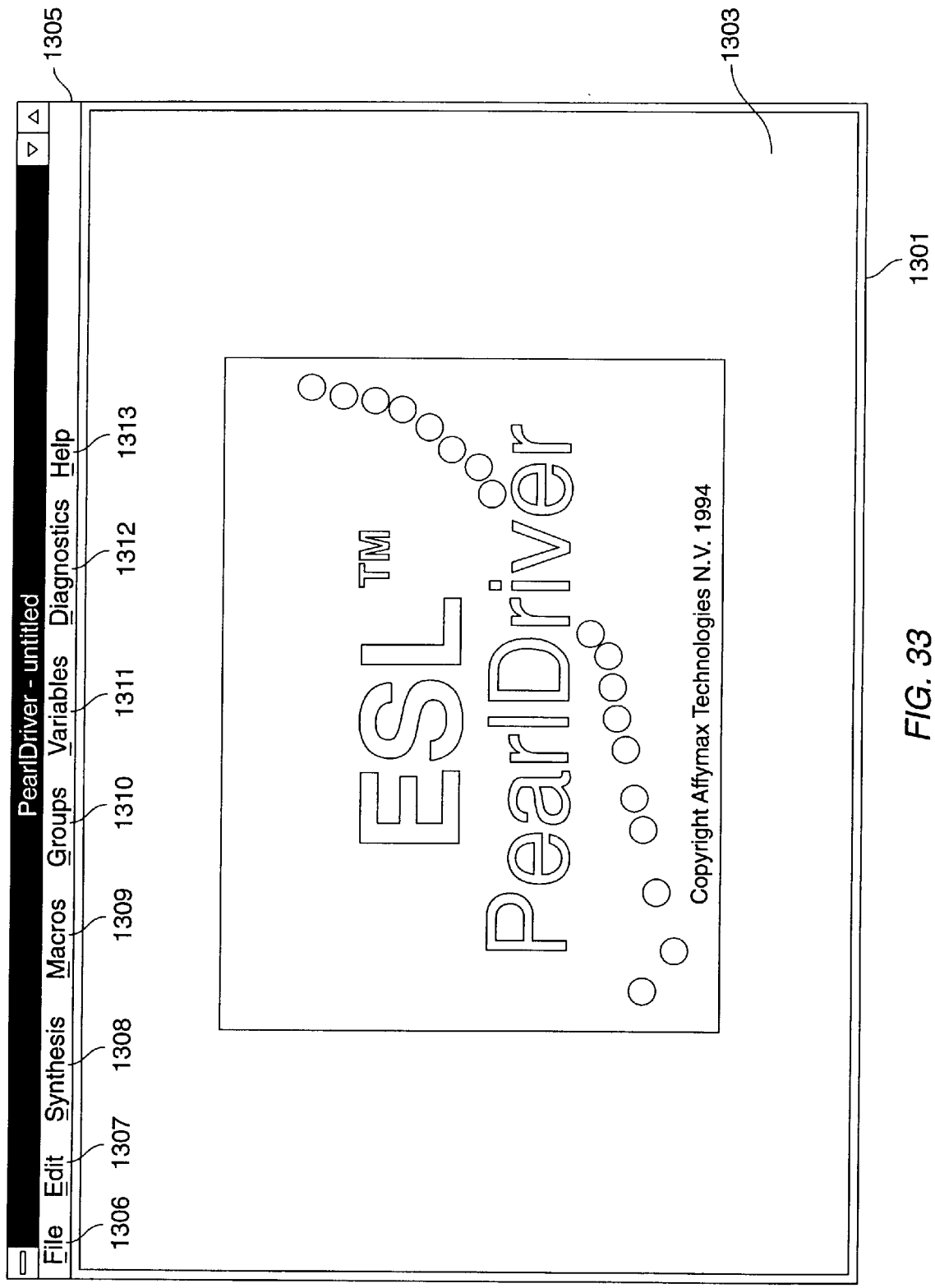
FIG. 33 illustrates a graphic user interface ("GUI") as implemented on the control computer. As shown, the GUI includes a rectangular window 1301 with a workspace 1303. At the top of the window is a menu bar 1305 with user command choices 1306–1313. Each of these command choices include additional submenus for controlling the operations of the synthesizer. A user can program the synthesizer by selecting the appropriate command choice with the mouse.

FIG. 33 illustrates a GUI as implemented on the control computer. The GUI includes a rectangular window 1301 with a workspace 1303. At the top of the window is a menu bar 1305 with user command choices 1306–1313. Each of these command choices include additional submenus containing commands for controlling the operations of the synthesizer. These command choices offer a user the flexibility of either performing a synthesis automatically or manually by invoking the appropriate commands with the mouse.

The GUI is designed with the intention of being a user friendly environment, thus minimizing efforts required for programming the synthesizer. For example, a dialog box object or a set of dialog box objects is associated with each command. When a command is invoked, the appropriate dialog objects are displayed in the workspace and interactively prompt the user to enter the necessary information. A Help command 1313 provides information to assist a user through the process. Using the dialog objects, the user may program the synthesizer without using traditional text commands.

Figure 34:
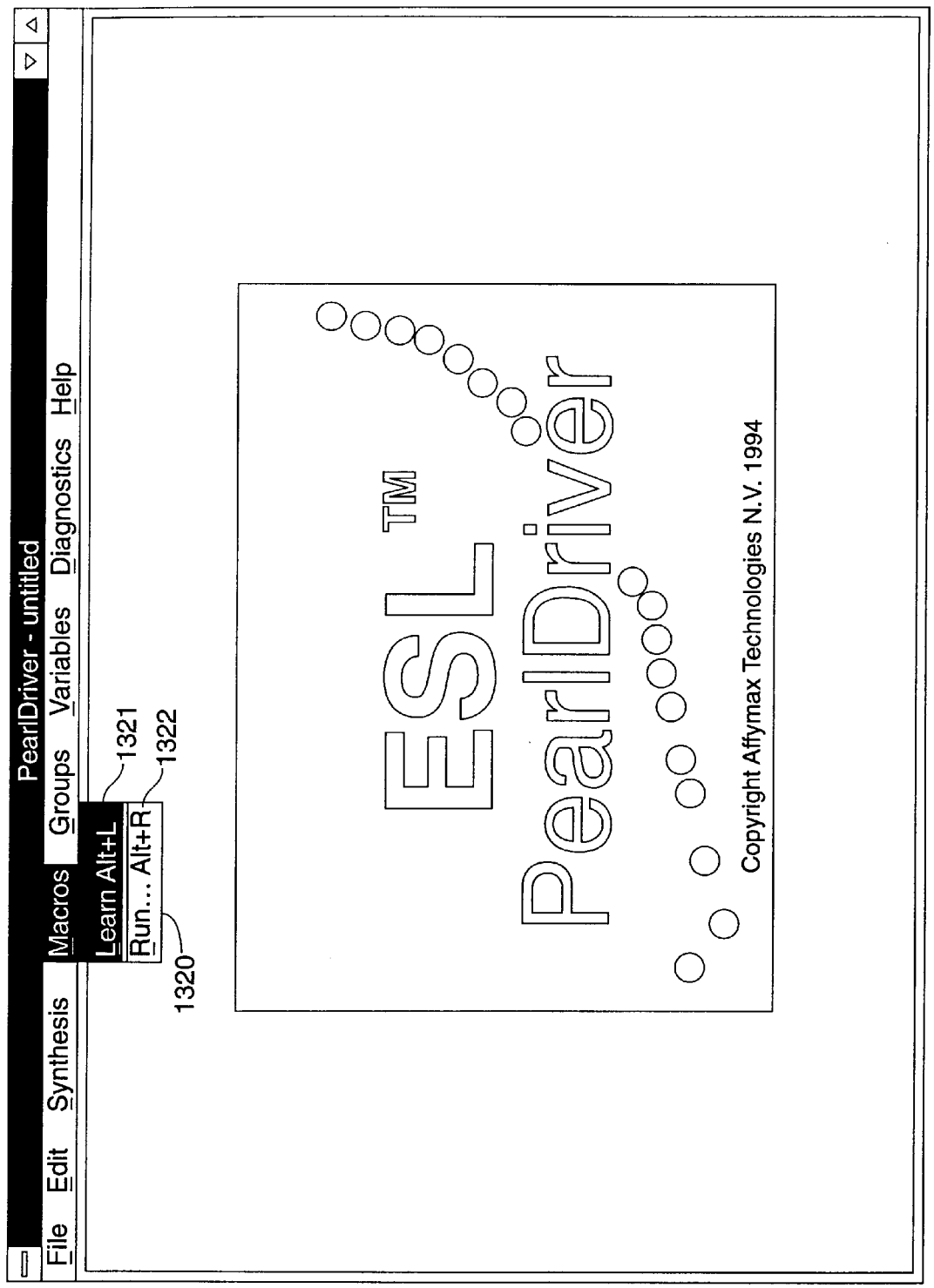
FIG. 34 depicts the GUI, showing the submenu options in the Macro menu.

FIG. 34 illustrates a submenu 1320 that is associated with the Macros option. A user may invoke either a Learn or Run command by clicking the mouse on submenu item 1321 or 1322, respectively. In the Windows environment, a macro is an object that contains a set of discrete commands, such as those discussed in connection with FIGS. 16–24, for controlling the synthesizer. Using the Learn command 1321, the user can define a macro to perform specific functions. The submenu may also identify the keystrokes assigned to invoke the available commands. For example, "Alt+L" is used to execute the Learn command.

Figure 35:
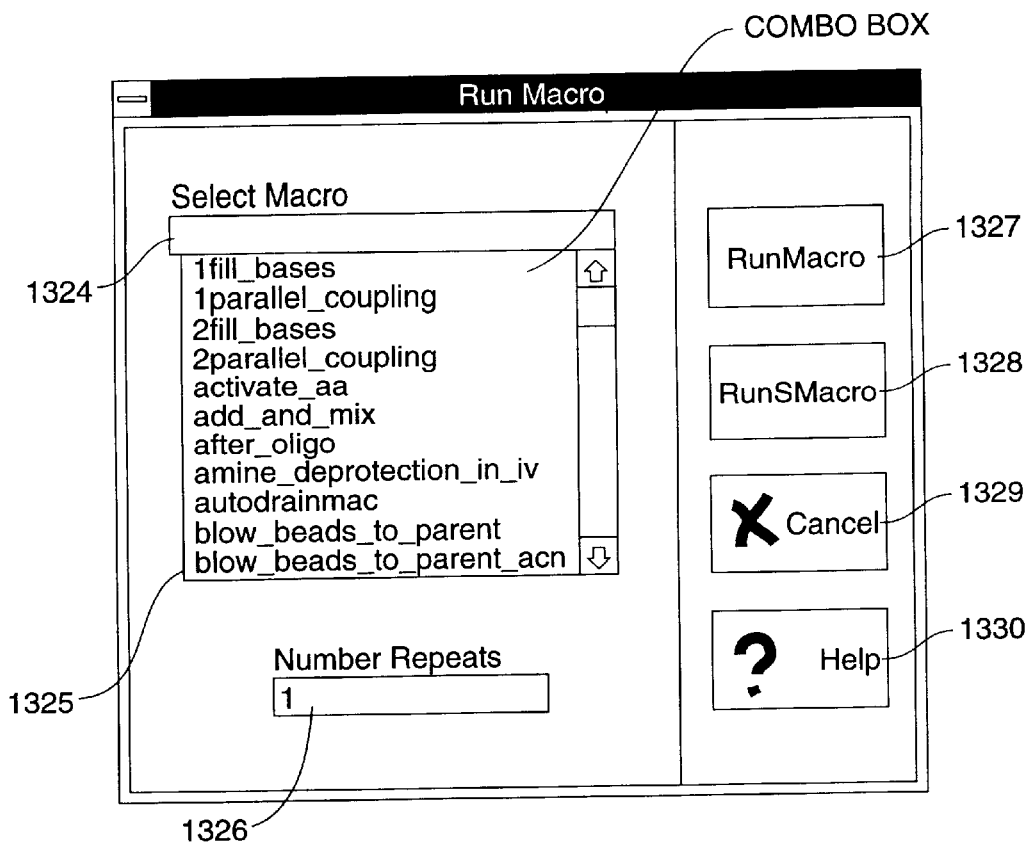
FIG. 35 depicts the dialog box for running a macro.

Once the macro is "learned," the Run command 1322 may be selected to execute the learned macro or any other macros which have been previously defined. FIG. 35 exemplifies a dialog box object that is displayed when the Run command is invoked. The dialog box object includes an area 1325 (combination box) which lists the available macros. To select a macro, the user enters the name of a macro in a Select Macro space 1324. Alternatively, the user may scroll, by clicking and dragging the mouse, until the desired macro file in space 1325 is selected. The user then enters the number of times the macro is to be repeated in space 1326. Finally, to run the macro, the user clicks the mouse on a RunMacro button 1327 or a RunSMacro button 1328. The RunSMacro command instructs the system to perform the macro functions serially, i.e., one reaction vessel at a time. The Cancel choice 1329, when selected, exits the dialog box object 1326. A Help choice 1330 provides information regarding the different choices in the dialog box object.

Figure 36:
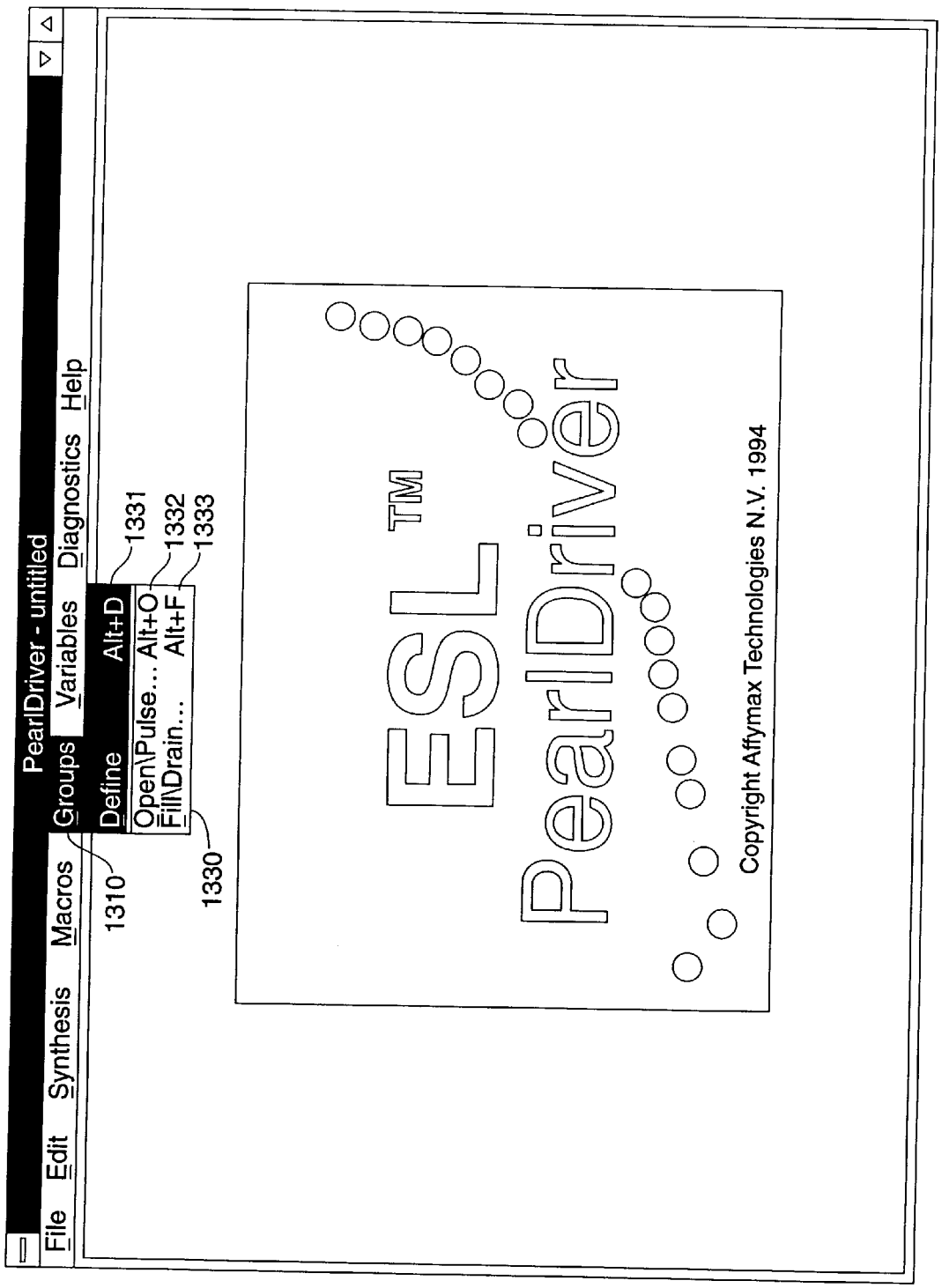
FIG. 36 depicts the GUI, showing the submenu options in the Groups menu.

FIG. 36 illustrates a submenu 1335 which is displayed when the Groups option 1310 on the menu bar is chosen. Submenu 1330 includes a Define command 1331 which is employed to define a set of valves associated with a group of specific reaction vessels. Once defined, the valve group is stored as a group object in memory. The computer's memory may contain many group objects, each defining a unique valve group.

Submenu 1330 also includes an Open/Pulse command 1332 to fill and drain the selected reaction vessels for a predefined time period. When invoked, a dialog object box associated with the Open/Pulse command is displayed. The dialog object box, somewhat akin to the one illustrated in FIG. 35, contains a combination box that lists the available group objects from which to choose. The user selects the desired group and inputs the desired time period to pulse the selected valves in an assigned space provided by the dialog object. To fill the reaction vessels, the user clicks an Open button to indicate that the valves are to be opened. Next, the user initiates the filling process by clicking either a Pulse or SPulse (to fill the reaction vessels serially) button. To drain the reaction vessels, the user clicks a Close button and either the Pulse or SPulse button.

The user, using a Fill/Drain command 1333, can fill or drain the vessels automatically using sensors. The Fill/Drain command, when selected, displays a dialog box object similar to that of the Open/Pulse command. The user selects the group of valves and clicks either an AutoFill or SAutoFill button to perform a fill function or an AutoDrain or SAutoDrain button to empty the reaction vessels. In some embodiments, a Time Delay option may be provided to delay the valves from being closed or opened after triggering the sensors. This function is particularly useful in situations where the reaction vessels are not quite at their desired levels when the sensors are activated. By setting the delay option with a specific delay period, the reaction vessels can be filled appropriately. As can be seen, the commands associated with the Group menu afford the user flexibility in choosing combinations of reaction vessels to employ during synthesis.

Figure 37:
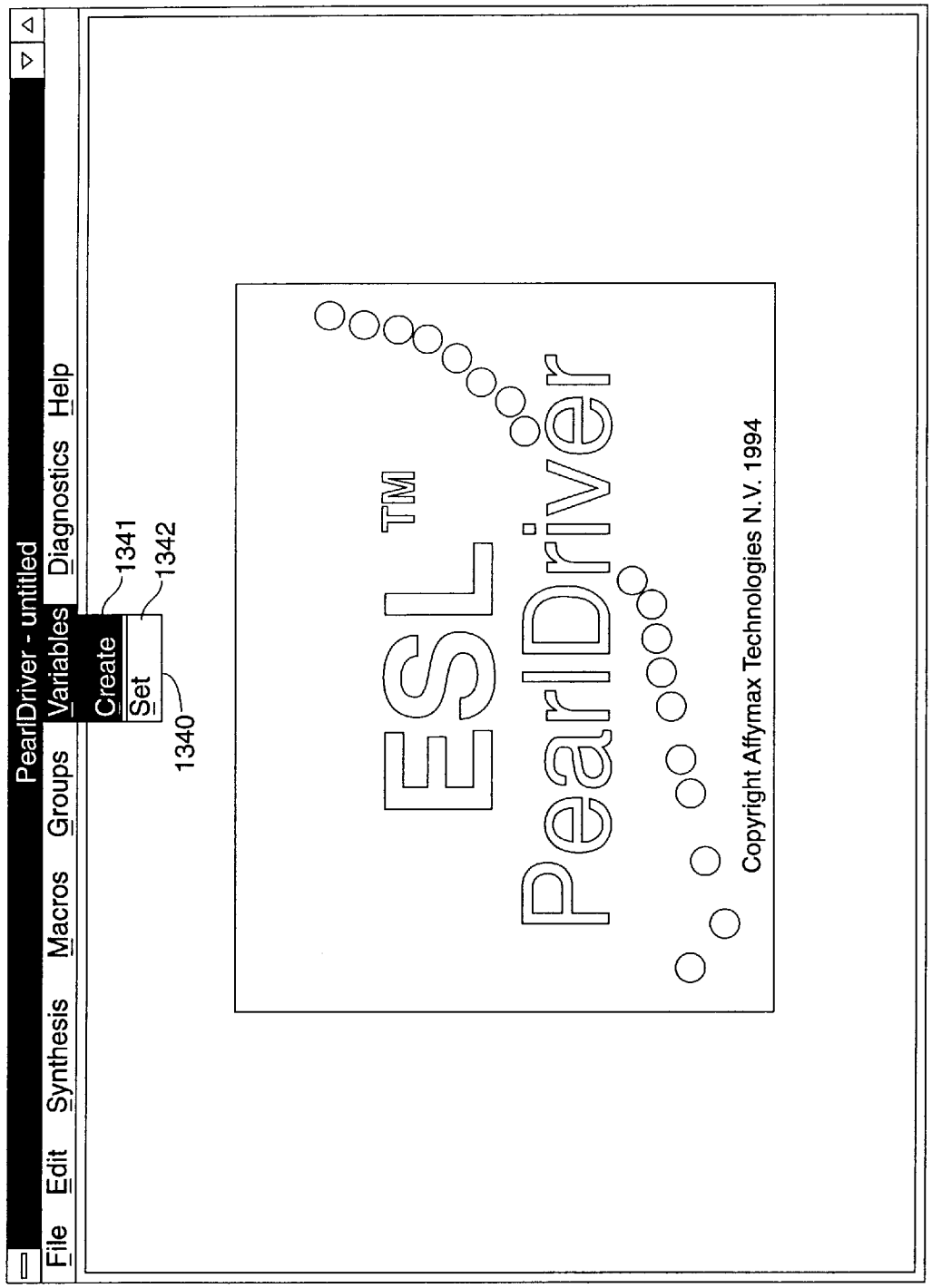
FIG. 37 depicts the GUI, showing the submenu options in the Variables menu.

FIG. 37 illustrates a submenu 1340 containing the options available for the Variables menu selection. A create command 1341 defines a variable which may be implemented in the macros. Variables are typically employed, for example, in situations where the value, such as time, may vary from one synthesis to another. Instead of creating a macro for each time value, a variable is simply defined to correspond to time. The variables are set to the desired value before each synthesis cycle using the set command 1342.

Figure 38:
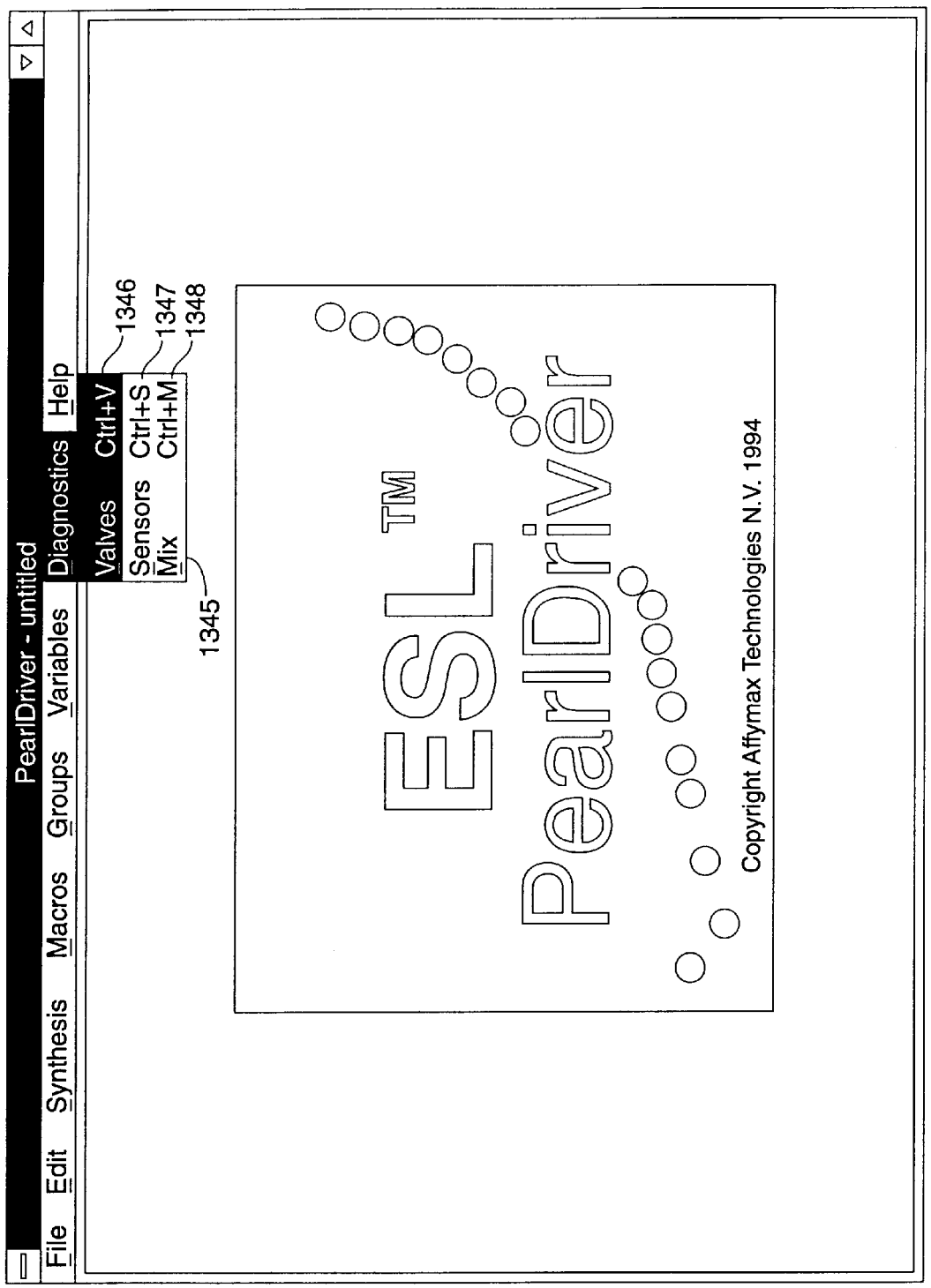
FIG. 38 depicts the GUI, showing the submenu options in the Diagnostics menu.

FIG. 38 illustrates a submenu 1345 that is associated with the Diagnostics option. Submenu 1345 includes Valves 1346, Sensors 1347, and Mix 1348 commands to gives a user intimate control of the synthesizer and access to information regarding the synthesizer for diagnostic purposes. The Mix command 1348, when selected, activates the vortex motor to mix the reaction vessels for a period of time as specified by the user.

Referring to FIG. 39, a Valve Diagnostic dialog box object 1390 is displayed when the Valves command is selected. The user, via dialog box object 1390, may control the operations of any valve in the synthesizer by selecting the entry with which the desired valve corresponds. For example, Valve 100 in Bank 1 is opened by clicking the cursor on ox 1391. For convenience, all the valves may be closed by selecting the Close All command 1397. A Cancel command 1398 closes the dialog box object 1390.

FIG. 40 illustrates a Sensor Diagnostics dialog box object 1391 corresponding to the sensor command. As shown, Dialog box object 1391 contains a box 1396 associated with each sensor. Boxes 1396 inform the user of the status of the corresponding sensors. For example, if a box has an "X" in it, this would indicate that the sensor with which it is associated is on. Conversely, an empty box would indicate that the sensor is off.

Figure 41:
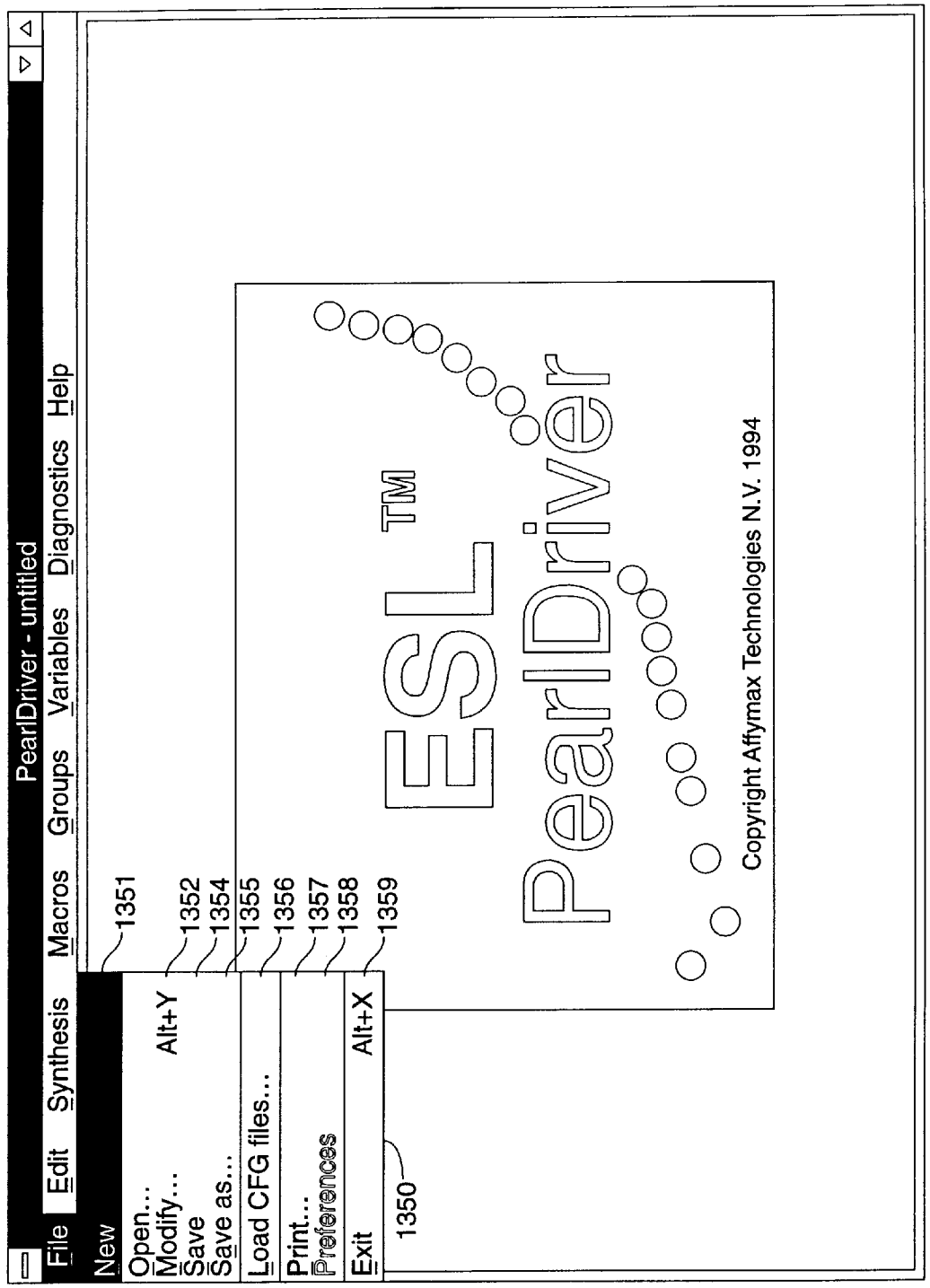
FIG. 41 depicts the GUI, showing the submenu options in the File menu.

FIG. 41 illustrates a submenu 1350 that is displayed when the File option is selected. A New command 1351 creates a new synthesis setup file for carrying out a synthesis and a Modify command 1352 allows a user to select a preexisting synthesis file for editing. Once the synthesis setup file is completed, the user invokes either the Save 1354 or Save As command 1355 for saving the file in memory. A Print command 1357 prints the selected synthesis file. A Print Setup command 1358 configures the printer to desired mode, such as printing the file in landscape mode. An Exit command 1359 is invoked to leave the File option.

In some instances, such as prior to each synthesis, or when a new valve group is selected, the user may wish to configure the system by invoking the Load CFG files command 1356. The system loads the appropriate files to inform which are the appropriate valves to use. In effect, CFG files map or "associate" the valves with each selected reaction vessel.

Figure 42:
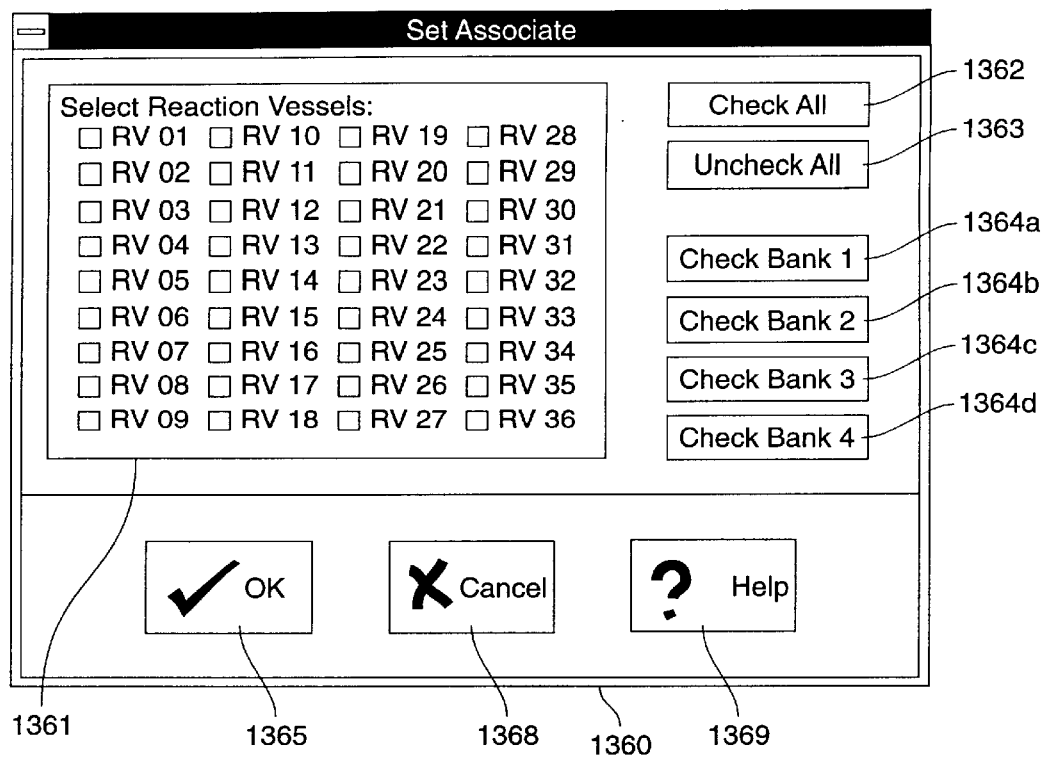
Figure 43:
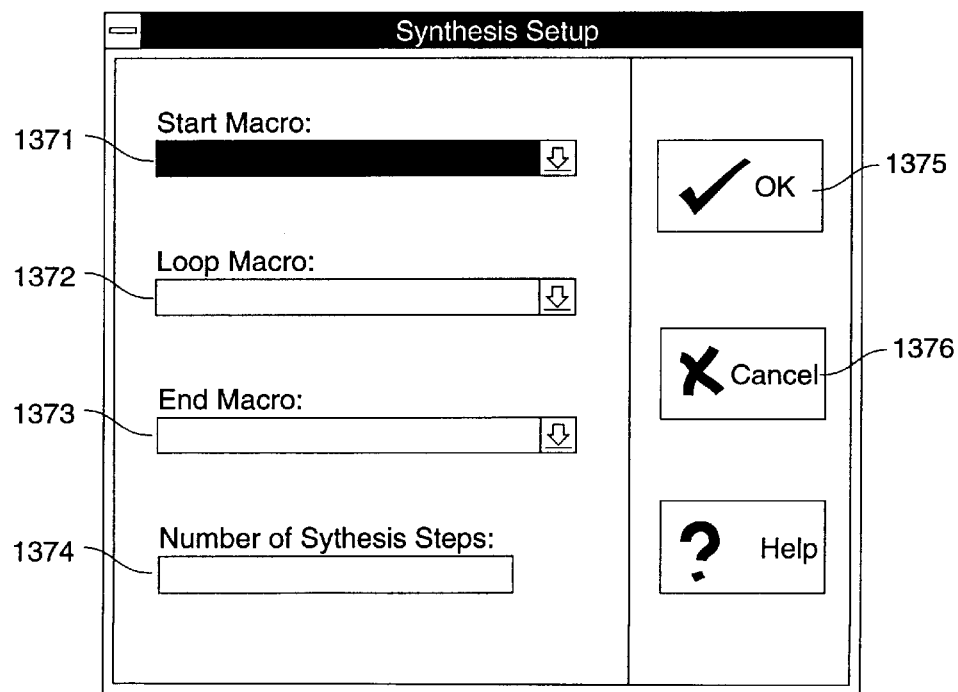

FIGS. 42-44 illustrate the dialog objects used in creating and modifying a synthesis setup file. Referring to FIG. 42, a Set Associate dialog box object 1360 allows the user to select the desired reaction vessels by checking the appropriate boxes contained in space 1361. For convenience, a Check All button 1362 and Uncheck All button 1363 are provided to easily select or de-select all the reaction vessels. Check Bank buttons 1364a-1364d allow the user to select all the reaction vessels belonging to a specific bank. A Cancel button 1368, when selected, aborts the synthesis setup process. A Help button 1369, as previously explained, provides information to assist the user through the process. To continue the synthesis setup process, the user clicks the OK button 1365 which closes the Set Associate dialog box object and displays a Synthesis Setup dialog box object.

FIG. 43 illustrates the Synthesis Setup dialog box object 1370 with which a user defines a Start Macro 1371, a Loop Macro 1372, and an End Macro 1373 for the synthesis. The Start Macro and End Macro, for example, include commands for washing the reaction vessels before and after each synthesis process. The Loop Macro contains commands to perform a synthesis. These commands include injecting the selected reaction vessels with amino acid building blocks and oligonucleotides, pooling the contents of the reaction vessels in the parent vessel and mixing them to form a bead suspension, and distributing the bead suspension to the selected reaction vessels. The injecting, pooling, and distributing steps constitute one synthesis cycle. The synthesis cycle is repeated according to the value entered in the Number Synthesis Steps parameter 1374. Once the Macros are defined, the user saves the contents of the Synthesis Setup dialog box object and continues the setup process by clicking an OK button 1375. Again, the user may abort the process by clicking a Cancel button 1376.

FIG. 44 illustrates the Amino & Oligo Setup dialog box object 1380. As shown, the box contains entries 1381 associated with each reaction vessel. The user enters the desired amino acid symbol and oligonucleotide code in the entries. For example, if the entry for reaction vessel 1. (RV01) contains "V ATGCCGA", this causes the synthesizer to inject amino acid V and oligonucleotide ATGCCGA into reaction vessel 1. After the appropriate codes are entered, the user clicks the OK button 1382 to complete the setup process. A Cancel button 1383 is provided to abort the process. As can been seen, a synthesis library can easily be created using the synthesis setup procedure.

Figure 45:
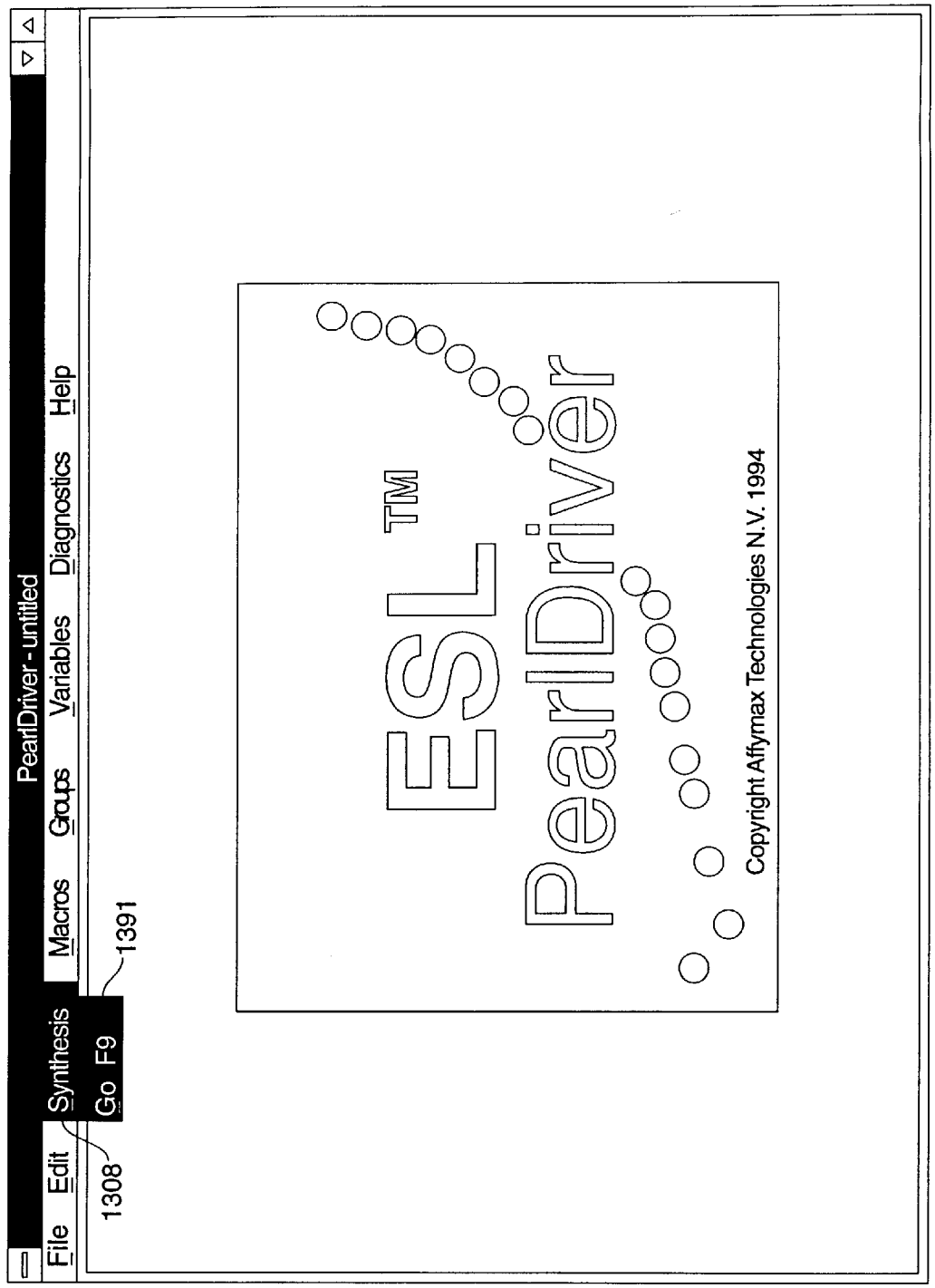
FIG. 45 depicts the GUI, showing the submenu options in the Synthesis menu.

Once the synthesis setup is completed, the user may initiate the synthesis process. Referring to FIG. 45, the user first selects the Synthesis option 1308 and then the Go command 1391 to begin the process. As an alternative, a user may build a single macro to perform functions similar to those saved in the synthesis files.

Figure 46:
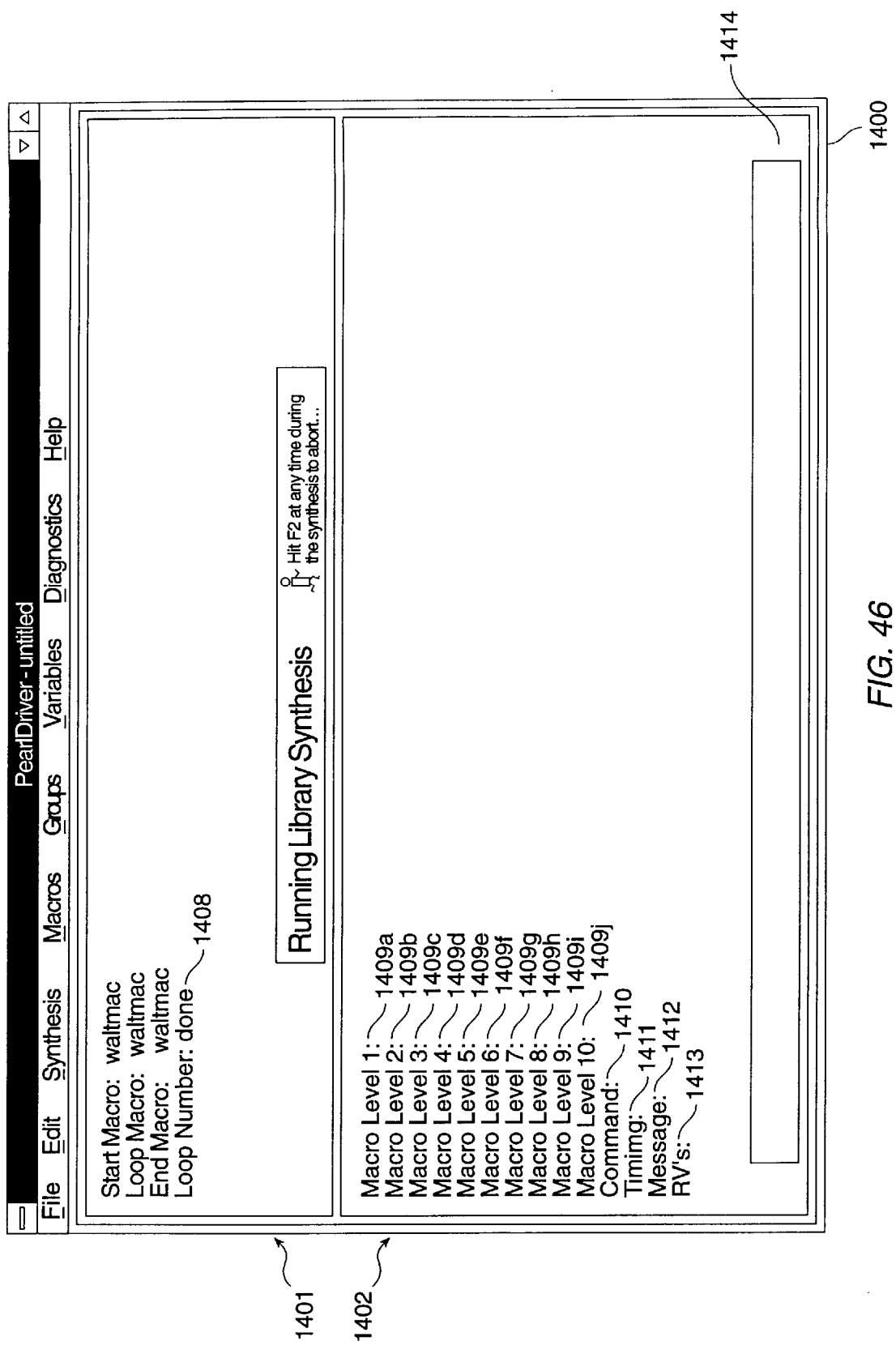
FIG. 46 depicts the status display during a synthesis or macro execution.

Referring to FIG. 46, the GUI displays a status screen 1400 during the synthesis or macro execution. As shown, the status screen is divided into two separate areas 1401 and 1402. The first area 1401 displays information relating to the synthesis. For example, the names of the Start Macro, Loop Macro, and End Macro are listed. Additionally, a Loop Number line 1408 informs the user as to the number of loops remaining in the synthesis.

The second area 1402 displays the filename of the Macro currently being executed. As previously described, a macro may be nested with other macros to perform higher level functions. The status screen may be designed to list up to 10 nested levels 1409a-1409j of macros being called. A Command line 1410, a Timing line 1411, Message line 1412, and RV's 1413 line may be provided to display additional status or configuration information. For example, the Command line may show which macro command is being executed; the Message line, when applicable, displays a text message as preprogrammed by the user. The Timing line displays the amount of time that remains in which the valves are opened or closed. The RV's line informs the user which reaction vessels are used. A Time to Complete bar 1414 informs the user as to the percentage of time remaining before the synthesis is completed.

Figure 47:
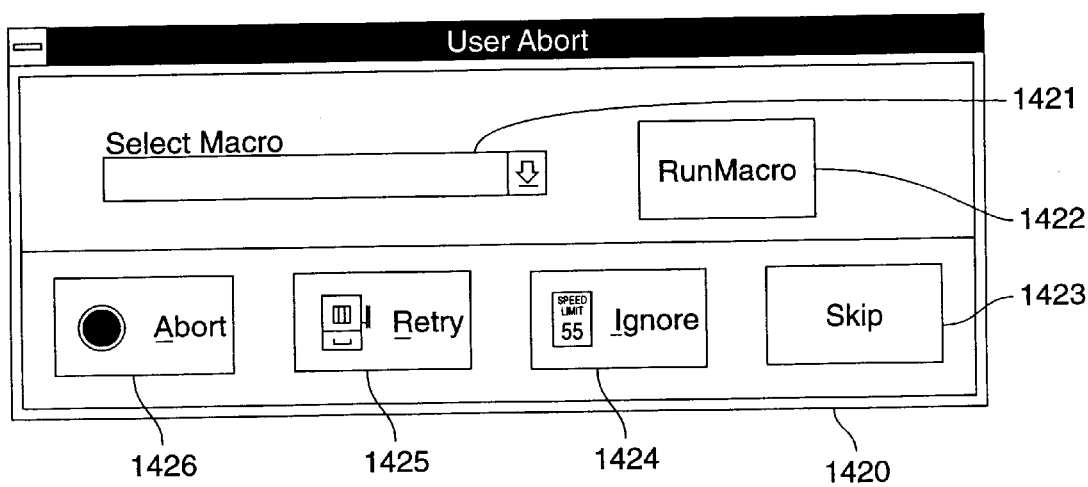
FIG. 47 depicts the User Abort dialog box.

At anytime during synthesis or macro execution, the user may switch into the "User Abort" mode by pressing a preassigned function key, i.e. F12. The User Abort mode allows the user to pause and execute macros that are not defined as part of the synthesis without having to abort the synthesis process. When invoked, the system temporarily pauses execution and displays the User Abort dialog box object 1420, as illustrated in FIG. 47. At this point, the user may insert any macro for execution. This can be done by typing the name of the desired macro in a Select Macro box 1421 and clicking the mouse on a Run Macro button 1422.

The User Abort dialog box object also provides an Ignore button 1424 which enables the user to continue the synthesis process as if the system had never entered into the User Abort mode. A skip option 1423 instructs the system to first skip over the current command in the macro before continuing the synthesis. A Retry button 1425 causes the system to execute the current macro from the beginning. An Abort button 1426 allows the user to cancel the synthesis.

Figure 48:
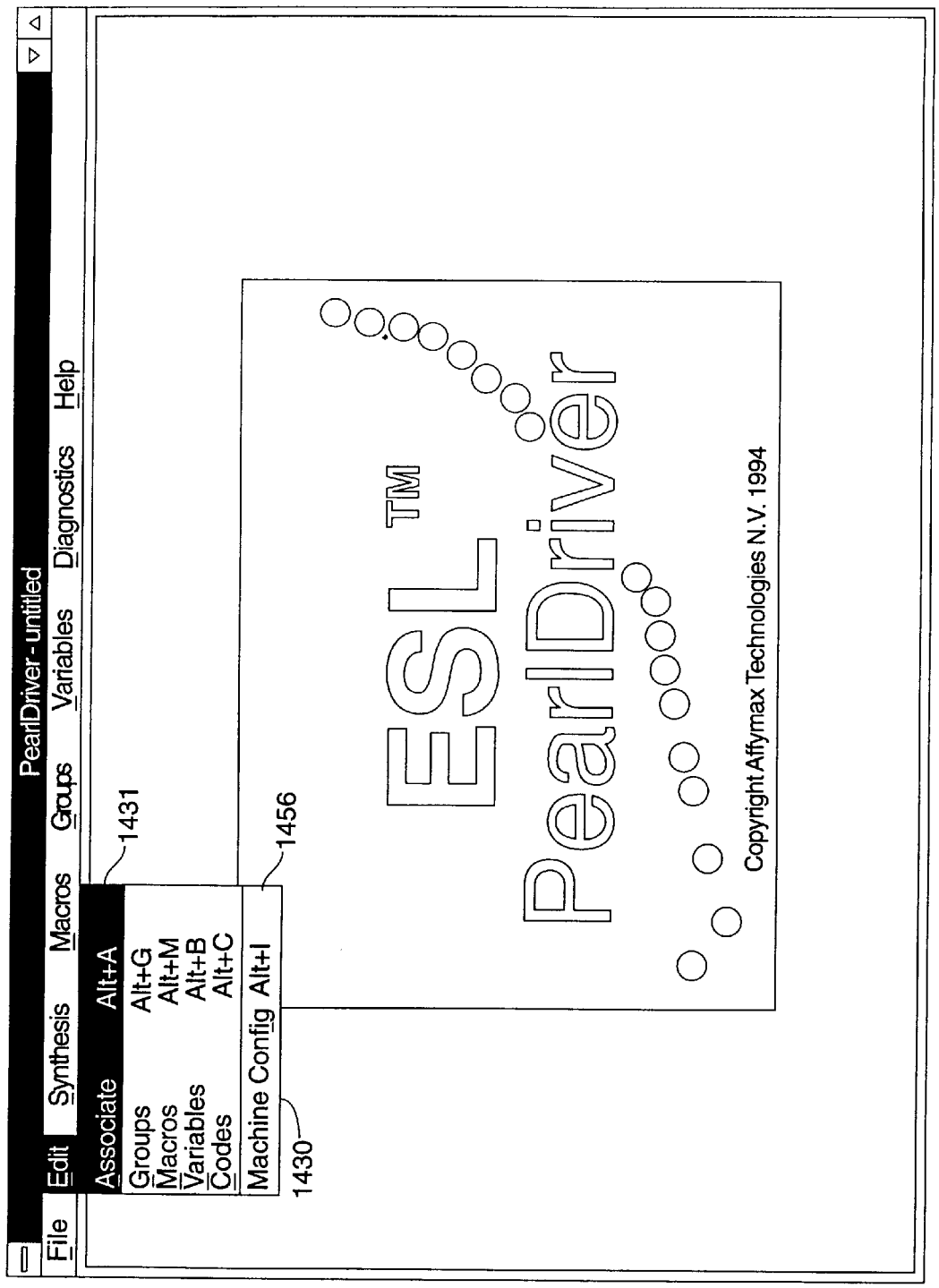
FIG. 48 depicts the GUI, showing the submenu options in the Edit menu.

FIG. 48 illustrates a submenu 1430 associated with the Edit command. The Edit command permits the user to easily access and modify the various objects by selecting the appropriate items listed in the submenu. An Associate command 1431, when selected, displays the dialog box object which lists the Set Associate objects stored in memory. By selecting the desired object, the Set Associate dialog box object is displayed. At this point, the user may edit the contents of the dialog box object with the mouse. When finished, the user clicks the OK button and the modifications are saved. Likewise, the user may edit the Group, Macro, Variable, and Code objects by selecting the desired object. The selected objects are then placed in an editor, allowing the user to modify the text.

As previously mentioned, the sensors may be inadvertently triggered by the presence of a drop of liquid. This may be a problem, particularly when the solution used during the synthesis cycle contains a high concentration of bubbles. To avoid or mitigate unintentional triggering of the sensors, their sensitivity may be programmed.

The sensors are programmed using a Machine Config command 1456. This command displays a Config dialog object box containing several entries, Fill %, Drain %, TimeOut %, and PtsAve. The Fill % specifies the percentage that the sensor remains on to determine when the reaction vessels are full. For example, if 80% is entered, the sensor must be on 80% of the time that it is read. The Drain % specifies the percentage that the sensor remains off to determine when the reaction vessels are empty. As an example, if 20% is entered, the sensor must be off 80% of the time that it is read. Timeout specifies the time period to delay before the sensors are switched on or off. PtsAve specifies the number of points or readings to use to determine the percentage of time that the sensors are on or off. The user may also specify the sensor or group of sensors from which to read. Thereafter, the user clicks an OK button which automatically configures the system according to the parameters.

Figure 49:
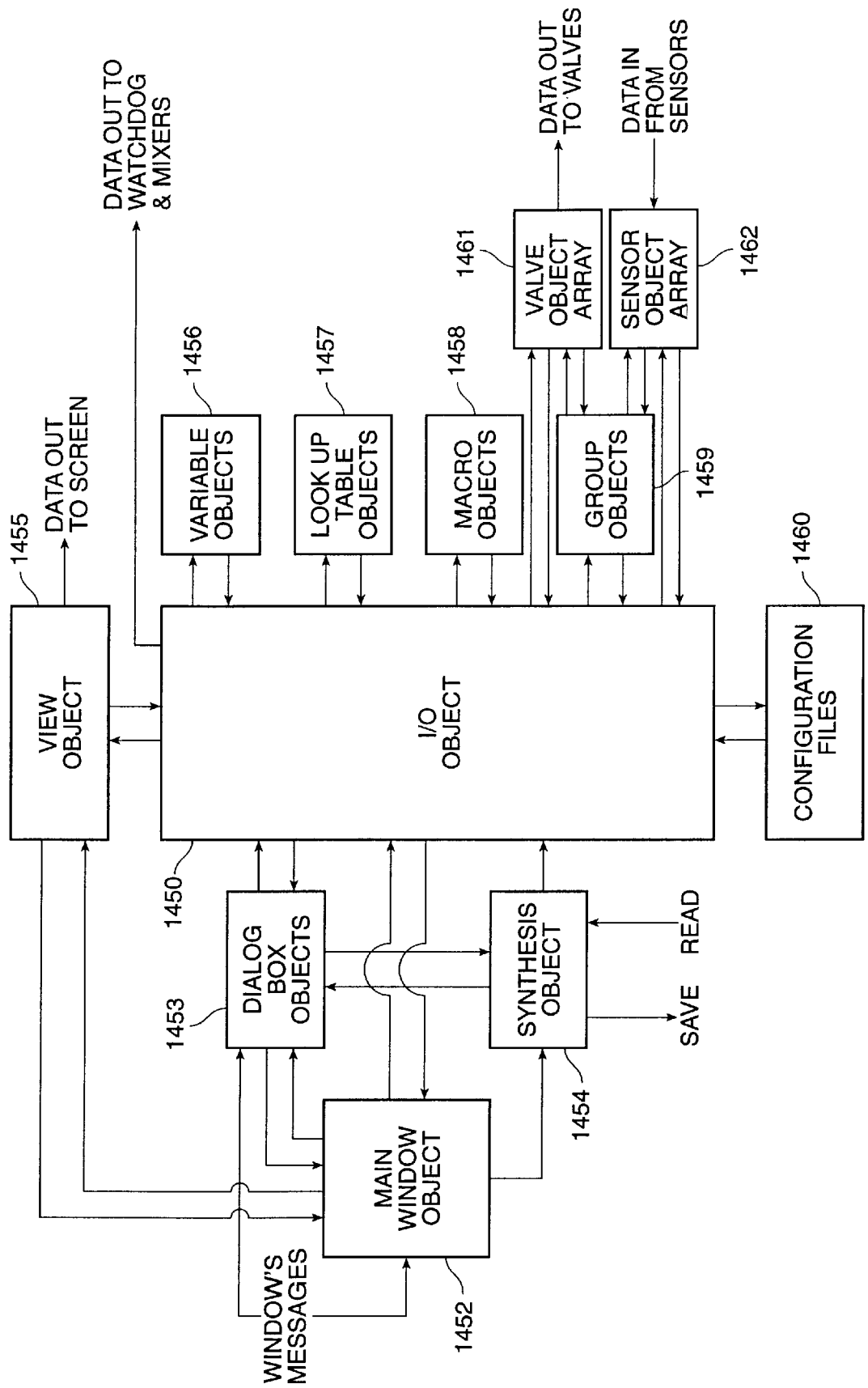
FIG. 49 schematically illustrates the data flow among the major modules of the control software in a Windows™ environment.

FIG. 49 is a flow chart illustrating the event-driven architecture of the control software as described in FIGS. 33–48. As shown, an I/O Object module 1450, which is the heart of the synthesizer's GUI, facilitates communication among the various object modules comprising the GUI. When the control software is initiated, a module 1460 loads the configuration files into the I/O Object module. These files are used to configure a Variable Objects module 1456, Lookup Table Objects module 1457, Macro Objects module 1458, Group Objects module 1459, Valve Object Array module 1461, and Sensor Object Array module 1462.

The Lookup Table Objects module contains a file used for mapping the valves and sensors to their corresponding reaction vessels so as to eliminate the need to manually address each individual valve or sensor relating to a specific reaction vessel. The Macro Objects module stores the list of defined macro; the Variable Objects module stores the defined variables while the defined group objects are stored in the Group Objects modules.

The Valve Object Array module stores an array identifying each individual valve in the system. To close or open a valve, the I/O Object module scans the Valve Object Array module until if finds a match. When a match is found, the Valve Object Array module outputs a signal to control that specific valve. To control a group of valves, the I/O module cooperates with the Group Objects module to scan the Valve Object Array, causing it to send the appropriate control signals to the selected valves.

The Sensor Object Array module stores an array identifying each individual sensor in the system. The I/O module may read a sensor by scanning the Sensor Object Array module until a match is found, causing it to read the specified sensor. To read a group of sensors, the I/O and Group Objects modules scan the Sensor Object Array module to determine the appropriate sensors to read.

The GUI also includes a Dialog Box Objects module 1453 and a Synthesis Object module 1454. The Dialog Box Objects module contains the dialog box objects which are displayed when certain commands are invoked. The Synthesis Object module stores the current synthesis setup file. To perform a different synthesis, the GUI reads the desired synthesis setup file from memory into the Synthesis Object module. Conversely, the contents in the Synthesis Object module are written to memory to save a synthesis setup file.

A Main Window Object (MWO) module 1452 communicates with a View Object module 1455 which displays the GUI's main window (FIG. 33) on the screen. A Message, in response to a user command, is sent to the MWO. This message is parsed to determine the appropriate command to execute. For example, if a Macros command is received, the MWO instructs the I/O object to retrieve the macros dialog box object from the Dialog Box Objects module and the lists of macros from the Macros Objects module. The View Object module receives this information from the I/O module and displays it on the GUI.

In one embodiment, the I/O module contains a Watchdog routine to shut down the synthesizer if the computer should malfunction. For example, the I/O object module may be programmed to send a pulse every 2 seconds to the synthesizer. If for any reason the synthesizer fails to receive these pulses, it will assume that the control computer has malfunctioned and will power down.

Figure 50:
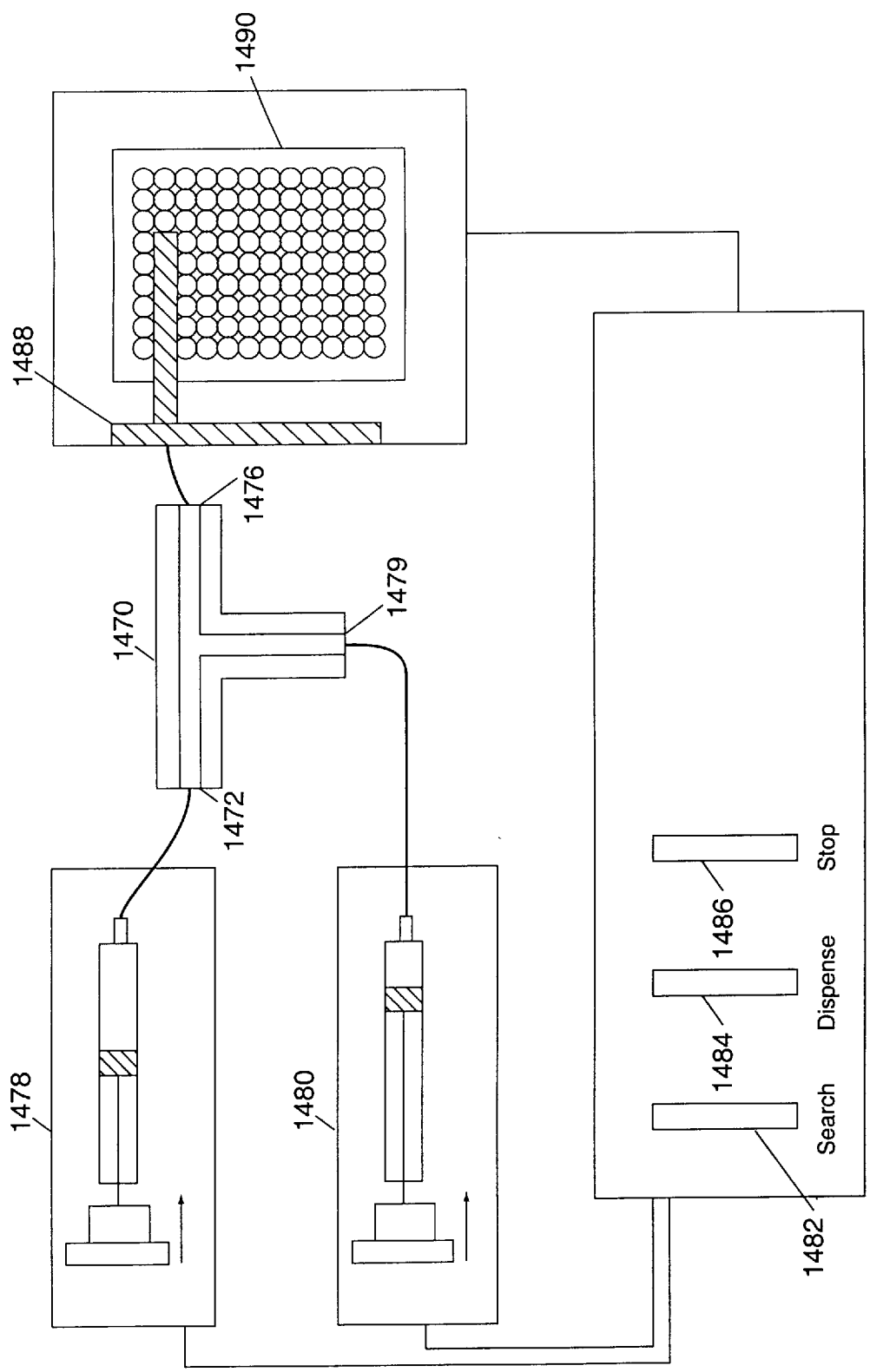
FIG. 50 shows a representation of a bead apportioning apparatus.
Figure 51:
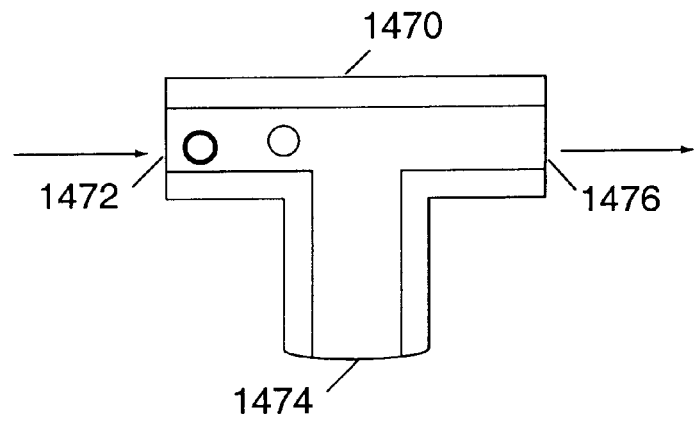
FIG. 51 shows a schematic representation of a bead dispensing/apportioning method. The figure shows the delivery of a suspension of beads to a flow cell or "detection tee" (top panel). Arrows indicate the direction of fluid flow. As individual or select numbers of multiple beads traverse the intersection of the two inlet channels (center panel), the bead delivery flow is stopped, and a dispensing fluid is flowed through the second inlet, to dispense the bead or beads that had traversed the intersection (bottom panel). The steps are repeated as desired.
Figure 51:
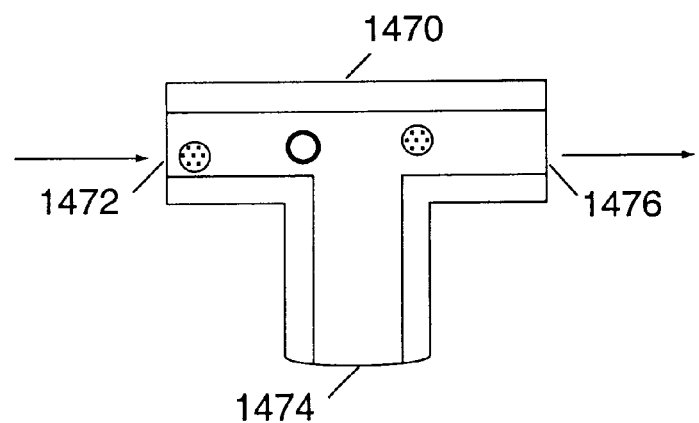
Figure 51:
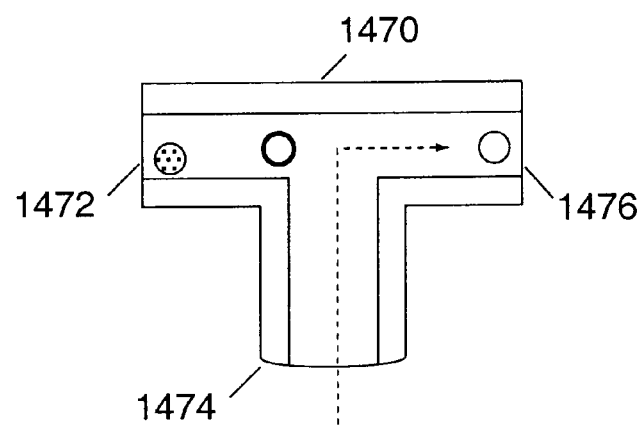

IX. Apparatus and Methods for Apportioning Individual or Select Number of Library Beads In addition to the foregoing, the present invention also provides methods and apparatus for apportioning individual, or select numbers of library beads. FIG. 50 illustrates a device useful in a method for apportioning individual or selected multiple numbers of beads. The device generally comprises a flow cell or "detection tee" 1470, having first and second inlet channels, 1472 and 1474, respectively, and an outlet, or "dispense" channel 1476. The apparatus provides a first fluid delivery means 1478 for delivering a suspension of beads through the first inlet channel, e.g., a syringe, a pump, or the like, until an individual bead, or select number of beads is observed to have passed the intersection of the first inlet channel 1472, with the second inlet channel, 1474. Once an individual or select number of beads is observed or detected as having passed this intersection, the flow through the first inlet channel is stopped or substantially slowed, and a second fluid delivery means 1480, e.g., a syringe or pump, delivers a volume of dispensing fluid through the second inlet channel, forcing the individual or select number of beads out of the detection tee, through the dispense channel 1476. A schematic representation of the device is shown in FIG. 50. To facilitate observation of the bead suspension, as it travels through the detection tee, typically, the detection tee will be in part translucent or transparent. Additionally, observation may be enhanced by use of microscopes, video cameras, optical sensors, or a combination thereof. A representation of the bead apportioning method is shown in FIG. 51.

The bead suspension and the dispensing fluid will typically be delivered to the detection tee by way of a pair of separate syringes, or pumps. Furthermore, in preferred aspects, the first inlet channel of the detection tee will have internal dimensions such that only a small number, e.g., from 1 to 5, beads may pass simultaneously. Typically, both the first inlet channel and the outlet channel will have the same internal dimensions. Accordingly, the size of a particular inlet or outlet channel can depend upon the particular bead size to be apportioned. For example, where Monobeads™ are used, the internal dimensions of the first inlet and outlet will generally be from greater than about 10 $\mu$m to about 40–50 $\mu$m in diameter, and preferably, from about 15 to about 20 $\mu$m. For larger bead sizes, e.g., 100–200 $\mu$m, larger internal dimensions are used. It will be readily appreciated to those skilled in the art, that most or all aspects of the selection methods may be automated. For example, a "search" switch 1482 may activate the first fluid delivery means which controls the delivery of a bead suspension to the first inlet channel of the detection tee. When a bead or select multiple beads are detected to have traversed the intersection of the two inlet channels, a second fluid delivery means, or dispense pump may be activated by a "dispense" switch 1484 which automatically deactivates the bead delivery pump, and delivers the dispense fluid to the detection tee. As a result of the dispense fluid flow, the individual or select multiple beads will be dispensed out through the outlet channel and collected. Typically, an exit tube will be attached to the outlet channel, which may be directed to dispense the individual or select multiple beads into the collection vessel 1490. A "stop" switch 1486 will shut off both pumps. The detection and switching operations may be performed manually, e.g., by microscopic observation and manual pump operation, or alternatively, may be computer controlled. For example, the detection tee may comprise a flow cell which measures, e.g., optical density of the solution flowing through the cell. When a bead crosses the flow cell, the higher optical density of the bead may trigger the switching of the pumps from the bead delivery pump to the dispense pump. In addition, the outlet or dispense channel may be manually placed into a collection vessel, or may be attached to a collection device which automatically switches collection vessels into which the beads will be dispensed, following each dispensing event, i.e. a fraction collector 1488. Furthermore, the various fluid delivery means may be calibrated for optimal flow rates for the apportioning of beads, and dispense volumes, to ensure proper apportioning of beads.

EXAMPLES

The following examples are provided as further illustration of the present invention and not as a limitation.

Example 1

Library Preparation and Screening

This Example illustrates how the products of a combinatorial peptide synthesis on resin beads can be explicitly specified by attaching an oligonucleotide identifier tag to the beads coincident with each amino acid coupling step in the synthesis. Each tag conveys which amino acid monomer was coupled in a particular step of the synthesis, and the overall sequence of a peptide on any bead can be deduced by reading the tag(s) on that bead. The collection of beads can be screened for binding to a fluorescently-labeled anti-peptide antibody using a fluorescence activated cell sorting (FACS) instrument. Those beads to which an antibody binds tightly can be isolated by FACS, and the oligonucleotide identifiers that are attached to individual sorted beads can be amplified by the PCR. The sequences of the amplified DNAs are determined to reveal the identity of the peptide sequences which bind to the antibody with high affinity. By combining high capacity, oligonucleotide code-based information storage, amplification methodology, and fluorescence-based sorting, the present method provides a means for specifying the identity of each member of a vast library of molecules synthesized from both natural and unnatural chemical building blocks and for quickly and efficiently isolating individual beads that bear high affinity ligands for biological receptors.

In this Example, single stranded oligonucleotides are used to encode a combinatorial peptide synthesis using both L- and D-amino acid building blocks and 10 μm diameter polystyrene beads. The oligonucleotide tags have a high information content, are amenable to very high sensitivity detection and decoding, and, with the present method, are stable to reagents used in peptide synthesis. Peptides and nucleotides are assembled in parallel, alternating syntheses so that each bead bears many copies of both a single peptide sequence and a unique oligonucleotide identifier tag. The oligonucleotides share common 5'- and 3'-PCR priming sites, and thus the beads can serve as templates for the PCR. The encoded synthetic library contains about $8.2 \times 10^5$ heptapeptides and is screened for binding to an anti-dynorphin B monoclonal antibody D32.39 (see Barrett & Goldstein, 1985, *Neuropeptides* 6: 113–120, incorporated herein by reference), using a fluorescence activated cell sorting (FACS) instrument to select individual beads that strongly bind the antibody. After PCR amplification of the oligonucleotide tags on sorted beads, the DNA is sequenced to determine the identity of the peptide ligands.

A. Reagents and General Methods

The monodisperse 10 μm diameter bead material used in this work was a custom-synthesized macroporous styrene-divinylbenzene copolymer functionalized with a 1,12-diaminododecane linker purchased from Pharmacia. The beads are Pharmacia Monobeads™ that have not been derivatized with Pharmacia's Gene Assembler Support linker. See Ugelstad and Mork, 1980, *Adv. Colloid Interface Sci.* 13: 101–140, incorporated herein by reference.

All protected amino acids were obtained from Bachem Bioscience Inc. PCR and sequencing primers were synthesized with an Applied Biosystems model 394 oligonucleotide synthesizer. Authentic samples of certain peptides were synthesized with an Applied Biosystems model 431A peptide synthesizer using Fmoc-protected amino acids, HBTU/HOBt in situ activation chemistry, and deprotection with 40:1:1 TFA/water/ethanedithiol. These peptides were purified by HPLC (>95% purity) on a Rainin $C_{18}$ reverse phase column using water/acetonitrile/0.1% TFA as eluant, and structures were verified by mass spectrometry.

B. Parallel Synthesis of a 69-base Oligonucleotide and the Opioid Peptide Dynorphin B The C-terminal seven amino acid fragment of the opioid peptide dynorphin B H-Arg-Gln-Phe-Lys-Val-Val-Thr-$NH_2$ (RQFKVVT) (SEQ ID NO:2) was synthesized in parallel with a 69-mer oligodeoxynucleotide (ST08) on 10 μm diameter beads. The sequence of ST08 was 5'-<u>ATC CAA TCT CTC CAC</u>(ATC TCT ATA CTA TCA) TCA CC [TA TC CT AT TT TT AC] CTC AC <u>T CAC TTC CAT TCC AC</u>-3' (SEQ ID NO:20). Underlined portions of this sequence correspond to PCR-priming sites while the region in parentheses is homologous to the primer used for sequencing this template. The 14-base sequence enclosed in brackets represents the coding region of the template.

The beads were first treated with a mixture of succinimidyl 4-O-DMT-oxybutyrate (Molecular Probes) and the 1-oxybenzotriazole ester of either N-Fmoc-2,4-dimethoxy-4'-(carboxymethyloxy)-benzhydrylamine (i.e. the acid-cleavable Knorr carboxamide linker) or N-Fmoc-Thr($^t$Bu)-OH (for non-cleavable experiments). The ratio of Fmoc-protected amino groups to DMT-protected hydroxyl residues on the beads was determined spectrophotometrically to be approximately 20:1. The beads were subjected to 20 cycles of oligonucleotide synthesis on an automated synthesizer using 3'-O-methyl-N,N-diisopropyl phosphoramidites of the following nucleosides: $N^6$-Bz-5'-O-DMT-(7-deaza)-2'-deoxyadenosine (Berry and Associates, Ann Arbor, Michigan), $N^4$-Bz-5'-O-DMT-2'-deoxycytidine, and 5'-O-DMT-thymidine (Glen Research).

The beads were then removed from the instrument and treated for 5 min. with 10% piperidine in DMF to remove the Fmoc protecting group. After coupling the first amino acid residue (N-Fmoc-Thr($^t$Bu)-OH), the beads were treated with a DMF solution of acetic anhydride and 1-methylimidazole to cap any unreacted amines. AU peptide coupling reactions were run for 20 min. and contained 0.11 M Fmoc-amino acid, 0.1 M HBTU, 0.1 M HOBt, and 0.3 M DIEA in DMF. The beads were then subjected to two cycles of nucleotide addition on the synthesizer (detritylation with TCA; tetrazole-catalyzed phosphitylation; capping with acetic anhydride; oxidation with iodine in acetonitrile/water). Sequential steps of amino acid coupling and dinucleotide addition were repeated until synthesis of the peptide sequence RQFKVVT (SEQ ID NO:2) and construction of the oligonucleotide coding region had been completed. After performing an additional 35 cycles of oligonucleotide synthesis, the beads were treated sequentially with piperidine/DMF (1:9 for 8 min), thiophenol/triethylamine/dioxane (1:2:2 for 4 hr), ethylenediamine/ethanol (1:1 for 5 hr at 55° C.), and TFA/water (20:1 for 1 hr) to deprotect fully both the peptide and oligonucleotide chains. In experiments using the acid-cleavable linker, the supernatant from the TFA deprotection reaction was concentrated in vacuo, and the isolated crude peptide was then analyzed by HPLC.

C. Construction of an Encoded Library

The parallel synthesis chemistry outlined above was used in the construction _of the library. The sites of peptide synthesis were differentiated from DNA synthesis sites in this experiment by coupling to all the beads a mixture of N-Fmoc-Thr($t$Bu)-OBt and succinimidyl 4-O-DMT-oxybutyrate as described above. Sequences of oligonucleotide tags in the library deviated from ST08 only within the coding region. The 3'-conserved region of the oligonucleotide ST08 was first synthesized on a total bead mass of 35 mg (~1.75×10$^8$ beads). The Fmoc protecting group was removed and the bead mass was divided into seven equal parts. To each aliquot was coupled one of seven different alpha-N-Fmoc-protected amino acids (side chain protecting groups are shown in parenthesis): Arg(N$^G$-Pmc), Gln(Trt), Phe, Lys($t$Boc), Val, D-Val and Thr($t$Bu). Each part was then subjected to two rounds of automated oligonucleotide synthesis. The respective sequences of the appended dinucleotides that specified uniquely each different amino acid residue were TA, TC, CT, AT, TT, CA and AC. The beads were then pooled, mixed thoroughly, and the entire bead mass subjected to Fmoc deprotection.

This cycle of bead partitioning, peptide coupling, oligonucleotide dimer synthesis, bead recombination and Fmoc removal was repeated for a total of seven times. The final Fmoc protecting group was not removed. Rather, the pooled bead mass was subjected to 35 cycles of oligonucleotide synthesis. The library was then fully deprotected as described above.

D. Library Staining and FACS Analysis

A portion of a library (typically 0.5–2 mg of beads) was suspended in blocking buffer (PBS, 1% BSA, 0.05% Tween-20) and incubated at room temperature for 1 hr. The beads were pelleted by centrifugation and resuspended in a solution of mAb D32.39 (10 mg/mL in blocking buffer). The suspension was incubated on ice for 30 min., pelleted by centrifugation, and washed with blocking buffer. The beads were then suspended in a solution of phycoerythrin-conjugated goat anti-mouse antibody (Molecular Probes) for 20 min. on ice. The beads were washed in blocking buffer and diluted in PBS for delivery into the fluorescence activated cell sorting (FACS) instrument (Becton Dickinson FACStar Plus). Beads which had bound the mAb D32.39 were identified by their acquired fluorescence. Individual beads from both the most brightly stained 0.17% of the library and from the region having the lowest fluorescence (ca. 98%) were sorted into PCR microfuge vials. Specific binding of D32.39 to the beads was blocked by preincubation of the mAb with the soluble peptide Ac-RQFKVVT-OH (SEQ ID NO:2) at a final concentration of 10 µM.

E. PCR of Bead-Bound Template

PCR amplifications were performed in the manufacturer supplied buffer system (50 mM KCl, 10 mM Tris-HCl, pH 9.0, 0.1% Triton X-100, 2 mM MgCl$_2$) with 0.2 mM dATP, dCTP, and dGTP, 0.8 mM dUTP, 2 mM each primer, 3 units 9 polymerase (Promega), and 1 unit of uracil DNA glycosylase (Gibco BRL) (total volume 70 L). The primer sequences, 5'-ATC CAA TCT CTC CAC-3' (SP13) (SEQ ID NO:21) and 5'-(biotin)-GTG GAA TGG AAG TGA-3' (SP14) (SEQ ID NO:22) were respectively homologous and complementary to the template ST08. PCR reactions consisted of 45 cycles of denaturation at 95° C. for 30 sec., primer annealing at 50° C. for 1 min., and extension at 72° C. for 1 min. Reactions were analyzed by electrophoresis in 20% acrylamide or 2% low melting point agarose gels.

F. Sequencing of PCR Product

Biotinylated PCR product from individual reactions was isolated with streptavidin-coated magnetic beads (Dynal, Inc.). After alkaline elution of the non-biotinylated strand and washing, each bead sample was treated with sequencing cocktail. Dideoxy sequencing was performed using the primer 5'-ATC TCT ATA CTA TCA-3' (SP15) (SEQ ID NO:23) and Bst polymerase (Bio-Rad) according to the manufacturer's instructions, with the exception that a 1:100 ratio of deoxy- to dideoxynucleotide triphosphates (Pharmacia) was employed.

G. Determination of Peptide Binding Affinities

The binding affinities of various peptides for the monoclonal antibody D32.39 were measured in a competition binding experiment. A tracer peptide (LRRASLGGGRRQFKVVT (SEQ ID NO:24); 50 pM) containing the known epitope for D32.39 fused to a consensus substrate sequence for cAMP-dependent protein kinase was radiolabeled to high specific activity with [g-$^{33}$P] ATP (see Li et al., 1989, Proc. Natl. Acad. Sci. USA 86: 558–562, incorporated herein by reference) and mixed with various concentrations of the peptide of interest (10 µM–1 pM). The peptide mixtures were added to polystyrene wells coated with D32.39 (0.1 µmg/mL). Samples were incubated 2 hr. at 4° C., the wells washed with PBS, and the radioactivity associated with each well was counted and used to generate a competitive binding curve. Under the conditions of the assay the IC$_{50}$ should be close to the dissociation constant (K$_d$) for the peptide.

Example 2

Synthesis and Stability Studies of Thiazolidinones

The following examples relate to the synthesis of thiazolidinones using the methods of the present invention. This synthesis is described in greater detail in U.S. patent application Ser. No. 08/265,090, filed Jun. 23, 1994, and incorporated herein by reference for all purposes.

A. Preparation of Double-Labeled Thiazolidinone

H$_2$N-S-TentaGel (500 mg), a commercially available polystyrene based resin (Rapp Polymere, Tubingen, Germany, 1 g, 0.30 mmol/g loading), was elaborated with Fmoc-Gly-OH labeled at the α-carbon (2-$^{13}$C, 99% from Cambridge Isotope Laboratories, Inc., Andover, Mass.). The resin was capped with Ac$_2$O, deprotected with piperidine, and the Fmoc-photolinker coupled as its OBt-activated ester. The resin was again capped, deprotected, and reacted with unlabeled Fmoc-Glycine-OH as its anhydride. An additional round of capping and deprotection generated the free amine resin. Reaction with 0.75 M PhCHO labeled at the carbonyl (carbonyl-$^{13}$C, 99% from Cambridge Isotope Laboratories, Inc., Andover, Mass.) and 2.0 M mercaptoacetic acid in ACN containing 3A molecular sieves for 2 hours at 70° C. generated the double labeled thiazolidinone resin. The resin was washed extensively (3×5 ml $CH_2Cl_2$, 3×5 ml DMF, 3×5 ml $CH_2Cl_2$, 3×5 ml MeOH, 3×5 ml $CH_2Cl_2$, 3×5 ml $Et_2O$) and dried under vacuum.

B. TFA Stability Studies

Figure 30:
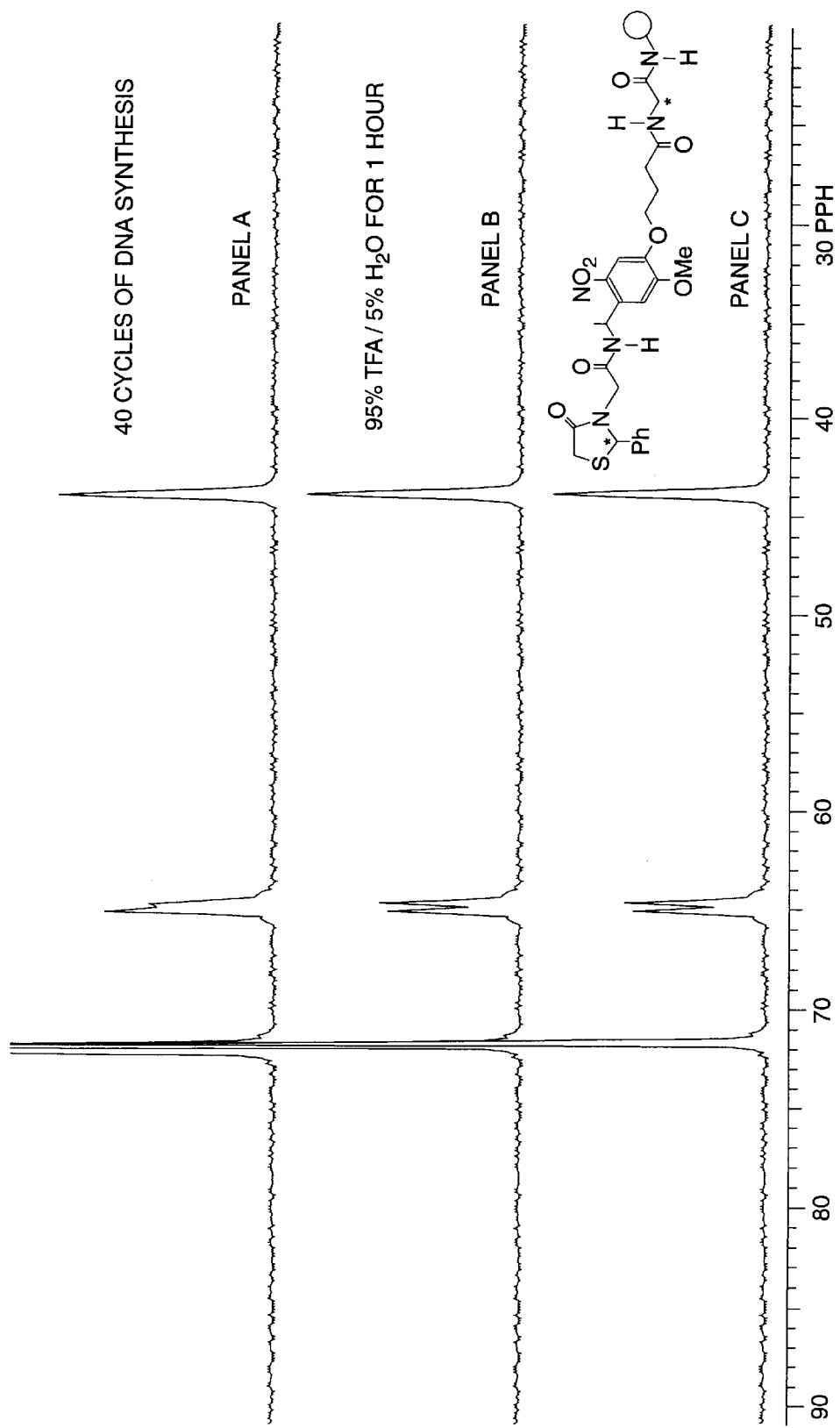
FIG. 30 illustrates the use of $^{13}$C NMR to monitor the stability of thiazolidinones. Panel C shows the $^{13}$C NMR spectrum of support bound thiazolidinone which has been doubly labeled with a $^{13}$C atom at the position 2 of the ring and at the position alpha to the carbonyl of the linker (labeled positions are indicated with a "*"). Panel B shows the $^{13}$C NMR spectrum of support-bound doubly labeled thiazolidinone after treatment with 95% TFA for 1 hour. Panel A shows $^{13}$C NMR spectrum of support bound doubly labeled thiazolidinone after 40 cycles of DNA synthesis.

A portion (20 mg) of the resin was treated with 95% TFA/5% $H_2O$ for 1 hour followed by washing with $CH_2Cl_2$, MeOH and $Et_2O$. Gel-$^{13}C$ NMR analysis of the resin indicated no loss of thiazolidinone, as evidenced by relative integration of the two labeled carbons. See Panel B, FIG. 30. Any destruction of either the photolinker or thiazolidinone would be expected to result in the integration of the benzylic carbon to decrease. This experiment demonstrated that both the thiazolidinone and the photolinker were stable to TFA treatment.

C. DNA Synthesis Stability Studies

Figure 31:
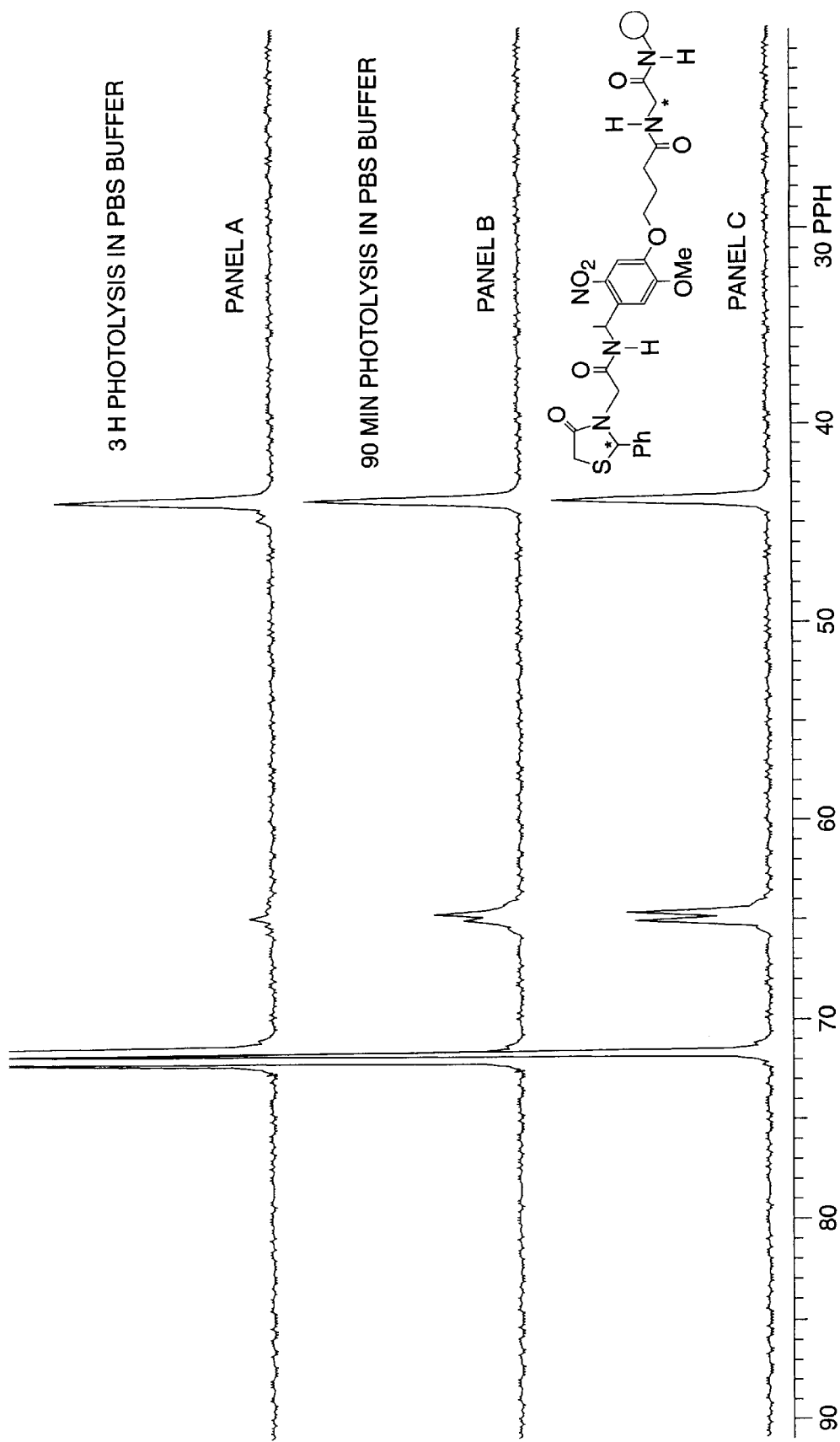
FIG. 31 further illustrates the use of $^{13}$C NMR to monitor the stability of thiazolidinones. Panel C shows the $^{13}$C NMR spectrum of support-bound thiazolidinone which has been doubly labeled with a $^{13}$C atom at the position 2 of the ring and at the position alpha to the carbonyl of the linker labeled positions are indicated with a "*"). Panel B shows the $^{13}$C NMR spectrum of support-bound doubly labeled thiazolidinone after 90 minute photolysis in PBS buffer. Panel A shows $^{13}$C NMR spectrum of support bound doubly labeled thiazolidinone after 3 hours of photolysis in PBS buffer.
Figure 32:
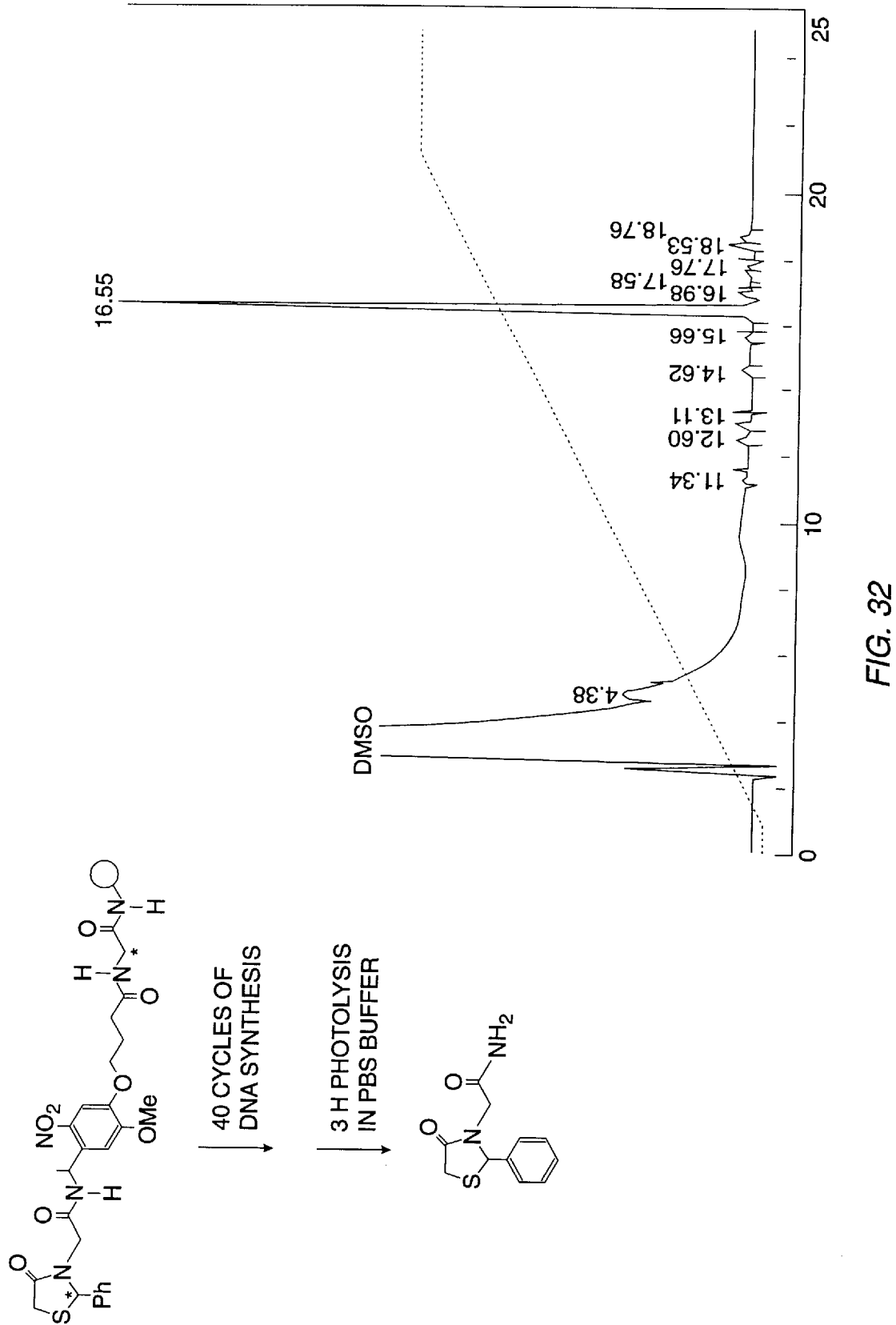
FIG. 32 shows an HPLC trace for the reaction mixture produced by subjecting a support-bound thiazolidinone to 40 cycles of DNA synthesis and 3 hour photolysis in PBS buffer.

A portion (20 mg) of the resin was loaded into the standard DNA synthesis cartridge and subjected to 40 cycles of DNA synthesis with A, C and T nucleosides employed as their phosphoramidites, followed by iodine oxidation after every cycle. "Mock" dimethoxytrityl (DMT) removal was accomplished by treating the resin 2% TFA/$CH_2Cl_2$ at the start of every cycle. The resin was removed from the cartridge, washed with DMF, and analyzed by gel-$^{13}C$ NMR spectroscopy. See Panel A, FIG. 30. The spectrum obtained revealed little or no destruction of either the photolinker or thiazolidinone molecules. A portion (2 mg) of the resin was also photolyzed for 3 hours in pH 7.4 PBS buffer and the liberated thiazolidinone analyzed by HPLC. See Panel A, FIG. 31 and FIG. 32. The data revealed that the thiazolidinone was released in high purity and that both the photolinker and thiazolidinone were not significantly altered upon treatment with standard DNA synthesis reagents.

Example 3

Combinatorial Synthesis

A combinatorial synthesis of YGGFL was performed using the synthesis device. The synthesis was done in reaction vessels 1–6; 7–9 were disconnected. The six amino acids added to the beads were L, E, G, Y, A, and F. YGGFL was specified along with other peptides. Beads were added to the parent vessel (29.5 mg) and suspended in DMF. Each synthesis cycle included steps of redistribution, peptide coupling, capping, amine deprotection, collection of deprotection for FMOC, rinsing with DMF, and recombination in the parent.

Following synthesis, the labeled Hertz antibody was introduced to the mixed beads. The Hertz antibody binds mostly with YGGFL. FACS analysis identified the presence of YGGFL, proving that this specified combination was synthesized by the synthesizer. The experiment shows that a diverse collection of peptides, including the YGGFL chain, can be specified and synthesized via the synthesizer.

Although the present invention has been described in some detail by way of illustration and example for purposes of clarity and understanding, it will be apparent that certain changes and modifications may be practiced within the scope of the appended claims.

Example 4

Determination of Bead Distribution Using the Apparatus of the Invention

To determine if mixed beads from the parent vessel were being evenly distributed to the reaction vessels, some beads were biotinylated. The biotinylated beads were manually deposited in one reaction vessel. Non-biotinylated beads were manually deposited in the other 8 reaction vessels. The synthesizer transfers all beads from 9 reaction vessels to the parent vessel. A sample was taken from the parent vessel, and fluoresced streptavidin was allowed to bind with biotin on the biotinylated beads. Florescence Activated Cell Sorter (FACS) analysis shows that approximately 9.1% of the beads in the parent vessel were biotinylated. The beads were then reallocated to 9 reaction vessels, and the percentage of biotinylated beads to total beads in each vessel was determined by a FACS analyzer. Table 5 shows that the mixed beads in each reaction vessel have approximately the same ratio of biotinylated beads to total beads as the parent vessel.

TABLE 5

|  | % Bright Beads |
| --- | --- |
| Parent | 9.1 |
| 1 | 9.7 |
| 2 | 9.7 |
| 3 | 9.4 |
| 4 | 8.7 |
| 5 | 9.4 |
| 6 | 8.9 |
| 7 | 9.1 |
| 8 | 8.9 |
| 9 | 9.3 |
| Average | 9.2 |
| Standard dev. | 0.32 |

Example 5

Screening Combinatorial Libraries For Imp Type II Dehydrogenase Inhibitors

In order to screen libraries for selective inhibitors of type II inhibitors of IMP dehydrogenase, two *E. coli* strains are constructed as follows:

Strain 1: guaB–, lacz+, Pho A–, carrying a plasmid which expresses type I IMP dehydrogenase.

Strain 2: guaB–, lacz–, Pho A–, carrying a plasmid which expresses type II IMP dehydrogenase.

The two strains are mixed and grown as a lawn on minimal medium plates lacking guanine, but containing lactose plus two color indicators: 2,3,5-triphenyl tetrazolium chloride, which produces a red color in response to lacz+ cells, and 5-bromo-4-chloro-3-indolyl-phosphate (XP), which produces a blue color in response to phoA+ cells. See Wanner, et al., *J. Bacteriol.* (1979) 140:229–239. Before plating, the cells are mixed with beads carrying a combinatorial library. Following plating, the library compounds are released from the beads by cleavage of the linker group, e.g., photolysis of a photocleavable linker group. Library compounds that are cytotoxic for *E. coli,* or that nonspecifically inhibit both enzyme types, produce a clear zone within the lawn. Compounds which inhibit type I IMP dehydrogenase inhibit the growth of cells which result in the production of the red color, and thus yield only a blue zone. Compounds which selectively inhibit the type II IMP dehydrogenase inhibit the growth of the cells which result in the blue color, resulting in a red zone around the library bead from which the compound is released. Beads which result in a red zone are collected and their tags are decoded to yield the structure of the compound which inhibited the type II IMP dehydrogenase according to the methods described in Example 1.

It is to be understood that the above description is intended to be illustrative and not restrictive. Many embodiments will be apparent to those of sell in the art upon reviewing the above description. The scope of the invention should, therefore, be determined not with reference to the above description, but should instead be determined with reference to the appended claims, along with the full scope of equivalents to which such claims are entitled. All publications and patent documents cited in this application are incorporated by reference in their entirety for all purposes to the same extent as if each individual publication or patent document were so individually denoted.

What is claimed is:

1. An apparatus for agitating reaction vessels, comprising:
   a reaction vessel bracket having a plurality of reaction vessels attached thereto;
   a non-concentric shaft having a first end and a second end, the first end being rotatably connected to the reaction vessel bracket;
   a mounting bracket rotatably engaging the second end of the shaft, with the reaction vessels being positioned between the reaction vessel bracket and the mounting bracket;
   a vortexing motor attached to the mounting bracket; and
   a transmission means for transmitting rotational force supplied by the motor to the second end of the shaft;
   wherein the rotational force causes the reaction vessel bracket to rotate in a circular path relative to the mounting bracket and thereby agitate contents of the reaction vessels.

2. The apparatus of claim 1, further including a second non-concentric shaft.

3. The apparatus of claim 2, wherein one of said shafts is mounted at a first end of the reaction vessel bracket, and the other of said shafts is mounted at a second end of the reaction vessel bracket.

4. The apparatus of claim 2, wherein said shafts are mounted inside of shaft housings.

5. The apparatus of claim 1, wherein said transmission means includes one or more elements selected from the group consisting of belts, chains and sprockets, pulleys, and gears.

6. The apparatus of claim 5, wherein said transmission means includes a belt and pulleys.

7. The apparatus of claim 1, wherein said vortexing motor is controlled by a control computer.

8. The apparatus of claim 1, wherein said reaction vessel bracket is a lower bracket said mounting bracket is an upper bracket, said reaction vessels have lower and upper ends, and said reaction vessels are attached to the lower bracket by their bottom ends.

9. The apparatus of claim 1, wherein said non-concentric shaft is connected to said mounting bracket via a fixed rotary support.

10. The apparatus of claim 9, wherein said fixed rotary support is a roller bearing.

11. The apparatus of claim 1, wherein said non-concentric shaft is designed so that the circular path has a radius of approximately 3.5 mm.

12. The apparatus of claim 1, wherein said vortexing motor is capable of rotating said reaction vessel bracket at approximately 1500 revolutions per minute.

13. The apparatus of claim 1, wherein said vortexing motor is selected from the group consisting of an electric motor and a pneumatic motor.

14. The apparatus of claim 1, wherein said vortexing motor is a stepper motor.

15. An apparatus for agitating reaction vessels, comprising:
   a reaction vessel bracket having a plurality of reaction vessels attached thereto;
   a non-concentric shaft having a first end and a second end, the first end being rotatably connected to the reaction vessel bracket;
   a mounting, bracket rotatably engaging the second end of the shaft;
   a vortexing motor attached to the mounting bracket; and
   a transmission means for transmitting rotational force supplied by the motor to the second end of the shaft;
   wherein the rotational force causes the reaction vessel bracket to rotate in a circular path relative to the mounting bracket and thereby agitate contents of the reaction vessels;
   wherein said reaction vessel bracket is a lower bracket said mounting bracket is an upper bracket, said reaction vessels have lower and upper ends, and said reaction vessels are attached to the lower bracket by their bottom ends.

16. An apparatus for agitating reaction vessels, comprising:
   a reaction vessel bracket having, a plurality of reaction vessels attached thereto, wherein each reaction vessel includes a bottom portion that is constructed of a length of flexible tubing, and wherein the bottom portion is attached to the reaction vessel bracket;

a non-concentric shaft having a first end portion and a second end portion, the first end portion being rotatably connected to the reaction vessel bracket;

a mounting, bracket rotatably holding the second end portion of the shaft;

a vortexing, motor; and a transmission assembly to transmit a rotational force supplied by the motor to the second end portion of the shaft to cause the shaft to rotate;

wherein rotation of the shaft causes the reaction vessel bracket to rotate in a circular path relative to the mounting, bracket and thereby agitate the contents of the reaction vessels.

* * * * *

```
                           SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:1:

Tyr Gly Gly Phe Leu Arg Arg Gln Phe Lys Val Val Thr
1               5                  10

(2) INFORMATION FOR SEQ ID NO:2:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:2:

Arg Gln Phe Lys Val Val Thr
1               5

(2) INFORMATION FOR SEQ ID NO:3:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:3:

Thr Phe Arg Gln Phe Lys Val Thr
1               5

(2) INFORMATION FOR SEQ ID NO:4:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide
```

```
    (xi) SEQUENCE DESCRIPTION: SEQ ID NO:4:

Thr Thr Arg Arg Phe Arg Val Thr
1               5

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Thr Val Arg Gln Phe Lys Thr Thr
1               5

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Gln Val Arg Gln Phe Lys Thr Thr
1               5

(2) INFORMATION FOR SEQ ID NO:7:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Arg Gln Phe Arg Thr Val Gln Thr
1               5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Lys Gln Phe Lys Val Thr Lys Thr
1               5

(2) INFORMATION FOR SEQ ID NO:9:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

```
        (ii) MOLECULE TYPE: peptide (xi) SEQUENCE DESCRIPTION: SEQ ID NO:9:

Gln Gln Phe Lys Val Val Gln Thr
1               5

(2) INFORMATION FOR SEQ ID NO:10:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Lys Gln Phe Lys Val Thr Gln Thr
1               5

(2) INFORMATION FOR SEQ ID NO:11:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Thr Gln Phe Lys Val Thr Lys Thr
1               5

(2) INFORMATION FOR SEQ ID NO:12:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Thr Phe Arg Val Phe Arg Val Thr
1               5

(2) INFORMATION FOR SEQ ID NO:13:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Phe Arg Arg Gln Phe Arg Val Thr
1               5

(2) INFORMATION FOR SEQ ID NO:14:

(i) SEQUENCE CHARACTERISTICS:
            (A) LENGTH: 8 amino acids
```

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Arg Gln Phe Lys Gln Val Gln Thr
1               5

(2) INFORMATION FOR SEQ ID NO:15:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Gln Thr Val Thr Val Lys Lys Thr
1               5

(2) INFORMATION FOR SEQ ID NO:16:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Gln Gln Val Gln Arg Gln Thr Thr
1               5

(2) INFORMATION FOR SEQ ID NO:17:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Lys Thr Gln Val Val Gln Phe Thr
1               5

(2) INFORMATION FOR SEQ ID NO:18:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Gln Val Thr Gln Val Arg Val Thr
1               5
```

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Phe Val Val Thr Val Arg Val Thr
1               5

(2) INFORMATION FOR SEQ ID NO:20:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:20:

ATCCAATCTC TCCACATCTC TATACTATCA TCACCTATCC TATTTTTAC        60

CCATTCCAC        69

(2) INFORMATION FOR SEQ ID NO:21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:21:

ATCCAATCTC TCCAC        15

(2) INFORMATION FOR SEQ ID NO:22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO:22:

GTGGAATGGA AGTGA        15

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:23:

ATCTCTATAC TATCA        15

(2) INFORMATION FOR SEQ ID NO:24:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:24:

```
Leu Arg Arg Ala Ser Leu Gly Gly Gly Arg Arg Gln Phe Lys Val Val
1               5                   10                  15
Thr
```